(12) United States Patent
Stoltz et al.

(10) Patent No.: US 11,390,585 B2
(45) Date of Patent: *Jul. 19, 2022

(54) QUATERNARY HETEROATOM CONTAINING COMPOUNDS

(71) Applicant: California Institute of Technology, Pasadena, CA (US)

(72) Inventors: Brian M. Stoltz, San Marino, CA (US); Scott C. Virgil, Pasadena, CA (US); David E. White, Wayne, PA (US); Taiga Yurino, Kyoto (JP); Yiyang Liu, Pasadena, CA (US); Douglas C. Behenna, Laguna Niguel, CA (US); Douglas Duquette, Los Angeles, CA (US); Christian Eidamshaus, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/164,204

(22) Filed: Feb. 1, 2021

(65) Prior Publication Data

US 2021/0155592 A1    May 27, 2021

Related U.S. Application Data

(63) Continuation of application No. 16/427,629, filed on May 31, 2019, now Pat. No. 10,906,875, which is a
(Continued)

(51) Int. Cl.
*C07D 211/78*    (2006.01)
*C07D 207/06*    (2006.01)
(Continued)

(52) U.S. Cl.
CPC .......... *C07D 211/78* (2013.01); *C07D 207/06* (2013.01); *C07D 207/08* (2013.01); *C07D 207/10* (2013.01); *C07D 207/16* (2013.01); *C07D 207/26* (2013.01); *C07D 207/263* (2013.01); *C07D 207/267* (2013.01); *C07D 207/27* (2013.01); *C07D 207/273* (2013.01); *C07D 207/277* (2013.01); *C07D 207/46* (2013.01); *C07D 211/16* (2013.01); *C07D 211/18* (2013.01); *C07D 211/22* (2013.01); *C07D 211/34* (2013.01); *C07D 211/38* (2013.01); *C07D 211/60* (2013.01); *C07D 211/76* (2013.01); *C07D 211/88* (2013.01);
(Continued)

(58) Field of Classification Search
CPC .............. C07D 211/78; C07D 211/16; C07D 211/18; C07D 211/22; C07D 211/34; C07D 211/38; C07D 211/60; C07D 211/76; C07D 211/88; C07D 211/90; C07D 211/94; C07D 211/96; C07D 207/06; C07D 207/08; C07D 207/10; C07D 207/16; C07D 207/26; C07D 207/263; C07D 207/267; C07D 207/27; C07D 207/273; C07D 207/277; C07D 207/46; C07D 223/04; C07D 223/10; C07D 241/04; C07D 241/08; C07D 241/52; C07D 265/30; C07D 265/32; C07D 309/04; C07D 309/30
See application file for complete search history.

(56) References Cited

U.S. PATENT DOCUMENTS 2,886,487 A    5/1959  Kupferberg et al.
4,639,462 A    1/1987  Kramer et al.
(Continued)

FOREIGN PATENT DOCUMENTS

DE          668489 C      12/1938
WO     WO-9525088 A1       9/1995
(Continued)

OTHER PUBLICATIONS

U.S. Appl. No. 16/219,214, Pending.
(Continued)

*Primary Examiner* — Timothy R Rozof
(74) *Attorney, Agent, or Firm* — Foley Hoag LLP; Janine S. Ladislaw

(57) ABSTRACT

The invention provides heterocyclic compounds with quaternary centers and methods of preparing compounds. Methods include the method for the preparation of a compound of Formula (II):

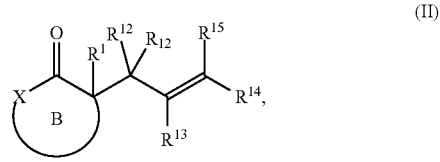

comprising treating a compound of Formula (I):

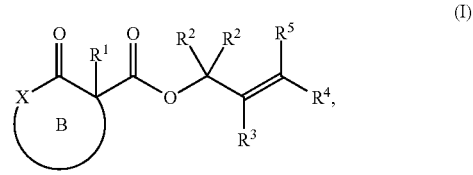

with a transition metal catalyst and under alkylation conditions as valence and stability permit.

14 Claims, 1 Drawing Sheet

Related U.S. Application Data continuation of application No. 16/049,434, filed on Jul. 30, 2018, now Pat. No. 10,343,996, which is a continuation of application No. 15/366,590, filed on Dec. 1, 2016, now Pat. No. 10,035,769, which is a continuation of application No. 13/797,736, filed on Mar. 12, 2013, now abandoned, which is a continuation of application No. 13/531,485, filed on Jun. 22, 2012, now Pat. No. 8,822,679.

(60) Provisional application No. 61/501,054, filed on Jun. 24, 2011.

(51) Int. Cl.

| | |
|---|---|
| C07D 207/08 | (2006.01) |
| C07D 207/10 | (2006.01) |
| C07D 207/16 | (2006.01) |
| C07D 207/26 | (2006.01) |
| C07D 207/263 | (2006.01) |
| C07D 207/267 | (2006.01) |
| C07D 207/27 | (2006.01) |
| C07D 207/273 | (2006.01) |
| C07D 207/277 | (2006.01) |
| C07D 207/46 | (2006.01) |
| C07D 211/16 | (2006.01) |
| C07D 211/18 | (2006.01) |
| C07D 211/22 | (2006.01) |
| C07D 211/34 | (2006.01) |
| C07D 211/38 | (2006.01) |
| C07D 211/60 | (2006.01) |
| C07D 211/76 | (2006.01) |
| C07D 211/88 | (2006.01) |
| C07D 211/90 | (2006.01) |
| C07D 211/94 | (2006.01) |
| C07D 211/96 | (2006.01) |
| C07D 233/04 | (2006.01) |
| C07D 233/10 | (2006.01) |
| C07D 241/04 | (2006.01) |
| C07D 241/08 | (2006.01) |
| C07D 241/52 | (2006.01) |
| C07D 265/30 | (2006.01) |
| C07D 265/32 | (2006.01) |
| C07D 309/04 | (2006.01) |
| C07D 309/30 | (2006.01) |
| C07D 223/10 | (2006.01) |
| C07D 223/04 | (2006.01) |

(52) U.S. Cl.
CPC .......... *C07D 211/90* (2013.01); *C07D 211/94* (2013.01); *C07D 211/96* (2013.01); *C07D 223/04* (2013.01); *C07D 223/10* (2013.01); *C07D 241/04* (2013.01); *C07D 241/08* (2013.01); *C07D 241/52* (2013.01); *C07D 265/30* (2013.01); *C07D 265/32* (2013.01); *C07D 309/04* (2013.01); *C07D 309/30* (2013.01)

(56) References Cited

U.S. PATENT DOCUMENTS

| | | | |
|---|---|---|---|
| 5,591,769 A | 1/1997 | Himmelsbach et al. | |
| 6,774,132 B1 | 8/2004 | Claesson et al. | |
| 7,235,698 B2 | 6/2007 | Behenna et al. | |
| 8,822,679 B2* | 9/2014 | Stoltz | C07D 223/04 540/529 |
| 9,518,034 B2 | 12/2016 | Stoltz et al. | |
| 10,035,769 B2* | 7/2018 | Stoltz | C07D 207/08 |
| 10,040,784 B2 | 8/2018 | Stoltz et al. | |
| 10,106,479 B2 | 10/2018 | Stoltz et al. | |
| 10,343,996 B2* | 7/2019 | Stoltz | C07D 207/16 |
| 10,358,422 B2 | 7/2019 | Stoltz et al. | |
| 10,421,696 B2 | 9/2019 | Stoltz et al. | |
| 10,745,354 B2 | 8/2020 | Stoltz et al. | |
| 10,906,875 B2* | 2/2021 | Stoltz | C07D 211/78 |
| 11,124,503 B2 | 9/2021 | Stoltz et al. | |
| 11,214,568 B2 | 1/2022 | Stoltz et al. | |
| 2006/0041004 A1 | 2/2006 | Gutman et al. | |
| 2006/0084820 A1 | 4/2006 | Behenna et al. | |
| 2010/0298293 A1 | 11/2010 | Allerheiligen et al. | |
| 2013/0267699 A1 | 10/2013 | Stoltz et al. | |
| 2015/0105552 A1 | 4/2015 | Stoltz et al. | |
| 2016/0096810 A1 | 4/2016 | Stoltz et al. | |
| 2016/0176773 A1 | 6/2016 | Stoltz et al. | |
| 2016/0280623 A1 | 9/2016 | Stoltz et al. | |
| 2020/0048201 A1 | 2/2020 | Stoltz et al. | |
| 2020/0157020 A1 | 5/2020 | Stoltz et al. | |
| 2020/0157049 A1 | 5/2020 | Stoltz et al. | |

FOREIGN PATENT DOCUMENTS

| | | |
|---|---|---|
| WO | WO-2003/062265 | 7/2003 |
| WO | WO-2005/012320 A2 | 2/2005 |
| WO | WO-2005/037823 A1 | 4/2005 |
| WO | WO-2009/013390 A1 | 1/2009 |
| WO | WO-2009/153178 A2 | 12/2009 |
| WO | WO-2011/153509 A1 | 12/2011 |
| WO | WO-2011/154374 A1 | 12/2011 |
| WO | WO-201 2/178129 A2 | 12/2012 |
| WO | WO-201 7/156239 A1 | 9/2017 |

OTHER PUBLICATIONS

U.S. Appl. No. 16/579,382, Pending.
U.S. Appl. No. 16/166,893, Pending.
U.S. Appl. No. 16/055,559, Pending.
U.S. Appl. No. 16/657,672, Allowed.
Amendment in Response to Non-Final Office Action Under 37 C.F.R. § 1.111, filed Jun. 15, 2021, U.S. Appl. No. 16/579,382.
Response to Non-Final Office Action, filed Mar. 11, 2021, U.S. Appl. No. 16/219,214.
Altman et al., "Orthogonal Pd- and Cu-based catalyst systems for C- and N-arylation of oxindoles," Journal of the American Chemical Society, 130(29):9613-9620 (2008).
Amat, et al., "Enantioselective Synthesis of 3,3-Disubstituted Piperidine Derivatives by Enolate Dialkylation of Phenylglycinol-derived oxazolopiperidone Lactams," J Org Chern, 72(12): 4431-4439 (2007).
Appeal Brief for U.S. Appl. No. 16/166,893 dated Feb. 11, 2020.
Appeal Brief for U.S. Appl. No. 16/055,559 filed Aug. 10, 2020.
Bach, et al., "Regioselective Reducing Ring Opening of 2-(2-Hydroxyphenyl)-3-[(trimethylsilyl)oxy]oxetanes at the More Substituted C-2-Position," Liebigs Annalen, 7:1529-1536 (1997).
Badillo, et al., "Enantioselective synthesis of substituted oxindoles and spirooxindoles with applications in drug discovery," Curr Opin Drug Discov Devel, 13(6): 758-776 (2010).
Baussanne, et al., "Diastereoselective Bis-Alkylation of Chiral Non-Racemic α,β-Unsaturated γ-Lactams," Tetrahedron Lett, 35(23): 3931-3934 (1994).
Behenna, et al., "Enantioselective construction of quaternary N-heterocycles by palladium-catalysed decarboxylative allylic alkylation of lactams," Nat Chem, 4(2): 130-133 (2012).
Behenna, et al., "Enantioselective Decarboxylative Alkylation Reactions: Catalyst Developement, Substrate Scope, and Mechanistic Studies," Chern Eur J, 17(50): 14199-14223 (2011).
Behenna, et al., "The Enantioselective Tsuji Allylation," J Am Chem Soc, 126(46): 15044-15045 (2004).
Bell, et al., "Organocatalytic asymmetric deconjugative Michael additions," J Org Chem, 71(14): 5407-5410 (2006).
Bennett, et al., "A Unified Approach to the Daucane and Sphenolobane Bicyclo[5.3.0]decane Core: Enantioselective Total Synthesis of

(56) References Cited

OTHER PUBLICATIONS

Daucene, Daucenal, Epoxydaucenal B, and 14-para-Anisoyloxydauc-4,8-diene", Chem Eur J, 19(52): 17745-17750 (2013).
Bennett, et al., "Expanding Insight into Asymmetric Palladium-Catalyzed Allylic Alkylation of N-Heterocyclic Molecules and Cyclic Ketones," Chem Eur J, 19(14): 4414-4418 (2013).
Bennett, et al., "Synthesis of enantioenriched γ-quaternary cycloheptenones using a combined allylic alkylation/Stork-Danheiser approach: preparation of mono-, bi-, and tricyclic systems", Org Biomol Chem, 10(1): 56-59 (2012).
Bobranski, et al., "Hydration of Phenyldiallylacetamide," Bulletin de l'Academie Polonaise de Sciences, Serie des Sciences, Chimiques, Geologiques et Geographiques, 7: 399-401 (1959).
Bulman Page, et al., "Short and Versatile Route to a Key Intermediate for Lactacystin Synthesis," Org Lett, 5(3): 353-355 (2003).
CAS Registry No. 1823805-71-5, (Entered STN: Dec. 6, 2015).
Chattopadhyay et al., "Mechanistic Origin of the Stereodivergence in Decarboxylative Allylation," Org Lett, 12(13): 3042-3045 (2010).
Coates, et al., "Efficient synthesis of 3-substituted lactams using Meerwein Eschenmoser Claisen [3,3] sigmatropic rearrangements," Tetrahedron Lett, 32(33): 4199-4202 (1991).
Dashkina et al., "Palladium-catalyzed allylation of salts of unsubstituted and substituted 5-nitro-1,3-dioxanes," Zhurnal Organicheskoi Khimii 30(11):1656-1659 (1994).
Day, et al., "The Catalytic Enantioselective Total Synthesis of (+)-Liphagal," Angew Chem Int Ed, 50(30): 6814-6818 (2011).
Desmaele, et al., "Stereocontrolled Elaboration of Quaternary Carbon Centers through the Asymmetric Michael-Type Alkylation of Chiral Imines/Secondary Enamines: Enantioselective Synthesis of (+)-Vincamine," J Org Chem, 62(12): 3890-3901 (1997).
Elz et al., "Synthesis, Biological in vitro evaluation and stereoselectivity of ondansetron analogues: novel 5-HT2A receptor antagonists," Bioorg Med Chem Letts 5(7):667-672 (1995).
Enders, et al., "Asymmetric Electrophilic Substitutions at the α-Position of γ- and δ-Lactams," Eur J Org Chem, 2001 (23): 4463-4477 (2001).
Enquist, et al., "The total synthesis of (−)-cyanthiwigin F by means of double catalytic enantioselective alkylation," Nature, 453(7199): 1228-1231 (2008).
Enquist, et al., "Total Syntheses of Cyanthiwigins B, F, and G," Chem Eur J, 17(36): 9957-9969 (2011).
Examiner's Answer to Appeal Brief for U.S. Appl. No. 16/055,559 dated Sep. 28, 2020.
Examiner's Answer to Appeal Brief for U.S. Appl. No. 16/166,893 dated Apr. 28, 2020.
Extended European Search Report for EP Application No. 18203943.8 dated Mar. 21, 2019.
Extended European Search Report for EP Application No. 19204164.8 dated Jul. 23, 2020.
Extended European Search Report for EP Application No. 20155322.9 dated Aug. 17, 2020.
Extended European Search Report for EP Application No. EP 17764072 dated Jul. 29, 2019.
Extended European Search Report for EP application No. EP12802759.6 mailed Mar. 14, 2016.
Extended European Search Report received for EP Patent Application No. 16773845.9, dated Oct. 9, 2018.
Ezquerra, et al., "Stereoselective Double Alkylation of Ethyl N-Boc-pyroglutamate," J Org Chem, 59(15): 4327-4331 (1994).
Fuji, et al., "Addition-elimination strategy for asymmetric induction: a chiral sulfoxide as a leaving group," Tetrahedron Lett, 31(17): 2419-2422 (1990). (CAS abstract).
Gartshore, et al., "Enantioselective Palladium-Catalyzed Decarboxylative Allylation of Carbazolones and Indolones: Formal Synthesis of (+)-Kopsihainanine A," Angew Chem Int Ed, 52(15): 4113-4116 (2013).
Groaning, et al., "Chiral Non-Racemic Bicyclic Lactams. Auxiliary-Based Asymmetric Reactions," Tetrahedron, 56(51): 9843-9873 (2000).

Ha et al., "Enantioselective Phase-Transfer Catalytic [α]-Benzylation and [α]-Allylation of [α]-tert-Butoxycarbonyl-lactones," Advanced Synthesis & Catalysis, 355(4): 637-642 (2013).
Hayashi et al., "Ni-Catalyzed Enantioselective C-Acylation of α-Substituted Lactams," J Am Chem Soc, 138(29):8997-9000 (2016).
Heathcock et al., "Daphniphyllum alkaloids. 15. Total syntheses of (±)-methyl homodaphniphyllate and (±)-daphnilactone A," J Org Chem, 57(9):2585-2594 (1992).
Helmchen, et al., "Phosphinooxazolines—A New Class of Versatile, Modular P,N-Ligands for Asymmetric Catalysis," Acc Chem Res, 33(6): 336-345 (2000).
Hong, et al., "Biosynthesis and Chemical Synthesis of Presilphiperfolanol Natural Products," Angew Chem Int Ed, 53(21): 5248-5260 (2014).
Hong, et al., "Enantioselective Total Synthesis of the Reported Structures of (−)-9-epi-Presilphiperfolan-1-ol and (−)-Presilphiperfolan-1-ol: Structural Confirmation and Reassignment and Biosynthetic Insights," Angew Chem Int Ed, 51(38): 9674-9678 (2012).
Hong, et al., "Palladium-catalyzed asymmetric alkylation in the synthesis of cyclopentanoid and cycloheptanoid core structures bearing all-carbon quaternary stereocenters," Tetrahedron, 67(52): 10234-10248 (2011).
Hong, et al., "The Construction of All-Carbon Quaternary Stereocenters by Use of Pd-Catalyzed Asymmetric Allylic Alkylation Reactions in Total Synthesis," Eur J Org Chem, 14: 2745-2759 (2013).
Imao, et al., "Easy Access to Esters with a Benzylic Quaternary Carbon Center from Diallyl Malonates by Palladium-Catalyzed Decarboxylative Allylation," J Org Chem, 72(5): 1652-1658 (2007).
International Search Report and Written Opinion for International Application No. PCT/US2012/043904 dated Feb. 1, 2013.
International Search Report and Written Opinion for International Application No. PCT/US2016/024238 dated Jul. 11, 2016.
International Search Report and Written Opinion for International Application No. PCT/US2017/021528 dated May 25, 2017.
Jakubec, et al., "Enantio- and diastereoselective Michael additions of C-succinimidyl esters to nitro olefins using cinchonine-derived bifunctional organocatalysts," Tetrahedron: Asymmetry, 22(11): 1147-1155 (2011).
Jette et al., "Palladium-catalyzed construction of quaternary stereocenters by enantioselective arylation of [gamma]-lactams with aryl chlorides and bromides," Angewandte Chemie Intl. Ed, 58(13):4297-4301 (2019).
Jing, et al.," Total Synthesis of (±)-Kopsihainanine A," Chem Eur J, 18(22): 6729-6732 (2012).
Johnson, et al., "Asymmetric carbon-carbon bond formations in conjugate additions of lithiated N-Boc allylic and benzylic amines to nitroalkenes: Enantioselective synthesis of substituted piperidines, pyrrolidines, and pyrimidinones," J Am Chem Soc, 124(39): 11689-11698 (2002).
Juaristi, et al., "Enantioselective synthesis of βamino acids. Part 9: Preparation of enantiopure α,α-disubstituted β-amino acids from 1-benzoyl-2(S)-tert-butyl-3-methylperhydropyrimidin-4-one," Tetrahedron: Asymmetry, 9(21): 3881-3888 (1998).
Kavitha et al., "Chemistry of cyclic imides: An overview on the past, present and future," Current Organic Chemistry, 20(19):1955-2001 (2016).
Keith, et al., "The Reaction Mechanism of the Enantioselective Tsuji Allylation: Inner-Sphere and Outer-Sphere Pathways, Internal Rearrangements, and Asymmetric C—C Bond Formation," J Am Chem Soc, 134(46): 19050-19060 (2012).
Kim, et al., "An Asymmetric Synthesis of (+)-Isonitramine by 'Triple Allylic Strain-Controlled' Intramolecular SN2 Alkylation," Tetrahedron Lett, 37(9): 1433-1434 (1996).
Kita et al., "Asymmetric Allylic Alkylation of β-ketoesters with allylic alcohols by a nickel/diphosphine catalyst," Angewandte Chemie International Edition, 55:1098-1101 (2016).
Korch et al., "Enantioselective synthesis of a-secondary and α-tertiary piperazin-2-ones and piperazines by catalytic asymmetric allylic alkylation," Angew Chem Int Edit, 54(1): 179-183 (2015).
Lakshmaiah et al., "Total Synthesis of (−)-Horsfiline via Asymmetric Nitroolefination," J. Org. Chem., 64: 1699-1704 (1999).

(56) References Cited

OTHER PUBLICATIONS

Lee et al., "Asymmetric synthesis and evaluation of [α]-quaternary chiral lactam derivatives as novel anticancer agents," Arch of Pharm Res, 37(10):1264-1270 (2014).
Li et al., "Synthesis of Mannich Bases of Meldrum's Acid and Its 5-Substituted Derivatives," Synthetic Commun, 30(13):2317-2323 (2000).
Li, et al., "Enantioselective Palladium-Catalyzed Decarboxylative Allylation of Carbazolones: Total Synthesis of (−)-Aspidospermidine and (+)-Kopsihainanine A," Angew Chem Int Ed, 52(15): 4117-4121 (2013).
Liu et al. "Formal total syntheses of classic natural product target molecules via palladium-catalyzed enantioselective alkylation." Beilstein J. Org. Chem. 2014, 10, 2501-2512.
Liu, et al., "Construction of Vicinal Tertiary and All-Carbon Quaternary Stereocenters via Ir-Catalyzed Regio-, Diastereo-, and Enantioselective Allylic Alkylation and Applications in Sequential Pd Catalysis," J Am Chem Soc, 135(29): 10626-10629 (2013).
Lu et al., "Metal-Catalyzed Enantioselective Allylation in Asymmetric Synthesis," Angew Chem Int Ed, 47(2): 258-297 (2008).
Lu et al., "Palladium-catalyzed enantioselective Csp3-Csp3 cross-coupling for the synthesis of (poly)fluorinated chiral building blocks," Organic Letters, 20(18):5657-5660 (2018).
Ma, et al., "Palladium-catalyzed decarboxylative allylic alkylation of diastereomeric β-ketoesters," Tetrahedron, 70(27): 4208-4212 (2014).
Mai et al., "Alpha-arylation of 3-aryloxindoles," Organic Letters, 12(10):2306-2309 (2010).
Mangunuru et al., "Enantioselective arylation of oxindoles using modified bi-dime ligands," Synthesis, 50(22):4435-4443 (2018).
Marziale et al., "An Efficient Protocol for the Palladium-Catalyzed Asymmetric Decarboxylative Allylic Alkylation Using Low Palladium Concentrations and a Palladium(II) Precatalyst," Adv Synth Catal, 357: 2238-2245 (2015).
McDougal, et al., "High-Throughput Screening of the Asymmetric Decarboxylative Alkylation Reaction of Enolate-Stabilized Enol Carbonates," Synlett 11:1712-1716 (2010).
McDougal, et al., "Rapid synthesis of an electron-deficient t-BuPHOX ligand: cross-coupling of aryl bromides with secondary phosphine oxides," Tetrahedron Lett, 51 (42): 5550-5554 (2010).
McFadden, et al., "The Catalytic Enantioselective, Protecting Group-Free Total Synthesis of (+)-Dichroanone," J Am Chem Soc, 128 (24): 7738-7739 (2006).
Melhado et al., "Gold(I)-Catalyzed Diastereo- and Enantioselective 1,3-Dipolar Cycloaddition and Mannich Reactions of Azlactones," J Am Chem Soc, 133(10):3517-3527 (2011).
Mertes, et al., "Glutarimides V: Synthesis of 2-Allyl-2-Phenylglutarimide," J Am Pharm Assoc, 67: 882-885 (1958). (CAS Abstract).
Meyers, et al., "Stereoselective Alkylations in Rigid Systems. Effect of Remote Substituents on pi-Facial Additions to Lactam Enolates. Stereoelectronic and Steric Effects," J Am Chem Soc, 120(30): 7429-7438 (1998).
Mohr, et al., "Deracemization of Quaternary Stereocenters by Pd-Catalyzed Enantioconvergent Decarboxylative Allylation of Racemic β-Ketoesters," Angew Chem Int Ed, 44 (42): 6924-6927 (2005).
Mohr, et al., "Enantioselective Tsuji Allylations," Chem Asian J, 2(12): 1476-1491 (2007).
Moss, et al., "Catalytic Enantio- and Diastereoselective Alkylations with Cyclic Sulfamidates," Angew Chem Int Ed, 49(3): 568-571 (2010).
Ngamnithiporn et al., "Nickel-catalyzed enantioselective allylic alkylation of lactones and lactams with unactivated allylic alcohols," Chemical Science, 9:2547-2551 (2018).
Notice of Allowance and Fees Due for U.S. Appl. No. 15/081,157 dated Jun. 14, 2018.
Notice of Allowance for U.S. Appl. No. 16/219,214 dated Jul. 1, 2020.
Notice of Allowance for U.S. Appl. No. 16/427,629 dated Nov. 24, 2020.
Notice of Allowance for U.S. Appl. No. 16/427,629 dated Sep. 30, 2020.
Notice of Allowance for U.S. Appl. No. 16/511,138 dated Apr. 8, 2020.
Notice of Allowance for U.S. Appl. No. 16/657,672 dated Apr. 19, 2021.
Numajiri, et al., "Enantioselective synthesis of α-quaternary Mannich adducts by palladium-catalyzed allylic alkylation: Total synthesis of (+)-sibirinine," J Am Chem Soc, 137(3): 1040-1043 (2015).
Numajiri, et al., "Enantioselective Synthesis of Dialkylated N-Heterocycles by Palladium-Catalyzed Allylic Alkylation," Organic Letters, 17(5):1082-1085 (2015).
Ojima, et al., "Asymmetric Synthesis with Chiral β-Lactams. Highly Stereoselective Alkylation and Aldol Reaction of a Chiral 3-Amino-4-Styryl-β-Lactam," Tetrahedrom Lett, 31(7): 977-980 (1990).
Padwa, et al., "A Novel Cycloaddition Reaction of α-Diazo-γ-amido Ketones Catalyzed by Rhodium (II) Acetate. Scope and Mechanistic Details of the Process," J Org Chem, 61 (7): 2283-2292 (1996). (CAS Abstract).
Park et al., "Highly Enantioselective Total Synthesis of (+)-Isonitramine," Organic Letters, 14(3):852-854 (2012).
Park, et al., "Highly Enantioselective Phase-Transfer Catalytic α-Alkylation of α-tert-Butoxycarbonyllactams: Construction of β-Quaternary Chiral Pyrrolidine and Piperidine Systems," Adv Synth Catal, 353(18): 3313-3318 (2011).
Patent Trial and Appeal Board Decision issued under Appeal No. 2020-005067 for U.S. Appl. No. 16/166,893 dated Oct. 20, 2020 (14 pages).
Pre-Appeal Brief Conference Request for Review for U.S. Appl. No. 16/166,893 dated Jul. 11, 2019.
Quirante et al., "Synthesis of Diazatricyclic Core of Madangamines from cis-Perhydroisoquinolines," J Org Chem, 73(2): 768-771 (2008).
Reeves, et al., "Development of (Trimethylsilyl)ethyl Ester Protected Enolates and Applications in Palladium-Catalyzed Enantioselective Allylic Alkylation: Intermolecular Cross-Coupling of Functionalized Electrophiles," Org Lett, 16(9): 2314-2317 (2014).
Reeves, et al., "Enantioselective Construction of α-Quaternary Cyclobutanones by Catalytic Asymmetric Allylic Alkylation," Angew Chem Int Ed, 52(26): 6718-6721 (2013).
Reply Brief for U.S. Appl. No. 16/166,893, filed Jun. 26, 2020.
Rodriguez, et al., ""Carba" Peptide Bond Surrogates/Different Approaches to Gly-ψ(CH$_2$-CH$_2$)-D,L-Xaa Pseudodipeptide Units," Int J Peptide Protein Res, 39(3): 273-277 (1992).
Ruggeri et al., "Synthesis of polycyclic lactam and lactone ethers by intramolecular Reformatskii reactions. A model for construction of the daphnilactone A ring system," J Org Chem, 52(26):5745-5746 (1987).
Sato et al., "N-Heterocyclic carbenes as ligands in palladium-catalyzed Tsuji-Trost allylic substitution," Journal of Organometallic Chemistry, 690(24-25): 5753-5758 (2005).
Schelwies et al., "Gold-Catalyzed Intermolecular Addition of Carbonyl Compounds to 1,6-Enynes: Reactivity, Scope, and Mechanistic Aspects," Chem Eur J 15(41):10888-10900 (2009).
Schwarz, et al., "Tandem α-Cyano Enamine/Enolate Alkylations on Bicyclic Lactams: Asymmetric Carbocycle and Heterocycle Synthesis," J Org Chem, 63(5): 1619-1629 (1998).
Seidel, et al., "Aldol and Claisen condensations with 1-(3,4-dichlorophenyl)-2-pyrrolidinone," J of Heterocyclic Chem, 3(3):311-314(1966).
Seto, et al., "Catalytic Enantioselective Alkylation of Substituted Dioxanone Enol Ethers: Ready Access to C(α)-Tetrasubstituted Hydroxyketones, Acids, and Esters," Angew Chem Int Ed, 47(36): 6873-6876 (2008).
Sherden, "Mechanistic investigations into the palladium-catalyzed decarboxylative allylic alkylation of ketone enolates using the PHOX ligand architecture," Chapter 1, Dissertation, California Institute of Technology (2011).
Shibuya, et al., "Enantioselective Synthesis of 5-6-7 Carbocyclic Core of the Gagunin Diterpenoids," Org Lett, 15(13): 3480-3483 (2013).

(56) References Cited

OTHER PUBLICATIONS

Sternativo, et al., "Synthesis of γ-lactams via a domino Michael addition/cyclization reaction of vinyl selenone with substituted amides." Tetrahedron Letters, 54(49):6755-6757 (2013).
Streuff, et al., "A palladium-catalysed enolate alkylation cascade for the formation of adjacent guaternary and tertiary stereocentres," Nat Chem, 2(3): 192-196 (2010).
Sun et al., "Enantioselective synthesis of gem-disubstituted N-Boc diazaheterocycles via decarboxylative asymmetric allylic alkylation," Chem Sci 10:788-792 (2019).
Supplemental European Search Report for EP application No. EP12802759 dated Oct. 28, 2014.
Takahashi, et al., "Atropisomeric lactam chemistry: catalytic enantioselective synthesis, application to asymmetric enolate chemistry and synthesis of key intermediates for NET inhibitors," Tetrahedron, 66(1): 288-296 (2010).
Tani, et al., "A Facile and Modular Synthesis of Phosphinooxazoline Ligands," Org Lett, 9(13): 2529-2531 (2007).
Tari, et al., "Recoverable Cinchona ammonium salts as organocatalysts in the enantioselective Michael addition of β-Keto esters," Tetrahedron: Asymmetry, 21(23): 2872-2878 (2010).
Tasker et al., "Recent advances in homogeneous nickel catalysis," Nature, 509:299-309 (2014).
Taylor et al., "Palladium-catalyzed enantioselective alpha-arylation and alpha-vinylation of oxindoles facilitated by an axially chiral p-stereogenic ligand," Journal of the American Chemical Society, 131(29):9900-9901 (2009).
Trost, "Asymmetric Allylic Alkylation, an Enabling Methodology," J Org Chem, 69(18): 5813-5837 (2004).
Trost, et al., "Asymmetric Synthesis of Oxindole and Indole Spirocyclic Alkaloid Natural Products," Synthesis, 18:3003-3025 (2009).
Trost, et al., "Enantioselective Synthesis of [α]-Tertiary Hydroxyaldehydes by Palladium-Catalyzed Asymmetric Allylic Alkylation of Enolates," J Am Chem Soc, 129(2): 282-283 (2007).
Tsuji et al., "Catalytic asymmetric synthesis of pentacyclic core of (−)-nakadomarin A via oxazolidine as an iminium cation equivalent," Org Biomol Chem, 12(40):7919-7922 (2014).
Varea, et al., "Asymmetric Synthesis. XXXV Synthesis of 2-Methyl 5-Substituted Piperidines from Chiral Non-racemic Lactams," Tetrahedron Lett, 36(7): 1035-1038 (1995).
Vijn, et al., "Highly Enantioselective Synthesis of a 2,3-Dihydroindole Mediated by N-Methylephedrine," Angew Chem Int Ed, 23(2): 165-166 (1984).
Weaver, et al., "Transition Metal-Catalyzed Decarboxylative Allylation and Benzylation Reactions," Chem Rev, 111(3): 1846-1913(2011).
White, et al., "The Catalytic Asymmetric Total Synthesis of Elatol," J Am Chem Soc, 130(3): 810-811 (2008).
Williams, et al., "Asymmetric synthesis of monosubstituted and α,α-disubstituted α-amino acids via diastereoselective glycine enolate alkylations," J Am Chem Soc, 113(24): 9276-9286 (1991).
Yamamoto et al., "Palladium-catalyzed asymmetric cyclization of methyl (E)-oxo-9-phenoxy-7-nonenoate and its analogs," Tetrahedron Letters, 23(30): 3089-3092 (1982).
Yang et al., "A new synthetic method for preparing Mannich bases of Meldrum's acid," Chinese J Org Chem, 22(7):525-527 (2002).
Yendapally, et al., "Design, synthesis, and evaluation of novel ethambutol analogues," Bioorg Med Chem Lett, 18(5):1607-1611 (2008).
Zawisza, et al., "An unexpected palladium-catalyzed cyclization of bis-hydroxy allylic alcohols to dioxabicyclo[2.2.2]octanes," Tetrahedron Lett, 47(19): 3271-3274 (2006).
Zawisza, et al., "Palladium-catalyzed formation of cyclic ethers—regio-, stereo- and enantioselectivity of the reaction," Eur J Org Chem, 2007(14): 2296-2309 (2007).
Zhang et al., "Asymmetric induction in Mn(III)-based oxidative free-radical cyclizations of phenylmethyl acetoacetates and 2,5-Dimethylpyrrolidine Acetoacetamides," J Org Chem 58:7640-7651 (1993).
Zhang et al., "Direct N-Acylation of Lactams, Oxazolidinones, and Imidazolidinones with Aldehydes by Shvo's Catalyst," Org Lett, 14(17): 4646-4649 (2012).
Zhou, et al., "Catalytic Asymmetric Synthesis of Oxindoles Bearing a Tetrasubstituted Stereocenter at the C-3 Position," Adv Synth Catal, 352(9): 1381-1407 (2010).
Liu et al., "Catalytic Enantioselective Construction of Quaternary Stereocenters: Assembly of Key Building Blocks for the Synthesis of Biologically Active Molecules," Acc. Chem. Res., 48: 740-751 (2015).
Notice of Allowance for U.S. Appl. No. 16/579,382 dated Mar. 9, 2022.
U.S. Appl. No. 13/531,485, Granted.
U.S. Appl. No. 13/797,736, Abandoned.
U.S. Appl. No. 15/366,590, Granted.
U.S. Appl. No. 16/049,434, Granted.
U.S. Appl. No. 16/427,629, Granted.
U.S. Appl. No. 14/514,001, Granted.
U.S. Appl. No. 16/219,214, Abandoned.
U.S. Appl. No. 14/877,496, Abandoned.
U.S. Appl. No. 14/972,475, Granted.
U.S. Appl. No. 16/579,382, Allowed.
U.S. Appl. No. 15/081,157, Granted.
U.S. Appl. No. 16/166,893, Abandoned.
U.S. Appl. No. 15/454,198, Granted.
U.S. Appl. No. 16/055,559, Granted.
U.S. Appl. No. 16/177,926, Granted.
U.S. Appl. No. 16/511,138, Granted.
U.S. Appl. No. 16/657,672, Granted.
U.S. Appl. No. 17/566,919, Pending.
U.S. Appl. No. 17/566,915, Pending.

* cited by examiner

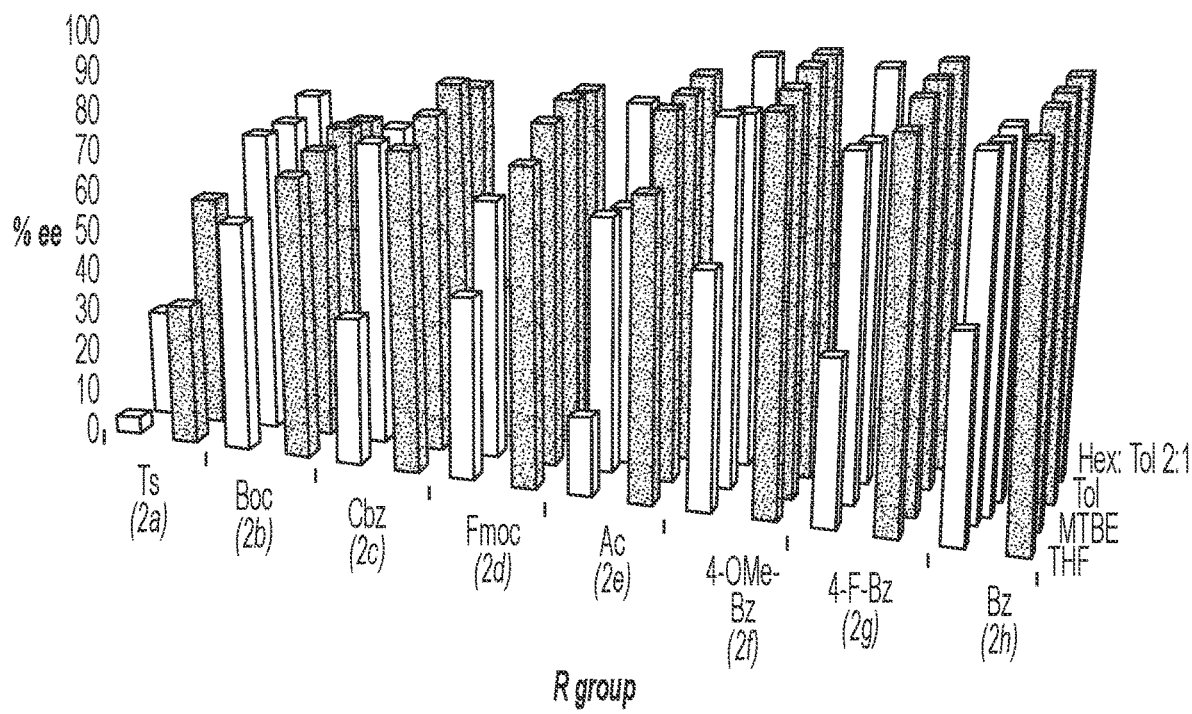
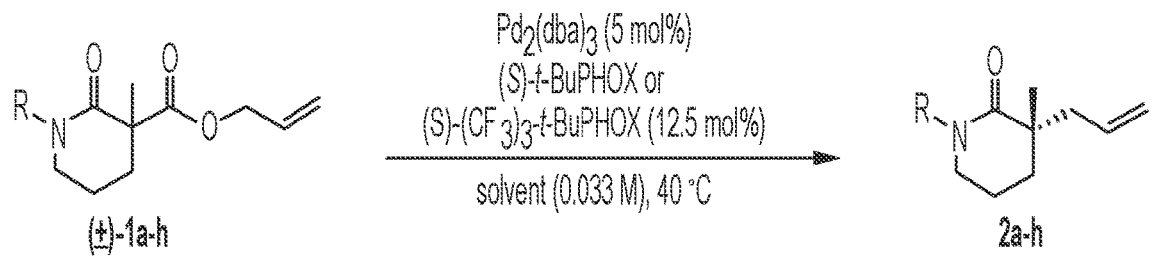
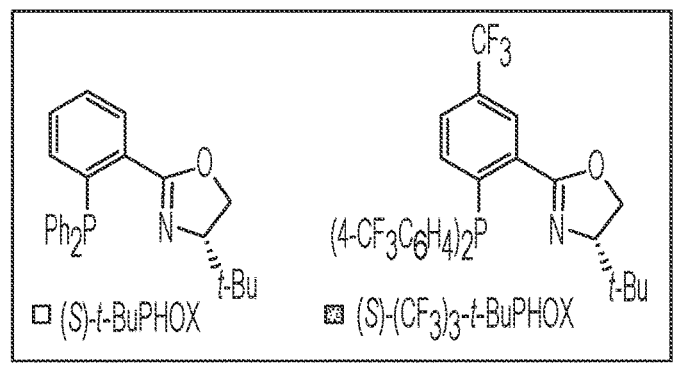

QUATERNARY HETEROATOM CONTAINING COMPOUNDS

CROSS REFERENCE TO RELATED APPLICATION

This application is a Continuation of U.S. application Ser. No. 16/427,629, filed on May 31, 2019, which is a Continuation of U.S. application Ser. No. 16/049,434, filed on Jul. 30, 2018, now U.S. Pat. No. 10,343,996, issued Jul. 9, 2019, which is a Continuation of U.S. application Ser. No. 15/366,590, filed on Dec. 1, 2016, now U.S. Pat. No. 10,035,769, issued Jul. 31, 2018, which is a Continuation of U.S. application Ser. No. 13/797,736, filed on Mar. 12, 2013, now abandoned, which is a Continuation-in-Part of U.S. application Ser. No. 13/531,485, filed Jun. 22, 2012, now U.S. Pat. No. 8,822,679, issued Sep. 2, 2014, which claims priority to and the benefit of U.S. Provisional Application Ser. No. 61/501,054, filed on Jun. 24, 2011, the entire contents of which are incorporated herein by reference.

STATEMENT REGARDING FEDERALLY SPONSORED RESEARCH

This invention was made with government support under Grant No. GM080269 awarded by the National Institutes of Health. The government has certain rights in the invention.

TECHNICAL FIELD

The disclosure relates to quaternary nitrogen compounds useful as building blocks in the synthesis of pharmaceuticals and other compounds.

BACKGROUND

Nitrogen-containing heterocycles are prevalent in numerous biologically active products that are the bases and templates for countless pharmaceuticals and other compounds used in many disciplines, including medicinal chemistry. A small sampling of some these compounds include aspidospermidine, fawcettimine, vinblastine, manzamine A, ethosuximide, aminoglutethimide and doxapram, depicted below.

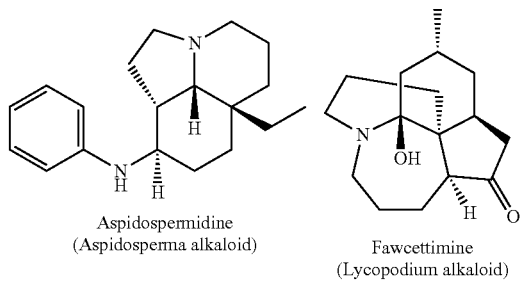

Aspidospermidine
(Aspidosperma alkaloid)

Fawcettimine
(Lycopodium alkaloid)

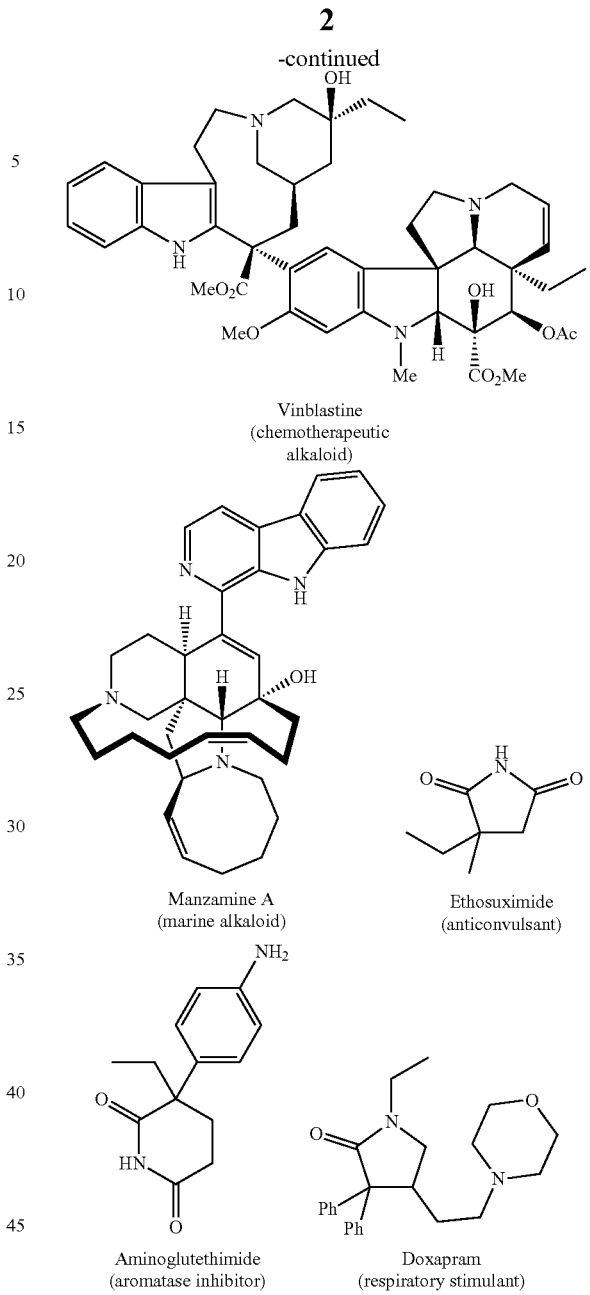

Vinblastine
(chemotherapeutic alkaloid)

Manzamine A
(marine alkaloid)

Ethosuximide
(anticonvulsant)

Aminoglutethimide
(aromatase inhibitor)

Doxapram
(respiratory stimulant)

Typically only one enantiomer of a compound exhibits biological activity, while the other enantiomer generally exhibits no activity, or substantially reduced activity. In addition, different stereoisomers of a compound often exhibit differences in biological activity. As such, a stereoselective and enantioselective synthesis of the target compound could theoretically produce pharmaceuticals or compounds with greater biological activity, and therefore, greater medicinal value. However, stereoselective and enantioselective syntheses of these types of compounds have proven very difficult. Indeed, most syntheses reported to date yield racemic mixtures of the various compounds. While some stereoselective methods for the synthesis of certain nitrogen containing heterocycles and their cyclic amine derivatives are known, only a sparse number of enantioselective methods exist. Additionally, most of these stereoselective methods use chiral auxiliary chemistry specific to the oxindole lactam nucleus or cyclic imides, both of which require enolate stabilization, thereby limiting the scope of each transformation.

SUMMARY

The invention provides heterocyclic compounds with quaternary centers and methods for preparing compounds with quaternary centers. The invention further provides methods for preparing compounds with quaternary centers. Specifically, the invention provides a method for the preparation of a compound of Formula (II):

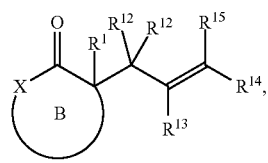
(II)

comprising treating a compound of Formula (I):

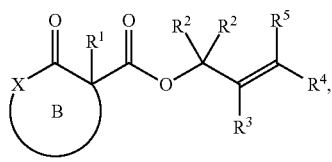
(I)

with a transition metal catalyst under alkylation conditions, wherein, as valence and stability permit, ring B represents an optionally substituted heterocycle;

X is a heteroatom;

$R^1$ is selected from optionally substituted alkyl, alkenyl, alkynyl, carbocyclyl, heterocycle, aryl, heteroaryl, and halogen;

$R^2$, $R^3$, $R^4$, $R^5$, $R^{12}$, $R^{13}$, $R^{14}$, and $R^{15}$ are independently selected at each occurrence from hydrogen, hydroxyl, halogen, nitro, alkyl, alkenyl, alkynyl, cyano, carboxyl, sulfate, amino, alkoxy, alkylamino, alkylthio, hydroxyalkyl, alkoxyalkyl, aminoalkyl, thioalkyl, ether, thioether, ester, amide, thioester, carbonate, carbamate, urea, sulfonate, sulfone, sulfoxide, sulfonamide, acyl, acyloxy, acylamino, aryl, heteroaryl, carbocyclyl, heterocyclyl, aralkyl, aralkyloxy, hetaralkyl, carbocyclylalkyl, and heterocyclylalkyl.

The invention further provides compounds represented by Formulas (I) and (II).

The present invention further provides a method of preparation of a compound of Formula (IV):

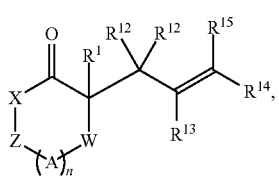
(IV)

comprising treating a compound of Formula (III):

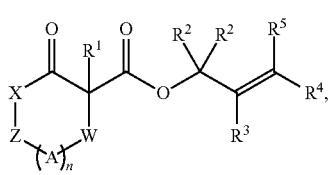
(III)

with a transition metal catalyst under alkylation conditions, wherein, as valence and stability permit, X is selected from —$NR^6$— and —O—;

Z is selected from —C(O)— and —$CR^7R^7$—;

A is independently selected at each occurrence from —$CR^8R^8$— and —$NR^9$—;

W is absent or selected from —O—, —$NR^{10}$—, and —$CR^{11}R^{11}$—;

$R^1$ is selected from optionally substituted alkyl, alkenyl, alkynyl, carbocyclyl, heterocycle, aryl, heteroaryl, and halogen;

$R^2$, $R^3$, $R^4$, $R^5$, $R^{12}$, $R^{13}$, $R^{14}$, and $R^{15}$ are independently selected at each occurrence from hydrogen, hydroxyl, halogen, nitro, alkyl, alkenyl, alkynyl, cyano, carboxyl, sulfate, amino, alkoxy, alkylamino, alkylthio, hydroxyalkyl, alkoxyalkyl, aminoalkyl, thioalkyl, ether, thioether, ester, amide, thioester, carbonate, carbamate, urea, sulfonate, sulfone, sulfoxide, sulfonamide, acyl, acyloxy, acylamino, aryl, heteroaryl, carbocyclyl, heterocyclyl, aralkyl, aralkyloxy, hetaralkyl, carbocyclylalkyl, and heterocyclylalkyl;

$R^7$, $R^8$, and $R^{11}$ are independently selected at each occurrence from hydrogen, halogen, nitro, alkyl, alkenyl, alkynyl, cyano, hydroxyl, thiol, carboxyl, sulfate, amino, alkoxy, alkylamino, alkylthio, hydroxyalkyl, alkoxyalkyl, aminoalkyl, thioalkyl, ether, thioether, ester, amide, thioester, carbonate, carbamate, urea, sulfonate, sulfone, sulfoxide, sulfonamide, acyl, acyloxy, acylamino, aryl, heteroaryl, carbocyclyl, heterocyclyl, aralkyl, aralkyloxy, hetaralkyl, carbocyclylalkyl, and heterocyclylalkyl;

wherein $R^7$ and $R^8$ may combine with the carbons to which they are bound to form an optionally substituted 3-8-membered ring, $R^8$ and $R^{11}$ may combine with the carbons to which they are bound to form an optionally substituted 3-8-membered ring, and when n is 2 or 3, $R^8$ attached to one carbon may combine with $R^8$ attached to another carbon to combine with the carbons to which they are bound to form a 3-8-membered ring;

$R^6$, $R^9$ and $R^{10}$ are independently selected at each occurrence from hydrogen, hydroxyl and optionally substituted alkyl, alkoxy, alkylthio, aryloxy, carbocyclyl, aryl, heteroaryl, aralkyl, heteroaralkyl, aralkyloxy, heteroaryloxy, acyl, arylcarbonyl, aralkylcarbonyl, acyloxy, sulfone, alkoxycarbonyl, aryloxycarbonyl, aralkoxycarbonyl, and amide; and n is 0-3.

The invention also comprises compounds represented by Formula (V):

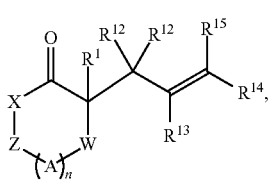
(V)

or a tautomer and/or a salt thereof, wherein:

X is selected from —NR$^6$— and —O—;

Z is selected from —C(O)— and —CR$^7$R$^7$—;

A is independently selected at each occurrence from —CR$^8$R$^8$— and —NR$^9$—;

W is absent or selected from —O—, —NR$^{10}$—, and —CR$^{11}$R$^{11}$—;

R$^1$ is selected from optionally substituted alkyl, alkenyl, alkynyl, carbocyclyl, heterocycle, aryl, heteroaryl, and halogen;

R$^{12}$, R$^{13}$, R$^{14}$ and R$^{15}$ are independently selected at each occurrence from hydrogen, hydroxyl, halogen, nitro, alkyl, alkenyl, alkynyl, cyano, carboxyl, sulfate, amino, alkoxy, alkylamino, alkylthio, hydroxyalkyl, alkoxyalkyl, aminoalkyl, thioalkyl, ether, thioether, ester, amide, thioester, carbonate, carbamate, urea, sulfonate, sulfone, sulfoxide, sulfonamide, acyl, acyloxy, acylamino, aryl, heteroaryl, carbocyclyl, heterocyclyl, aralkyl, aralkyloxy, hetaralkyl, carbocyclylalkyl, and heterocyclylalkyl;

R$^7$, R$^8$, and R$^{11}$ are independently selected at each occurrence from hydrogen, halogen, nitro, alkyl, alkenyl, alkynyl, cyano, hydroxyl, thiol, carboxyl, sulfate, amino, alkoxy, alkylamino, alkylthio, hydroxyalkyl, alkoxyalkyl, aminoalkyl, thioalkyl, ether, thioether, ester, amide, thioester, carbonate, carbamate, urea, sulfonate, sulfone, sulfoxide, sulfonamide, acyl, acyloxy, acylamino, aryl, heteroaryl, carbocyclyl, heterocyclyl, aralkyl, aralkyloxy, hetaralkyl, carbocyclylalkyl, and heterocyclylalkyl;

wherein R$^7$ and R$^8$ may combine with the carbons to which they are bound to form an optionally substituted 3-8-membered ring, R$^8$ and R$^{11}$ may combine with the carbons to which they are bound to form an optionally substituted 3-8-membered ring, and when n is 2 or 3, R$^8$ attached to one carbon may combine with R$^8$ attached to another carbon to combine with the carbons to which they are bound to form a 3-8-membered ring;

R$^6$, R$^9$ and R$^{10}$ are independently selected at each occurrence from hydrogen, hydroxyl and optionally substituted alkyl, alkoxy, alkylthio, aryloxy, carbocyclyl, aryl, heteroaryl, aralkyl, heteroaralkyl, aralkyloxy, heteroaryloxy, acyl, arylcarbonyl, aralkylcarbonyl, acyloxy, sulfone, alkoxycarbonyl, aryloxycarbonyl, aralkoxycarbonyl, and amide; and n is 0-3.

The invention further comprises compounds represented by Formula (VI):

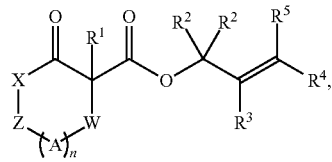

(VI)

or a tautomer and/or a salt thereof, wherein:

X is selected from —NR$^6$— and —O—;

Z is selected from —C(O)— and —CR$^7$R$^7$—;

A is independently selected at each occurrence from —CR$^8$R$^8$— and —NR$^9$—;

W is absent or selected from —O—, —NR$^{10}$—, and —CR$^{11}$R$^{11}$—;

R$^1$ is selected from optionally substituted alkyl, alkenyl, alkynyl, carbocyclyl, heterocycle, aryl, heteroaryl, and halogen;

R$^2$, R$^3$, R$^4$ and R$^5$ are independently selected at each occurrence from hydrogen, hydroxyl, halogen, nitro, alkyl, alkenyl, alkynyl, cyano, carboxyl, sulfate, amino, alkoxy, alkylamino, alkylthio, hydroxyalkyl, alkoxyalkyl, aminoalkyl, thioalkyl, ether, thioether, ester, amide, thioester, carbonate, carbamate, urea, sulfonate, sulfone, sulfoxide, sulfonamide, acyl, acyloxy, acylamino, aryl, heteroaryl, carbocyclyl, heterocyclyl, aralkyl, aralkyloxy, hetaralkyl, carbocyclylalkyl, and heterocyclylalkyl;

R$^7$, R$^8$, and R$^{11}$ are independently selected at each occurrence from hydrogen, halogen, nitro, alkyl, alkenyl, alkynyl, cyano, hydroxyl, thiol, carboxyl, sulfate, amino, alkoxy, alkylamino, alkylthio, hydroxyalkyl, alkoxyalkyl, aminoalkyl, thioalkyl, ether, thioether, ester, amide, thioester, carbonate, carbamate, urea, sulfonate, sulfone, sulfoxide, sulfonamide, acyl, acyloxy, acylamino, aryl, heteroaryl, carbocyclyl, heterocyclyl, aralkyl, aralkyloxy, hetaralkyl, carbocyclylalkyl, and heterocyclylalkyl;

wherein R$^7$ and R$^8$ may combine with the carbons to which they are bound to form an optionally substituted 3-8-membered ring, R$^8$ and R$^{11}$ may combine with the carbons to which they are bound to form an optionally substituted 3-8-membered ring, and when n is 2 or 3, R$^8$ attached to one carbon may combine with R$^8$ attached to another carbon to combine with the carbons to which they are bound to form a 3-8-membered ring;

R$^6$, R$^9$ and R$^{10}$ are independently selected at each occurrence from hydrogen, hydroxyl and optionally substituted alkyl, alkoxy, alkylthio, aryloxy, carbocyclyl, aryl, heteroaryl, aralkyl, heteroaralkyl, aralkyloxy, heteroaryloxy, acyl, arylcarbonyl, aralkylcarbonyl, acyloxy, sulfone, alkoxycarbonyl, aryloxycarbonyl, aralkoxycarbonyl, and amide; and n is 0-3.

In embodiments of the present invention, a compound is represented by Formula A, Formula A(ii), Formula D or Formula D(i).

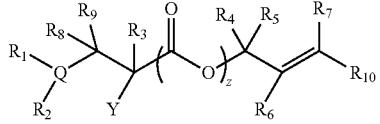

Formula A

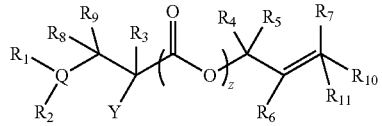

Formula A(ii)

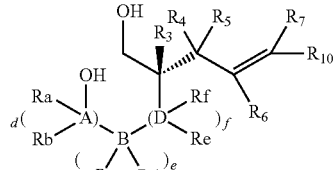

Formula D

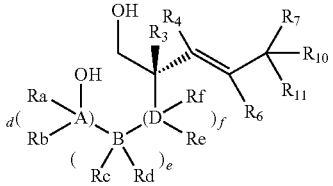

Formula D(i)

In Formula A, A(ii), D and D(i), z is 0 or 1; Q is a heteroatom; each of R1 through R11 and Ra through Rf is independently hydrogen, a substituted or unsubstituted hydrocarbyl group, a substituted or unsubstituted heteroatom containing hydrocarbyl group, or a functional group; each of d, e and f is independently an integer of 0 or greater; each of A, B and D is independently a carbon atom or a heteroatom; and two or more groups selected from R1 though R11, Ra through Rf and Y optionally combine to form a ring. In some embodiments, R8 and R9 combine to form a carbonyl group. In some embodiments, R2 and Y combine to form a ring with Q, and the ring may be saturated or may include at least one double bond. In some embodiments, Q is N or O. When Q is N, R1 may be an amine protecting group. In some embodiments, however, R1 may be H or OH. For example, in some embodiments, z is 0 and R1 is either H or OH.

In some exemplary embodiments, the compound of Formula A may be a compound represented by Formula C.

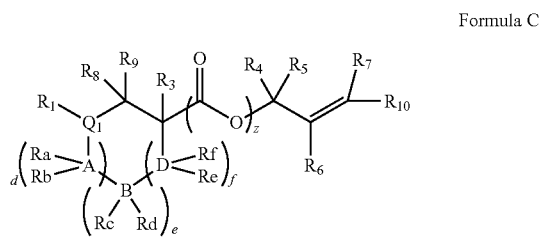

Formula C

In Formula C, z is 0 or 1; each of d, e and f is independently an integer of 0 or greater; Q1 is a heteroatom; and each of A, B and D is independently a heteroatom or a carbon atom. In some embodiments, R1 may be H or OH. For example, z is 0 and R1 is either H or OH. In Formula C, R8 and R9 may optionally combine to form a carbonyl group such that the compound of Formula C is represented by Formula C(i).

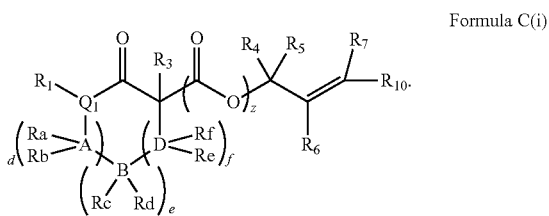

Formula C(i)

In Formulae C and C(i), R1 and one Ra may combine to form a double bond, or one Rb and one Rc may combine to form a double bond, or one Rd and one Re may combine to form a double bond. In some embodiments, in Formulae C and C(i), one Ra and one Rb may combine to form a carbonyl group, or one Rc and one Rd may combine to form a carbonyl group, or one Re and one Rf may combine to form a carbonyl group. Also, in some embodiments, R1 is H or OH. In some embodiments, the compound of Formula A, A(ii), D or D(i) is racemic, i.e., the compound includes a generally equimolar mixture of the (+) and (−) enantiomers of the compound. For example, in some embodiments, e.g., those in which z is 1, the compound is racemic. However, in some other embodiments, the compound of Formula A, A(ii), D or D(i) is enantioenriched, i.e., the compound includes more of one enantiomer than the other. For example, in some embodiments, e.g., in which z is 0, the compound may be an enantioenriched compound in which the compound includes one of the (+) or the (−) enantiomer in an enantiomeric excess of greater than 50%, for example greater than 60%, or greater than 70%, or greater than 80%, or greater than 90%.

According to some embodiments of the present invention, a method of making an enantioenriched heteroatom containing compound includes subjecting the compound of claim 1 to palladium catalyzed decarboxylative alkylation using an electron poor ligand, a palladium-based catalyst, and a solvent. The electron poor ligand may be a ligand including an electron poor moiety selected from fluorine atoms, partially or fully fluorinated hydrocarbyl groups, partially or fully fluorinated heteroatom containing hydrocarbyl groups, $NO_2$ groups and $SO_2R$ groups, wherein R is hydrogen, a substituted or unsubstituted hydrocarbyl group, a substituted or unsubstituted heteroatom containing hydrocarbyl group, or a functional group. For example, the electron poor ligand may be a R'—PHOX ligand, where R' is selected from $(CF_3)_3$ groups, partially or fully fluorinated hydrocarbyl groups, partially or fully fluorinated heteroatom containing hydrocarbyl groups, $NO_2$ groups and $SO_2R$ groups, wherein R is hydrogen, a substituted or unsubstituted hydrocarbyl group, a substituted or unsubstituted heteroatom containing hydrocarbyl group, or a functional group.

BRIEF DESCRIPTION OF THE DRAWINGS

These and other features and advantages of the present invention will be better understood by reference to the following detailed description when considered in conjunction with the following drawing, in which:

FIG. 1 is a graph comparing the enantiomeric excess of different compounds prepared via a palladium catalyzed decarboxylative alkylation process according to embodiments of the present invention.

DETAILED DESCRIPTION

I. Definitions

The term "acyl" is art-recognized and refers to a group represented by the general formula hydrocarbyl-C(O)—, such as alkyl-C(O)—.

The term "acylamino" is art-recognized and refers to an amino group substituted with an acyl group and may be represented, for example, by the formula hydrocarbyl-C(O)NH—.

The term "acyloxy" is art-recognized and refers to a group represented by the general formula hydrocarbyl-C(O)O—, preferably alkyl-C(O)O—.

The term "alkoxy" refers to an alkyl group having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone, e.g., $C_1$-$C_{30}$ for straight chains, $C_3$-$C_{30}$ for branched chains, and more preferably 20 or fewer, e.g., $C_1$-$C_3$, $C_1$-$C_6$, $C_1$-$C_9$, $C_1$-$C_{12}$, $C_1$-$C_{15}$ and $C_1$-$C_{18}$. Likewise, preferred cycloalkyls have from 3-10 carbon atoms in their ring structure, and more preferably have 5, 6 or 7 carbons in the ring structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing one or more hydrogen atoms on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" or "$C_x$ to $C_y$-alkyl" when used in conjunction with a chemical moiety, such as, acyl, acyloxy, alkyl, alkenyl, alkynyl, or alkoxy is meant to include groups that contain from x to y carbons in the chain. For example, the term "$C_x$ to $C_y$-alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. The terms "$C_x$ to $C_y$-alkenyl" and "$C_x$ to $C_y$-alkynyl" refer to substituted or unsubstituted unsaturated aliphatic groups analogous in length and possible substitution to the alkyls described above, but that contain at least one double or triple bond respectively. Within a range of $C_{x-y}$, subranges are also generally envisioned. For example, for the range $C_1$ to $C_{15}$-alkyl, ranges falling within this range such as $C_1$ to $C_2$-alkyl and $C_2$ to $C_8$-alkyl are also included.

The term "alkylamino", as used herein, refers to an amino group substituted with at least one alkyl group.

The term "alkylthio", as used herein, refers to a thiol group substituted with an alkyl group and may be represented by the general formula alkyl-S—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

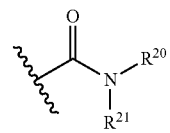

wherein $R^{20}$ and $R^{21}$ each independently represent a hydrogen or hydrocarbyl group, or $R^{20}$ and $R^{21}$ taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

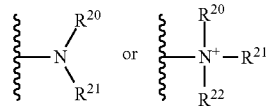

wherein $R^{20}$, $R^{21}$, and $R^{22}$ each independently represent a hydrogen or a hydrocarbyl group, or $R^{20}$ and $R^{21}$ taken together with the N atom to which they are attached complete a heterocycle having from 4 to 8 atoms in the ring structure. The terms "amine" and "amino" are intended to include amine groups that may be protected by a protecting group such as a carbobenzyloxy group (Cbz), a tert-butyloxycarbonyl group (BOC), a 9-fluorenylmethyloxycarbonyl group (FMOC), an acetyl group, a benzoyl group, a benzyl group, and a tosyl group.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which one or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

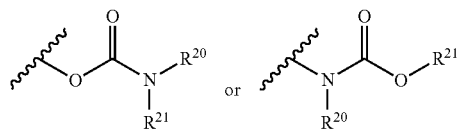

wherein $R^{20}$ and $R^{21}$ independently represent hydrogen or a hydrocarbyl group.

The terms "carbocycle", "carbocyclyl", and "carbocyclic", as used herein, refers to a non-aromatic saturated or unsaturated ring in which each atom of the ring is carbon. Preferably a carbocycle ring contains from 3 to 10 atoms, more preferably from 5 to 7 atoms.

The term "carbocyclylalkyl", as used herein, refers to an alkyl group substituted with a carbocycle group.

The term "carbonate" is art-recognized and refers to a group —OCO$_2$—R$^{20}$, wherein R$^{20}$ represents a hydrocarbyl group.

The term "carboxyl", as used herein, refers to a group represented by the formula —CO$_2$H. The term "ester", as used herein, refers to a group —C(O)OR$^{20}$ wherein R$^{20}$ represents a hydrocarbyl group such as an aryl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The term "haloalkyl" as used herein includes from one halo substituent up to perhalo substitution. Exemplary haloalkyls includes —CFH$_2$, —CClH$_2$, —CBrH$_2$, —CF$_2$H, —CCl$_2$H, —CBr$_2$H, —CF$_3$, —CCl$_3$, —CBr$_3$, —CH$_2$CH$_2$F, —CH$_2$CH$_2$Cl, —CH$_2$CH$_2$Br, —CH$_2$CHF$_2$, —CHFCH$_3$, —CHClCH$_3$, —CHBrCH$_3$, —CF$_2$CHF$_2$, —CF$_2$CHCl$_2$, —CF$_2$CHBr$_2$, —CH(CF$_3$)$_2$, and —C(CF$_3$)$_3$. Perhaloalkyl, for example, includes —CF$_3$, —CCl$_3$, —CBr$_3$, —CF$_2$CF$_3$, —CCl$_2$CF$_3$ and —CBr$_2$CF$_3$.

The terms "hetaralkyl" and "heteroaralkyl", as used herein, refers to an alkyl group substituted with a hetaryl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Exemplary heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 8-membered rings, whose ring structures include at least one heteroatom, preferably one to four heteroatoms, more preferably one or two heteroatoms. The terms "heterocyclyl", "heterocycle" and "heterocyclic" also include polycyclic ring systems having two or more cyclic rings in which one or more carbons are common to two adjoining rings wherein at least one of the rings is heterocyclic, e.g., the other cyclic rings can be selected from cycloalkyl, cycloalkenyl, cycloalkynyl, aryl, heteroaryl, and/or heterocyclyl. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to optionally substituted alkyl, alkenyl, alkynyl, carbocycle and aryl and combinations thereof.

The term "hydroxyl" or "hydroxy", as used herein, refers to an OH group. The term "hyrdoxy" or "hydroxyl" is intended to include groups that may be protected by a protecting group such as a TBDMS or TIPS protecting groups.

The term "hydroxyalkyl", as used herein, refers to an alkyl group substituted with a hydroxy group. The term "hydroxyalkyl" is intended to include hydroxyl groups that may be protected by a protecting group such as a TBDMS or TIPS protecting groups.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

A "protecting group" as used herein has the meaning ascribed in the field. A protecting group is a group that is covalently bound to a functional group in order to maintain chemoselectivity in a subsequent chemical reaction. Protecting groups for nitrogen atoms include "amine protecting groups" and "amide protecting groups". Protecting groups for hydroxyl groups include "hydroxyl protecting groups". The need for protection and deprotection, and the selection of appropriate protecting groups can be readily determined by one skilled in the art. The chemistry of protecting groups can be found, for example, in Greene and Wuts, *Protective Groups in Organic Synthesis,* 4th. Ed., Wiley & Sons, 2007, which is incorporated herein by reference in its entirety. Those of ordinary skill in the art would readily understand what is meant by "amine protecting group" and "amide protecting groups", however, some nonlimiting examples of nitrogen protecting groups include carboxybenzyl (Cbz) groups, p-methoxybenzyl carbonyl (Moz or MeOZ) groups, tert-butyloxycarbonyl (BOC) groups, fluorenylmethyloxycarbonyl (FMOC) groups, acetyl (Ac) groups, benzoyl (Bz)

groups, benzyl (Bn) groups, carbamate groups, p-methoxybenzyl (PMB) groups, dimethoxybenzyl (DMPM) groups, p-methoxyphenyl (PMP) groups, tosyl (Ts) groups, sulfonamide (Nosyl & Nps) groups, methoxybenzoyl groups (OMe-Bz), and fluorobenzoyl groups (F-Bz). For example, in some embodiments, the amine protecting group is selected from tosyl groups (Ts), butyloxycarbonyl groups (BOC), carbobenzyloxy groups (Cbz), fluoreneylmethyloxycarbonyl groups (FMOC), acetyl groups (Ac), methoxybenzoyl groups (OMe-Bz), and fluorobenzoyl groups (F-Bz). Those of ordinary skill in the art would readily understand what is meant by "hydroxyl protecting group", however, some nonlimiting examples of hydroxyl protecting groups include an acetyl (Ac) group, a benzoyl (Bz) group, a benzyl (Bn) group, a β-methoxyethoxy methyl (MEM) group, a methoxy methyl (MOM) group, a silyl group such as a trimethylsilyl (TMS) group, a tert-butyldimethylsilyl (TBDMS) group, and a triisopropylsilyl (TIPS) group.

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "substituted" refers to moieties having substituents replacing a hydrogen on one or more carbons of the backbone. It will be understood that "substitution" or "substituted with" includes, except for where otherwise provided, the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted at a position can themselves be substituted, if appropriate.

The term "sulfate" is art-recognized and refers to the group —$OSO_3H$, or a pharmaceutically acceptable salt thereof.

The term "sulfonamide" is art-recognized and refers to the group represented by the general formulae

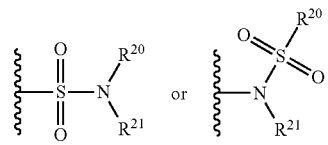

wherein $R^{20}$ and $R^{21}$ independently represents hydrogen or hydrocarbyl.

The term "sulfoxide" is art-recognized and refers to the group —S(O)—$R^{20}$, wherein $R^{20}$ represents a hydrocarbyl.

The term "sulfonate" is art-recognized and refers to the group $SO_3H$, or a pharmaceutically acceptable salt thereof.

The term "sulfone" is art-recognized and refers to the group —$S(O)_2$—$R^{20}$, wherein $R^{20}$ represents a hydrocarbyl.

The term "tautomer" as used herein is art-recognized and refers to the formal migration of a hydrogen atom, accompanied by a switch of a single bond and adjacent double bond. When used herein to describe a compound or genus of compounds, tautomer includes any portion of a compound or the entire compound such as a single substituent of a compound, multiple substituents of a compound or, for example, the entire compound. For example, the tautomer of a compound that includes a hydroxyalkene (A) is the aldehyde (B):

The term "thioalkyl", as used herein, refers to an alkyl group substituted with a thiol group.

The term "thioester", as used herein, refers to a group —C(O)S$R^{20}$ or —SC(O)$R^{20}$ wherein $R^{20}$ represents a hydrocarbyl.

The term "thioether", as used herein, is equivalent to an ether, wherein the oxygen is replaced with a sulfur.

The term "urea" is art-recognized and may be represented by the general formula

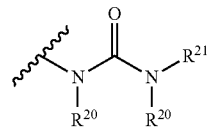

wherein $R^{20}$ and $R^{21}$ independently represent hydrogen or a hydrocarbyl.

II. Description of the Invention

Nitrogen-containing heterocycles are ubiquitous in natural products, pharmaceuticals, and materials science. Given the abundance of these heterocycles in nature, pharmacology, and materials science, stereoselective methods for the synthesis of 3,3-disubstituted pyrrolidinones, piperidinones, and caprolactams, in addition to their corresponding amines, would, in theory, be valuable for the preparation of a wide array of important structures in these areas of research. The general formulae for such disubstituted pyrrolidinones, piperidinones, and caprolactams are depicted below.

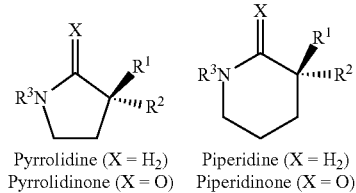

Pyrrolidine (X = H₂)  Piperidine (X = H₂)
Pyrrolidinone (X = O)  Piperidinone (X = O)

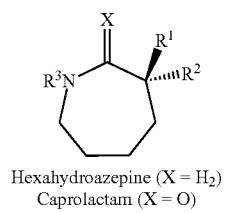

Hexahydroazepine (X = H₂)
Caprolactam (X = O)

A small sample of the products these disubstituted pyrrolidinones, piperidinones and caprolactams could theoretically be used to prepare includes those depicted below.

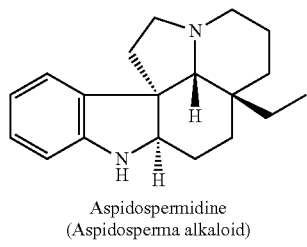

Aspidospermidine
(Aspidosperma alkaloid)

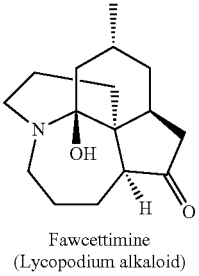

Fawcettimine
(Lycopodium alkaloid)

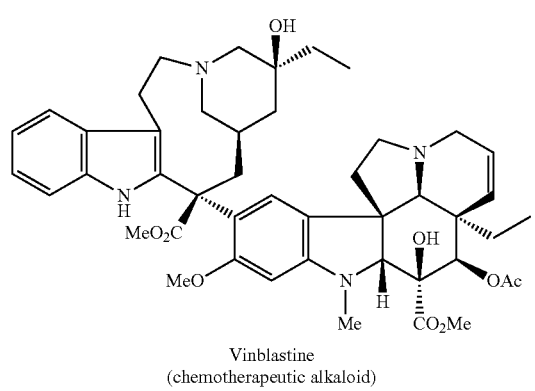

Vinblastine
(chemotherapeutic alkaloid)

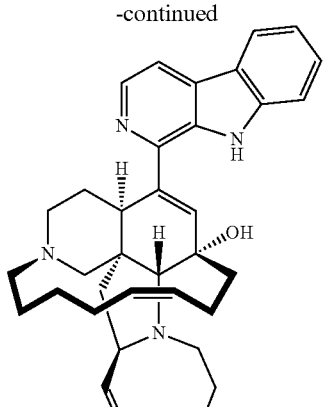

Manzamine A
(marine alkaloid)

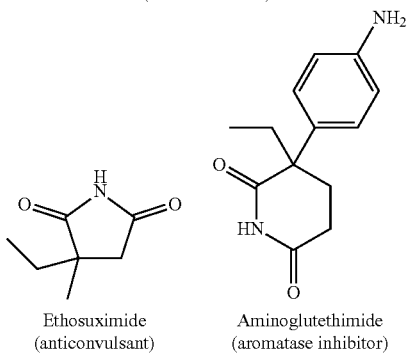

Ethosuximide          Aminoglutethimide
(anticonvulsant)      (aromatase inhibitor)

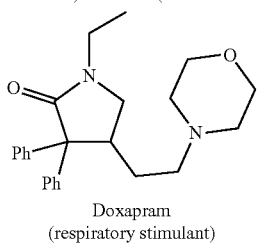

Doxapram
(respiratory stimulant)

However, as can be seen from the small sample depicted above, many of the target compounds include quaternary centers, e.g., C(α)-quaternary centers. Unfortunately, a paucity of enantioselective lactam syntheses leading to such C(α)-quaternary centers is known. Indeed, most known methods rely on chiral auxiliary chemistry, and although a few catalytic examples exist, they are specific to the oxindole lactam nucleus, α-carbonyl stabilized enolates, or cyclic imides. Importantly, enolate stabilization is critical for success in these catalytic systems, thereby limiting the scope of each transformation. To date, there are no examples of catalytic asymmetric alkylations of simple piperidinone, pyrrolidinone, and caprolactam scaffolds (or other nitrogen containing compounds, e.g., acyclic compounds) for the formation of C(α)-quaternary or C(α)-tetrasubstituted tertiary centers.

Transition metal-catalyzed allylic alkylation is a key method for the enantioselective preparation of chiral substances and ranks among the best general techniques for the catalytic alkylation of prochiral enolates. Given the importance of α-quaternary lactams (discussed above), embodiments of the present invention are directed to a general method for catalytic asymmetric α-alkylation of cyclic and acyclic quaternary heteroatom containing compounds (including nitrogen containing compounds, e.g., lactams, and their structurally analogous oxygen containing compounds, e.g., lactones). Over the past several years, methods for the synthesis of α-quaternary ketones have been reported, and the use of these methods has been demonstrated in a number of complex molecule syntheses. See Mohr, et al., "Deracemization of quaternary stereocenters by Pd-catalyzed enantioconvergent decarboxylative allylation of racemic β-ketoesters," *Angew. Chem., Int. Ed.* 44, 6924-6927 (2005); Seto, et al., "Catalytic enantioselective alkylation of substituted dioxanone enol ethers: ready access to C(α)-tetrasubstituted hydroxyketones, acids, and esters," *Angew. Chem. Int. Ed.* 47, 6873-6876 (2008); Streuff, et al., "A Palladium-catalysed enolate alkylation cascade for the formation of adjacent quaternary and tertiary stereocenters," *Nature Chem.* 2, 192-196 (2010); McFadden, et al., "The catalytic enantioselective, protecting group-free total synthesis of (+)-dichroanone," *J. Am. Chem. Soc.* 128, 7738-7739 (2006); White, et al., "The catalytic asymmetric total synthesis of elatol," *J. Am. Chem. Soc.* 130, 810-811 (2008); Enquist, et al., "The total synthesis of (−)-cyanthiwigin F via double catalytic enantioselective alkylation," *Nature* 453, 1228-1231 (2008); Day, et al., "The catalytic enantioselective total synthesis of (+)-liphagal," *Angew. Chem. Int. Ed.* 50, in press (2011), the entire content of all of which are incorporated herein by reference. Related allylic alkylation methods have also been developed. See Trost, et al., "Regio- and Enantioselective Pd-Catalyzed Allylic Alkylation of Ketones through Allyl Enol Carbonates," *J. Am. Chem. Soc.* 127, 2846-2847 (2005); Trost, et al., "Palladium-Catalyzed Asymmetric Allylic α-Alkylation of Acyclic Ketones," *J. Am. Chem. Soc.* 127, 17180-17181 (2005); Trost, et al., "Asymmetric Allylic Alkylation of Cyclic Vinylogous Esters and Thioesters by Pd-Catalyzed Decarboxylation of Enol Carbonate and β-Ketoester Substrates," *Angew. Chem., Int. Ed.* 45, 3109-3112 (2006); Trost, et al., "Enantioselective Synthesis of α-Tertiary Hydroxyaldehydes by Palladium-Catalyzed Asymmetric Allylic Alkylation of Enolates." *J. Am. Chem. Soc.* 129, 282-283 (2007); Trost, et al., "Palladium-Catalyzed Decarboxylative Asymmetric Allylic Alkylation of Enol Carbonates," *J. Am. Chem. Soc.* 131, 18343-18357 (2009); Nakamura, et al., "Synthesis of Chiral α-Fluoroketones through Catalytic Enantioselective Decarboxylation," *Angew. Chem., Int. Ed.* 44, 7248-7251 (2005); Burger, et al., "Catalytic Asymmetric Synthesis of Cyclic α-Allylated α-Fluoroketones," *Synlett* 2824-2826 (2006); Belanger, et al., "Enantioselective Pd-Catalyzed Allylation Reaction of Fluorinated Silyl Enol Ethers," *J. Am. Chem. Soc.* 129, 1034-1035 (2007); Schulz, et al., "Palladium-Catalyzed Synthesis of Substituted Cycloheptane-1,4-diones by an Asymmetric Ring-Expanding Allylation (AREA)," *Angew. Chem., Int. Ed.* 46, 3966-3970 (2007), the entire content of all of which are incorporated herein by reference.

According to embodiments of the present invention, a wide range of structurally-diverse, functionalized heteroatom containing compounds (e.g., nitrogen containing lactams and oxygen containing lactones) are prepared by a stereoselective method including palladium-catalyzed enantioselective enolate alkylation. This chemistry is important to the synthesis of bioactive alkaloids, and the transformation is useful for the construction of novel building blocks for medicinal and polymer chemistry. Indeed, in some embodiments of the present invention, these novel building blocks include heteroatom containing compounds useful as precursors to (or reactants leading to the preparation of) numerous biologically active and important natural and pharmaceutical products. While embodiments of the present invention are directed to the novel building blocks achieved from the transition-metal catalyzed allylic alkylation reaction, other embodiments of the present invention are directed to novel heteroatom containing substrates used in the transition-metal catalyzed allylic alkylation reaction to form the building blocks. Indeed, in some embodiments of the present invention, a method of making a building block compound comprises reacting a substrate compound with a ligand in the presence of a palladium-based catalyst and a solvent. The palladium-based catalysts, ligands and solvents useful in this reaction are described in more detail below in the section entitled "Palladium-Catalyzed Decarboxylative Alkylation." The substrates used in the reaction, and the building block compounds made from the reaction are described here, and in the below sections entitled "Heteroatom Containing Substrate Compounds" and "Heteroatom Containing Building Block Compounds."

III. Compounds and Methods of the Invention

The present invention provides a method for the preparation of a compound of Formula (II):

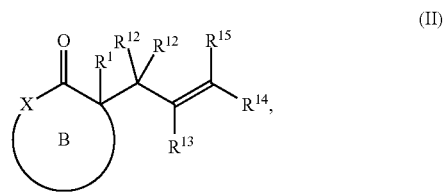

comprising treating a compound of Formula (I):

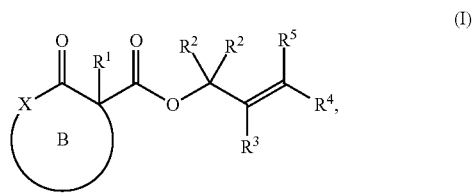

with a transition metal catalyst and under alkylation conditions, wherein, as valence and stability permit,
ring B represents an optionally substituted heterocycle;
X is a heteroatom;
$R^1$ is selected from optionally substituted alkyl, alkenyl, alkynyl, carbocyclyl, heterocycle, aryl, heteroaryl, and halogen;
$R^2$, $R^3$, $R^4$, $R^5$, $R^{12}$, $R^{13}$, $R^{14}$, and $R^{15}$ are independently selected at each occurrence from hydrogen, halogen, nitro, alkyl, alkenyl, alkynyl, cyano, carboxyl, sulfate, alkoxy, alkylamino, alkylthio, hydroxyalkyl, alkoxyalkyl, aminoalkyl, thioalkyl, ether, thioether, ester, amide, thioester, carbonate, carbamate, urea, sulfonate, sulfone, sulfoxide, sulfonamide, acyl, acyloxy, acylamino, aryl, heteroaryl, carbocyclyl, heterocyclyl, aralkyl, aralkyloxy, hetaralkyl, carbocyclylalkyl, and heterocyclylalkyl.

In addition to methods for preparing compounds of Fomula (II), the invention further discloses compounds represented by Formula (I) and Formula (II). The following discussion of Ring B as well as variables X, $R^2$, $R^3$, $R^4$, $R^5$, $R^{12}$, $R^{13}$, $R^{14}$, and $R^{15}$ refers to both the method of preparing a compound of Formula (II) from a compound of Formula (I) and the compounds of Formula (I) and (II).

Ring B of the compound of Formula (I) or (II) may contain one or more heteroatoms selected from O, N, S, P, B, or Si. In certain embodiments, X of ring B is nitrogen or oxygen wherein nitrogen is optionally substituted. In addition to X, ring B may contain one or more additional heteroatoms such as a nitrogen or an oxygen. Ring B may represent a substituted 4-8 membered ring or preferably a substituted 5-7 membered ring. In particular, ring B may represent an optionally substituted 5-7-membered lactam ring. Alternatively, ring B may represent an optionally substituted 5-7 membered lactone ring.

As valence and stability permit, ring B may be saturated or contain unsaturation with, for example, one or more multiple bonds. Substituents on ring B may be selected from at least: a halogen, a hydroxyl, a carbonyl (such as a carboxyl, an alkoxycarbonyl, an arylcarbonyl, an aryloxycarbonyl, an aralkoxycarbonyl, a formyl, or an acyl), a thiocarbonyl (such as a thioester, a thioacetate, or a thioformate), an alkoxyl, a phosphoryl, a phosphate, an aryloxy, an aralkyloxy, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. In addition, one or more of the substituents on ring B may also be substituted by one or more substituents.

While not wishing to be bound by a particular mechanism, the reactions disclosed herein may proceed by directly linking the carbon bearing $R^2$ to the carbon bearing $R^1$. Accordingly, in some embodiments, the carbon bearing the $R^2$ groups in a compound of Formula (I) may be the carbon bearing the $R^{12}$ groups in a compound of Formula (II), and thus $R^{12}$ in the product is the same as $R^2$ in the reactant. Similarly, in these embodiments, the carbon bearing $R^4$ and $R^5$ in a compound of Formula (I) may be the carbon bearing $R^{14}$ and $R^{15}$ groups in a compound of Formula (II) (so that $R^{14}$ in the product is the same as $R^4$ in the reactant, and $R^{15}$ in the product is the same as $R^5$ in the reactant) and the carbon bearing $R^3$ in a compound of Formula (I) may be the carbon bearing $R^{13}$ in a compound of Formula (II) (making $R^{13}$ in the product the same as $R^3$ in the reactant).

Alternatively, the reactions disclosed herein may proceed through an allylic rearrangement of the allyl ester. In such embodiments, the carbon bearing the $R^2$ groups in a compound of Formula (I) may be the carbon bearing the $R^{14}$ and $R^{15}$ groups in a compound of Formula (II) (meaning that $R^{14}$ and $R^{15}$ in the product are the same as the two $R^2$ groups in the reactant). Similarly, in these embodiments, the carbon bearing $R^4$ and $R^5$ in a compound of Formula (I) may be the carbon bearing $R^{12}$ groups in a compound of Formula (II) (meaning that the two $R^2$ groups in the product are the same as $R^4$ and $R^5$ in the reactant) and the carbon bearing $R^3$ in a compound of Formula (I) may be the carbon bearing $R^{13}$ in a compound of Formula (II) (such that $R^{13}$ in the product is the same as $R^3$ in the reactant).

In preferred embodiments, wherein $R^2$, $R^4$, $R^5$, $R^{12}$, $R^{14}$, and $R^{15}$ are all hydrogen, the product is the same regardless of which mechanism applies, and regardless of the presence or absence of a non-hydrogen substituent at $R^3$ and/or $R^{13}$. In other embodiments, at least one of $R^2$, $R^4$, $R^5$, $R^{12}$, $R^{14}$, and $R^{15}$ is a non-hydrogen substituent.

The present invention also provides a method of preparation of a compound of Formula (IV):

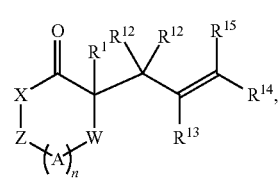

comprising treating a compound of Formula (III):

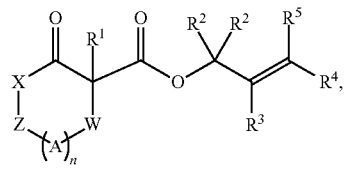

with a transition metal catalyst and under alkylation conditions, wherein, as valence and stability permit, X is selected from $-NR^6-$ and $-O-$;

Z is selected from $-C(O)-$ and $-CR^7R^7-$;

A is independently selected at each occurrence from $-CR^8R^8-$ and $-NR^9-$;

W is absent or selected from $-O-$, $-NR^{10}-$, and $-CR^{11}R^{11}-$;

$R^1$ is selected from optionally substituted alkyl, alkenyl, alkynyl, carbocyclyl, heterocycle, aryl, heteroaryl, and halogen;

$R^2$, $R^3$, $R^4$, $R^5$, $R^{12}$, $R^{14}$, and $R^{15}$ are independently selected at each occurrence from hydrogen, halogen, nitro, alkyl, alkenyl, alkynyl, cyano, carboxyl, sulfate, alkoxy, alkylamino, alkylthio, hydroxyalkyl, alkoxyalkyl, aminoalkyl, thioalkyl, ether, thioether, ester, amide, thioester, carbonate, carbamate, urea, sulfonate, sulfone, sulfoxide, sulfonamide, acyl, acyloxy, acylamino, aryl, heteroaryl, carbocyclyl, heterocyclyl, aralkyl, aralkyloxy, hetaralkyl, carbocyclylalkyl, and heterocyclylalkyl;

$R^7$, $R^8$, and $R^{11}$ are independently selected at each occurrence from hydrogen, halogen, nitro, alkyl, alkenyl, alkynyl, cyano, hydroxyl, thiol, carboxyl, sulfate, amino, alkoxy, alkylamino, alkylthio, hydroxyalkyl, alkoxyalkyl, aminoalkyl, thioalkyl, ether, thioether, ester, amide, thioester, carbonate, carbamate, urea, sulfonate, sulfone, sulfoxide, sulfonamide, acyl, acyloxy, acylamino, aryl, heteroaryl, carbocyclyl, heterocyclyl, aralkyl, aralkyloxy, hetaralkyl, carbocyclylalkyl, and heterocyclylalkyl;

wherein $R^7$ and $R^8$ may combine with the carbons to which they are bound to form an optionally substituted 3-8-membered ring; $R^8$ and $R^{11}$ may combine with the carbons to which they are bound to form an optionally substituted 3-8-membered ring; and when n is 2 or 3, $R^8$ attached to one carbon may combine with $R^8$ attached to another carbon to combine with the carbons to which they are bound to form a 3-8-membered ring;

$R^6$, $R^9$ and $R^{10}$ are independently selected at each occurrence from hydrogen, hydroxyl and optionally substituted alkyl, alkoxy, alkylthio, aryloxy, carbocyclyl, aryl, heteroaryl, aralkyl, heteroaralkyl, aralkyloxy, heteroaryloxy, acyl, arylcarbonyl, aralkylcarbonyl, acyloxy, sulfone, alkoxycarbonyl, aryloxycarbonyl, aralkoxycarbonyl, and amide; and n is 0-3.

While not wishing to be bound by a particular mechanism, the reactions disclosed herein may proceed by directly linking the carbon bearing $R^2$ to the carbon bearing $R^1$. Accordingly, in some embodiments, the carbon bearing the $R^2$ groups in a compound of Formula (III) may be the carbon bearing the $R^{12}$ groups in a compound of Formula (IV), and thus $R^{12}$ in the product is the same as $R^2$ in the reactant. Similarly, in these embodiments, the carbon bearing $R^4$ and $R^5$ in a compound of Formula (III) may be the carbon bearing $R^{14}$ and $R^{15}$ groups in a compound of Formula (IV) (so that $R^{14}$ in the product is the same as $R^4$ in the reactant, and $R^{15}$ in the product is the same as $R^5$ in the reactant) and the carbon bearing $R^3$ in a compound of Formula (III) may be the carbon bearing $R^{13}$ in a compound of Formula (IV) (making $R^{13}$ in the product the same as $R^3$ in the reactant).

Alternatively, the reactions disclosed herein may proceed through an allylic rearrangement of the allyl ester. In such embodiments, the carbon bearing the $R^2$ groups in a compound of Formula (III) may be the carbon bearing the $R^{14}$ and $R^{15}$ groups in a compound of Formula (IV) (meaning that $R^{14}$ and $R^{15}$ in the product are the same as the two $R^2$ groups in the reactant). Similarly, in these embodiments, the carbon bearing $R^4$ and $R^5$ in a compound of Formula (III) may be the carbon bearing $R^{12}$ groups in a compound of Formula (IV) (meaning that the two $R^2$ groups in the product are the same as $R^4$ and $R^5$ in the reactant) and the carbon bearing $R^3$ in a compound of Formula (III) may be the carbon bearing $R^{13}$ in a compound of Formula (IV) (such that $R^{13}$ in the product is the same as $R^3$ in the reactant). In preferred embodiments, wherein $R^2$, $R^4$, $R^5$, $R^{12}$, $R^{14}$, and $R^{15}$ are all hydrogen, the product is the same regardless of which mechanism applies, and regardless of the presence or absence of a non-hydrogen substituent at $R^3$ and/or $R^{13}$. In other embodiments, at least one of $R^2$, $R^4$, $R^5$, $R^{12}$, $R^{14}$, and $R^{15}$ is a non-hydrogen substituent.

The invention also comprises compounds represented by Formula (V):

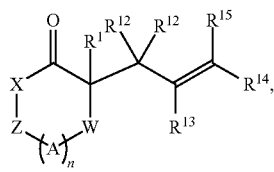

or a tautomer and/or a salt thereof, wherein:

X is selected from —NR$^6$— and —O—;

Z is selected from —C(O)— and —CR$^7$R$^7$—;

A is independently selected at each occurrence from —CR$^8$R$^8$— and —NR$^9$—;

W is absent or selected from —O—, —NR$^{10}$—, and —CR$^{11}$R$^{11}$—;

$R^1$ is selected from optionally substituted alkyl, alkenyl, alkynyl, carbocyclyl, heterocycle, aryl, heteroaryl, and halogen;

$R^{12}$, $R^{13}$, $R^{14}$ and $R^{15}$ are independently selected at each occurrence from hydrogen, hydroxyl, halogen, nitro, alkyl, alkenyl, alkynyl, cyano, carboxyl, sulfate, amino, alkoxy, alkylamino, alkylthio, hydroxyalkyl, alkoxyalkyl, aminoalkyl, thioalkyl, ether, thioether, ester, amide, thioester, carbonate, carbamate, urea, sulfonate, sulfone, sulfoxide, sulfonamide, acyl, acyloxy, acylamino, aryl, heteroaryl, carbocyclyl, heterocyclyl, aralkyl, aralkyloxy, hetaralkyl, carbocyclylalkyl, and heterocyclylalkyl;

$R^7$, $R^8$, and $R^{11}$ are independently selected at each occurrence from hydrogen, halogen, nitro, alkyl, alkenyl, alkynyl, cyano, hydroxyl, thiol, carboxyl, sulfate, amino, alkoxy, alkylamino, alkylthio, hydroxyalkyl, alkoxyalkyl, aminoalkyl, thioalkyl, ether, thioether, ester, amide, thioester, carbonate, carbamate, urea, sulfonate, sulfone, sulfoxide, sulfonamide, acyl, acyloxy, acylamino, aryl, heteroaryl, carbocyclyl, heterocyclyl, aralkyl, aralkyloxy, hetaralkyl, carbocyclylalkyl, and heterocyclylalkyl;

wherein $R^7$ and $R^8$ may combine with the carbons to which they are bound to form an optionally substituted 3-8-membered ring; $R^8$ and $R^{11}$ may combine with the carbons to which they are bound to form an optionally substituted 3-8-membered ring; and when n is 2 or 3, $R^8$ attached to one carbon may combine with $R^8$ attached to another carbon to combine with the carbons to which they are bound to form a 3-8-membered ring;

$R^6$, $R^9$ and $R^{10}$ are independently selected at each occurrence from hydrogen, hydroxyl and optionally substituted alkyl, alkoxy, alkylthio, aryloxy, carbocyclyl, aryl, heteroaryl, aralkyl, heteroaralkyl, aralkyloxy, heteroaryloxy, acyl, arylcarbonyl, aralkylcarbonyl, acyloxy, sulfone, alkoxycarbonyl, aryloxycarbonyl, aralkoxycarbonyl, and amide; and n is 0-3.

The invention also comprises compounds represented by Formula (VI):

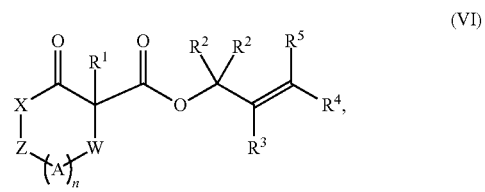

or a tautomer and/or a salt thereof, wherein:

X is selected from —NR$^6$— and —O—;

Z is selected from —C(O)— and —CR$^7$R$^7$—;

A is independently selected at each occurrence from —CR$^8$R$^8$— and —NR$^9$—;

W is absent or selected from —O—, —NR$^{10}$—, and —CR$^{11}$R$^{11}$—;

$R^1$ is selected from optionally substituted alkyl, alkenyl, alkynyl, carbocyclyl, heterocycle, aryl, heteroaryl, and halogen;

$R^2$, $R^3$, $R^4$ and $R^5$ are independently selected at each occurrence from hydrogen, halogen, nitro, alkyl, alkenyl, alkynyl, cyano, carboxyl, sulfate, amino, alkoxy, alkylamino, alkylthio, hydroxyalkyl, alkoxyalkyl, aminoalkyl, thioalkyl, ether, thioether, ester, amide, thioester, carbonate, carbamate, urea, sulfonate, sulfone, sulfoxide, sulfonamide, acyl, acyloxy, acylamino, aryl, heteroaryl, carbocyclyl, heterocyclyl, aralkyl, aralkyloxy, hetaralkyl, carbocyclylalkyl, and heterocyclylalkyl;

$R^7$, $R^8$, and $R^{11}$ are independently selected at each occurrence from hydrogen, halogen, nitro, alkyl, alkenyl, alkynyl, cyano, hydroxyl, thiol, carboxyl, sulfate, amino, alkoxy, alkylamino, alkylthio, hydroxyalkyl, alkoxyalkyl, aminoalkyl, thioalkyl, ether, thioether, ester, amide, thioester, carbonate, carbamate, urea, sulfonate, sulfone, sulfoxide, sulfonamide, acyl, acyloxy, acylamino, aryl, heteroaryl, carbocyclyl, heterocyclyl, aralkyl, aralkyloxy, hetaralkyl, carbocyclylalkyl, and heterocyclylalkyl;

wherein $R^7$ and $R^8$ may combine with the carbons to which they are bound to form an optionally substituted 3-8-membered ring; $R^8$ and $R^{11}$ may combine with the carbons to which they are bound to form an optionally substituted 3-8-membered ring; and when n is 2 or 3, $R^8$ attached to one carbon may combine with $R^8$ attached to another carbon to combine with the carbons to which they are bound to form a 3-8-membered ring; $R^6$, $R^9$ and $R^{10}$ are independently selected at each occurrence from hydrogen, hydroxyl and optionally substituted alkyl, alkoxy, alkylthio, aryloxy, carbocyclyl, aryl, heteroaryl, aralkyl, heteroaralkyl, aralkyloxy, heteroaryloxy, acyl, arylcarbonyl, aralkylcarbonyl, acyloxy, sulfone, alkoxycarbonyl, aryloxycarbonyl, aralkoxycarbonyl, and amide; and n is 0-3.

$R^1$ of a compound of Formula (I)-(VI) may be selected from halogen and an optionally substituted group selected from alkyl, carbocyclyl, carbocyclylalkyl, cyanoalkyl, aralkyl, heteroaralkyl, hydroxyalkyl, haloalkyl, acylalkyl, alkoxycarbonylalkyl, and aryloxycarbonylalkyl. In particular, $R^1$ may be selected from halogen, alkyl, optionally substituted aralkyl, optionally substituted alkoxycarbonylalkyl, optionally substituted cyanoalkyl, and optionally substituted hydroxyalkyl. In particular, $R^1$ may be selected from halogen and optionally substituted alkyl, wherein alkyl is substituted by one or more of: halogen, hydroxyl, cyano, alkoxy, aryloxy, alkylsilyloxy, aryl, alkyl-substituted aryl, haloalkyl-substited aryl, alkylthio, carbocyclyl, arylcarbonyl, aralkylcarbonyl, heteroaryl, aralkyloxy, heteroaryloxy, acyl, arylcarbonyl, aralkylcarbonyl, acyloxy, alkyl sulfonyl, aryl sulfonyl, alkoxycarbonyl, aryloxycarbonyl, aralkoxycarbonyl, and amide.

When $R^1$ is optionally substituted alkyl in any of Formulas (I)-(VI), alkyl may be selected from optionally substituted $C_1$ to $C_{10}$-alkyl, such as optionally substituted $C_1$ to $C_5$-alkyl. In particular, $R^1$ is optionally substituted alkyl and alkyl is selected from optionally substituted $C_1$ to $C_3$-alkyl. When $R^1$ is halogen, $R^1$ may be selected from chloro, bromo and fluoro. In certain embodiments, $R^1$ may be fluoro.

$R^2$ and $R^{12}$ of a compound of Formula (I)-(VI) may be independently selected at each occurrence from hydrogen, halogen, hydroxyl, haloalkyl, cyano, alkyl, alkoxy, alkylthio, amide, amine, and carbocyclyl. In particular, $R^2$ and $R^{12}$ may be selected at each occurrence from hydrogen, halogen, haloalkyl and hydroxyl. For example, $R^2$ and $R^{12}$ at each occurrence is hydrogen.

$R^3$, $R^4$, $R^5$, $R^{13}$, $R^{14}$, and $R^{15}$ of a compound of Formula (I)-(VI) may be independently selected at each occurrence from hydrogen, halogen, haloalkyl, cyano, alkyl, alkoxy, alkylthio, amide, amine, aryloxy, and aralkyloxy. In particular, $R^3$, $R^4$, $R^5$, $R^{13}$, $R^{14}$, and $R^{15}$ may be independently selected at each occurrence from hydrogen, halogen, haloalkyl, cyano, alkyl, and alkoxy. For example, $R^3$, $R^4$, $R^5$, $R^{13}$, $R^{14}$, and $R^{15}$ may be independently selected at each occurrence from chloro, bromo, fluoro, and $C_1$ to $C_5$-alkyl wherein alkyl is optionally substituted with one or more halogens or hydroxyls.

Two of $R^2$, $R^3$, $R^4$, $R^5$, $R^{12}$, $R^{13}$, $R^{14}$, and $R^{15}$ of a compound of Formula (I)-(VI), may be taken together with the carbons to which they are bound to form a ring. For example, $R^3$ and $R^4$ may combine with the carbons to which they are bound to form an optionally substituted 5-8-membered ring, $R^{13}$ and $R^{14}$ may combine with the carbons to which they are bound to form an optionally substituted 5-8-membered ring, $R^4$ and $R^5$ may combine with the carbons to which they are bound to form a 3-8-membered ring, $R^{14}$ and $R^{15}$ may combine with the carbons to which they are bound to form a 3-8-membered ring, $R^2$ together with $R^3$, $R^4$ or $R^5$ may combine with the carbons to which they are bound to form a 5-8-membered ring, and $R^{12}$ together with $R^{13}$, $R^{14}$, or $R^{15}$ may combine with the carbons to which they are bound to form a 5-8-membered ring. A ring formed by any two of $R^2$, $R^3$, $R^4$ and $R^5$ and any two of $R^{12}$, $R^{13}$, $R^{14}$ and $R^{15}$ may be optionally substituted with one or more substituents selected from halogen, hydroxyl, haloalkyl, cyano, alkyl, alkoxy, alkylthio, amide, amine.

$R^7$, $R^8$, and $R^{11}$ of a compound of Formula (III)-(VI) may be independently selected at each occurrence from hydrogen, halogen, hydroxyl, haloalkyl, cyano, alkyl, alkoxy, alkylthio, amide, amine, and carbocyclyl. In particular, $R^7$, $R^8$, and $R^{11}$ may be independently selected at each occurrence from hydrogen, halogen, haloalkyl and hydroxyl. In particular embodiments when two of $R^7$, $R^8$, and $R^{11}$ combine with the atoms to which they are bound to form a ring, the ring may be substituted by one or more of halogen, hydroxyl, haloalkyl, cyano, alkyl, alkoxy, alkylthio, amide, amine.

$R^6$, $R^9$, and $R^{10}$ of a compound of Formula (III)-(VI) may be independently selected at each occurrence from hydrogen, hydroxyl, and an optionally substituted groups selected from alkyl, alkoxy, alkylthio, aryloxy, carbocyclyl, aryl, arylcarbonyl, aralkylcarbonyl, heteroaryl, aralkyl, heteroaralkyl, aralkyloxy, heteroaryloxy, acyl, arylcarbonyl, aralkylcarbonyl, acyloxy, alkyl sulfonyl, aryl sulfonyl, alkoxycarbonyl, aryloxycarbonyl, aralkoxycarbonyl, and amide. In certain embodiments, $R^6$, $R^9$, and $R^{10}$ are independently selected from an optionally substituted amine or amide protecting group. In particular, $R^6$, $R^9$, and $R^{10}$ may be independently selected at each occurrence from optionally substituted aralkyloxy, aralkoxycarbonyl, heteroaryloxy, acyl, arylcarbonyl, aralkylcarbonyl, arylsulfonyl, alkoxycarbonyl, and aryloxycarbonyl, wherein the substituents may be selected from one or more of halogen, alkyl, alkoxy, haloalkyl, phenyl and hydroxyl.

For a compound of any of Formulas (III)-(VI), X may be —$NR^6$—; Z may be selected from —C(O)— and —$CR^7R^7$—; A at each occurrence may be —$CR^8R^8$—; W may be selected from —$NR^{10}$— and —$CR^{11}R^{11}$—; and n may be 0-2. In such embodiments, $R^1$ may be selected from halogen, alkyl, optionally substituted aralkyl, optionally substituted alkoxycarbonylalkyl, optionally substituted cyanoalkyl, and optionally substituted hydroxyalkyl; $R^2$ and $R^{12}$ may be selected at each occurrence from hydrogen, halogen, hydroxyl, haloalkyl, cyano, alkyl, alkoxy, alkylthio, amide, amine, and carbocyclyl; $R^3$, $R^4$, $R^5$, $R^{13}$, $R^{14}$, and $R^{15}$ may be independently selected at each occurrence from hydrogen, halogen, haloalkyl, cyano, alkyl, alkoxy, alkylthio, amide, amine, aryloxy, and aralkyloxy; $R^7$, $R^8$, and $R^{11}$ may be independently selected at each occurrence from hydrogen, halogen, hydroxyl, haloalkyl, cyano, alkyl, alkoxy, alkylthio, amide, amine, and carbocyclyl; and $R^6$ and $R^{10}$ may be independently selected at each occurrence from hydrogen, hydroxyl, and an optionally substituted groups selected from alkyl, alkoxy, alkylthio, aryloxy, carbocyclyl, aryl, arylcarbonyl, aralkylcarbonyl, heteroaryl, aralkyl, heteroaralkyl, aralkyloxy, heteroaryloxy, acyl, arylcarbonyl, aralkylcarbonyl, acyloxy, alkyl sulfonyl, aryl sulfonyl, alkoxycarbonyl, aryloxycarbonyl, aralkoxycarbonyl, and amide.

For a compound of any of Formulas (III)-(VI), X may be —$NR^6$—; Z may be —$CR^7R^7$—; A may be —$CR^8R^8$—; W may be —NR$^{10}$—; and n may be 1. The compound of Formula (IV) or (V) may be represented by the Formula (IVa):

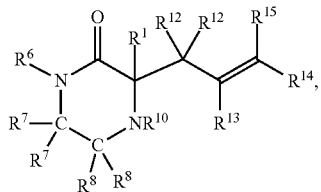
(IVa)

and the compound of Formula (III) and (VI) may be represented by the Formula (IIIa):

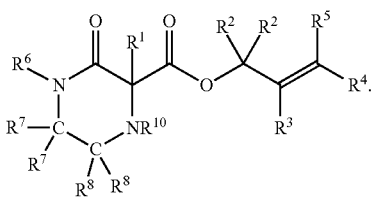
(IIIa)

In such embodiments, R$^1$ may be selected from halogen, alkyl, optionally substituted aralkyl, optionally substituted alkoxycarbonylalkyl, optionally substituted cyanoalkyl, and optionally substituted hydroxyalkyl; R$^2$ and R$^{12}$ may be independently selected at each occurrence from hydrogen, halogen, hydroxyl, haloalkyl, cyano, alkyl, alkoxy, alkylthio, amide, amine, and carbocyclyl; R$^3$, R$^4$, R$^5$, R$^{13}$, R$^{14}$, and R$^{15}$ may be independently selected at each occurrence from hydrogen, halogen, haloalkyl, cyano, alkyl, alkoxy, alkylthio, amide, amine, aryloxy, and aralkyloxy; R$^7$ and R$^8$ may be independently selected at each occurrence from hydrogen, halogen, hydroxyl, haloalkyl, cyano, alkyl, alkoxy, alkylthio, amide, amine, and carbocyclyl; and R$^6$ and R$^{10}$ may be independently selected at each occurrence from an amine or amide protecting group, hydrogen, hydroxyl, and an optionally substituted groups selected from alkyl, alkoxy, alkylthio, aryloxy, carbocyclyl, aryl, arylcarbonyl, aralkylcarbonyl, heteroaryl, aralkyl, heteroaralkyl, aralkyloxy, heteroaryloxy, acyl, arylcarbonyl, aralkylcarbonyl, acyloxy, alkylsulfonyl, arylsulfonyl, alkoxycarbonyl, aryloxycarbonyl, aralkoxycarbonyl, and amide.

In certain embodiments, for a compound of any of Formulas (III)-(VI), X is —NR$^6$—; Z is selected from —C(O)— and —CR$^7$R$^7$—; A at each occurrence is —CR$^8$R$^8$—; W is —CR$^{11}$R$^{11}$—, and n is 0-2. In such embodiments, R$^1$ may be selected from halogen, alkyl, optionally substituted aralkyl, optionally substituted alkoxycarbonylalkyl, optionally substituted cyanoalkyl, and optionally substituted hydroxyalkyl; R$^2$ and R$^{12}$ may be independently selected at each occurrence from hydrogen, halogen, hydroxyl, haloalkyl, cyano, alkyl, alkoxy, alkylthio, amide, amine, and carbocyclyl; R$^3$, R$^4$, R$^5$. R$^{13}$, R$^{14}$, and R$^{15}$ may be independently selected at each occurrence from hydrogen, halogen, haloalkyl, cyano, alkyl, alkoxy, alkylthio, amide, amine, aryloxy, and aralkyloxy; R$^7$, R$^8$, and R$^{11}$ may be independently selected at each occurrence from hydrogen, halogen, hydroxyl, haloalkyl, cyano, alkyl, alkoxy, alkylthio, amide, amine, and carbocyclyl; and R$^6$ may be selected from hydrogen, hydroxyl, and an optionally substituted group selected from alkyl, alkoxy, alkylthio, aryloxy, carbocyclyl, aryl, arylcarbonyl, aralkylcarbonyl, heteroaryl, aralkyl, heteroaralkyl, aralkyloxy, heteroaryloxy, acyl, arylcarbonyl, aralkylcarbonyl, acyloxy, alkyl sulfonyl, aryl sulfonyl, alkoxycarbonyl, aryloxycarbonyl, aralkoxycarbonyl, and amide.

For a compound of any of Formulas (III)-(VI), X may be —NR$^6$—; Z may be —CR$^7$R$^7$; A may be —CR$^8$R$^8$—; W may be —CR$^{11}$R$^{11}$—, and n may be 0-2. The compound of Formula (IV) or (V) may be represented by the Formula (IVb):

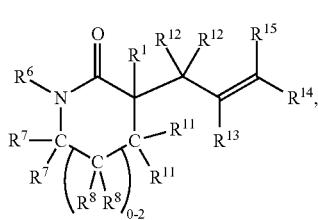
(IVb)

and the compound of Formula (III) or (VI) may be represented by the Formula (IIIb):

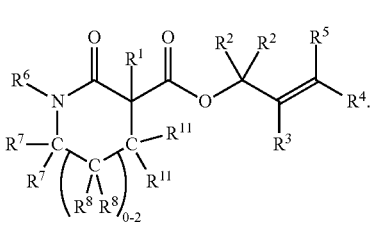
(IIIb)

In such embodiments, R$^1$ may be selected from halogen, alkyl, optionally substituted aralkyl, optionally substituted alkoxycarbonylalkyl, optionally substituted cyanoalkyl, and optionally substituted hydroxyalkyl; R$^2$ and R$^{12}$ may be independently selected at each occurrence from hydrogen, halogen, hydroxyl, haloalkyl, cyano, alkyl, alkoxy, alkylthio, amide, amine, and carbocyclyl; R$^3$, R$^4$, R$^5$, R$^{13}$, R$^{14}$, and R$^{15}$ may be independently selected at each occurrence from hydrogen, halogen, haloalkyl, cyano, alkyl, alkoxy, alkylthio, amide, amine, aryloxy, and aralkyloxy; R$^7$ and R$^8$ may be independently selected at each occurrence from hydrogen, halogen, hydroxyl, haloalkyl, cyano, alkyl, alkoxy, alkylthio, amide, amine, and carbocyclyl; and R$^6$ may be selected from an amine or amide protecting group, hydrogen, hydroxyl, and an optionally substituted groups selected from alkyl, alkoxy, alkylthio, aryloxy, carbocyclyl, aryl, arylcarbonyl, aralkylcarbonyl, heteroaryl, aralkyl, heteroaralkyl, aralkyloxy, heteroaryloxy, acyl, arylcarbonyl, aralkylcarbonyl, acyloxy, alkyl sulfonyl, aryl sulfonyl, alkoxycarbonyl, aryloxycarbonyl, aralkoxycarbonyl, and amide.

In certain embodiments, for a compound of any of Formulas (III)-(VI), X is —NR$^6$— or —O—; Z is —C(O)— and —CR$^7$R$^7$—; A is independently selected at each occurrence from —CR$^8$R$^8$— and —NR$^9$—; W is absent or selected from —O—, —NR$^{10}$—, and —CR$^{11}$R$^{11}$; and n is 0-3, with the proviso that when X is —NR$^6$—, and Z is selected from —C(O)— and —CR$^7$R$^7$—, at least one A is —NR$^9$— or W is —NR$^{10}$—. In such embodiments, R$^1$ may be selected from halogen, alkyl, optionally substituted aralkyl, optionally substituted alkoxycarbonylalkyl, optionally substituted cyanoalkyl, and optionally substituted hydroxyalkyl; R$^2$ and R$^{12}$ may be independently selected at each occurrence from hydrogen, halogen, hydroxyl, haloalkyl, cyano, alkyl, alkoxy, alkylthio, amide, amine, and carbocyclyl; R$^3$, R$^4$, R$^5$, R$^{13}$, R$^{14}$, and R$^{15}$ may be independently selected at each occurrence from hydrogen, halogen, haloalkyl, cyano, alkyl, alkoxy, alkylthio, amide, amine, aryloxy, and aralkyloxy; R$^7$, R$^8$, and R$^{11}$ may be independently selected at each occurrence from hydrogen, halogen, hydroxyl, haloalkyl, cyano, alkyl, alkoxy, alkylthio, amide, amine, and carbocyclyl; and R$^6$, R$^9$, and R$^{10}$ may be selected from hydrogen, hydroxyl, and an optionally substituted group selected from alkyl, alkoxy, alkylthio, aryloxy, carbocyclyl, aryl, arylcarbonyl, aralkylcarbonyl, heteroaryl, aralkyl, heteroaralkyl, aralkyloxy, heteroaryloxy, acyl, arylcarbonyl, aralkylcarbonyl, acyloxy, alkyl sulfonyl, aryl sulfonyl, alkoxycarbonyl, aryloxycarbonyl, aralkoxycarbonyl, and amide.

For any of Formulas (III), (Ma), (IIIb), (IV), (IVa), (IVb), (V) and (VI), R$^6$ may be selected from:

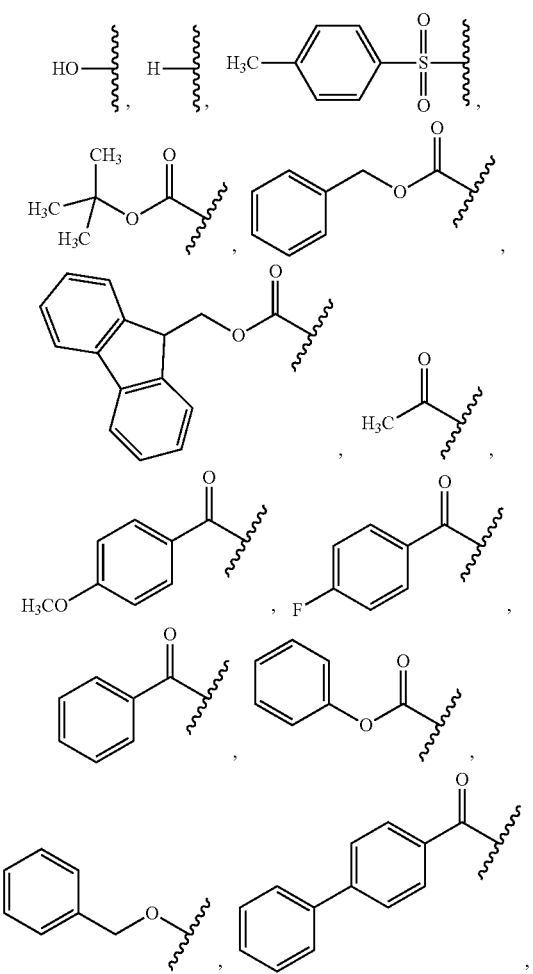

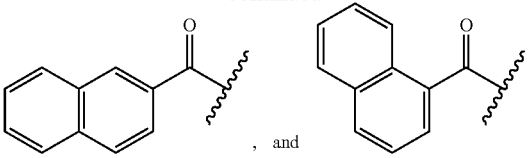

For any of Formulas (I), (II), (III), (Ma), (IIIb), (IV), (IVa) and (IVb), R$^1$ may be selected from:

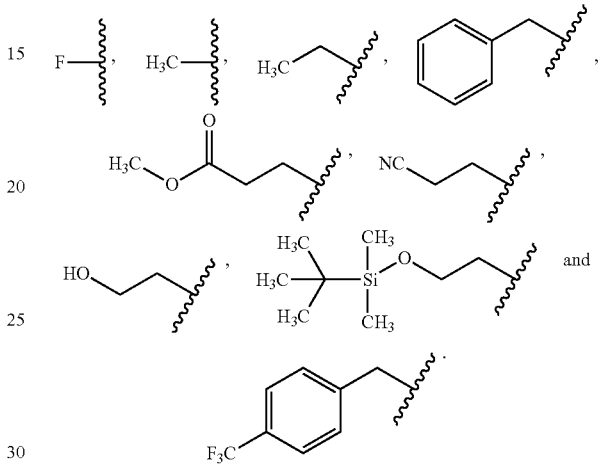

While not being bound by a particular mechanism, any of the alkylation reactions discussed herein may proceed with or without a rearrangement of the allylic group. In the absence of an allylic rearrangement it is envisioned that compounds subjected to the alkylation conditions described herein, where a compound of Formula (I) is converted to (II), a compound of Formula (III) is converted to (IV), a compound of Formula (Ma) is converted to (IVa) and a compound of Formula (IIIb) is converted to (IVb), will otherwise display a substitution pattern in the product that is the same as the substitution pattern in the substrate. For example, ring B, X, Z, A, W, n, and R$^6$ to R$^{11}$ will not be altered from the substrate to the product under the reaction conditions and the carbons bearing R$^{12}$ and R$^{15}$ in the product will correspond with the carbons bearing R$^2$ and R$^5$ in the substrate, respectively.

In the event of an allylic rearrangement, it is envisioned that compounds subjected to the alkylation conditions described herein, where a compound of Formula (I) is converted to (II), a compound of Formula (III) is converted to (IV), a compound of Formula (Ma) is converted to (IVa) and a compound of Formula (IIIb) is converted to (IVb), will otherwise display a substitution pattern in the product that is the same as the substitution pattern in the substrate except that the substitution pattern in the product at the carbons bearing R$^{12}$, R$^{14}$ and R$^{15}$ is transposed relative to the starting material. That is, the carbon bearing R$^4$ and R$^5$ in the substrate becomes the carbon bearing the R$^{12}$ groups in the product, the carbon bearing the R$^2$ groups in the substrate becomes the carbon bearing R$^{14}$ and R$^{15}$ in the product, and the carbon bearing R$^3$ in the substrate becomes the carbon bearing R$^{11}$ in the product. For example, ring B, X, Z, A, W, n, R$^1$ and R$^6$ to R$^{11}$ will not be altered from the substrate to the product under the reaction conditions but the carbons bearing $R^{12}$ to $R^{15}$ in the product are transposed relative to the carbons bearing $R^2$ to $R^5$ in the substrate.

Under some circumstances, one or more substituents may be altered on the product relative to the substrate. For example, a protected hydroxyl group in the starting material may become deprotected under the alkylation conditions of the method. Accordingly, in the various embodiments disclosed herein, $R^{12}$, $R^{13}$, $R^{14}$, and $R^{15}$ may be hydroxy in addition to the other options disclosed above; for $R^{13}$, $R^{14}$, and $R^{15}$, the resulting hydroxyalkene may tautomerize to the corresponding carbonyl, such as to a ketone or aldehyde, as would be well understood. Under some circumstances, a protected amino group in the starting material may become deprotected under the alkylation conditions of the method. Accordingly, in the various embodiments disclosed herein, $R^{12}$, $R^{13}$, $R^{14}$, and $R^{15}$ may be amino in addition to the other options disclosed above; for $R^{13}$, $R^{14}$, and $R^{15}$, the resulting aminoalkene may tautomerize to the corresponding imine, such as to a ketimine or aldimine, as would be well understood.

A compound of any of Formulas (I), (II), (III), (Ma), (IIIb), (IV), (IVa), (IVb), (V) and (VI) may contain one or more asymmetric centers, chiral axes and chiral planes and may thus give rise to enantiomers, diastereomers, and other stereoisomeric forms and may be defined in terms of absolute stereochemistry, such as (R)- or (S)- or, as (D)- or (L)- for amino acids. The present invention is intended to include all such possible isomers, as well as their racemic and optically pure forms. Optically active (+) and (−), (R)- and (S)-, or (D)- and (L)-isomers, e.g., ligands or substrates for the methods described herein, may be prepared using chiral synthons or chiral reagents, or resolved using conventional techniques, such as reverse phase HPLC. The racemic mixtures may be prepared and thereafter separated into individual optical isomers or these optical isomers may be prepared by chiral synthesis. The enantiomers may be resolved by methods known to those skilled in the art, for example by formation of diastereoisomeric salts which may then be separated by crystallization, gas-liquid or liquid chromatography, selective reaction of one enantiomer with an enantiomer specific reagent.

The compounds of the invention may be racemic or in certain embodiments, compounds of the invention may be enriched in one enantiomer. For example, a compound of any of Formulas (I), (II), (III), (Ma), (IIIb), (IV), (IVa), (IVb), (V) and (VI) such as a substrate or product of the methods described herein, may have 30% ee or greater, 40% ee or greater, 50% ee or greater, 60% ee or greater, 70% ee or greater, 80% ee or greater, 90% ee or greater, 95% ee or greater, or even 98% ee or greater. In certain embodiments, compounds of the invention may have more than one stereocenter. In certain such embodiments, compounds of the invention may be enriched in one or more diastereomer. For example, a compound of the invention may have 30% de or greater, 40% de or greater, 50% de or greater, 60% de or greater, 70% de or greater, 80% de or greater, 90% de or greater, 95% de or greater, or even 98% de or greater.

Transition Metal Catalysts

Preferred transition metal catalysts of the invention are complexes of transition metals wherein the metal is selected from Groups 6, 8, 9 and 10 in the periodic table. In preferred embodiments, the metal of the transition metal catalyst is selected from molybdenum, tungsten, iridium, rhenium, ruthenium, nickel, platinum, and palladium. In more preferred embodiments, the metal is palladium.

In one embodiment of the invention, a complex of a neutral transition metal is employed directly in the reaction. It should be appreciated that the air and moisture sensitivity of many complexes of neutral transition metals will necessitate appropriate handling precautions. This may include the following precautions without limitation: minimizing exposure of the reactants to air and water prior to reaction; maintaining an inert atmosphere within the reaction vessel; properly purifying all reagents; and removing water from reaction vessels prior to use. Exemplary neutral transition metal catalysts include, without limitation, $Mo(CO)_6$, $Mo(MeCN)_3(CO)_3$, $W(CO)_6$, $W(MeCN)_3(CO)_3$, [Ir(1,5-cyclooctadiene)Cl]$_2$, [Ir(1,5-cyclooctadiene)Cl]$_2$, [Ir(1,5-cyclooctadiene)Cl]$_2$, $Rh(PPh_3)_3Cl$, [Rh(1,5-cyclooctadiene)Cl]$_2$, $Ru(pentamethylcyclopentadienyl)(MeCN)_3PF_6$, $Ni(1,5-cyclooctadiene)_2$, $Ni[P(OEt)_3]_4$, tris(dibenzylideneacetone)dipalladium(0), tris(dibenzylideneacetone)dipalladium(0)-chloroform adduct, bis(4-methoxybenzylidene)acetone)dipalladium(0), $Pd(OC(=O)CH_3)_2$, $Pd(3,5$-dimethyoxy-dibenzylideneacetone$)_2$, $PdCl_2(R^{23}CN)_2$; $PdCl_2(PR^{24}R^{25}R^{26})_2$; $[Pd(\eta^3$-allyl$)Cl]_2$; and $Pd(PR^{24}R^{25}R^{26})_4$, wherein $R^{23}$, $R^{24}$, $R^{25}$, and $R^{26}$ are independently selected from H, hydrocarbyl, substituted hydrocarbyl, heteroatom-containing hydrocarbyl, and substituted heteroatom-containing hydrocarbyl. In particular embodiments, the transition metal catalyst tris(dibenzylideneacetone)dipalladium, $Pd_2(dba)_3$, or bis(4-methoxybenzylidene)acetone) dipalladium, $Pd_2(pmdba)_3$, is preferred.

To improve the effectiveness of the catalysts discussed herein, additional reagents may be employed as needed, including, without limitation, salts, solvents, and other small molecules. Preferred additives include $AgBF_4$, $AgOSO_2CF_3$, $AgOC(=O)CH_3$, $PPh_3$, $P(n-Bu)_3$, and bipyridine. These additives are preferably used in an amount that is in the range of about 1 equivalent to about 5 equivalents relative to the amount of the catalyst.

The neutral oxidation state of the transition metal can also be obtained in situ, by the reduction of transition metal complexes that are initially in a higher oxidation level. An exemplary method for reduction of the transition metal complex is with the use of nucleophilic reagents including, without limitation, NBu4OH, tetrabutylammonium difluorotriphenylsilicate (TBAT), tetrabutylammonium fluoride (TBAF), 4-dimethylaminopyridine (DMAP), $NMe_4OH$ $(H_2O)_5$, KOH/1,4,7,10,13,16-Hexaoxacyclooctadecane, EtONa, TBAT/Trimethyl-(2-methyl-cyclohex-1-enyloxy)-silane, and mixtures thereof. When a nucleophilic reagent is needed for the reduction of the metal complex, the nucleophilic reagent is used in an amount in the range of about 1 mol % to about 20 mol % relative to the reactant, more preferably in the range of about 1 mol % to about 10 mol % relative to the substrate, and most preferably in the range of about 5 mol % to about 8 mol % relative to the substrate.

Exemplary transition metal complexes with a +2 oxidation state include, without limitation, allylchloro[1,3-bis(2,6-di-i-propylphenyl)imidazol-2-ylidene]palladium(II), ([2S,3S]-bis[diphenylphosphino]butane)($\eta^3$-allyl)palladium(II) perchlorate, [S]-4-tert-butyl-2-(2-diphenylphosphanyl-phenyl)-4,5-dihydro-oxazole($\eta^3$-allyl)palladium(II) hexafluorophosphate (i.e., [Pd(S-tBu-PHOX)(allyl)]$PF_6$), and cyclopentadienyl($\eta^3$-allyl) palladium(II), with [Pd(s-tBu-PHOX)(allyl)]$PF_6$ and cyclopentadienyl($\eta^3$-allyl)palladium(II) being most preferred. The amount of catalyst to be used in the reactions of the invention is generally measured in relation to the amount of substrate that is present. For the reactions of the invention, the metal from the catalyst is present in an amount ranging from about 1 mol % to about 20 mol % relative to the substrate. More preferably, the metal from the catalyst is present in an amount ranging from about 1 mol % to about 10 mol %, such as about 2 mol % to about 7 mol %, such as about 5 mol % relative to the substrate. By "metal from the catalyst" is meant the equivalents (relative to the substrate) of transition metal atoms. Thus, for example, 5 mol % of tris(dibenzylideneacetone) dipalladium(0) provides 10 mol % of metal atoms relative to the substrate. In certain embodiments, the amount of catalyst in relation to the substrate is selected from 2-8 mol %, such as about 5 mol %.

Ligands

One aspect of the invention is the enantioselectivity of the methods. Enantioselectivity is a result of the presence of chiral ligands during the reactions. Without being bound by theory, enantioselectivity results from the asymmetric environment that is created around the metal center by the presence of chiral ligands. The chiral ligand forms a complex with the transition metal, thereby occupying one or more of the coordination sites on the metal and creating an asymmetric environment around the metal center. This complexation may or may not involve the displacement of achiral ligands already complexed to the metal. When displacement of one or more achiral ligands occurs, the displacement may proceed in a concerted fashion, i.e., with both the achiral ligand decomplexing from the metal and chiral ligand complexing to the metal in a single step. Alternatively, the displacement may proceed in a stepwise fashion, i.e., with decomplexing of the achiral ligand and complexing of the chiral ligand occurring in distinct steps. Complexation of the chiral ligand to the transition metal may be allowed to occur in situ, i.e., by admixing the ligand and metal before adding the substrate. Alternatively, the ligand-metal complex can be formed separately, and the complex isolated before use in the alkylation reactions of the present invention. Once coordinated to the transition metal center, the chiral ligand influences the orientation of other molecules as they interact with the transition metal catalyst. Coordination of the metal center with a π-allyl group, and reaction of the substrate with the π-allyl-metal complex are dictated by the presence of the chiral ligand. The orientation of the reacting species determines the stereochemistry of the products.

Many factors determine the ability of the chiral ligand to influence the orientation of the reacting species, and thereby determine the stereochemistry of the products. For example, shape and size (i.e., sterics), denticity (mono- or bidentate), and electronic properties affect the ligand-metal complex as well as the interaction of the metal-ligand complex with the nucleophile. These factors can vary substantially between ligands, resulting in correspondingly large differences in the success of the ligands as promoters of enantioselective alkylation. For any given substrate, some ligands might provide relatively high product yield, while other ligands affect relatively high enantiopurity of the product. Still other ligands may provide both high yield and high enantiopurity, while still other ligands might provide neither. It should be understood that proper ligand selection for any given substrate will influence the products of the reaction.

Generally, the chiral ligand is present in an amount in the range of about 0.75 equivalents to about 10 equivalents relative to the amount of metal from the catalyst, preferably in the range of about 0.75 to about 5 equivalents relative to the amount of metal from the catalyst, and most preferably in the range of about 0.75 to about 1.25, such as about 1.25 equivalents relative to the amount of metal from the catalyst. Alternatively, the amount of the chiral ligand can be measured relative to the amount of the substrate. Then, the chiral ligand is present in an amount ranging from about 1 mol % to about 20 mol %, more preferably from about 2.5 mol % to about 13 mol % such as about 12.5 mol % relative to the substrate.

Chiral ligands of the invention may be bidentate or monodentate or ligands with higher denticity (i.e., tridentate, tetradentate, etc.) can be used. Preferably, the ligand will be substantially enantiopure. By "enantiopure" is meant that only a single enantiomer is present. In many cases, substantially enantiopure ligands can be purchased from commercial sources.

Exemplary chiral ligands may be found in U.S. Pat. No. 7,235,698, the entirely of which is incorporated herein by reference. Preferred chiral ligands of the invention include the PHOX-type chiral ligands such as (R)-2-[2-(diphenylphosphino)phenyl]-4-isopropyl-2-oxazoline, (R)-2-[2-(diphenylphosphino)phenyl]-4-phenyl-2-oxazoline, (S)-2-[2-(diphenylphosphino)phenyl]-4-benzyl-2-oxazoline, (S)-2-[2-(diphenylphosphino)phenyl]-4-tert-butyl-2-oxazoline ((S)-t-BuPHOX) and (S)-2-(2-(bis(4-(Trifluoromethyl)phenyl)phosphino)-5-(trifluoromethyl)phenyl)-4-(tert-butyl)-4,5-dihydrooxazole ((S)—(CF$_3$)$_3$-t-BuPHOX). In preferred embodiments, the PHOX type chiral ligand is selected from (S)-t-BuPHOX and (S)—(CF$_3$)$_3$-t-BuPHOX).

Where a chiral ligand is used, the reactions of the invention may enrich the stereocenter bearing $R^1$ in the product relative to the enrichment at this center, if any, of the starting material. For example, a product of the methods described herein may have 30% ee or greater, 40% ee or greater, 50% ee or greater, 60% ee or greater, 70% ee or greater, 80% ee or greater, 90% ee or greater, 95% ee or greater, or even 98% ee or greater, even where this % ee is greater than the % ee of the starting material, such as 0% ee (racemic). In embodiments where the starting material has more than one stereocenter, reactions of the invention may enrich the stereocenter bearing $R^1$ relative to the enrichment at this center, if any, of the starting material, and substantially independently of the stereochemical disposition/enrichment of any other stereocenters of the molecule. For example, a product of the methods described herein may have 30% de or greater, 40% de or greater, 50% de or greater, 60% de or greater, 70% de or greater, 80% de or greater, 90% de or greater, 95% de or greater, or even 98% de or greater at the stereocenter of the product bearing $R^1$.

Alkylation Conditions

The reactions of the invention are preferably carried out in solvent under an inert atmosphere. Appropriate solvents include, without limitation, hydrocarbons, substituted hydrocarbons, heteroatom-containing hydrocarbons, and substituted heteroatom-containing hydrocarbons. Preferred solvents include ethers, amines, ketones, aromatic hydrocarbons, heteroatom-containing aromatic hydrocarbons, and substituted aromatic hydrocarbons. In certain embodiments, the solvent is selected from one or more polar aprotic and nonpolar solvents. Examples of preferred solvents include 1,4-dioxane, tetrahydrofuran, methyl-tert-butyl ether, diethyl ether, toluene, hexanes, benzene, diisopropyl ether, ethyl acetate, triethylamine, anisole, acetone, fluorobenzene, and diglyme or mixtures thereof. Supercritical fluids can also be used as solvents, with carbon dioxide representing one such solvent. Reaction temperatures range from 0° C. to 100° C., with 20° C. to 60° C. being preferred, and 20° C. to 25° C. (i.e., room temperature) being particularly preferred. In particular embodiments, the reaction temperature is is below about 60° C., below about 50° C., below about 40° C., or below about 30° C. The reaction time will generally be in the range of 1 hour to 24 hours. In certain embodiments, instruments such as a microwave reactor may be used to accelerate the reaction time. Pressures range from atmospheric to pressures typically used in conjunction with supercritical fluids, with the preferred pressure being atmospheric.

IV. Additional Compounds and Methods of the Invention

According to embodiments of the present invention compounds useful as either substrates for the creation of building blocks leading to target compounds or as building blocks include compounds represented by the following Chemical Formula A. As discussed here, these compounds can be used as substrate compounds useful in the method noted above and described in detail below. Also, these compounds may be used as reactants in other methods and reaction schemes to make other compounds, e.g., some naturally occurring compounds that may be biologically active. Chemical Formula A

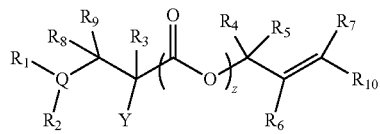

In Chemical Formula A, z is either 0 or 1, and Q is a heteroatom, for example, N, O, P, S or a halogen such as Cl, I, Br or F. In some embodiments, for example, Q is N or O. Each of R1 through R10 is independently selected from hydrogen, substituted or unsubstituted hydrocarbyl groups, substituted or unsubstituted heteroatom containing hydrocarbyl groups, or functional groups. However, in some embodiments, R3 is not hydrogen. In some embodiments, in which z is 0 and R8 and R9 combine to form a carbonyl group (as discussed further below), R3 is also not phenyl or substituted phenyl. In yet other embodiments, in which z is 0 and R8 and R9 combine to form a carbonyl group (as discussed further below), R3 is not a simple carbonyl group. However, in some embodiments, R3 may be a substituted carbonyl group, e.g., a carbonyl group substituted hydrocarbyl group or heteroatom containing hydrocarbyl group or functional group. In some embodiments, though, R3 does not include any carbonyl groups, whether substituted or unsubstituted. In yet other embodiments, in which z is 0 and R8 and R9 combine to form a carbonyl group (as discussed further below), R3 is not an ethyl group. However, in some embodiments, R3 may be a substituted ethyl group, and R3 may be any other alkyl group (or other group as described above). In some embodiments, though, R3 is not an ethyl group or a substituted ethyl group. Also, in some embodiments, the carbon atom to which the R3 group is attached is a chiral, stereogenic center, i.e., R3 and Y are not the same.

Y may be selected from hydrogen, heteroatoms, substituted or unsubstituted hydrocarbyl groups, substituted or unsubstituted heteroatom containing hydrocarbyl groups, or functional groups. Additionally, any two or more adjacent R and Y groups can optionally combine to form a carbonyl group on the underlying atom. For example, in some embodiments, R8 and R9 combine to form a carbonyl group, as shown in the below Formula A(i).

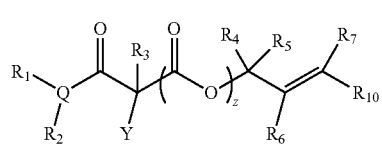

Also, any two or more adjacent R and Y groups can optionally combine to form a ring, e.g., a cyclic, heterocyclic, aryl or heteroaryl ring. Indeed, in some embodiments, although Formula 1 depicts an acyclic heteroatom containing compound, Formula 1 also encompasses cyclic, heterocyclic, aryl and heteroaryl compounds. Also, in some embodiments, while R6 and R10 may combine to form nearly any ring structure, R6 and R10 do not form a substituted or unsubstituted benzene ring. Similarly, in some embodiments, while R4 and R6 may combine to form nearly any ring structure, R4 and R6 do not form a substituted or unsubstituted benzene ring. In other embodiments, R6 and R10 do not form any aromatic ring, and R4 and R6 do not form any aromatic ring.

In embodiments in which R2 and Y combine to form a ring, in some embodiments, the atom in the ring directly adjacent the Q atom (i.e., the atom on the opposite side of the Q atom to the carbon atom carrying the R8 and R9 groups) is not a chiral center. More specifically, any substituents on that atom are the same as each other, and that atom does not include two different substituents.

For example, in some embodiments, the R2 group on the Q atom, and the Y group combine to form a ring with the Q atom, the carbon atom to which the Y group is attached, and the intervening carbon atom. The ring formed between the R2 group and the Y group can be any type of ring with any number of ring atoms. However, the ring formed from the combination of R2 and Y does not form a benzene ring or ortho-disubstituted benzene ring. In some embodiments, though, R2 and Y may form other substituted benzene rings. In other embodiments, however, R2 and Y do not form any kind of benzene ring.

In some exemplary embodiments, for example, the ring formed between the R2 group and the Y group may include one or more additional heteroatoms (i.e., additional to the Q atom depicted in Formula 1). In these embodiments, the compounds of Formula 1 may be represented by Formula B, below.

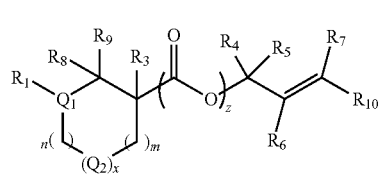

Formula B

In Formula B, z is 0 or 1, and R1 through R10 are the same as defined above with respect to Formula A. Each of Q1 and Q2 are as defined above with respect to Q1, and are each independently selected from heteroatoms, e.g., N, O, S, P or halogens, such as Cl, I, F or Br. In some embodiments, for example, each of Q1 and Q2 is independently selected from N or O. Additionally, similar to that described above with respect to Formulae 1 and 1(a), any two or more adjacent R groups can optionally combine to form a carbonyl group on the underlying atom. For example, in some embodiments, R8 and R9 combine to form a carbonyl group, as shown in the below Formula 2(a).

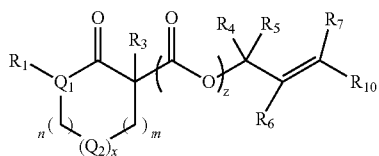

Formula B(i)

Also, in Formula B, each of x, n and m can be any integer of 0 or greater. When x is greater than 1, the plurality of Q2 heteroatoms may be the same as or different from each other. In some embodiments, for example, each of x, n and m is independently 0, 1, 2, 3 or 4. In some exemplary embodiments, when x and n are both 0, m may be 1, 2, 3 or 4. Conversely, when x and m are both 0, n may be 1, 2, 3 or 4. These configurations yield compounds having the Formulae B(ii) or B(iii) (where R8 and R9 combine to form a carbonyl group) below. Also, while m and n are defined here such that the ring depicted in Formula B has up to 7 ring atoms, it is understood that the size of the ring in Formula B is not particularly limited, and n and m can be any integers corresponding to any ring size. For example, in some embodiments, n and m are integers such that the resulting ring depicted in Formula B has from 3 to 12 ring atoms. In some embodiments for example, n and m are integers such that the resulting ring has from 3 to 10 ring atoms. In other embodiments, n and m are integers such that the resulting ring has from 5 to 7 ring atoms.

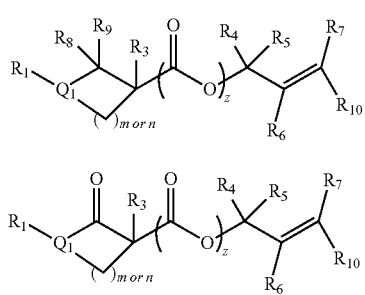

Formula B(ii)

Formula B(iii)

Alternatively, in some embodiments, when x is 1, n and m may be any integer from 0 to 4 such that the sum of n and m may be 0, 1, 2 or 3. For example, in some embodiments, when x is 1, n may be 0 and m may be 0, 1, 2 or 3. In other embodiments, when x is 1, n may be 1 and m may be 0, 1 or 2. In still other embodiments, when x is 1, n may be 2 and m may be 0 or 1. In yet other embodiments, when x is 1, n may be 3 and m may be 0. Conversely, in some embodiments, when x is 1, m may be 0 and n may be 0, 1, 2 or 3. In other embodiments, when x is 1, m may be 1 and n may be 0, 1 or 2. In still other embodiments, when x is 1, m may be 2 and n may be 0 or 1. In yet other embodiments, when x is 1, m may be 3 and n may be 0. These configurations yield compounds of Formula B in which there are two heteroatoms, and include all configurations of the two heteroatoms on the ring. Specifically, these configurations cover every possible position of the second heteroatom (Q2) on the ring depicted in Formula B. Also, while m and n are defined here such that the ring depicted in Formula B has up to 7 ring atoms, it is understood that the size of the ring in Formula B is not particularly limited, and n and m can be any integers corresponding to any ring size, as discussed above. For example, in some embodiments, n and m are integers such that the resulting ring depicted in Formula B has from 3 to 12 ring atoms, for example 3 to 10 ring atoms or 5 to 7 ring atoms.

In some embodiments, the ring may include the Q atom depicted in Formulae A and B as the only heteroatom, and include any number of additional carbon atoms in the ring. Alternatively, however, the ring depicted in Formulae B and B(i) through B(iii) can have any number of heteroatoms positioned anywhere on the ring. For example, as shown in Formula B and B(i) above, the ring may include the heteroatom depicted in Formulae A and B separated from a group of one or more additional heteroatoms by one or more carbon atoms, or the ring may include two or more heteroatoms that are adjacent each other within the ring. However, according to other embodiments, the ring depicted in Formula B may include three or more heteroatoms which may be adjacent one another or separated from each other by at least one carbon atom. This configuration is depicted in Formulae B(iv) and B(v) (where R8 and R9 combine to form a carbonyl group) below.

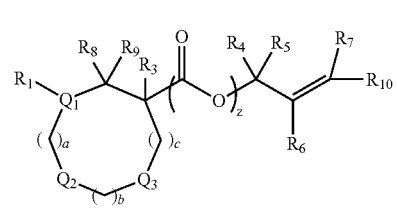

Formula B(iv)

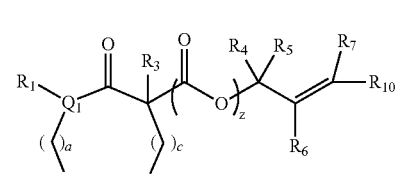

Formula B(v)

In Formula B(iv) and B(v), z is 0 or 1, each of Q1, Q2 and Q3 is as defined above with respect to Q1, and are each independently a heteroatom, for example, O, N, S, P, or a halogen such as Cl, I, Br or F. Each of R1 through R10 is also as described above with respect to Formulae A, B and B(i) through 2(iii). Each of a, b and c is independently an integer of 0 or greater. In some exemplary embodiments, each of a, b and c may be independently an integer of 0, 1 or 2. For example, in some embodiments, each of a, b and c is 0, yielding a five membered ring including three adjacent heteroatoms. In other embodiments, a is 1 and b and c are both 0, yielding a six membered ring in which Q2 and Q3 are adjacent one another and Q2 is separated from Q1 by a carbon atom. In still other embodiments, a is 2 and b and c are both 0, yielding a seven membered ring in which Q2 and Q3 are adjacent one another and Q2 is separated from Q1 by two carbon atoms.

According to other embodiments, b is 1 and a and c are both 0, yielding a six membered ring in which Q1 and Q2 are adjacent one another and Q2 is separated from Q3 by a carbon atom. In still other embodiments, b is 2 and a and c are both 0, yielding a seven membered ring in which Q1 and Q2 are adjacent one another and Q2 is separated from Q3 by two carbon atoms.

In other embodiments, c is 1 and a and b are both 0, yielding a six membered ring in which Q1, Q2 and Q3 are adjacent one another. In still other embodiments, c is 2 and a and b are both 0, yielding a seven membered ring in which Q1, Q2 and Q3 are adjacent one another. Also, while a, b and c are defined here such that the ring depicted in Formulae B, B(iv) and B(v) has up to 7 ring atoms, it is understood that the size of the ring in Formulae B, B(iv) and B(v) is not particularly limited, and a, b and c can be any integers corresponding to any ring size, as discussed above. For example, in some embodiments, a, b and c are integers such that the resulting ring depicted in Formulae B, B(iv) and B(v) has from 3 to 12 ring atoms, for example 3 to 10 ring atoms or 5 to 7 ring atoms.

In some exemplary embodiments, the ring depicted in Formula B may include four heteroatoms, and the four heteroatoms may be placed on the ring in any manner. For example, some of the heteroatoms may be spaced from each other by one or more ring carbon atoms while others are adjacent, or all heteroatoms may be adjacent each other, or all heteroatoms may be spaced from each other by one or more ring carbon atoms.

Additionally, although the rings discussed above are depicted and described as fully saturated, according to some embodiments of the present invention, any of the rings may be unsaturated (i.e., mono- or poly-unsaturated). To account for these compounds, the heteroatom containing substrate of Formula A may be represented by Formulae C or C(i) (where R8 and R9 combine to form a carbonyl group) below.

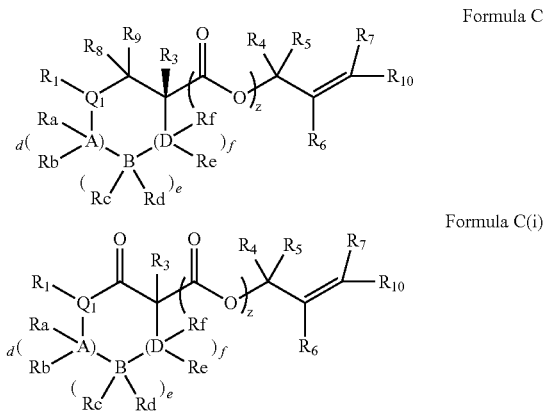

Formula C

Formula C(i)

In Formulae C and C(i), z is 0 or 1, and Q1 and R1 through R10 are as defined above with respect to Formulae A, B and B(i) through B(v). Each of A, B and D is independently a carbon atom or a heteroatom. However, in some embodiments, in which d is 1 or greater, the A atom located directly adjacent the Q1 atom is not a chiral center. More specifically, the Ra and Rb substituents on that atom are the same as each other, and are not two different substituents. Also, the ring formed from Q1, A, B and D is not a benzene ring or an ortho-disubstituted benzene ring. In some embodiments, though, the ring may be any other substituted benzene ring. In other embodiments, however, the ring is not any kind of benzene ring.

Each of Ra, Rb, R, Rd, Re and Rf may be independently selected from hydrogen atoms, substituted or unsubstituted hydrocarbyl groups, substituted or unsubstituted heteroatom containing hydrocarbyl groups, halogens or functional groups. However, as discussed above, in some embodiments, in which d is 1 or greater, the A atom located directly adjacent the Q1 atom is not a chiral center, and the Ra and Rb substituents on that atom are the same as each other. In some embodiments, however, one R group on each of two adjacent ring atoms can combine to form a bond, thereby creating a double bond within the ring structure. Specifically, each of Ra through Rf is either: independently hydrogen, a substituted or unsubstituted hydrocarbyl group, a substituted or unsubstituted heteroatom containing hydrocarbyl group, or a functional group; or combines with another of Ra through Rf to form a double bond. For example, R1 and one of the Ra groups may combine to form a double bond, or one of the Rb groups and one of the Rc groups may combine to form a double bond within the ring, or one of the Rd groups and one of the Re groups may combine to form a double bond within the ring. Any number of double bonds may be formed within the ring structure, and the ring structure may be heteroaryl in nature. Alternatively or additionally, two adjacent R groups on the same ring atom (e.g., Ra and Rb, or Rc and Rd, or Re and Rf) can combine to form a carbonyl group on the ring atom.

Each of d, e and f is independently an integer of 0 or greater, for example, an integer of 0, 1, 2, 3, or 4. When d, e or f is greater than 1, the plurality of A, B or D atoms, and the plurality of Ra, Rb, Rc, Rd, Re or Rf groups may be the same as or different from each other. Also, although Formulae C and C(i) above depict a six membered ring, it is understood from the definitions of d, e and f that the ring is not limited to six members, and can have any number of ring atoms, as discussed above with respect to Formulae A, B and B(i) through B(v). Indeed, in some embodiments, the ring has from 3 to 12 ring atoms, for example 3 to 10 ring atoms or 5 to 7 ring atoms.

Also, in the rings discussed above, any of the ring atoms, whether carbon or heteroatom, can be substituted with a substituted or unsubstituted hydrocarbyl group, substituted or unsubstituted heteroatom containing hydrocarbyl group, a halogen or a functional group. Indeed, although the rings depicted in Formulae B and B(i) through B(v) above are depicted with hydrogen atoms on each of the ring atoms, any or all of the hydrogen atoms on any or all of the ring atoms may be substituted with the substituents described above. As shown in Formula C, for example, each of the ring atoms (Q1, A, B and/or D) may include R groups that can be hydrogen, a substituted or unsubstituted hydrocarbyl group, a substituted or unsubstituted heteroatom containing hydrocarbyl group, a halogen or a functional group.

In some embodiments of the present invention, building block compounds created from substrate compounds of Formula A are represented by the below Formula D. The compounds of Formula D include compounds created by the palladium catalyzed decarboxylative alkylation of substrate compounds represented by Formula A in which z is 1, Q (or Q1) is O and R8 and R9 combine to form a carbonyl group.

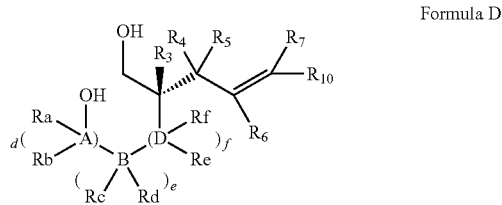

Formula D

As noted above, compounds of Formula D can be made through the palladium catalyzed decarboxylative alkylation of a lactone satisfying one of Formulae A, B or C above. Specifically, the compound of Formula D will result when a compound of Formula C (in which z is 1, Q1 is O and R8 and R9 combine to form a carbonyl group) is subjected to palladium catalyzed decarboxylative alkylation. In Formula D, A, B, D, Ra, Rb, Rc, Rd, Re, Rf, R3, R4, R5, R6, R7 and R10 are as described above with respect to A through C. Each of Ra, Rb, R, Rd, Re and Rf may be independently selected from hydrogen atoms, substituted or unsubstituted hydrocarbyl groups, substituted or unsubstituted heteroatom containing hydrocarbyl groups, halogens or functional groups. However, similar to that discussed above with respect to Formulae A through C, in some embodiments, in which d is 1 or greater, the A atom that is directly adjacent the OH group is not a chiral center. More specifically, the Ra and Rb groups on the A atom that is directly adjacent the OH group are the same as each other. In some embodiments, however, one R group on each of two adjacent ring atoms can combine to form a bond, thereby creating a double bond within the ring structure. Specifically, each of Ra through Rf is either: independently hydrogen, a substituted or unsubstituted hydrocarbyl group, a substituted or unsubstituted heteroatom containing hydrocarbyl group, or a functional group; or combines with another of Ra through Rf to form a double bond.

In Formulae A, A(i), B, B(i) through B(v), C, C(i), and D above, the heteroatom containing compounds are depicted and described as including a terminal alkenyl group. This position of the alkenyl group may be important in the palladium catalyzed decarboxylative alkylation reaction. However, for other uses of the heteroatom containing compounds described here (e.g., as reactants in other reactions), the alkenyl group need not be positioned at the terminal end of the compound.

Instead, the alkenyl group can be positioned elsewhere in the compound. Also, the position of the alkenyl group can be modified after the completion of the palladium catalyzed decarboxylative alkylation reaction. For example, in compounds of Formula A through C in which z is 0, the alkenyl group can be positioned as shown in the below Formulae A(ii) and A(iii) (where R8 and R9 combine to form a carbonyl group) in which z is 0.

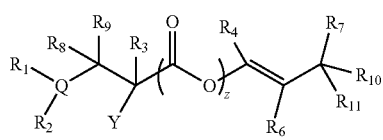

Formula A(ii)

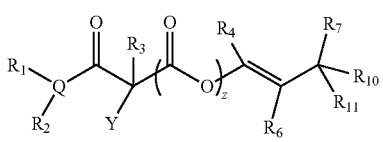

Formula A(iii)

In Formula A(ii) and A(iii), Q, Y and R1 through R10 are as described above with respect to Formulae 1, 2, 2(a), 2(b) and 3. However, in Formulae A(ii) and A(iii), z is 0. Also, R11 is selected from the same substituents described above for R1 through R10. Specifically, each of R1 through R11 may be independently selected from hydrogen, substituted or unsubstituted hydrocarbyl groups, substituted or unsubstituted heteroatom containing hydrocarbyl groups, halogens or functional groups.

In other embodiments, in which the compound is analogous to the compound represented by Formula D, the alkenyl group can be positioned as shown in the below Formula D(i).

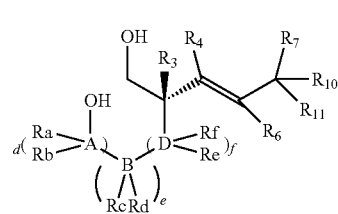

Formula D(i)

In Formula D(i), A, B, D, Ra through Rf, d, e, f, and R3 through R10 are as described above. Also, R11 is selected from the same substituents described above for R1 through R10. Specifically, each of R1 through R11 may be independently selected from hydrogen, substituted or unsubstituted hydrocarbyl groups, substituted or unsubstituted heteroatom containing hydrocarbyl groups, halogens or functional groups. Each of Ra, Rb, Rc, Rd, Re and Rf may be independently selected from hydrogen atoms, substituted or unsubstituted hydrocarbyl groups, substituted or unsubstituted heteroatom containing hydrocarbyl groups, halogens or functional groups. However, similar to that discussed above with respect to Formulae A through C, in some embodiments, in which d is 1 or greater, the A atom that is directly adjacent the OH group is not a chiral center. More specifically, the Ra and Rb groups on the A atom that is directly adjacent the OH group are the same as each other. In some embodiments, however, one R group on each of two adjacent ring atoms can combine to form a bond, thereby creating a double bond within the ring structure. Specifically, each of Ra through Rf is either: independently hydrogen, a substituted or unsubstituted hydrocarbyl group, a substituted or unsubstituted heteroatom containing hydrocarbyl group, or a functional group; or combines with another of Ra through Rf to form a double bond. In Formulae A, A(i), B, B(i) through B(v), C, C(i), and D above, the terminal alkenyl group can be reacted (e.g., hydrogenated) to make a corresponding alkyl derivative having the below Formula A(iv) and A(v) (in which the R8 and R9 groups combine to form a carbonyl group, and in which z is 0.

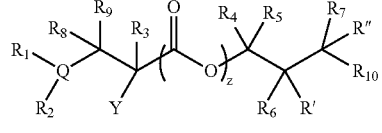

Formula A(iv)

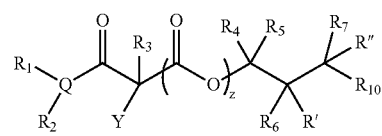

Formula A(v)

In Formula A(iv) and A(v), Q, Y and R1 through R11 are as described above with respect to Formulae A through C. Also, R' and R" are independently selected from the same substituents described above for R1 through R11. Specifically, each of R1 through R11 and R' and R" may be independently selected from hydrogen, substituted or unsubstituted hydrocarbyl groups, substituted or unsubstituted heteroatom containing hydrocarbyl groups, halogens or functional groups. Also, it is understood that although Formula A through C are discussed and depicted above as including the terminal alkenyl group, any of those formulae may instead include the terminal alkyl discussed here and depicted in Formulae A(iv) and A(v).

In some embodiments of the present invention in which the heteroatom is a nitrogen atom, the R group on the heteroatom (i.e., Q, Q1, Q2, Q3, or other heteroatoms in the substrates of Formulae A through C) can be an amine protecting group. Those of ordinary skill in the art would readily understand what is meant by "amine protecting group." However, some nonlimiting examples of suitable amine protecting groups include carboxybenzyl (Cbz) groups, p-methoxybenzyl carbonyl (Moz or MeOZ) groups, tert-butyloxycarbonyl (BOC) groups, fluorenylmethyloxycarbonyl (FMOC) groups, acetyl (Ac) groups, benzoyl (Bz) groups, benzyl (Bn) groups, carbamate groups, p-methoxybenzyl (PMB) groups, dimethoxybenzyl (DMPM) groups, p-methoxyphenyl (PMP) groups, tosyl (Ts) groups, sulfonamide (Nosyl & Nps) groups, methoxybenzoyl groups (OMe-Bz), and fluorobenzoyl groups (F-Bz). For example, in some embodiments, the amine protecting group is selected from tosyl groups (Ts), butyloxycarbonyl groups (BOC), carbobenzyloxy groups (Cbz), fluoreneylmethyloxycarbonyl groups (FMOC), acetyl groups (Ac), methoxybenzoyl groups (OMe-Bz), fluorobenzoyl groups (F-Bz), and benzoyl groups (Bz).

In some alternate embodiments, however, the R group(s) on the N can be hydrogen, a substituted or unsubstituted hydrocarbyl group, a substituted or unsubstituted heteroatom containing hydrocarbyl group, or a functional group. For example, in some embodiments, the R group(s) on the N atom may be H or OH. In some exemplary embodiments, for example, z is 0 and R1 is H or OH.

As used herein, the term "hydrocarbyl groups" refers to univalent hydrocarbon radicals containing from 1 to 30 carbon atoms, for example, from 1 to 24 carbon atoms or 1 to 12 carbon atoms. The term "hydrocarbyl groups" includes linear, branched, cyclic, saturated and unsaturated species, for example, alkyl groups, alkenyl groups, alkynyl groups, aryl groups, and the like. Also, as used herein, the term "substituted," as in "substituted hydrocarbyl groups," refers to a hydrocarbyl group in which one or more hydrogen atoms (bonded to a carbon atom) is replaced with one or more non-hydrogen functional groups.

The term "functional groups" would be readily understood to those of ordinary skill in the art. However, some nonlimiting examples of suitable functional groups for use in the Formulae and substrates described above include halogens, hydroxyl groups, sulfhydryl groups, alkoxy groups (e.g., having from 1 to 24 carbon atoms), alkenyloxy groups (e.g., having from 2 to 24 carbon atoms), alkynyloxy groups (e.g., having from 2 to 24 carbon atoms), aryloxy groups (e.g., having from 5 to 24 carbon atoms), acyl groups including alkylcarbonyl groups of the formula —CO-alkyl (e.g., having from 2 to 24 carbon atoms) and arylcarbonyl groups of the formula —CO-aryl (e.g., having from 6 to 24 carbon atoms), acyloxy groups having the formula —O-acyl, alkoxycarbonyl groups having the formula —(CO)—O-alkyl (e.g., having from 2 to 24 carbon atoms), carbonyl groups (including aldehyde moieties having the formula —(CO)—H) and ketone moieties having the formula —(CO)—R where R is any hydrocarbyl group), aryloxycarbonyl groups having the formula —(CO)—O-aryl (e.g., having from 6 to 24 carbon atoms), halocarbonyl groups having the formula —CO—X (where X is a halogen), alkylcarbonato groups having the formula —O—(CO)—O-alkyl (e.g., having from 2 to 24 carbon atoms), arylcarbonato groups having the formula —O—(CO)—O-aryl (e.g., having from 6 to 24 carbon atoms), carboxyl groups having the formula —COOH, carboxylato groups having the formula —COO$^-$, carbamoyl groups having the formula —(CO)—NH$_2$, mono-alkyl substituted carbamoyl groups having the formula —(CO)—NH-alkyl (e.g., the alkyl group having from 1 to 24 carbon atoms), di-alkyl substituted carbamoyl groups having the formula —(CO)—N-alkyl$_2$ (e.g., each alkyl group having from 1 to 24 carbon atoms), mono-aryl substituted carbamoyl groups having the formula —(CO)—NH-aryl (e.g., the aryl group having from 6 to 24 carbon atoms), di-aryl substituted carbamoyl groups having the formula —(CO)—N-aryl$_2$ (e.g., each aryl group having from 6 to 24 carbon atoms), di-N(alkyl)-N(aryl) substituted carbamoyl groups having the formula —(CO)—N-(alkyl)(aryl), thiocarbamoyl groups having the formula —(CS)—NH$_2$, carbamido groups having the formula —NH—(CO)—NH$_2$, cyano groups, isocyano groups, cyanato groups, isocyanato groups, isothiocyanato groups, azido groups, formyl groups, thioformyl groups, amino groups, mono-alkyl substituted amino groups (e.g., the alkyl group having from 1 to 24 carbon atoms), di-alkyl substituted amino groups (e.g., the alkyl group having from 1 to 24 carbon atoms), mono-aryl substituted amino groups (e.g., the aryl group having from 6 to 24 carbon atoms), di-aryl substituted amino groups (e.g., each aryl group having from 6 to 24 carbon atoms), alkylamido groups having the formula —NH—(CO)-alkyl (e.g., having from 2 to 24 carbon atoms), arylamido groups having the formula —NH—(CO)-aryl (e.g., having from 6 to 24 carbon atoms), imino groups having the formula —CR=NH (where R is hydrogen, alkyl, aryl, alkaryl, aralkyl, etc.), alkyl imino groups having the formula —CR=N-alkyl (where R is hydrogen, alkyl, aryl, aralkyl, alkaryl, etc.), aryl imino groups having the formula —CR=N-aryl (where R is hydrogen, alkyl, aryl, aralkyl, alkaryl, etc.), nitro groups, nitroso groups having the formula —NO, sulfo groups having the formula —SO$_2$—OH, sulfonato groups having the formula —SO$_2$—O$^-$, alkylsulfanyl groups having the formula —S-alkyl (also called, interchangeably, alkylthio groups), arylsulfanyl groups having the formula —S-aryl (also called, interchangeably, arylthio groups), alkylsulfinyl groups having the formula —(SO)-alkyl, arylsulfinyl groups having the formula —(SO)-aryl, alkylsulfonyl groups having the formula —SO$_2$-alkyl, arylsulfonyl groups having the formula —SO$_2$-aryl, boryl groups having the formula —BH$_2$, borono groups having the formula —B(OH)$_2$, boronato groups having the formula —B(OR)$_2$ (where R is alkyl or another hydrocarbyl group), phosphono groups having the formula —P(O)(OH)$_2$, phosphonato groups having the formula —P(O)(O$^-$)$_2$, phosphinato groups having the formula —P(O)(O$^-$), phospho groups having the formula —PO$_2$, and phosphino groups having the formula —PH$_2$.

In addition to, or instead of, being substituted with a functional group, the substituted species may be substituted with hydrocarbyl groups, for example, alkyl groups (e.g., having from 1 to 24 carbon atoms, or from 1 to 12 carbon atoms, or from 1 to 6 carbon atoms), alkenyl groups (e.g., having from 2 to 24 carbon atoms, or from 2 to 13 carbon atoms, or from 2 to 6 carbon atoms), alkynyl groups (e.g., having from 2 to 24 carbon atoms, or from 2 to 12 carbon atoms, or from 2 to 6 carbon atoms), aryl groups (e.g., having from 5 to 24 carbon atoms, or from 5 to 14 carbon atoms), alkaryl groups (i.e., aryl with an alkyl substituent, e.g., having from 6 to 24 carbon atoms, or from 6 to 16 carbon atoms), and/or aralkyl groups (i.e., alkyl with an aryl substituent, e.g., having from 6 to 24 carbon atoms, or from 6 to 16 carbon atoms). Also, any of the functional groups or hydrocarbyl group substituents may be further substituted (if the group permits) with one or more additional functional groups or hydrocarbyl groups.

Nonlimiting examples of compounds satisfying the above formulae include heteroatom containing substrates, and heteroatom containing building blocks, both of which are described in more detail below.

Heteroatom Containing Substrates

As discussed above, transition metal-catalyzed allylic alkylation can be used for the enantioselective preparation of chiral substances. According to embodiments of the present invention, heteroatom containing substrates useful in the transition metal-catalyzed allylic alkylation reaction include cyclic and acyclic heteroatom containing compounds represented by Formula 1.

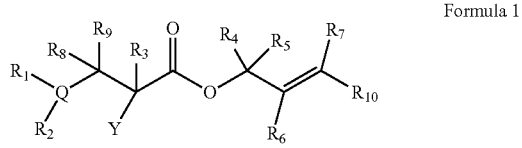

Formula 1

In Formula 1, Q is a heteroatom, for example, N, O, P, S or a halogen such as Cl, I, Br or F. In some embodiments, for example, Q is N or O. Each of R1 through R10 is independently selected from hydrogen, substituted or unsubstituted hydrocarbyl groups, substituted or unsubstituted heteroatom containing hydrocarbyl groups, or functional groups. However, in some embodiments, R3 is not hydrogen. In some embodiments, in which R8 and R9 combine to form a carbonyl group (as discussed below), R3 is also not phenyl or substituted phenyl. In yet other embodiments, in which R8 and R9 combine to form a carbonyl group (as discussed below), R3 is not a simple carbonyl group. However, in some embodiments, in which R8 and R9 combine to form a carbonyl group (as discussed below), R3 may be a substituted carbonyl group, e.g., a carbonyl group substituted hydrocarbyl group or heteroatom containing hydrocarbyl group or functional group. In some embodiments, though, R3 does not include any carbonyl groups, whether substituted or unsubstituted. In yet other embodiments, in which R8 and R9 combine to form a carbonyl group (as discussed below), R3 is not an ethyl group. However, in some embodiments, R3 may be a substituted ethyl group, and R3 may be any other alkyl group (or other group as described above). In some embodiments, though, R3 is not an ethyl group or a substituted ethyl group. Also, in some embodiments, the carbon atom to which the R3 group is attached is a chiral, stereogenic center, i.e., R3 and Y are not the same.

Y may be selected from hydrogen, heteroatoms, substituted or unsubstituted hydrocarbyl groups, substituted or unsubstituted heteroatom containing hydrocarbyl groups, or functional groups. Additionally, any two or more adjacent R and Y groups can optionally combine to form a carbonyl group on the underlying atom. For example, in some embodiments, R8 and R9 combine to form a carbonyl group, as shown in the below Formula 1(a).

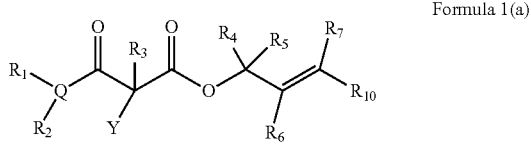

Formula 1(a)

Also, any two or more adjacent R and Y groups can optionally combine to form a ring, e.g., a cyclic, heterocyclic, aryl or heteroaryl ring. Indeed, in some embodiments, although Formula 1 depicts an acyclic heteroatom containing compound, Formula 1 also encompasses cyclic, heterocyclic, aryl and heteroaryl compounds. Also, in some embodiments, while R6 and R10 may combine to form nearly any ring structure, R6 and R10 do not form a substituted or unsubstituted benzene ring. In some embodiments, R6 and R10 do not form any aromatic ring. Similarly, in some embodiments, while R4 and R6 may combine to form nearly any ring structure, R4 and R6 do not form a substituted or unsubstituted benzene ring. In some embodiments, R4 and R6 do not form any aromatic ring.

In embodiments in which R2 and Y combine to form a ring, in some embodiments, the atom in the ring directly adjacent the Q atom (i.e., the atom on the opposite side of the Q atom to the carbon atom carrying the R8 and R9 groups) is not a chiral center. More specifically, any substituents on that atom are the same as each other, and that atom does not include two different substituents.

For example, in some embodiments, the R2 group on the Q atom, and the Y group combine to form a ring with the Q atom, the carbon atom to which the Y group is attached, and the intervening carbon atom. The ring formed between the R2 group and the Y group can be any type of ring with any number of ring atoms. However, the ring formed from the combination of R2 and Y does not form a benzene ring or ortho-disubstituted benzene ring. In some embodiments, though, R2 and Y may form other substituted benzene rings. In other embodiments, however, R2 and Y do not form any kind of benzene ring.

In some exemplary embodiments, for example, the ring formed between the R2 group and the Y group may include one or more additional heteroatoms (i.e., additional to the Q atom depicted in Formula 1). In these embodiments, the compounds of Formula 1 may be represented by Formula 2, below.

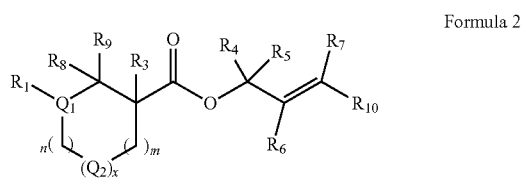

Formula 2

In Formula 2, R1 through R10 are the same as defined above with respect to Formula 1. Each of Q1 and Q2 are as defined above with respect to Q1, and are each independently selected from heteroatoms, e.g., N, O, S, P or halogens, such as Cl, I, F or Br. In some embodiments, for example, each of Q1 and Q2 is independently selected from N or O. Additionally, similar to that described above with respect to Formulae 1 and 1(a), any two or more adjacent R groups can optionally combine to form a carbonyl group on the underlying atom. For example, in some embodiments, R8 and R9 combine to form a carbonyl group, as shown in the below Formula 2(a).

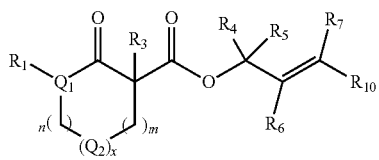

Formula 2(a)

Also, in Formula 2, each of x, n and m can be any integer of 0 or greater. When x is greater than 1, the plurality of Q2 heteroatoms may be the same as or different from each other. In some embodiments, for example, each of x, n and m is independently 0, 1, 2, 3 or 4. In some exemplary embodiments, when x and n are both 0, m may be 1, 2, 3 or 4. Conversely, when x and m are both 0, n may be 1, 2, 3 or 4. These configurations yield compounds having the Formulae 2(b) or 2(c) (where R8 and R9 combine to form a carbonyl group) below. Also, while m and n are defined here such that the ring depicted in Formula 2 has up to 7 ring atoms, it is understood that the size of the ring in Formula 2 is not particularly limited, and n and m can be any integers corresponding to any ring size. For example, in some embodiments, n and m are integers such that the resulting ring depicted in Formula 2 has from 3 to 12 ring atoms. In some embodiments for example, n and m are integers such that the resulting ring has from 3 to 10 ring atoms. In other embodiments, n and m are integers such that the resulting ring has from 5 to 7 ring atoms.

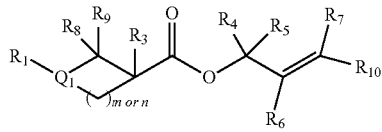

Formula 2(b)

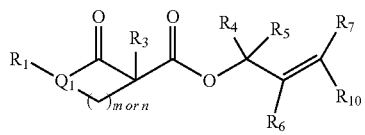

Formula 2(c)

Alternatively, in some embodiments, when x is 1, n and m may be any integer from 0 to 4 such that the sum of n and m may be 0, 1, 2 or 3. For example, in some embodiments, when x is 1, n may be 0 and m may be 0, 1, 2 or 3. In other embodiments, when x is 1, n may be 1 and m may be 0, 1 or 2. In still other embodiments, when x is 1, n may be 2 and m may be 0 or 1. In yet other embodiments, when x is 1, n may be 3 and m may be 0. Conversely, in some embodiments, when x is 1, m may be 0 and n may be 0, 1, 2 or 3. In other embodiments, when x is 1, m may be 1 and n may be 0, 1 or 2. In still other embodiments, when x is 1, m may be 2 and n may be 0 or 1. In yet other embodiments, when x is 1, m may be 3 and n may be 0. These configurations yield compounds of Formula 2 in which there are two heteroatoms, and cover all configurations of the two heteroatoms. Specifically, these configurations cover every possible position of the second heteroatom (Q2) on the ring depicted in Formula 2. Also, while m and n are defined here such that the ring depicted in Formula 2 has up to 7 ring atoms, it is understood that the size of the ring in Formula 2 is not particularly limited, and n and m can be any integers corresponding to any ring size, as discussed above. For example, in some embodiments, n and m are integers such that the resulting ring depicted in Formula 2 has from 3 to 12 ring atoms, for example 3 to 10 ring atoms or 5 to 7 ring atoms.

In some embodiments, the ring may include the Q atom depicted in Formulae 1 and 2 as the only heteroatom, and include any number of additional carbon atoms in the ring. Alternatively, however, the ring depicted in Formulae 2 and 2(a) through 2(c) can have any number of heteroatoms positioned anywhere on the ring. For example, as shown in Formula 2 and 2(a) above, the ring may include the heteroatom depicted in Formulae 1 and 2 separated from a group of one or more additional heteroatoms by one or more carbon atoms, or the ring may include two or more heteroatoms that are adjacent each other within the ring. However, according to other embodiments, the ring depicted in Formula 2 may include three or more heteroatoms which may be adjacent one another or separated from each other by at least one carbon atom. This configuration is depicted in Formulae 2(d) and 2(e) (where R8 and R9 combine to form a carbonyl group) below.

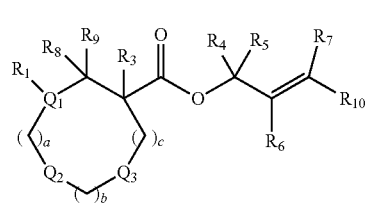

Formula 2(d)

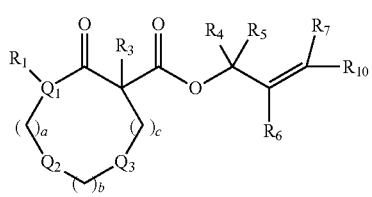

Formula 2(e)

In Formula 2(d) and 2(e), each of Q1, Q2 and Q3 is as defined above with respect to Q1, and are each independently a heteroatom, for example, O, N, S, P, or a halogen such as Cl, I, Br or F. Each of R1 through R10 is also as described above with respect to Formulae 1, 2 and 2(a) through 2(c). Each of a, b and c is independently an integer of 0 or greater. In some exemplary embodiments, each of a, b and c may be independently an integer of 0, 1 or 2. For example, in some embodiments, each of a, b and c is 0, yielding a five membered ring including three adjacent heteroatoms. In other embodiments, a is 1 and b and c are both 0, yielding a six membered ring in which Q2 and Q3 are adjacent one another and Q2 is separated from Q1 by a carbon atom. In still other embodiments, a is 2 and b and c are both 0, yielding a seven membered ring in which Q2 and Q3 are adjacent one another and Q2 is separated from Q1 by two carbon atoms.

According to other embodiments, b is 1 and a and c are both 0, yielding a six membered ring in which Q1 and Q2 are adjacent one another and Q2 is separated from Q3 by a carbon atom. In still other embodiments, b is 2 and a and c are both 0, yielding a seven membered ring in which Q1 and Q2 are adjacent one another and Q2 is separated from Q3 by two carbon atoms.

In other embodiments, c is 1 and a and b are both 0, yielding a six membered ring in which Q1, Q2 and Q3 are adjacent one another. In still other embodiments, c is 2 and a and b are both 0, yielding a seven membered ring in which Q1, Q2 and Q3 are adjacent one another. Also, while a, b and c are defined here such that the ring depicted in Formulae 2, 2(d) and 2(e) has up to 7 ring atoms, it is understood that the size of the ring in Formulae 2, 2(d) and 2(e) is not particularly limited, and a, b and c can be any integers corresponding to any ring size, as discussed above. For example, in some embodiments, a, b and c are integers such that the resulting ring depicted in Formulae 2, 2(d) and 2(e) has from 3 to 12 ring atoms, for example 3 to 10 ring atoms or 5 to 7 ring atoms.

In some exemplary embodiments, the ring depicted in Formula 2 may include four heteroatoms, and the four heteroatoms may be placed on the ring in any manner. For example, some of the heteroatoms may be spaced from each other by one or more ring carbon atoms while others are adjacent, or all heteroatoms may be adjacent each other, or all heteroatoms may be spaced from each other by one or more ring carbon atoms.

Additionally, although the rings discussed above are depicted and described as fully saturated, according to some embodiments of the present invention, any of the rings may be unsaturated (i.e., mono- or poly-unsaturated). To account for these compounds, the heteroatom containing substrate of Formula 1 may be represented by Formulae 3 or 3(a) (where R8 and R9 combine to form a carbonyl group) below.

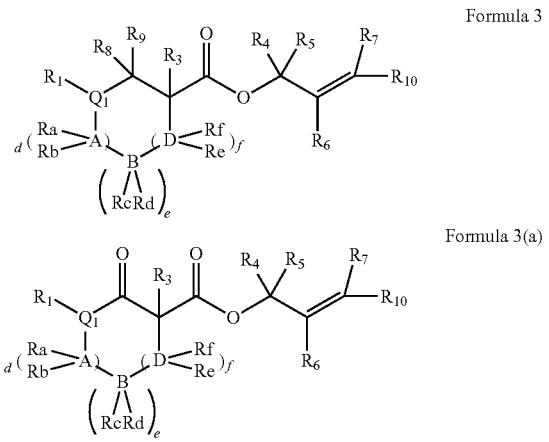

In Formulae 3 and 3(a), Q1 and R1 through R10 are as defined above with respect to Formulae 1, 2 and 2(a) through 2(e). Each of A, B and D is independently a carbon atom or a heteroatom. However, in some embodiments, in which d is 1 or greater, the A atom located directly adjacent the Q1 atom is not a chiral center. More specifically, the Ra and Rb substituents on that atom are the same as each other, and are not two different substituents. Also, the ring formed from Q1, A, B and D is not a benzene ring or an ortho-disubstituted benzene ring. In some embodiments, though, the ring may be any other substituted benzene ring. In other embodiments, however, the ring is not any kind of benzene ring.

Each of Ra, Rb, R, Rd, Re and Rf may be independently selected from hydrogen atoms, substituted or unsubstituted hydrocarbyl groups, substituted or unsubstituted heteroatom containing hydrocarbyl groups, halogens or functional groups. However, as discussed above, in some embodiments, in which d is greater than 1, the A atom located directly adjacent the Q1 atom is not a chiral center, and the Ra and Rb substituents on that atom are the same as each other. In some embodiments, however, one R group on each of two adjacent ring atoms can combine to form a bond, thereby creating a double bond within the ring structure. Specifically, each of Ra through Rf is either: independently hydrogen, a substituted or unsubstituted hydrocarbyl group, a substituted or unsubstituted heteroatom containing hydrocarbyl group, or a functional group; or combines with another of Ra through Rf to form a double bond. For example, R1 and one of the Ra groups may combine to form a double bond, one of the Rb groups and one of the Rc groups may combine to form a double bond within the ring, or one of the Rd groups and one of the Re groups may combine to form a double bond within the ring. Any number of double bonds may be formed within the ring structure, and the ring structure may be heteroaryl in nature. Alternatively or additionally, two adjacent R groups on the same ring atom (e.g., Ra and Rb, or Rc and Rd, or Re and Rf) can combine to form a carbonyl group on the ring atom. Each of d, e and f is independently an integer of 0 or greater, for example, an integer of 0, 1, 2, 3, or 4. When d, e or f is greater than 1, the plurality of A, B or D atoms, and the plurality of Ra, Rb, Rc, Rd, Re or Rf groups may be the same as or different from each other. Also, although Formulae 3 and 3(a) above depict a six membered ring, it is understood from the definitions of d, e and f that the ring is not limited to six members, and can have any number of ring atoms, as discussed above with respect to Formulae 1, 2 and 2(a) through 2(e). Indeed, in some embodiments, the ring has from 3 to 12 ring atoms, for example 3 to 10 ring atoms or 5 to 7 ring atoms.

Also, in the rings discussed above, any of the ring atoms, whether carbon or heteroatom, can be substituted with a substituted or unsubstituted hydrocarbyl group, substituted or unsubstituted heteroatom containing hydrocarbyl group, a halogen or a functional group. Indeed, although the rings depicted in Formulae 2 and 2(a) through 2(e) above are depicted with hydrogen atoms on each of the ring atoms, any or all of the hydrogen atoms on any or all of the ring atoms may be substituted with the substituents described above. As shown in Formula 3, for example, each of the ring atoms (Q1, A, B and/or D) may include R groups that can be hydrogen, a substituted or unsubstituted hydrocarbyl group, a substituted or unsubstituted heteroatom containing hydrocarbyl group, a halogen or a functional group.

In Formulae 1, 1(a), 2, 2(a) through 2(b), 3 and 3(a) above, the heteroatom containing substrates are depicted and described as including a terminal alkenyl group. This position of the alkenyl group may be important for the palladium catalyzed decarboxylative alkylation reaction used to create the building blocks described below. However, for other uses of the heteroatom containing substrates described here (e.g., as reactants in other reactions), the alkenyl group need not be positioned at the terminal end of the compound. Instead, the alkenyl group can be positioned elsewhere in the compound. For example, the alkenyl group can be positioned as shown in the below Formulae 1(b) and 1(c) (where R8 and R9 combine to form a carbonyl group).

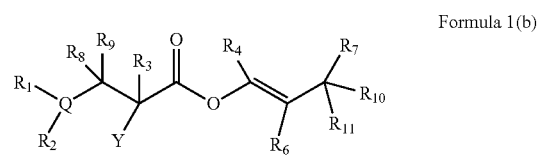

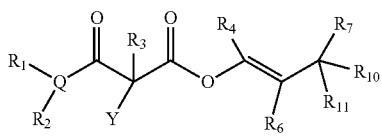

Formula 1(c)

In Formula 1(a), Q, Y and R1 through R10 are as described above with respect to Formulae 1, 2, 2(a), 2(b) and 3. Also, R11 is selected from the same substituents described above for R1 through R9. Specifically, each of R1 through R10 may be independently selected from hydrogen, substituted or unsubstituted hydrocarbyl groups, substituted or unsubstituted heteroatom containing hydrocarbyl groups, halogens or functional groups.

In Formulae 1 through 3 above, the terminal alkenyl group can be reacted (e.g., hydrogenated) to make a corresponding alkyl derivative having the below Formula 1(d) and 1(e) (in which the R8 and R9 groups combine to form a carbonyl group, and in which z is 0.

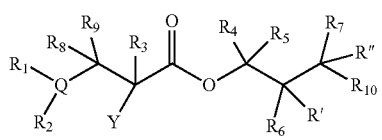

Formula 1(d)

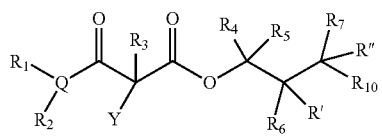

Formula 1(e)

In Formula 1(d) and 1(e), Q, Y and R1 through R11 are as described above with respect to Formulae A through C. Also, R' and R" are independently selected from the same substituents described above for R1 through R11. Specifically, each of R1 through R11 and R' and R" may be independently selected from hydrogen, substituted or unsubstituted hydrocarbyl groups, substituted or unsubstituted heteroatom containing hydrocarbyl groups, halogens or functional groups. Also, it is understood that although Formula 1 through 3 are discussed and depicted above as including the terminal alkenyl group, any of those formulae may instead include the terminal alkyl discussed here and depicted in Formulae 1(d) and 1(e).

In some embodiments of the present invention in which the heteroatom is a nitrogen atom, the R group on the heteroatom (i.e., Q, Q1, Q2, Q3, or other heteroatoms in the substrates of Formulae 1 through 3) can be an amine protecting group. Those of ordinary skill in the art would readily understand what is meant by "amine protecting group." However, some nonlimiting examples of suitable amine protecting groups include carbobenzyloxy (Cbz) groups, p-methoxybenzyl carbonyl (Moz or MeOZ) groups, tert-butyloxycarbonyl (BOC) groups, fluorenylmethyloxycarbonyl (FMOC) groups, acetyl (Ac) groups, benzoyl (Bz) groups, benzyl (Bn) groups, carbamate groups, p-methoxybenzyl (PMB) groups, dimethoxybenzyl (DMPM) groups, p-methoxyphenyl (PMP) groups, tosyl (Ts) groups, sulfonamide (Nosyl & Nps) groups, methoxybenzoyl groups (OMe-Bz), and fluorobenzoyl groups (F-Bz). For example, in some embodiments, the amine protecting group is selected from tosyl groups (Ts), butyloxycarbonyl groups (BOC), carbobenzyloxy groups (Cbz), fluoreneylmethyl-oxycarbonyl groups (FMOC), acetyl groups (Ac), methoxybenzoyl groups (OMe-Bz), fluorobenzoyl groups (F-Bz), and benzoyl groups (Bz).

Also, the substrate compounds are generally racemic, i.e., an equimolar mixture of the (+) and (−) enantiomers of the compound. However, in some embodiments, the substrates may be enantioenriched compounds in which one of the (+) or (−) enantiomers is present in an enantiomeric excess. Indeed, as used herein, the term "enantionriched" refers to an enantiomeric excess of the particular enantiomer of the compound. Specifically, the substrate compounds according to some embodiments of the present invention include on eof (+) or (−) enantiomers in an enantiomeric excess, thus creating an "enantioenriched" substrate compound. In some embodiments, for example, the enantioenriched substrate compound may include one of the (+) or (−) enantiomers in an enantiomeric excess of greater than 50%, for example, about 60% or greater, or about 70% or greater, or about 80%. or greater According to some embodiments, the enantioenriched substrate compound may include one of the (+) or (−) enantiomers in an enantiomeric excess of about 90% or greater. In other embodiments, the enantioenriched substrate compound may include one of the (+) or (−) enantiomers in an enantiomeric excess of about 90% to about 99%.

Some nonlimiting examples of substrates satisfying the above formulae, according to embodiments of the present invention, include the compounds depicted below. It is understood that although some of the nitrogen atoms in some of the nitrogen containing—compounds listed below include protecting groups, the nitrogen atoms do not necessarily include a protecting group. Indeed, in some embodiments of the present invention, a hydrogen atom is attached to the nitrogen atom. In each of the examples listed below, the protecting group on any of the nitrogen atoms can be replaced with a hydrogen atom.

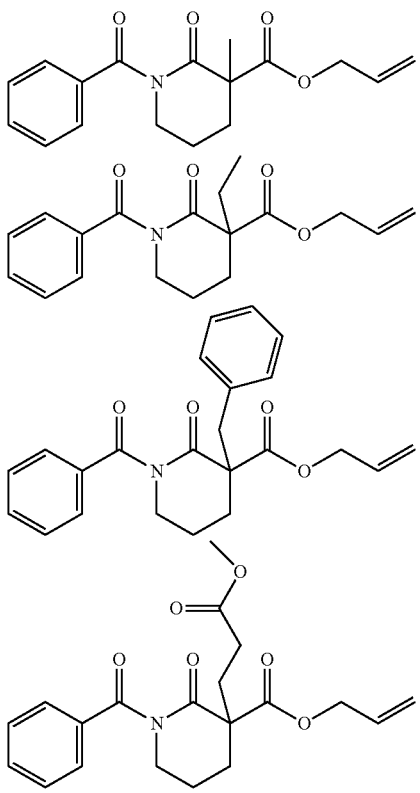

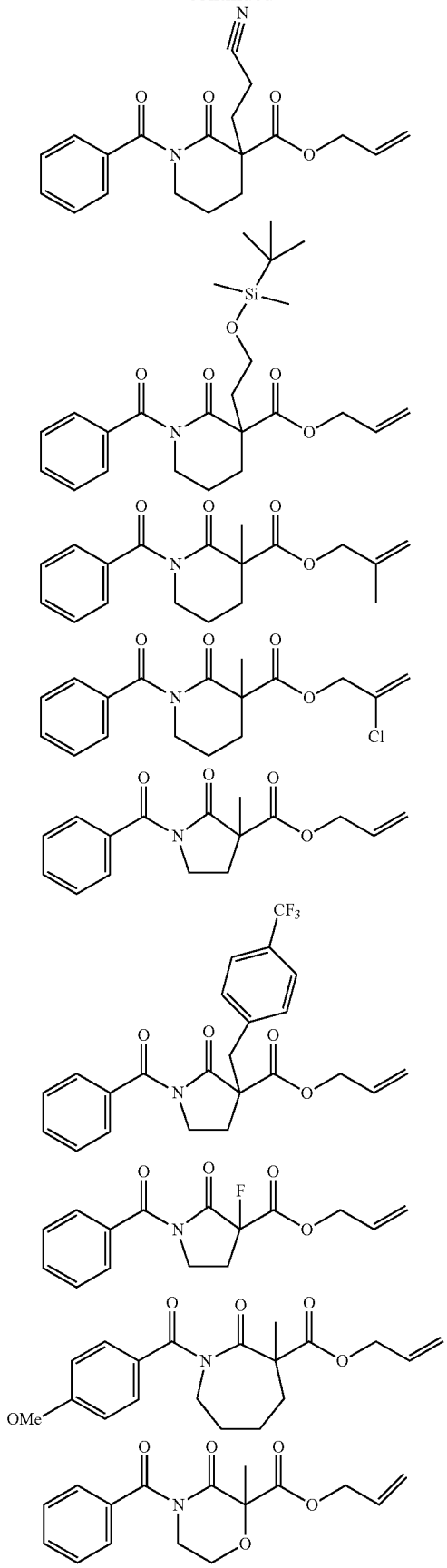
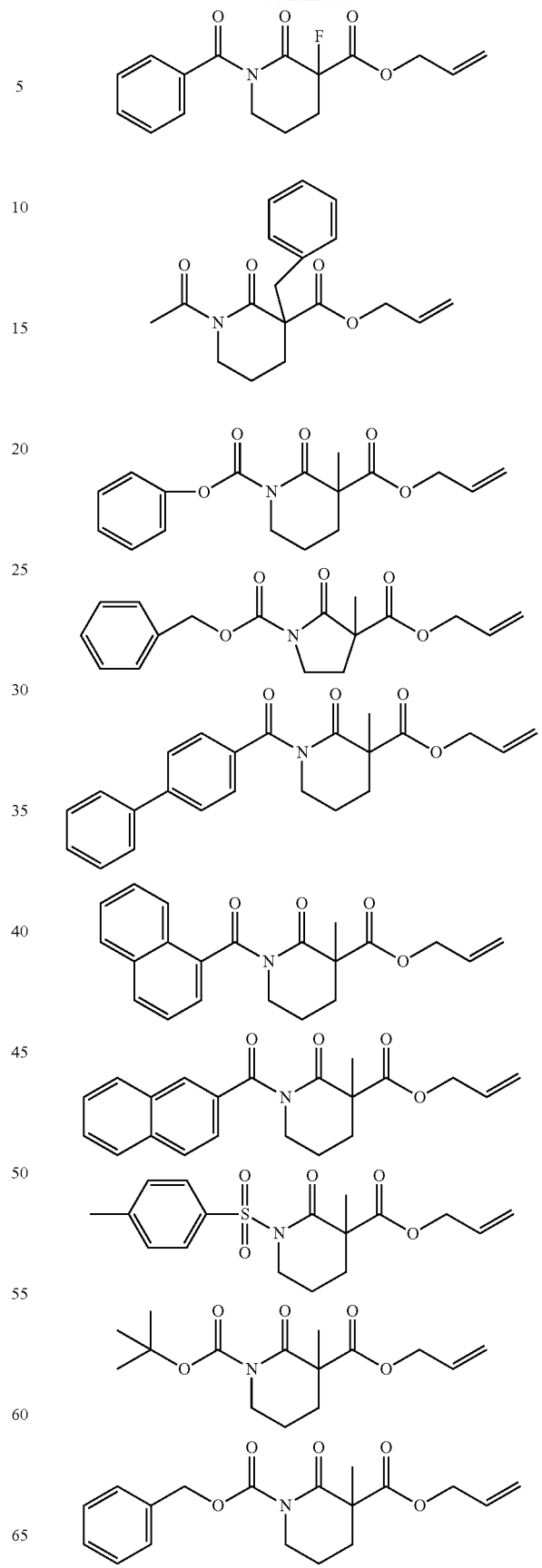

53
-continued
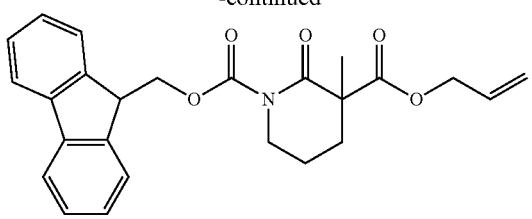
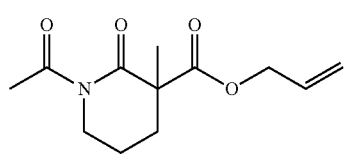
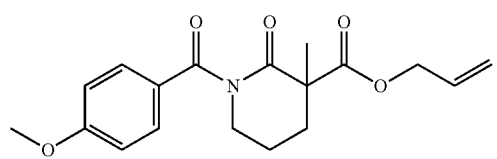
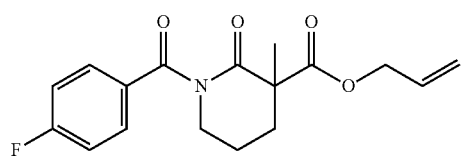
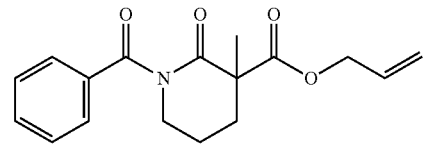
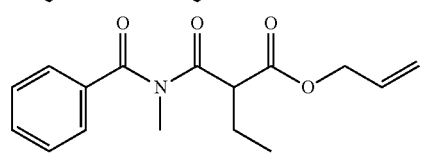
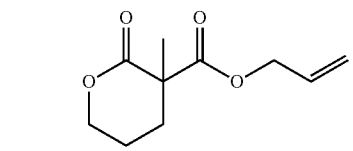
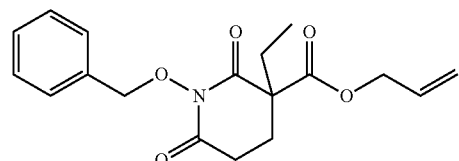
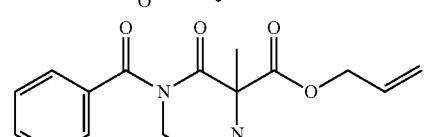
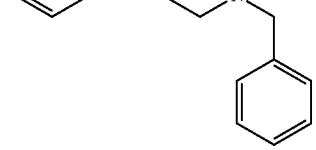
54
-continued
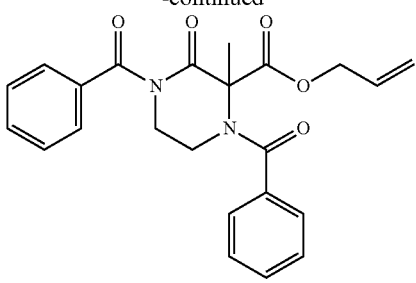
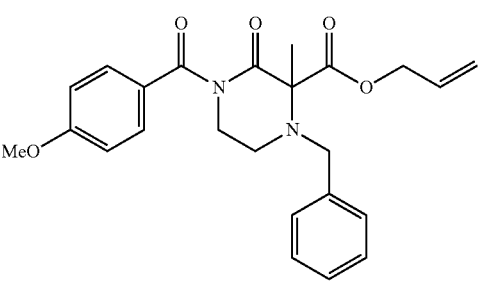
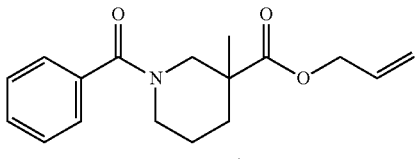
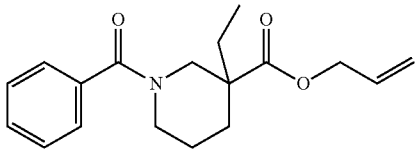
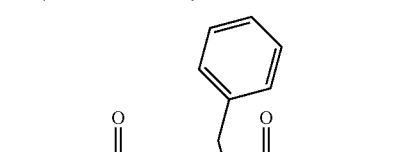
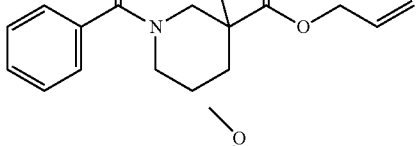
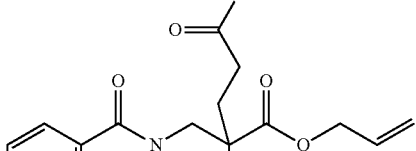
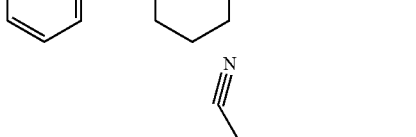
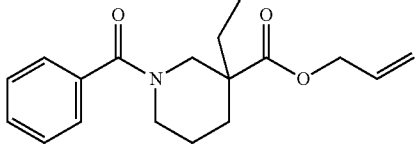

55
-continued
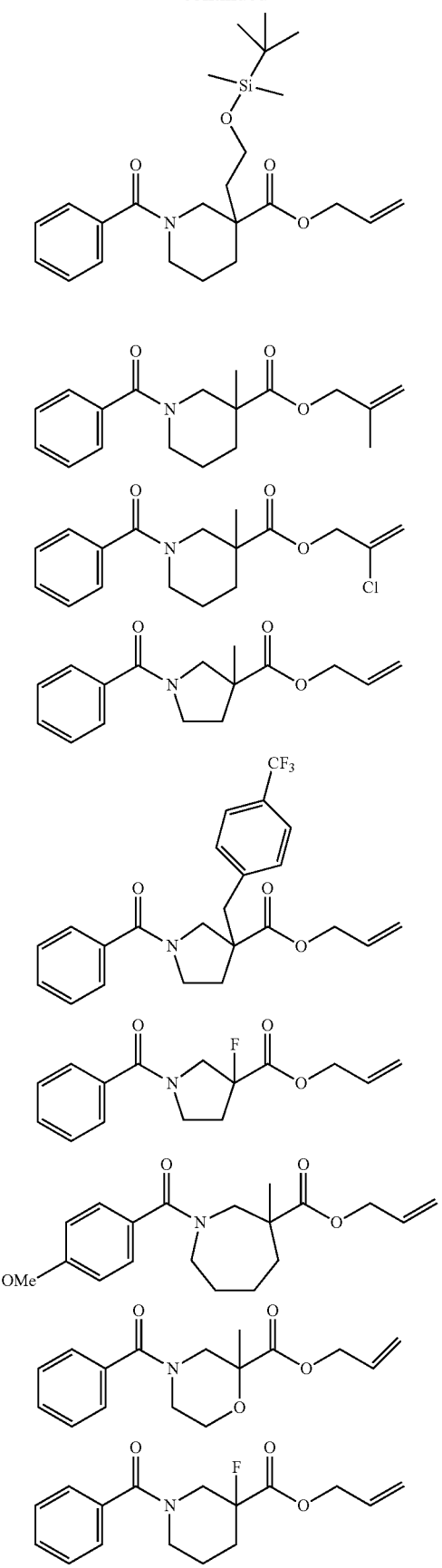
56
-continued
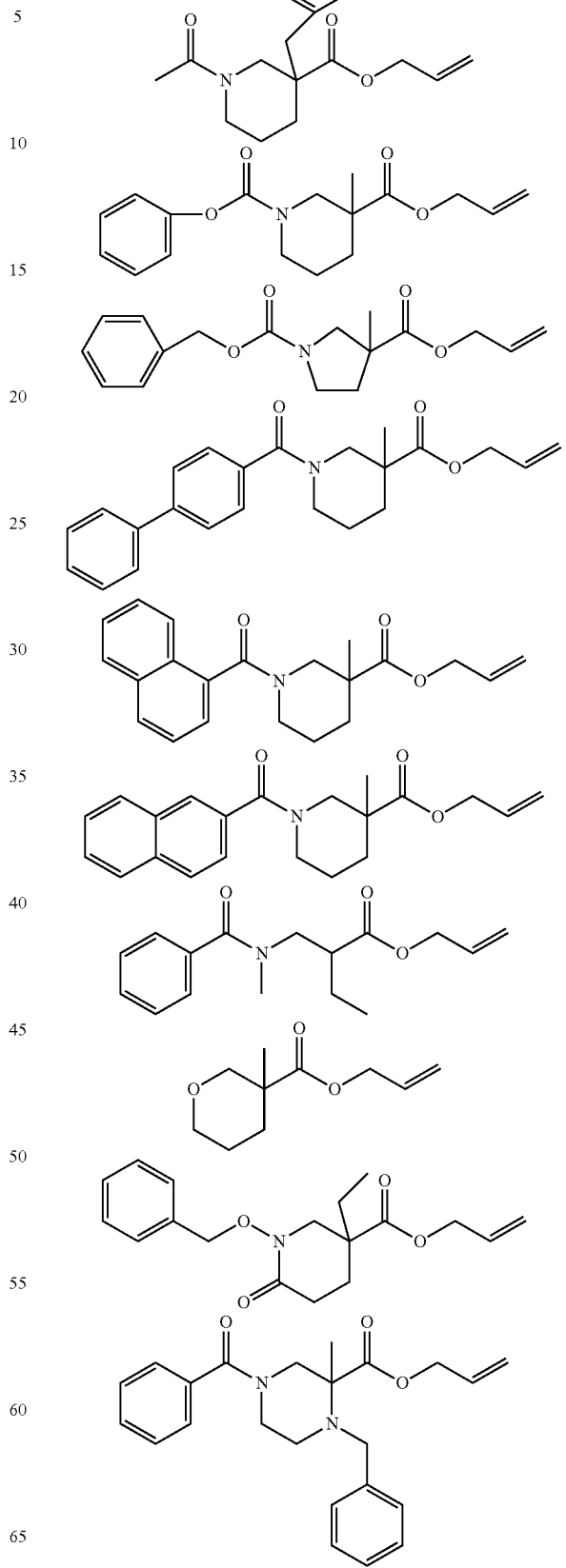

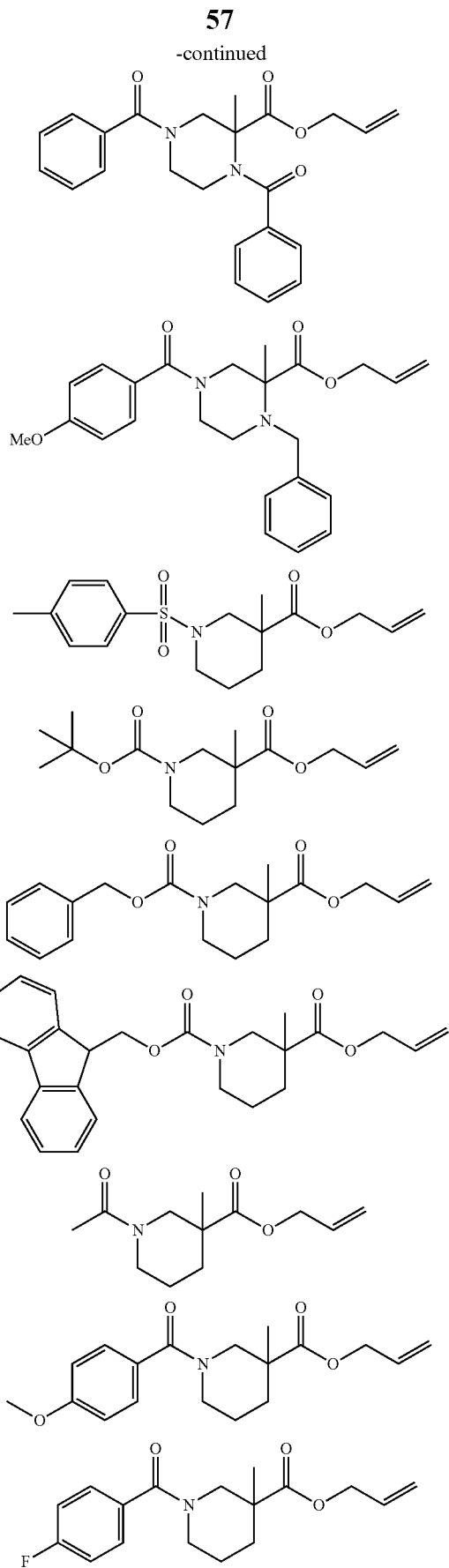

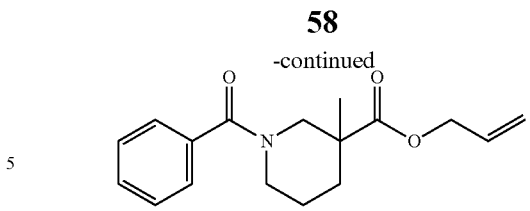

Heteroatom Containing Building Blocks

The heteroatom containing substrates described above may be used to create novel building block compounds useful in the formation of numerous other chemical and pharmaceutical compounds. Indeed, the novel substrates discussed above are designed to create the novel building blocks discussed here via palladium-catalyzed decarboxylative alkylation reactions. These reactions, when performed on racemic compositions of the substrates described above yield enantioenriched compositions of the building block compounds. As the building blocks discussed here are the result of palladium-catalyzed decarboxylative alkylation of the substrates discussed above, the structures of these compounds are similar in many respects to their corresponding substrates. However, as would be recognized by those of ordinary skill in the art based on the differences in the structures, the stereochemistry, enantioselectivity and chemical and physical properties of the building blocks can be significantly different from those of their corresponding substrates.

According to embodiments of the present invention, heteroatom containing building blocks useful in the creation of target compounds include cyclic and acyclic heteroatom containing building blocks represented by Formula 4.

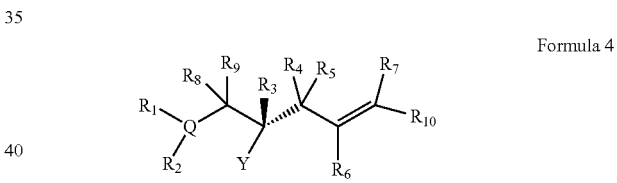

Formula 4

In Formula 4, as in Formula 1 (of the counterpart heteroatom containing substrates), Q is a heteroatom, for example, N, O, P, S or a halogen such as Cl, I, Br or F. In some embodiments, for example, Q is N or O. Each of $R_1$ through $R_{10}$ is independently selected from hydrogen, substituted or unsubstituted hydrocarbyl groups, substituted or unsubstituted heteroatom containing hydrocarbyl groups, or functional groups. However, in some embodiments, $R_3$ is not hydrogen. In some embodiments, in which z is 0 and $R_8$ and $R_9$ combine to form a carbonyl group, $R_3$ is also not phenyl or substituted phenyl. In yet other embodiments, in which z is 0 and $R_8$ and $R_9$ combine to form a carbonyl group, $R_3$ is not a simple carbonyl group. However, in some embodiments, $R_3$ may be a substituted carbonyl group, e.g., a carbonyl group substituted hydrocarbyl group or heteroatom containing hydrocarbyl group or functional group. In some embodiments, though, $R_3$ does not include any carbonyl groups, whether substituted or unsubstituted. In yet other embodiments, in which z is 0 and $R_8$ and $R_9$ combine to form a carbonyl group, $R_3$ is not an ethyl group. However, in some embodiments, $R_3$ may be a substituted ethyl group, and $R_3$ may be any other alkyl group (or other group as described above). In some embodiments, though, $R_3$ is not an ethyl group or a substituted ethyl group. Also, in some embodiments, the carbon atom to which the R3 group is attached is a chiral, stereogenic center, i.e., R3 and Y are not the same.

Y may be selected from hydrogen, heteroatoms, substituted or unsubstituted hydrocarbyl groups, substituted or unsubstituted heteroatom containing hydrocarbyl groups, or functional groups. Additionally, any two or more adjacent R and Y groups can optionally combine to form a carbonyl group on the underlying atom. For example, in some embodiments, R8 and R9 combine to form a carbonyl group, as shown in the below Formula 4(a).

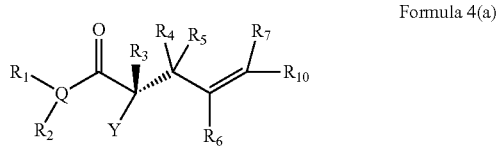

Formula 4(a)

Also, any two or more adjacent R and Y groups can optionally combine to form a ring, e.g., a cyclic, heterocyclic, aryl or heteroaryl ring. Indeed, in some embodiments, although Formula 4 depicts an acyclic heteroatom containing compound, Formula 4 also encompass cyclic, heterocyclic, aryl and heteroaryl compounds. Also, in some embodiments, while R6 and R10 may combine to form nearly any ring structure, R6 and R10 do not form a substituted or unsubstituted benzene ring. In some embodiments, R6 and R10 do not form any aromatic ring. Similarly, in some embodiments, while R4 and R6 may combine to form nearly any ring structure, R4 and R6 do not form a substituted or unsubstituted benzene ring. In some embodiments, R4 and R6 do not form any aromatic ring.

In embodiments in which R2 and Y combine to form a ring, in some embodiments, the atom in the ring directly adjacent the Q atom (i.e., the atom on the opposite side of the Q atom to the carbon atom carrying the R8 and R9 groups) is not a chiral center. More specifically, any substituents on that atom are the same as each other, and that atom does not include two different substituents.

For example, in some embodiments, the R2 group on the Q atom, and the Y group combine to form a ring with the Q atom, the carbon atom to which the Y group is attached, and the intervening carbon atom. The ring formed between the R2 group and the Y group can be any type of ring with any number of ring atoms. However, the ring formed from the combination of R2 and Y does not form a benzene ring or ortho-disubstituted benzene ring. In some embodiments, though, R2 and Y may form other substituted benzene rings. In other embodiments, however, R2 and Y do not form any kind of benzene ring.

In some exemplary embodiments, for example, the ring formed between the $R_2$ group and the Y group may include one or more additional heteroatoms (i.e., additional to the Q atom depicted in Formula 4). In these embodiments, the compounds of Formula 4 may be represented by Formula 5, below.

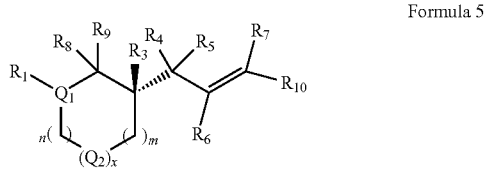

Formula 5

In Formula 5, R1 through R10 are the same as defined above with respect to Formula 4. Each of Q1 and Q2 are as defined above with respect to Q1, and are each independently selected from heteroatoms, e.g., N, O, S, P or halogens, such as Cl, I, F or Br. In some embodiments, for example, each of Q1 and Q2 is independently selected from N or O. Additionally, similar to that described above with respect to Formulae 4 and 4(a), any two or more adjacent R groups can optionally combine to form a carbonyl group on the underlying atom. For example, in some embodiments, R8 and R9 combine to form a carbonyl group, as shown in the below Formula 5(a).

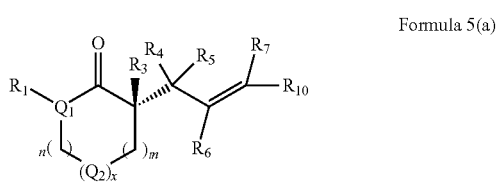

Formula 5(a)

Also, in Formula 5, each of x, n and m can be any integer of 0 or greater. When x is greater than 1, the plurality of Q2 heteroatoms may be the same as or different from each other. In some embodiments, for example, each of x, n and m is independently 0, 1, 2, 3 or 4. In some exemplary embodiments, when x and n are both 0, m may be 1, 2, 3 or 4. Conversely, when x and m are both 0, n may be 1, 2, 3 or 4. These configurations yield compounds having the Formulae 5(b) or 5(c) (where R8 and R9 combine to form a carbonyl group) below. Also, while m and n are defined here such that the ring depicted in Formula 5 has up to 7 ring atoms, it is understood that the size of the ring in Formula 5 is not particularly limited, and n and m can be any integers corresponding to any ring size. For example, in some embodiments, n and m are integers such that the resulting ring depicted in Formula 5 has from 3 to 12 ring atoms. In some embodiments for example, n and m are integers such that the resulting ring has from 3 to 10 ring atoms. In other embodiments, n and m are integers such that the resulting ring has from 5 to 7 ring atoms.

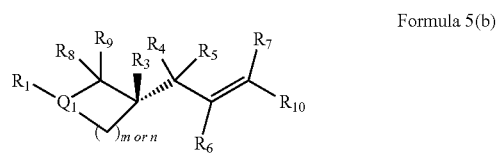

Formula 5(b)

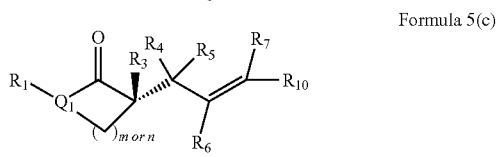

Formula 5(c)

Alternatively, in some embodiments, when x is 1, n and m may be any integer from 0 to 4 such that the sum of n and m may be 0, 1, 2 or 3. For example, in some embodiments, when x is 1, n may be 0 and m may be 0, 1, 2 or 3. In other embodiments, when x is 1, n may be 1 and m may be 0, 1 or 2. In still other embodiments, when x is 1, n may be 2 and m may be 0 or 1. In yet other embodiments, when x is 1, n may be 3 and m may be 0. Conversely, in some embodiments, when x is 1, m may be 0 and n may be 0, 1, 2 or 3. In other embodiments, when x is 1, m may be 1 and n may be 0, 1 or 2. In still other embodiments, when x is 1, m may be 2 and n may be 0 or 1. In yet other embodiments, when x is 1, m may be 3 and n may be 0. These configurations yield compounds of Formula 5 in which there are two heteroatoms, and cover all configurations of the two heteroatoms. Specifically, these configurations cover every possible position of the second heteroatom (Q2) on the ring depicted in Formula 5. Also, while m and n are defined here such that the ring depicted in Formula 5 has up to 7 ring atoms, it is understood that the size of the ring in Formula 5 is not particularly limited, and n and m can be any integers corresponding to any ring size, as discussed above. For example, in some embodiments, n and m are integers such that the resulting ring depicted in Formula 5 has from 3 to 12 ring atoms, for example 3 to 10 ring atoms or 5 to 7 ring atoms.

In some embodiments, the ring may include the Q atom depicted in Formulae 4 and 5 as the only heteroatom, and include any number of additional carbon atoms in the ring. Alternatively, however, the ring depicted in Formulae 5 and 5(a) through 5(c) can have any number of heteroatoms positioned anywhere on the ring. For example, as shown in Formula 5 and 5(a) above, the ring may include the heteroatom depicted in Formulae 4 and 5 separated from a group of one or more additional heteroatoms by one or more carbon atoms, or the ring may include two or more heteroatoms that are adjacent each other within the ring. However, according to other embodiments, the ring depicted in Formula 5 may include three or more heteroatoms which may be adjacent one another or separated from each other by at least one carbon atom. This configuration is depicted in Formulae 5(d) and 5(e) (where R8 and R9 combine to form a carbonyl group) below.

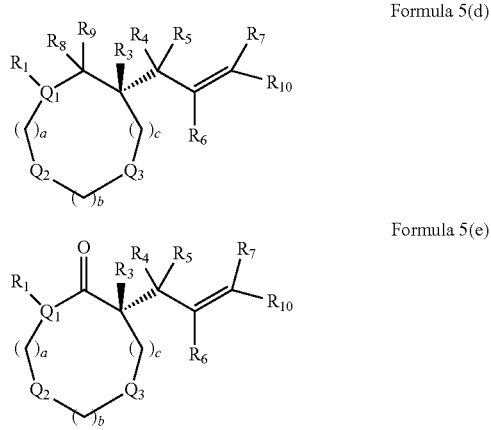

Formula 5(d)

Formula 5(e)

In Formula 5(d) and 5(e), each of Q1, Q2 and Q3 is as defined above with respect to Q1, and each is independently a heteroatom, for example, O, N, S, P, or a halogen such as Cl, I, Br or F. Each of R1 through R10 is also as described above with respect to Formulae 4, 5 and 5(a) through 5(c). Each of a, b and c is independently an integer of 0 or greater. In some exemplary embodiments, each of a, b and c may be independently an integer of 0, 1 or 2. For example, in some embodiments, each of a, b and c is 0, yielding a five membered ring including three adjacent heteroatoms. In other embodiments, a is 1 and b and c are both 0, yielding a six membered ring in which Q2 and Q3 are adjacent one another and Q2 is separated from Q1 by a carbon atom. In still other embodiments, a is 2 and b and c are both 0, yielding a seven membered ring in which Q2 and Q3 are adjacent one another and Q2 is separated from Q1 by two carbon atoms.

According to other embodiments, b is 1 and a and c are both 0, yielding a six membered ring in which Q1 and Q2 are adjacent one another and Q2 is separated from Q3 by a carbon atom. In still other embodiments, b is 2 and a and c are both 0, yielding a seven membered ring in which Q1 and Q2 are adjacent one another and Q2 is separated from Q3 by two carbon atoms.

In other embodiments, c is 1 and a and b are both 0, yielding a six membered ring in which Q1, Q2 and Q3 are adjacent one another. In still other embodiments, c is 2 and a and b are both 0, yielding a seven membered ring in which Q1, Q2 and Q3 are adjacent one another. Also, while a, b and c are defined here such that the ring depicted in Formulae 5, 5(d) and 5(e) has up to 7 ring atoms, it is understood that the size of the ring in Formulae 5, 5(d) and 5(e) is not particularly limited, and a, b and c can be any integers corresponding to any ring size, as discussed above. For example, in some embodiments, a, b and c are integers such that the resulting ring depicted in Formulae 5, 5(d) and 5(e) has from 3 to 12 ring atoms, for example 3 to 10 ring atoms or 5 to 7 ring atoms.

In some exemplary embodiments, the ring depicted in Formula 5 may include four heteroatoms, and the four heteroatoms may be placed on the ring in any manner. For example, some of the heteroatoms may be spaced from each other by one or more ring carbon atoms while others are adjacent, or all heteroatoms may be adjacent each other, or all heteroatoms may be spaced from each other by one or more ring carbon atoms.

Additionally, although the rings discussed above may be depicted and described as fully saturated, according to some embodiments of the present invention, any of the rings may be unsaturated (i.e., mono- or poly-unsaturated). To account for these compounds, the heteroatom containing substrate of Formula 4 may be represented by Formulae 6 or 6(a) (where R8 and R9 combine to form a carbonyl group) below.

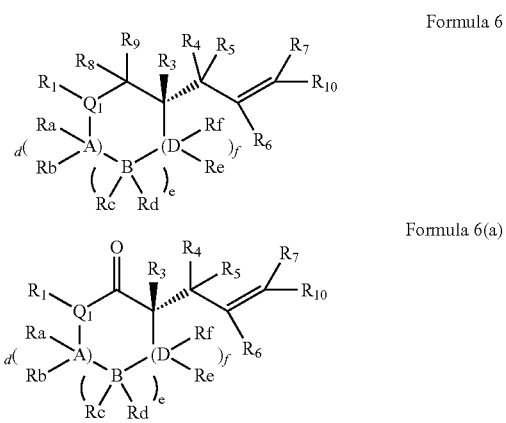

Formula 6

Formula 6(a)

In Formulae 6 and 6(a), Q1 and R1 through R10 are as defined above with respect to Formulae 4, 5 and 5(a) through 5(e). Each of A, B and D is independently a carbon atom or a heteroatom. However, in some embodiments, in which d is 1 or greater, the A atom located directly adjacent the Q1 atom is not a chiral center. More specifically, the Ra and Rb substituents on that atom are the same as each other, and are not two different substituents. Also, the ring formed from Q1, A, B and D is not a benzene ring or an ortho-disubstituted benzene ring. In some embodiments, though, the ring may be any other substituted benzene ring. In other embodiments, however, the ring is not any kind of benzene ring.

Each of Ra, Rb, Rc, Rd, Re and Rf may be independently selected from hydrogen atoms, substituted or unsubstituted hydrocarbyl groups, substituted or unsubstituted heteroatom containing hydrocarbyl groups, halogens or functional groups. However, as discussed above, in some embodiments, in which d is greater than 1, the A atom located directly adjacent the Q1 atom is not a chiral center, and the Ra and Rb substituents on that atom are the same as each other. In some embodiments, however, one R group on each of two adjacent ring atoms can combine to form a bond, thereby creating a double bond within the ring structure. Specifically, each of Ra through Rf is either: independently hydrogen, a substituted or unsubstituted hydrocarbyl group, a substituted or unsubstituted heteroatom containing hydrocarbyl group, or a functional group; or combines with another of Ra through Rf to form a double bond. For example, R1 and one of the Ra groups may combine to form a double bond, one of the Rb groups and one of the Rc groups may combine to form a double bond within the ring, or one of the Rd groups and one of the Re groups may combine to form a double bond within the ring. Any number of double bonds may be formed within the ring structure, and the ring structure may be heteroaryl in nature. Alternatively or additionally, two adjacent R groups on the same ring atom (e.g., Ra and Rb, or Rc and Rd, or Re and Rf) can combine to form a carbonyl group on the ring atom. Each of d, e and f is independently an integer of 0 or greater, for example, an integer of 0, 1, 2, 3, or 4. When d, e or f is greater than 1, the plurality of A, B or D atoms, and the plurality of Ra, Rb, Rc, Rd, Re or Rf groups may be the same as or different from each other. Also, although Formulae 6 and 6(a) above depict a six membered ring, it is understood from the definitions of d, e and f that the ring is not limited to six members, and can have any number of ring atoms, as discussed above with respect to Formulae 4, 4 and 4(a) through 4(e). Indeed, in some embodiments, the ring has from 3 to 12 ring atoms, for example 3 to 10 ring atoms or 5 to 7 ring atoms.

Also, in the rings discussed above, any of the ring atoms, whether carbon or heteroatom, can be substituted with a substituted or unsubstituted hydrocarbyl group, substituted or unsubstituted heteroatom containing hydrocarbyl group, a halogen or a functional group. Indeed, although the rings depicted in Formulae 5 and 5(a) through 5(e) above are depicted with hydrogen atoms on each of the ring atoms, any or all of the hydrogen atoms on any or all of the ring atoms may be substituted with the substituents described above. As shown in Formula 6, for example, each of the ring atoms (Q1, A, B and/or D) may include R groups that can be hydrogen, a substituted or unsubstituted hydrocarbyl group, a substituted or unsubstituted heteroatom containing hydrocarbyl group, a halogen or a functional group.

In some embodiments of the present invention, the building block compounds can have an alternate structure represented by the below Formulae D. The compounds of Formula D include compounds created by the palladium catalyzed decarboxylative alkylation of substrate compounds represented by Formula 1(a), 2(a) or 3(a) in which Q (or Q1) is O.

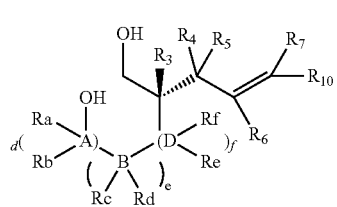

Formula D

As noted above, compounds of Formula D can be made through the palladium catalyzed decarboxylative alkylation of a lactone satisfying one of Formulae 1(a), 2(a) or 3(a) above. Specifically, the compound of Formula D will result when a compound of Formula 3(a) (in which Q1 is O) is subjected to palladium catalyzed decarboxylative alkylation. In Formula D, A, B, D, Ra, Rb, Rc, Rd, Re, Rf, R3, R4, R5, R6, R7 and R10 are as described above with respect to Formulae 1 through 3. For example, each of Ra, Rb, R, Rd, Re and Rf may be independently selected from hydrogen atoms, substituted or unsubstituted hydrocarbyl groups, substituted or unsubstituted heteroatom containing hydrocarbyl groups, halogens or functional groups. However, similar to that discussed above with respect to Formulae A through C and 4 through 6, in some embodiments, in which d is 1 or greater, the A atom that is directly adjacent the OH group is not a chiral center. More specifically, the Ra and Rb groups on the A atom that is directly adjacent the OH group are the same as each other. In some embodiments, however, one R group on each of two adjacent ring atoms can combine to form a bond, thereby creating a double bond within the ring structure. Specifically, each of Ra through Rf is either: independently hydrogen, a substituted or unsubstituted hydrocarbyl group, a substituted or unsubstituted heteroatom containing hydrocarbyl group, or a functional group; or combines with another of Ra through Rf to form a double bond. In Formulae 4, 4(a), 5, 5(a) through 5(b), 6 and 6(a) above, the heteroatom containing building blocks are depicted and described as including a terminal alkenyl group. This position of the alkenyl group may be imparted by the palladium catalyzed decarboxylative alkylation reaction used to create the building blocks. However, after creation via the palladium catalyzed decarboxylative alkylation reaction, the building blocks can be further modified to move the alkenyl group to a position other than the terminal end of the compound. For example, the alkenyl group can be positioned as shown in the below Formulae 4(b) and 4(c) (where R8 and R9 combine to form a carbonyl group).

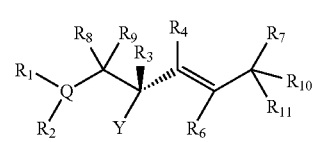

Formula 4(b)

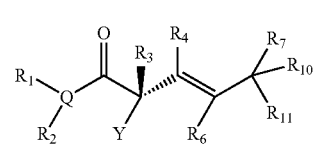

Formula 4(c)

In Formula 4(a), Q, Y and R1 through R10 are as described above with respect to Formulae 4, 5, 5(a) through 5(e), 6 and 6(a). Also, R11 is selected from the same substituents described above for R1 through R9. Specifically, each of R1 through R11 may be independently selected from hydrogen, substituted or unsubstituted hydrocarbyl groups, substituted or unsubstituted heteroatom containing hydrocarbyl groups, halogens or functional groups.

In other embodiments, in which the compound is analogous to the compound represented by Formula D, the alkenyl group can be positioned as shown in the below Formula D(i).

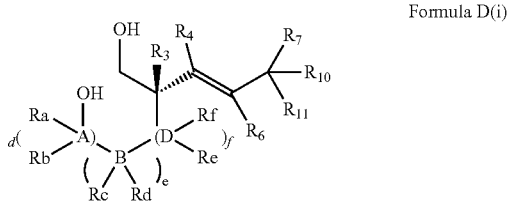

Formula D(i)

In Formula D(i), A, B, D, Ra through Rf, d, e, f, and R3 through R10 are as described above. Also, R11 is selected from the same substituents described above for R1 through R10. Specifically, each of R1 through R11 may be independently selected from hydrogen, substituted or unsubstituted hydrocarbyl groups, substituted or unsubstituted heteroatom containing hydrocarbyl groups, halogens or functional groups. However, similar to that discussed above with respect to Formulae A through C and 4 through 6, in some embodiments, in which d is 1 or greater, the A atom that is directly adjacent the OH group is not a chiral center. More specifically, the Ra and Rb groups on the A atom that is directly adjacent the OH group are the same as each other. In some embodiments, however, one R group on each of two adjacent ring atoms can combine to form a bond, thereby creating a double bond within the ring structure. Specifically, each of Ra through Rf is either: independently hydrogen, a substituted or unsubstituted hydrocarbyl group, a substituted or unsubstituted heteroatom containing hydrocarbyl group, or a functional group; or combines with another of Ra through Rf to form a double bond.

Additionally, in Formulae 4, 4(a), 5, 5(a) through 5(b), 6 and 6(a) above, the heteroatom containing building blocks are depicted and described as potentially including non-hydrogen R groups (R7 and or R10) on the terminal alkenyl group. In embodiments in which the building blocks include such a non-hydrogen R group on the terminal alkenyl group, the R group is added via a reaction occurring after the palladium catalyzed decarboxylative alkylation reaction used to create the building block. Specifically, while the palladium catalyzed decarboxylative alkylation reaction may result in building blocks including only hydrogen on the terminal alkenyl, if desired, the building block furnished by the palladium catalyzed decarboxylative alkylation reaction can be further modified to substitute one or both of the hydrogen atoms on the terminal alkenyl group with a substituted or unsubstituted hydrocarbyl, a substituted or unsubstituted heteroatom containing hydrocarbyl, a halogen or a functional group.

In Formulae 4 through 6 above, the terminal alkenyl group can be reacted (e.g., hydrogenated) to make a corresponding alkyl derivative having the below Formula 4(d) and 4(e) (in which the R8 and R9 groups combine to form a carbonyl group) in which z is 0.

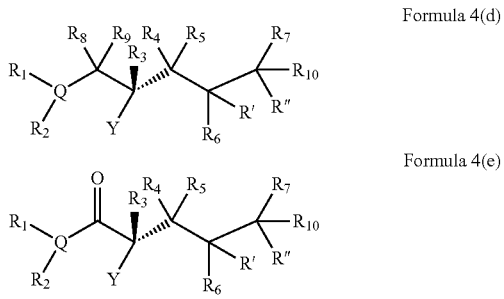

Formula 4(d)

Formula 4(e)

In Formula 4(d) and 4(e), Q, Y and R1 through R11 are as described above with respect to Formulae A through C. Also, R' and R" are independently selected from the same substituents described above for R1 through R11. Specifically, each of R1 through R11 and R' and R" may be independently selected from hydrogen, substituted or unsubstituted hydrocarbyl groups, substituted or unsubstituted heteroatom containing hydrocarbyl groups, halogens or functional groups. Also, it is understood that although Formula 4 through 6 are discussed and depicted above as including the terminal alkenyl group, any of those formulae may instead include the terminal alkyl discussed here and depicted in Formulae 4(d) and 4(e).

In some embodiments of the present invention in which the heteroatom is a nitrogen atom, the R group on the heteroatom (i.e., Q, Q1, Q2, Q3, or other heteroatoms in the building blocks of Formulae 4 through 6) can be an amine protecting group. Those of ordinary skill in the art would readily understand what is meant by "amine protecting group." However, some nonlimiting examples of suitable amine protecting groups include carbobenzyloxy (Cbz) groups, p-methoxybenzyl carbonyl (Moz or MeOZ) groups, tert-butyloxycarbonyl (BOC) groups, fluorenylmethyloxycarbonyl (FMOC) groups, acetyl (Ac) groups, benzoyl (Bz) groups, benzyl (Bn) groups, carbamate groups, p-methoxybenzyl (PMB) groups, dimethoxybenzyl (DMPM) groups, p-methoxyphenyl (PMP) groups, tosyl (Ts) groups, sulfonamide (Nosyl & Nps) groups, methoxybenzoyl groups (OMe-Bz), and fluorobenzoyl groups (F-Bz). For example, in some embodiments, the amine protecting group is selected from tosyl groups (Ts), butyloxycarbonyl groups (BOC), carbobenzyloxy groups (Cbz), fluoreneylmethyloxycarbonyl groups (FMOC), acetyl groups (Ac), methoxybenzoyl groups (OMe-Bz), fluorobenzoyl groups (F-Bz), and benzoyl groups (Bz).

In some alternate embodiments, however, the R group(s) on the N can be hydrogen, a substituted or unsubstituted hydrocarbyl group, a substituted or unsubstituted heteroatom containing hydrocarbyl group, or a functional group. For example, in some embodiments, the R group(s) on the N atom may be H or OH.

Also, the building blocks described above are generally formed from the racemic form of the corresponding substrate compound. The resulting building block compounds may also be racemic, however, in some embodiments, the palladium catalyzed decarboxylative alkylation procedures result in enantioenriched building block compounds. As used herein, the term "enantionriched" refers to an enantiomeric excess of the particular enantiomer of the compound. Specifically, the building block compounds according to embodiments of the present invention include on eof (+) or (−) enantiomers in an enantiomeric excess, thus creating an "enantioenriched" building block compound. In some embodiments, for example, the enantioenriched building block compound may include one of the (+) or (−) enantiomers in an enantiomeric excess of greater than 50%, for example, about 60% or greater, or about 70% or greater, or about 80%. or greater According to some embodiments, the enantioenriched building block compound may include one of the (+) or (−) enantiomers in an enantiomeric excess of about 90% or greater. In other embodiments, the enantioenriched building block compound may include one of the (+) or (−) enantiomers in an enantiomeric excess of about 90% to about 99%.

Some nonlimiting examples of building blocks satisfying the above formula, according to embodiments of the present invention, include the compounds depicted below. It is understood that although some of the nitrogen atoms in some of the nitrogen containing-compounds listed below include protecting groups, the nitrogen atoms do not necessarily include protecting groups. Indeed, in some embodiments of the present invention, hydrogen atoms are attached to the nitrogen atoms. In each of the examples listed below, the protecting group on any of the nitrogen atoms can be replaced with a hydrogen atom.

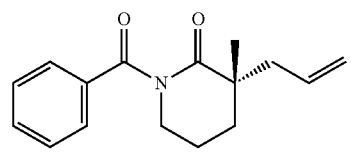

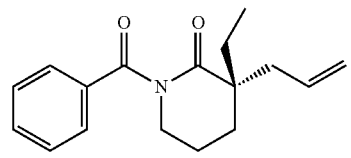

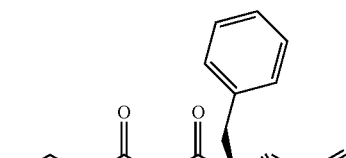

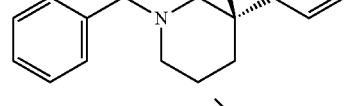

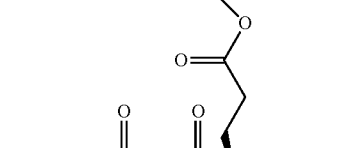

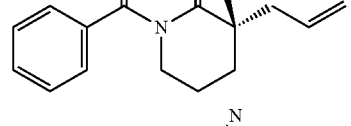

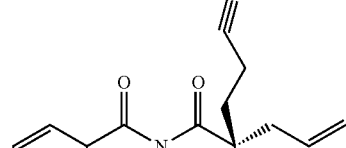

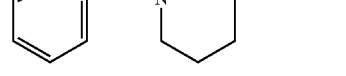

-continued

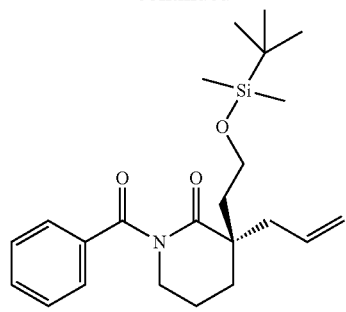

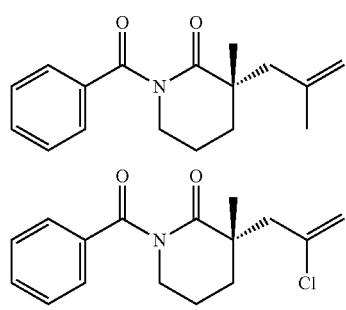

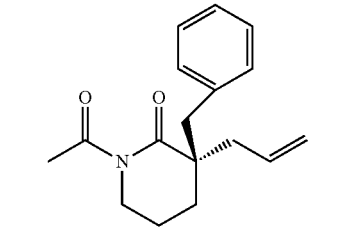

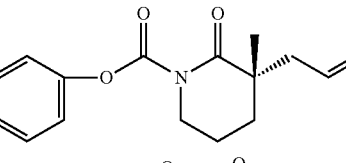

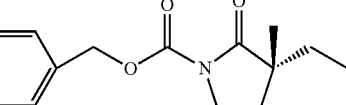

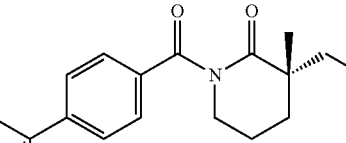

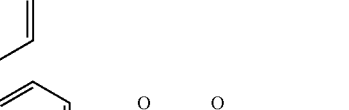

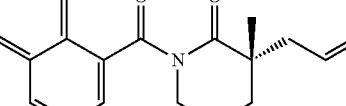

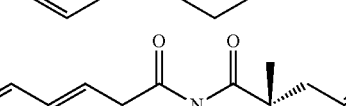

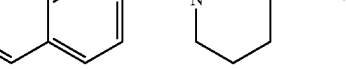

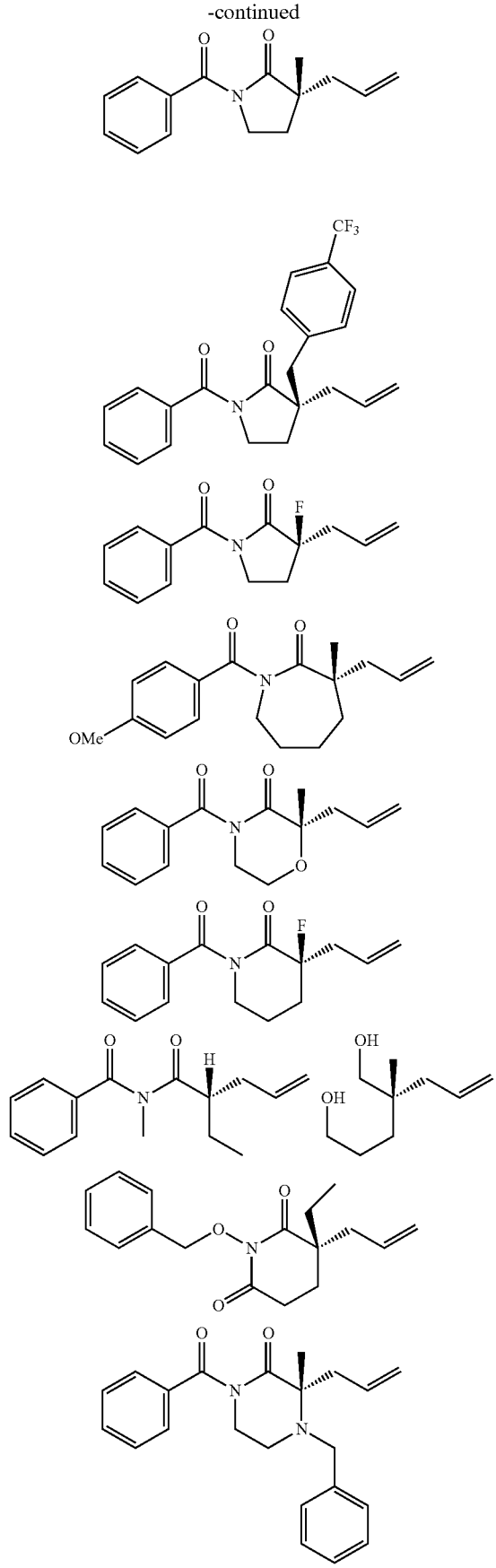
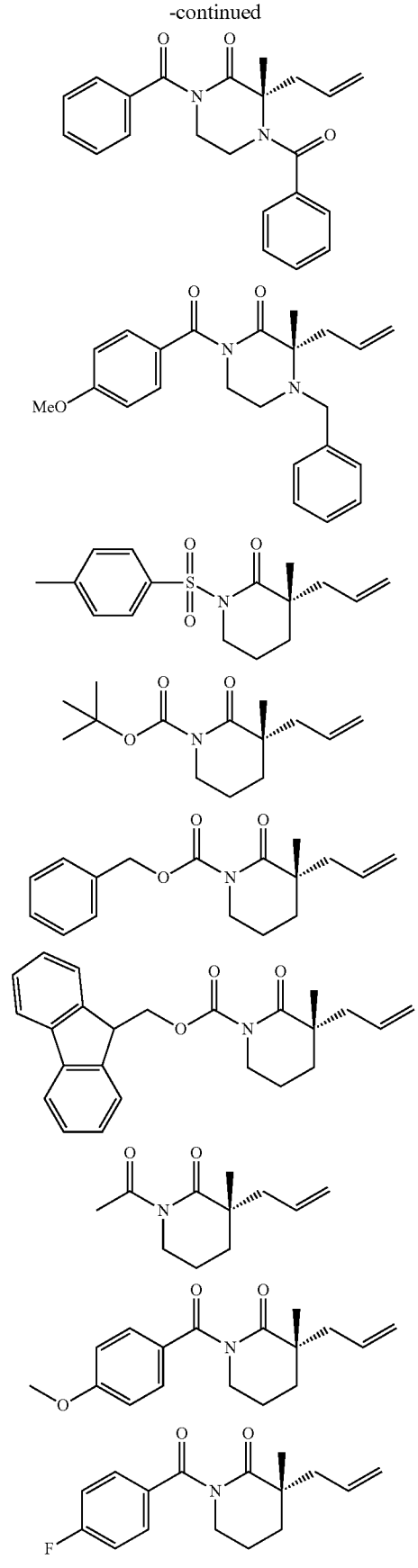

71
-continued
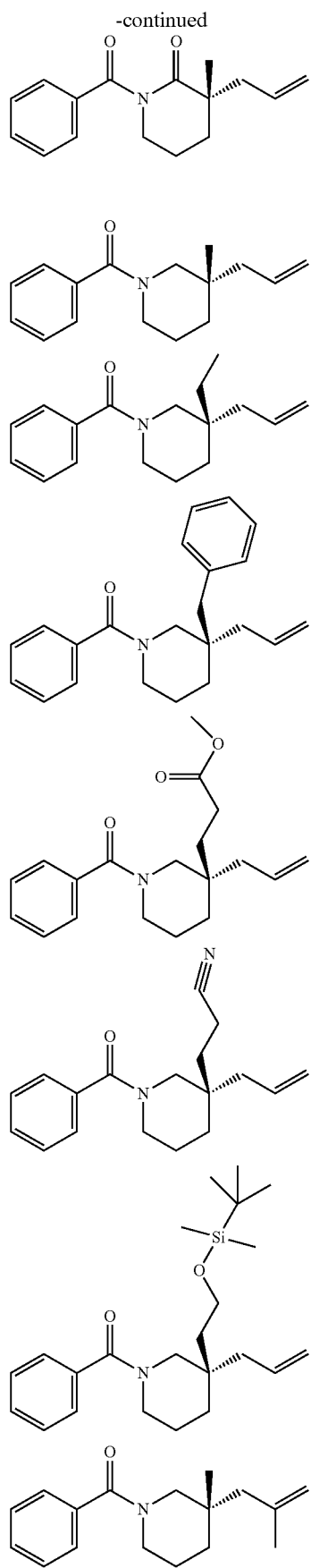
72
-continued
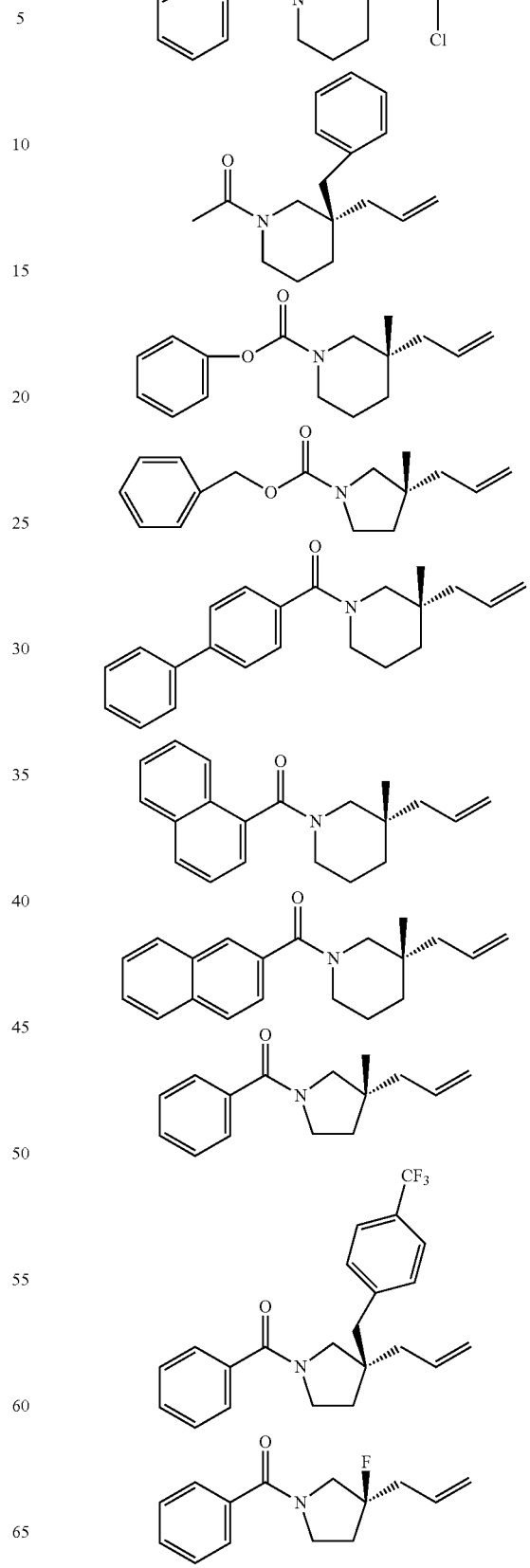

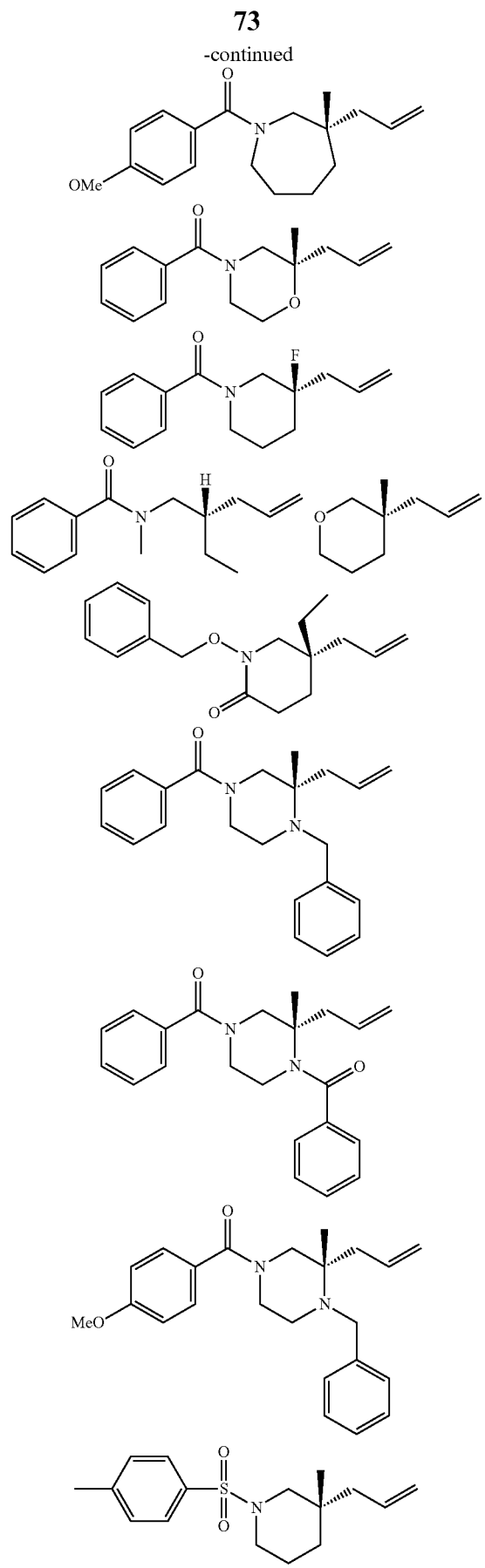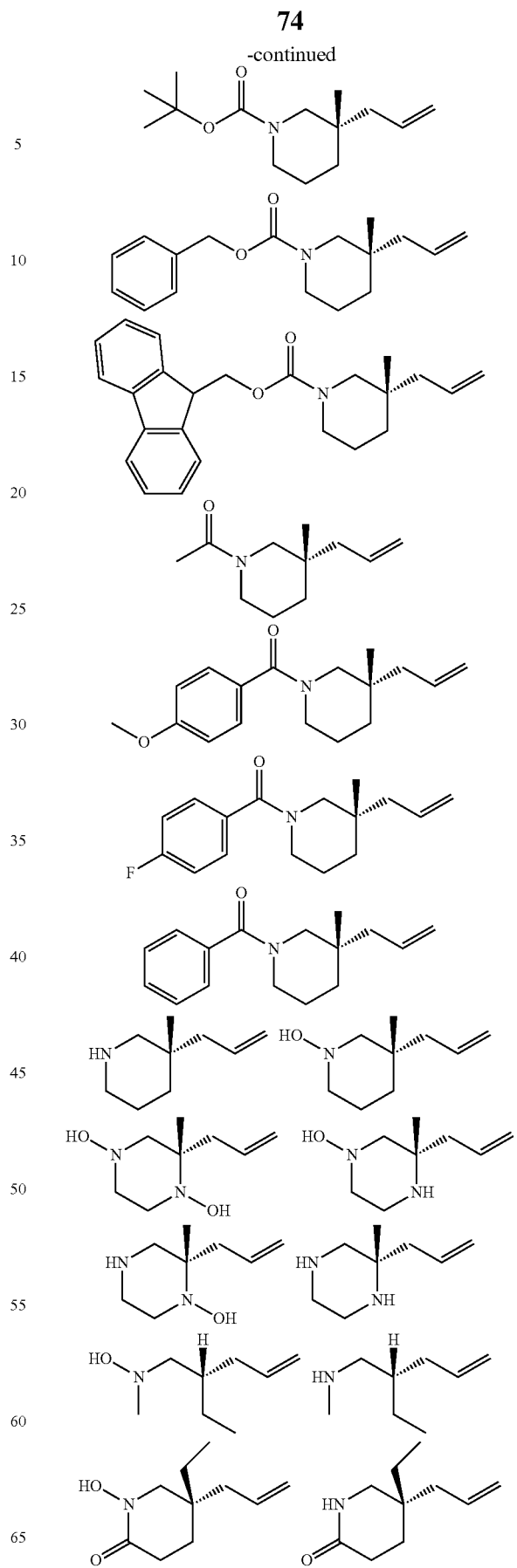

75
-continued
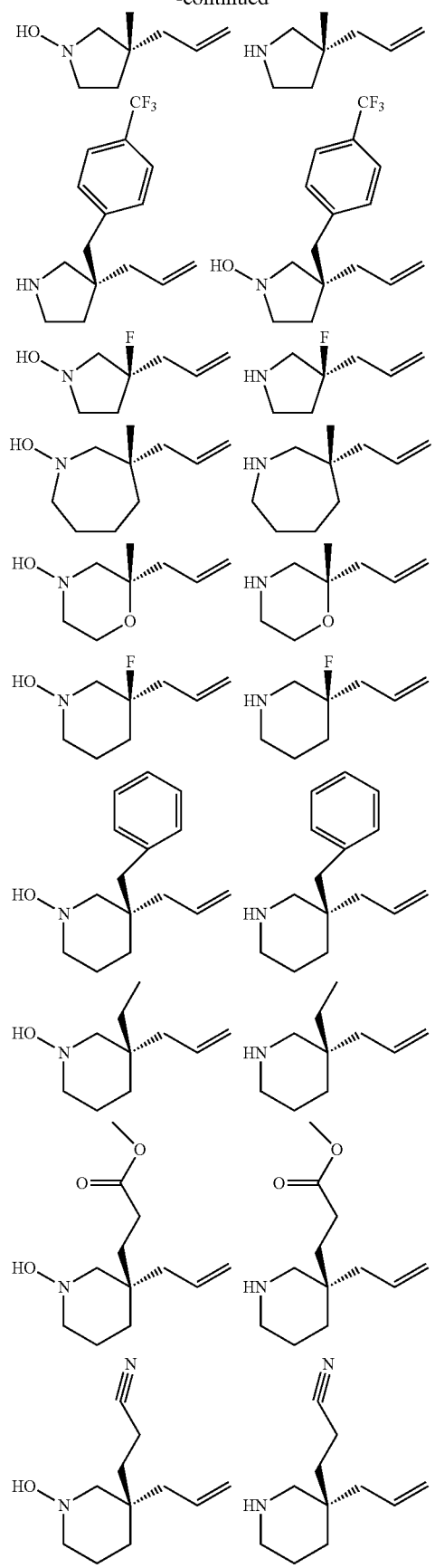
76
-continued
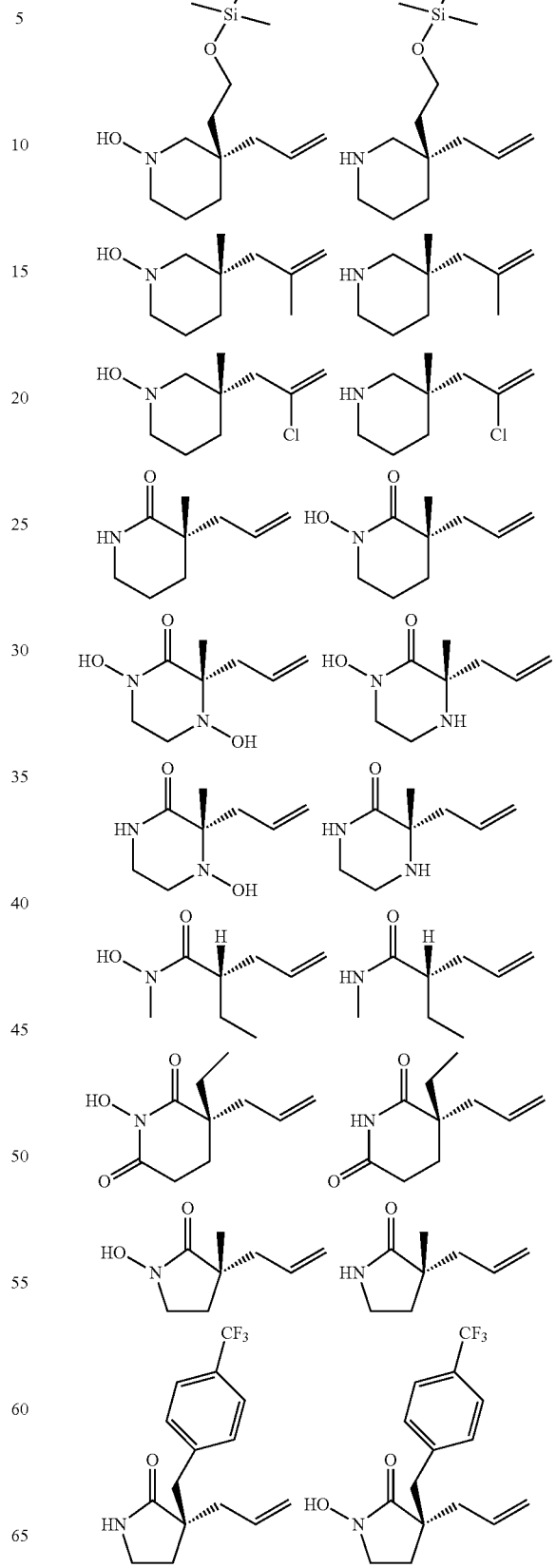

-continued

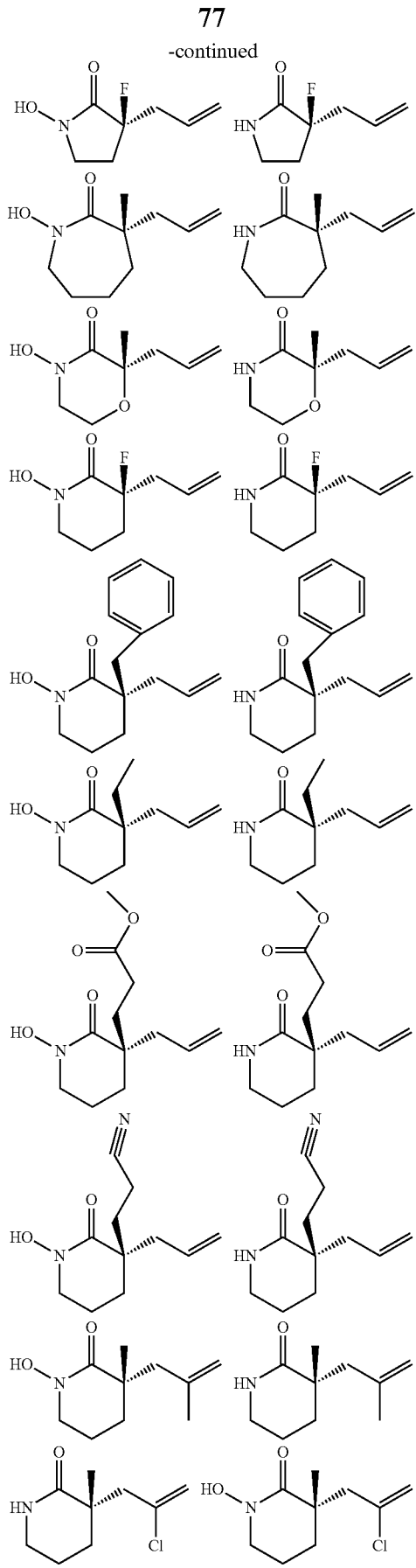

-continued

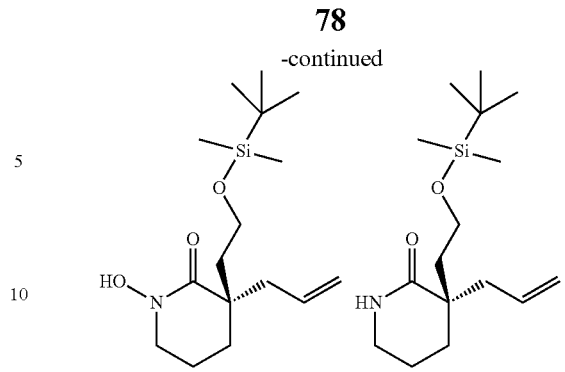

Palladium Catalyzed Decarboxylative Alkylation Reaction

As discussed above, decarboxylative alkylation chemistry, and related allylic alkylation methods have been used in the creation of certain classes of compounds, e. g., α-quaternary ketones.

The building blocks according to embodiments of the present invention, discussed in detail above, can be prepared by the transition metal catalyzed decarboxylative alkylation processes discussed in the references cited above. However, further investigation into the known ketone allylic alkylation reactions (and other related reactions), as discussed here, led to increased enantio- and stereo-selectivity of the reaction to yield highly enantioenriched building block compounds.

In the course of investigating the ketone enolate allylic alkylation and other alkylation processes, interesting ligand electronic effects and, in certain cases, pronounced solvent effects were encountered. McDougal, et al., "High-throughput screening of the asymmetric decarboxylative alkylation reaction of enolate-stabilized enol carbonates," *Synlett* 1712-1716 (2010), the entire content of which is incorporated herein by reference. For example, it was found that for inductively- and resonance-stabilized enolates, highly electron deficient ligands and non-polar solvents are desired. With these findings as a backdrop, further probing of these subtle effects involved examination of enolate reactivity in a lactam series that would be amenable to both steric and electronic fine-tuning. This further probing led to ligand and solvent designs useful for the alkylation of N-heterocycles (and other nitrogen containing compounds) and the construction of the novel building block compounds (discussed above) that are useful for medicinal and polymer chemistry.

Preliminary data suggested that electron rich N-alkyl lactam derivatives were poor substrates for decarboxylative alkylation due to low reactivity. Thus, electron withdrawing N-protecting groups were chosen. These substrates were screened across a series of four solvents (THF, MTBE, toluene, and 2:1 hexane-toluene) while employing two electronically distinct ligands on Pd. Specifically, the reactions used in the screening were carried out using racemic lactams 1a through 1h (depicted below) as the reactants, a Pd2(dba)3 catalyst (5 mol %), a solvent and a ligand. For each of the lactam compounds 1a through 1h, eight experiments were carried out. Specifically, four experiments were carried out using the same first ligand, i.e., (S)-t-BuPHOX (12.5 mol %), but varying the solvent (0.033 M) between THF, MTBE, toluene, and 2:1 hexane-toluene. The other four experiments for each lactam compound were carried out using the same second ligand, i.e., (S)—(CF3)3-t-BuPHOX (12.5 mol %), but varying the solvent (0.033 M) between THF, MTBE, toluene, and 2:1 hexane-toluene. Each experiment was carried out at 40° C.

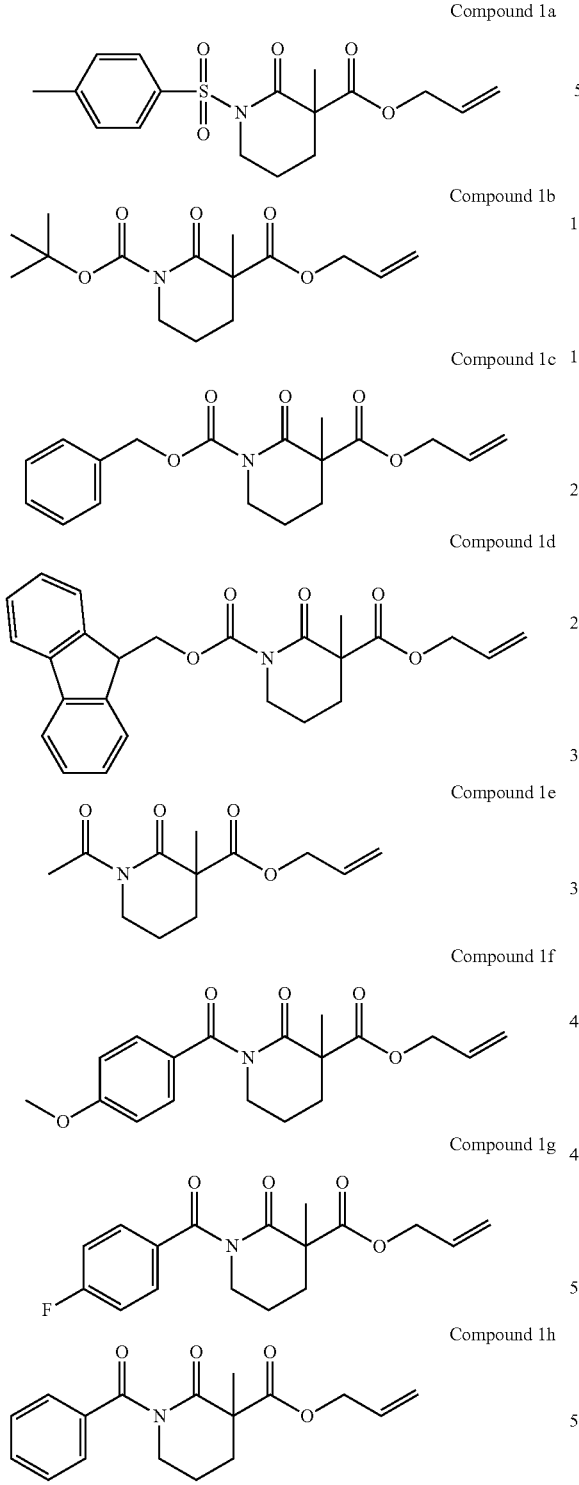

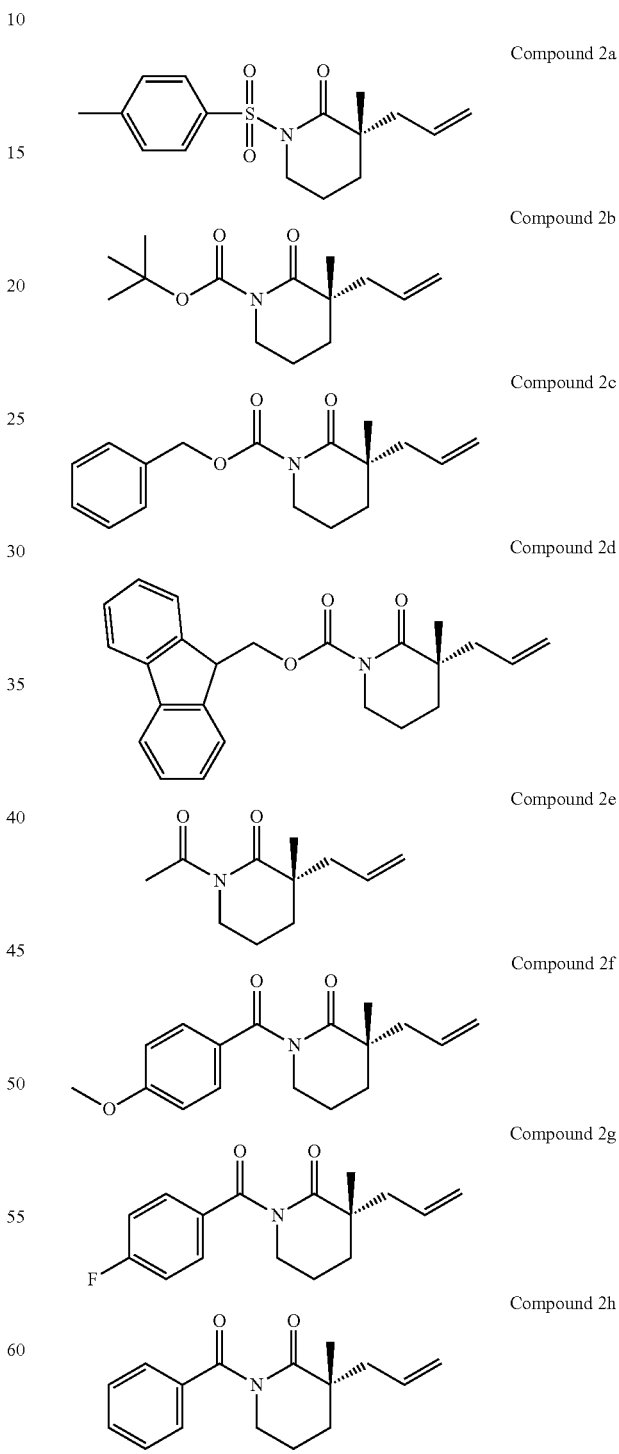

pound 2d corresponds to the compound made from the reaction of Compound 1d, Compound 2e corresponds to the compound made from the reaction of Compound 1e, Compound 2f corresponds to the compound made from the reaction of Compound 1f, Compound 2g corresponds to the compound made from the reaction of Compound 1g, and Compound 2h corresponds to the compound made from the reaction of Compound 1h.

The compounds resulting from the palladium catalyzed decarboxylative alkylation reactions of Compounds 1a through 1h, described above, are depicted below as Compounds 2a through 2h, where Compound 2a corresponds to the compound made from the reaction of Compound 1a, Compound 2b corresponds to the compound made from the reaction of Compound 1b, Compound 2c corresponds to the compound made from the reaction of Compound 1c, Com- The results of this broad screen were highly encouraging, as shown in FIG. 1 (depicting the enantiomeric excess of the compounds prepared using the lactam reactants (Compounds 1a through 1h) with the various ligands and solvents discussed above). Reactivity across all substrates with either ligand was uniformly good, as all of the compounds were completely converted to the desired product. Strikingly, as the N-substituent group was changed from sulfonyl to carbamoyl to acyl functionalities, the enantioselectivity rose from nearly zero to nearly perfect. There was also a difference between the two ligands, and electron poor (S)—(CF$_3$)$_3$-t-BuPHOX was the better choice. As the solvent system became less polar, a distinct increase in enantiomeric excess was observed, however, this effect was substantially less pronounced for reactions employing the electron poor ligand and for reactions varying the N-substituent. Ultimately, with the N-benzoyl group (Bz) on the substrate (i.e., Compound 1h) and (S)—(CF$_3$)$_3$-t-BuPHOX as ligand, the reaction produced the lactam of Compound 2h in >96% ee in each of the four solvents.

Given these results, investigation of the reaction scope was performed by exploring a range of substituted N-acyl lactam derivatives. These derivatives are shown in Table 1 below.

TABLE 1

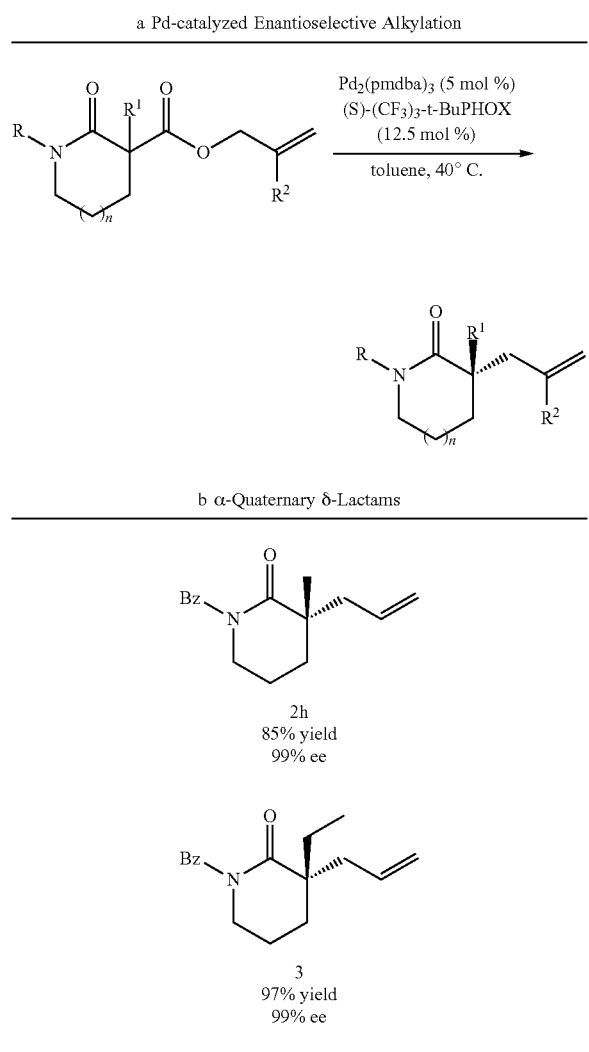

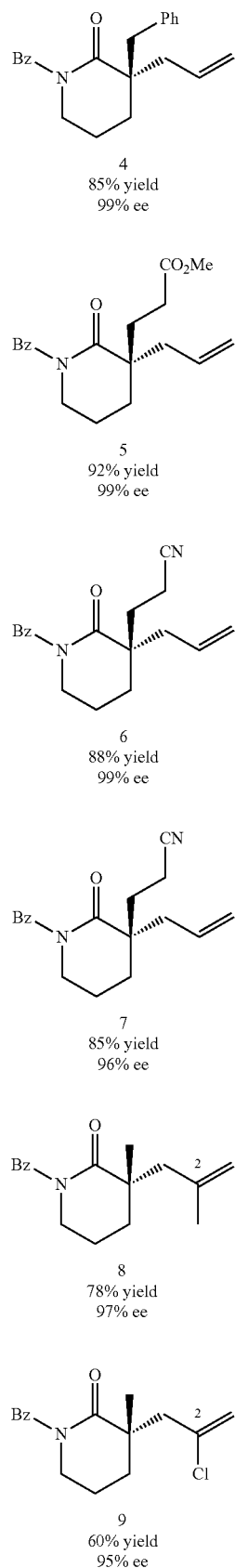

TABLE 1-continued
c Other Ring Sizes and Frameworks
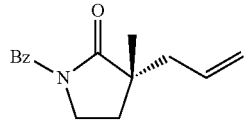
10
90% yield
98% ee
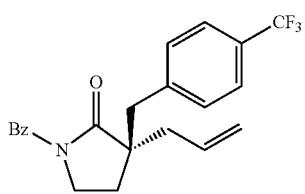
11
89% yield
93% ee
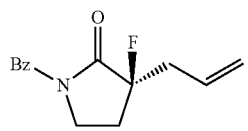
12
86% yield
98% ee
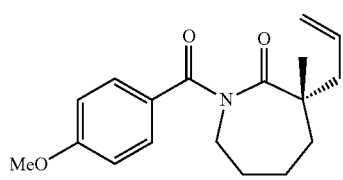
13
83% yield
93% ee
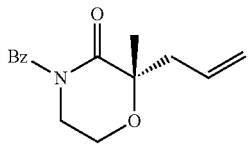
14
91% yield
99% ee
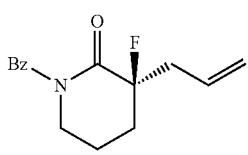
15
89% yield
99% ee
TABLE 1-continued
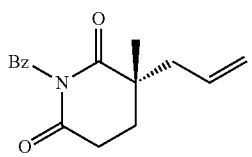
16
81% yield
94% ee
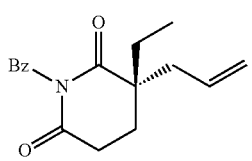
17
86% yield
96% ee
d Other N-acyl Groups
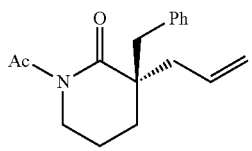
18
90% yield
88% ee
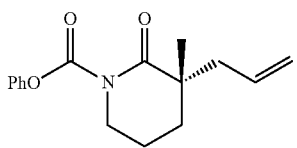
19
82% yield
94% ee
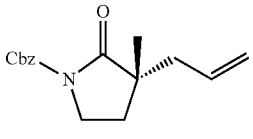
20
86% yield
91% ee
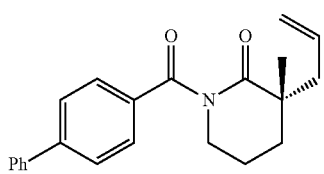
21
85% yield
99% ee TABLE 1-continued

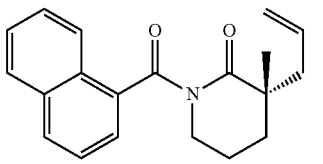

22
86% yield
99% ee

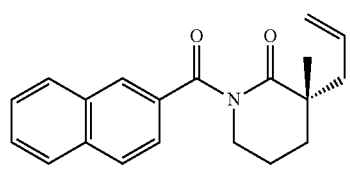

23
82% yield
97% ee

Importantly, reproducing the screening reaction on preparative scale furnishes the N-Bz piperidinone of Compound 2h in 85% isolated yield and 99% ee (see box (b) in Table 1 above). Alteration of the C(α)-group to other alkyl and functionalized alkyl units (e.g., —CH$_2$CH$_3$ and —CH$_2$Ph), as well as to moieties possessing additional acidic protons (e.g., —CH$_2$CH$_2$CO$_2$Me and —CH$_2$CH$_2$CN) leads to high yields of the lactams of Compounds 3 through 6 (see box b in Table 1 above) in uniformly good enantioenrichment (99% ee). Common silyl protecting groups are tolerated in the transformation and the lactam of Compound 7 is furnished in 85% yield and 96% ee. Substituted allyl groups can be incorporated, however only at C(2), leading to products such as the methallyl lactam of Compound 8 and the chloroallyl lactam of Compound 9 in good yield and enantioselectivity (≥95% ee).

Beyond piperidinones, pyrrolidinones and caprolactams are also good substrate classes, furnishing the heterocycles of Compounds 10 through 13 (see box c of Table 1 above) in good yield and ee. Additionally, the morpholine-derived product of Compound 14, containing a C(α)-tetrasubstituted tertiary center, is produced in 91% yield and 99% ee. C(a)-Fluoro substitution is readily introduced into the 1,3-dicarbonyl starting material and is viable in the enantioselective reaction leading to the fluoropyrrolidinone of Compound 12 (86% yield, 98% ee) and the fluoropiperidinone of Compound 15 (89% yield, 99% ee). Moreover, N-Bz glutarimides serve as good substrates smoothly reacting to provide the cyclic imides of Compounds 16 and 17 in high yield and enantioselectivity. Finally, alteration of the N-Bz group is possible (see box d in Table 1 above), giving lactams with an N-acetyl group (Compound 18), N-carbamates (Compounds 19 and 20), and a variety of N-aroyl derivatives (Compounds 21 through 23).

These screening procedures highlight certain methods according to the present invention. In particular, as can be seen from the screening procedures described above, according to some embodiments of the present invention, modifying the traditional transition metal catalyzed decarboxylative alkylation reaction by using an electron poor ligand yields enantioenriched compounds. As used herein, the term "electron poor" is used in its art-recognized sense, and not as a term of degree or approximation. Indeed, those of ordinary skill in the art would readily understand what is meant by the term "electron poor." However, in some embodiments, the electron poor ligand may be a (S)-t-BuPHOX in which one or more of the hydrogen atoms on the t-Bu moiety is substituted with a fluorine atom or other electron poor functional group, such as, for example, a partially or fully fluorinated hydrocarbyl or heteroatom containing hydrocarbyl group, a NO$_2$ group, or a SO$_2$R group (in which R in SO$_2$R is any substituted or unsubstituted hydrocarbyl, heteroatom containing hydrocarbyl, or functional group). In some embodiments, for example, the t-Bu moiety may be replaced, yielding a R'—PHOX (e.g., a (S)—R'—PHOX) ligand, in which R' may be a partially or fully fluorinated hydrocarbyl or heteroatom containing hydrocarbyl group, a NO$_2$ group, a SO$_2$R group (in which R in SO$_2$R is any substituted or unsubstituted hydrocarbyl, heteroatom containing hydrocarbyl, or functional group), or a hydrocarbyl or heteroatom containing hydrocarbyl group in which at least one of the hydrogen atoms is replaced by an electron poor group, such as, for example, a fluorine atom, a NO$_2$ group, or a SO$_2$R group (in which R in SO$_2$R is any substituted or unsubstituted hydrocarbyl, heteroatom containing hydrocarbyl, or functional group.

Accordingly, in some embodiments of the present invention, a method of preparing an enantioenriched heteroatom containing building block compound includes reaction of a heteroatom containing substrate compound with a palladium-based catalyst and an electron poor ligand in the presence of a solvent. The electron poor ligand is as described above, and the palladium catalyst is not particularly limited, and those of ordinary skill in the art would be able to select a suitable catalyst. However, nonlimiting examples of suitable catalysts include Pd$_2$(dba)$_3$ and Pd$_2$(pmdba)$_3$ (dba=dibenzylidene acetone; pmdba=di(p-methoxybenzylidene) acetone). The solvent is also not particularly limited, and can be any solvent normally used in metal catalyzed decarboxylative alkylation procedures. Some nonlimiting examples of suitable solvents include THF, MTBE, toluene, and hexane:toluene (2:1). Additional ligands, catalysts and solvents useful in the reactions according to embodiments of the present invention, and additional reaction particulars, are disclosed in U.S. Pat. No. 7,235,698 to Behenna, et al., the entire content of which is incorporated herein by reference.

The enantioenriched products formed by the catalytic asymmetric alkylation chemistry according to embodiments of the present invention can be of broad utility in synthetic chemistry. To illustrate this point, the lactam of Compound 3 can be transformed into the *Aspidosperma* alkaloid (+)-quebrachamine by modification of a previous route that employed a chiral auxiliary. See Amat, et al., "Enantioselective Synthesis of 3,3-Disubstituted Piperidine Derivatives by Enolate Dialkylation of Phenylglycinol-Derived Oxazolopiperidone Lactams," *J. Org. Chem.* 72, 4431-4439 (2007), the entire content of which is incorporated herein by reference. Additionally, cleavage of the N-Bz group of the lactam of Compound 3 produces the chiral lactam of Compound 24, a compound previously used as a racemate in the synthesis of rhazinilam, a microtubule-disrupting agent that displays similar cellular characteristics to paclitaxel. Edler, et al., "Demonstration of microtubule-like structures formed with (−)-rhazinilam from purified tubulin outside of cells and a simple tubulin-based assay for evaluation of analog activity," *Arch. Biochem. and Biophys.* 487, 98-104 (2009); Magnus, et al., "Concise synthesis of (±)-rhazinilam," *Tetrahedron* 57, 8647-8651 (2001), the entire contents of both of which are incorporated herein by reference. The below Synthesis Reaction Scheme depicts routes to the (+)-Quebrachamine and (+)-Rhazinilam. Finally, reduction of the lactam of Compound 24 produces the C(3)-quaternary piperidine of Compound 25 and demonstrates access to the corresponding amine building blocks.

Synthesis Reaction Scheme

| Terms Table | |
|---|---|
| Shorthand | Meaning |
| Ts | Tosyl |
| Boc | Tert-butyloxy carbonyl group |
| Cbz | Carboxy benzyl group |
| Fmoc | Fluorenyl methyloxy carbonyl group |
| Ac | Acetyl group |
| 4-OMe-Bz | 4-methoxy-benzoyl group |
| 4-F-Bz | 4-fluoro-benzoyl group |
| Bz | Benzoyl group |

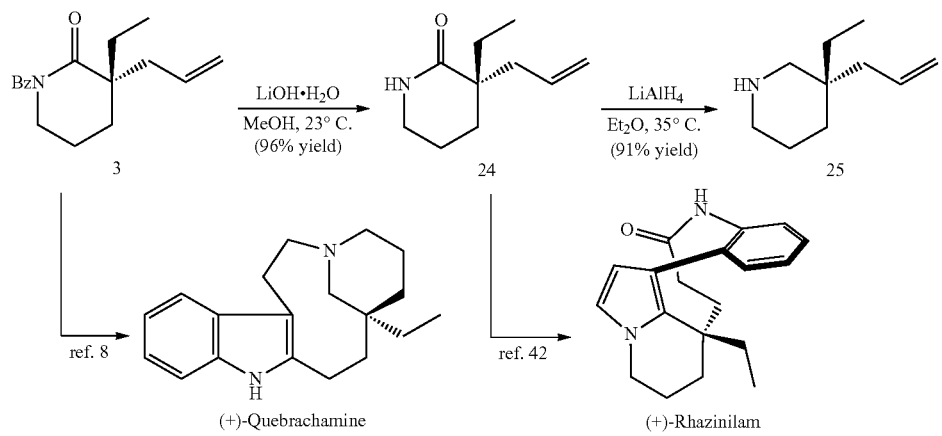

In summary, embodiments of the present invention are directed to substrates useful in preparing enantioenriched quaternary N-containing compounds, and other embodiments are directed to the enantioenriched quaternary N-containing compounds. Additionally, embodiments of the present invention are directed to methods for the catalytic enantioselective alkylation of nitrogen containing derivatives (e.g., monocyclic 5-, 6-, and 7-membered lactam enolate derivatives) to form quaternary N-containing compounds (e.g., α-quaternary and α-tetrasubstituted tertiary lactams). The reaction discovery process was enabled by parallel screening of reaction parameters and led to the identification of a sterically and electronically tuned system for highly enantioselective alkylation. This method has been applied to the catalytic asymmetric synthesis of key intermediates previously employed for the construction of *Aspidosperma* alkaloids. Finally, the asymmetric products formed according to embodiments of the present invention are widely useful as building blocks for the preparation of a wide range of nitrogen containing compounds (including heterocycles) prevalent in materials science, medicinal chemistry and natural products.

Experimental

The following examples and experimental procedures are presented for illustrative purposes only, and do not limit the scope of the present invention. In the examples below and description throughout, certain terms are used as shorthand. The shorthand terms are known to those of ordinary skill in the art, however, the following Terms Table lists the shorthand used and its corresponding meaning.

-continued

| Terms Table | |
|---|---|
| Shorthand | Meaning |
| THF | Tetrahydrofuran |
| MTBE | Methyl tert-butyl ether |
| Tol | Toluene |
| Hex:Tol | Mixed hexane and toluene solvent |
| Ph | Phenyl group |
| OPh (or PhO) | Phenyloxy group |

Materials and Methods

Unless otherwise stated, reactions were performed in flame-dried glassware under an argon or nitrogen atmosphere using dry, deoxygenated solvents. Solvents were dried by passage through an activated alumina column under argon. Brine solutions are saturated aqueous sodium chloride solutions. Tris(dibenzylideneacetone)dipalladium(0) ($Pd_2(dba)_3$) was purchased from Strem and stored in a glove box. Lithium bis(trimethylsilyl)amide was purchased from Aldrich and stored in a glove box. Tris[bis(p-methoxybenzylidene)-acetone]dipalladium(0) ($Pd_2(pmdba)_3$) was prepared by known methods and stored in a glovebox. See McDougal, et al., "High-throughput screening of the asymmetric decarboxylative alkylation reaction of enolate-stabilized enol carbonates,"*Synlett* 1712-1716. (2010), the entire content of which has already been incorporated herein by reference. (S)-t-BuPHOX, (S)—(CF$_3$)$_3$-t-BuPHOX, and allyl cyanoformate were prepared by known methods. See Helmchen, et al., "Phosphinooxazolines—a new class of versatile, modular P,N-ligands for asymmetric catalysis," *Acc. Chem. Res.* 33, 336-345 (2000); Tani, et al., "A facile and modular synthesis of phosphinooxazoline ligands," *Org. Lett.* 9, 2529-2531 (2007); McDougal, et al., "Rapid synthesis of an electron-deficient t-BuPHOX ligand: cross-coupling of aryl bromides with secondary phosphine oxides," *Tetrahedron Lett.* 51, 5550-5554 (2010), the entire contents of all of which have already been incorporated herein by reference.

Selectfluor, methyl iodide, and ethyl iodide were purchased from Aldrich, Acros Organics, Strem, or Alfa Aesar and used as received unless otherwise stated. Sodium hydride (NaH) was purchased as a 60% dispersion in mineral oil from Acros and used as such unless otherwise stated. Triethylamine was distilled from $CaH_2$ prior to use. Acrolein, acrylonitrile, methyl acrylate, and benzoyl chloride were distilled prior to use.

Reaction temperatures were controlled by an IKAmag temperature modulator. Thin-layer chromatography (TLC) was performed using E. Merck silica gel 60 F254 precoated plates (0.25 mm) and visualized by UV fluorescence quenching, anisaldehyde, $KMnO_4$, or CAM staining. ICN Silica gel (particle size 0.032-0.063 mm) was used for flash chromatography. Analytical chiral HPLC was performed with an Agilent 1100 Series HPLC utilizing a Chiralpak (AD-H or AS) or Chiralcel (OD-H, OJ-H, or OB-H) columns (4.6 mm×25 cm) obtained from Daicel Chemical Industries, Ltd. with visualization at 220 or 254 nm. Analytical chiral SFC was performed with a JACSO 2000 series instrument utilizing Chiralpak (AD-H or AS-H) or Chiralcel (OD-H, OJ-H, or OB-H) columns (4.6 mm×25 cm), or a Chiralpak IC column (4.6 mm×10 cm) obtained from Daicel Chemical Industries, Ltd with visualization at 210 or 254 nm. Optical rotations were measured with a Jasco P-2000 polarimeter at 589 nm.

$^1$H and $^{13}$C NMR spectra were recorded on a Varian Inova 500 (at 500 MHz and 126 MHz, respectively) or a Mercury 300 (at 300 MHz and 75 MHz, respectively), and are reported relative to residual protio solvent ($CDCl_3$=7.26 and 77.0 ppm and $C_6D_6$=7.16 and 128.0 ppm, respectively). Data for $^1$H NMR spectra are reported as follows: chemical shift (δ ppm) (multiplicity, coupling constant (Hz), integration). IR spectra were recorded on a Perkin Elmer Paragon 1000 spectrometer and are reported in frequency of absorption (cm$^{-1}$). High resolution mass spectra were obtained using an Agilent 6200 Series TOF with an Agilent G1978A Multimode source in electrospray ionization (ESI), atmospheric pressure chemical ionization (APCI) or mixed (MM) ionization mode or from the Caltech Mass Spectral Facility.

Preparation of Substrates for the Ligand, Protecting Group and Solvent Screening The reactions used to probe the ligand, protecting group and solvent effects (discussed above) involved preparing a collection of racemic lactam substrates (i.e., Compounds 1a through 1h satisfying the formula for Compound 1, depicted below) for palladium-catalyzed decarboxylative allylic alkylation, and screening these substrates for reactivity and enantioselectivity across an array of solvents employing two chiral ligands, (S)-t-BuPHOX and (S)—(CF$_3$)$_3$-t-BuPHOX. For a description of the structure and synthesis of these ligands, see Helmchen, et al., "Phosphinooxazolines—a new class of versatile, modular P,N-ligands for asymmetric catalysis," *Acc. Chem. Res.* 33, 336-345 (2000); Tani, et al., "A facile and modular synthesis of phosphinooxazoline ligands," *Org. Lett.* 9, 2529-2531 (2007); McDougal, et al., "Rapid synthesis of an electron-deficient t-BuPHOX ligand: cross-coupling of aryl bromides with secondary phosphine oxides," *Tetrahedron Lett.* 51, 5550-5554 (2010), the entire contents of all of which are incorporated herein by reference. The preparation of these compounds, and the screening reactions performed to make the enantioenriched Compounds 2a through 2h are described here.

Compound 1—Generic Formula for Compounds 1a through 1h

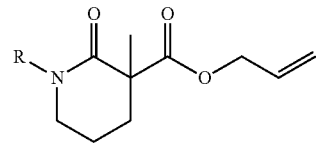

Some derivatives of Compound 1 (above) were made by a diallyl malonate method, i.e., the method represented by the below Diallyl Malonate Method Reaction Scheme.

Diallyl Malonate Method Reaction Scheme

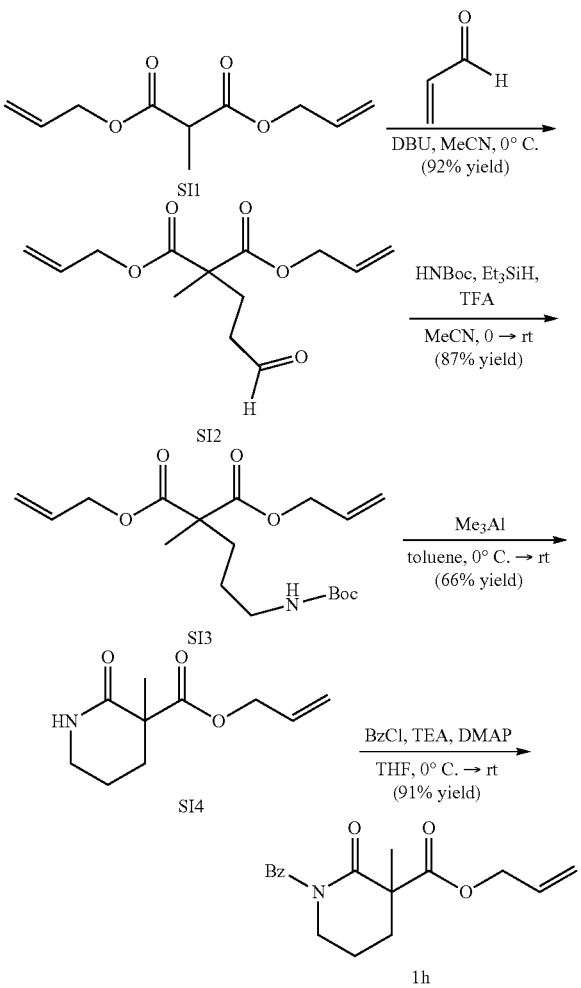

In the above Diallyl Malonate Method Reaction Scheme, aldehyde SI2, carbamate SI3, and lactam SI4 were prepared according to the following procedures. Also, although the final reaction depicted in the Diallyl Malonate Method Reaction Scheme describes the reaction used to form Compound 1h, analogous reactions can be used to form Compounds 1a through 1g, as also described below.

Aldehyde SI2: To a cooled (0° C.) solution of diallyl 2-methylmalonate (SI1)$^5$ (17.0 g, 84.7 mmol, 1.00 equiv)

and acrolein (6.23 mL, 93.2 mmol, 1.10 equiv) in MeCN (282 mL) was added DBU (253 mL, 1.70 mmol, 0.02 equiv). After 15 min, the reaction mixture was diluted with saturated aqueous NH$_4$Cl (200 mL) and EtOAc (100 mL) and the phases were separated. The aqueous phase was extracted with EtOAc (3×200 mL) and the combined organic phases were dried (Na$_2$SO$_4$), filtered, and concentrated under reduced pressure. The resulting oil was purified by flash chromatography (8×16 cm SiO$_2$, 10 to 20% EtOAc in hexanes) to afford aldehyde SI2 as a colorless oil (19.7 g, 92% yield). R$_f$=0.32 (20% EtOAc in hexanes); $^1$H NMR (300 MHz, CDCl$_3$) d 9.71 (t, J=1.2 Hz, 1H), 5.83 (ddt, J=17.2, 10.5, 5.7 Hz, 2H), 5.26 (dq, J=17.2, 1.5 Hz, 2H), 5.19 (dq, J=10.4, 1.3 Hz, 2H), 4.57 (dt, J=5.6, 1.4 Hz, 4H), 2.55-2.45 (m, 2H), 2.20-2.10 (m, 2H), 1.41 (s, 3H); $^{13}$C NMR (75 MHz, CDCl$_3$) d 200.6, 171.2, 131.3, 118.5, 65.9, 52.8, 39.2, 27.7, 20.3; IR (Neat Film NaCl) 2988, 2945, 1732, 1230, 1186, 1116, 984, 935 cm$^{-1}$; HRMS (MM: ESI-APCI) m/z calc'd for C$_{13}$H$_{19}$O$_5$ [M+H]$^+$: 255.1227, found 255.1223.

Carbamate SI3: To a cooled (0° C.) solution of aldehyde SI2 (19.7 g, 77.5 mmol, 1.00 equiv), BocNH$_2^6$ (22.7 g, 194 mmol, 2.50 equiv), and Et$_3$SiH (31.0 mL, 194 mmol, 2.50 equiv) in MeCN (310 mL) was added trifluoroacetic acid (12.1 mL, 163 mmol, 2.10 equiv) dropwise over 5 min. The reaction mixture was stirred at 0° C. for 2 h and at ambient temperature for an additional 18 h, at which point the reaction mixture was cooled (0° C.), treated with saturated aqueous NaHCO$_3$ (150 mL), stirred for 40 min, and concentrated under reduced pressure to remove MeCN (~250 mL). The remaining material was diluted with Et$_2$O (200 mL) and the phases were separated. The aqueous phase was extracted with Et$_2$O (4×100 mL) and EtOAc (1×150 mL), and the combined organic phases were washed with brine (2×150 mL), dried over Na$_2$SO$_4$, filtered, and concentrated under reduced pressure. The resulting oil was purified by flash chromatography (8×25 cm SiO$_2$, 5 to 15% EtOAc in hexanes) to afford carbamate SI3 as a colorless oil (23.0 g, 87% yield). R$_f$=0.32 (20% EtOAc in hexanes); $^1$H NMR (300 MHz, CDCl$_3$) δ 5.88 (ddt, J=17.3, 10.4, 5.7 Hz, 2H), 5.30 (dq, J=17.2, 1.6, 1.5 Hz, 2H), 5.23 (dq, J=10.4, 1.3, 1.3 Hz, 2H), 4.61 (dt, J=5.6, 1.4 Hz, 4H), 4.55 (br s, 1H), 3.12 (q, J=6.7 Hz, 2H), 2.00-1.75 (m, 2H), 1.44 (m, 14H); $^{13}$C NMR (75 MHz, CDCl$_3$) δ 171.6, 155.8, 131.5, 118.4, 79.0, 65.7, 53.4, 40.4, 32.7, 28.3, 24.9, 19.9; IR (Neat Film NaCl) 3403, 2977, 2939, 1734, 1517, 1366, 1250, 1173, 985, 934 cm$^{-1}$; HRMS (MM: ESI-APCI) m/z calc'd for C$_{18}$H$_{29}$NO$_6$Na [M+Na]$^+$: 378.1887, found 378.1892.

Lactam SI4: To a cooled (0° C.) solution of carbamate SI3 (10.4 g, 30.6 mmol, 1.00 equiv) in toluene (306 mL) was added trimethylaluminum (11.7 mL, 61.1 mmol, 2.00 equiv) dropwise over 10 min. After 5 h the reaction was allowed to warm to ambient temperature and stirred for an additional 17 h. The reaction was cooled (0° C.), treated with brine (100 mL, CAUTION: Gas evolution and exotherm) in a dropwise manner over 30 min, and stirred until gas evolution ceased. The reaction mixture was then treated with saturated aqueous sodium potassium tartrate (200 mL) and stirred for 4 h. The phases were separated and the aqueous phase was extracted with EtOAc (5×150 mL). The combined organic phases were dried over Na$_2$SO$_4$, filtered, and concentrated under reduced pressure. The resulting oil was purified by flash chromatography (5×16 cm SiO$_2$, 45 to 65% EtOAc in hexanes) to afford lactam SI4 as a colorless oil (3.99 g, 66% yield). R$_f$=0.41 (100% EtOAc); $^1$H NMR (300 MHz, CDCl$_3$) δ 6.85 (s, 1H), 6.00-5.75 (m, 1H), 5.30 (d, J=17.1 Hz, 1H), 5.20 (d, J=10.4 Hz, 1H), 4.70-4.50 (m, 2H), 3.40-3.20 (m, 2H), 2.30-2.15 (m, 1H), 1.94-1.59 (m, 3H), 1.48 (s, 3H); $^{13}$C NMR (75 MHz, CDCl$_3$) δ 173.1, 172.0, 131.7, 118.1, 65.7, 50.1, 42.3, 33.0, 22.4, 19.3; IR (Neat Film NaCl) 3207, 3083, 2942, 2873, 1737, 1668, 1254, 1194, 1132 cm$^{-1}$; HRMS (MM: ESI-APCI) m/z calc'd for C$_{10}$H$_{16}$NO$_3$ [M+H]$^+$: 198.1125, found 198.1117.

As discussed in more detail below with respect to the specific Compounds 1a through 1h, reactions were performed with Compound 1 (33.6 mmol), Pd$_2$(dba)$_3$ (5 mol %), and ligand (12.5 mol %) in solvent (1.0 mL) at 40° C. for 72 h (dba=dibenzylideneacetone). In all cases, complete consumption of starting material and product formation was observed by thin layer chromatography on silica gel. Pd$_2$(pmdba)$_3$ (5 mol %) was used for Compounds 1a and 1b at 50° C. (pmdba=bis(4-methoxybenzylidene)acetone). Enantiomeric excess (ee) was determined by chiral GC, SFC, or HPLC.

Compound 1h—R is Benzoyl

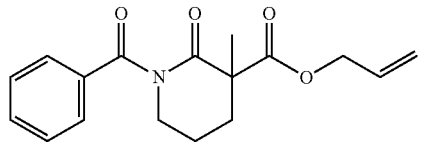 [SMILES: C=CCOC(=O)C1(C)CCCN(C(=O)c2ccccc2)C1=O]

To a cooled (0° C.) solution of lactam SI4 (394 mg, 2.00 mmol, 1.00 equiv), triethylamine (840 mL, 6.00 mmol, 3.00 equiv), and DMAP (25.0 mg, 205 mmol, 0.102 equiv) in THF (8.00 mL) was added benzoyl chloride (470 mL, 4.00 mmol, 2.00 equiv) dropwise over 5 min. The reaction mixture was allowed to warm to ambient temperature and stirred for 14 h. The reaction mixture was then diluted with brine (10 mL) and EtOAc (10 mL), and the phases were separated. The aqueous phase was extracted with EtOAc (3×15 mL), and the combined organic phases were washed with brine (2×30 mL), dried over Na$_2$SO$_4$, filtered, and concentrated under reduced pressure. The resulting oil was purified by flash chromatography (3×25 cm SiO$_2$, 15 to 25% Et$_2$O in hexanes) to afford benzoyl lactam 1h as an amorphous solid (550 mg, 91% yield). R$_f$=0.38 (25% EtOAc in hexanes); $^1$H NMR (500 MHz, CDCl$_3$) δ 7.78-7.63 (m, 2H), 7.52-7.42 (m, 1H), 7.42-7.32 (m, 2H), 5.98 (ddt, J=17.2, 10.4, 5.9 Hz, 1H), 5.40 (dq, J=17.2, 1.4 Hz, 1H), 5.33 (dq, J=10.4, 1.2 Hz, 1H), 4.72 (dt, J=6.0, 1.3 Hz, 2H), 3.93-3.82 (m, 1H), 3.83-3.73 (m, 1H), 2.56-2.43 (m, 1H), 2.13-1.90 (m, 2H), 1.87-1.76 (m, 1H), 1.49 (s, 3H); $^{13}$C NMR (126 MHz, CDCl$_3$) δ 174.9, 172.8, 172.4, 135.9, 131.6, 131.4, 128.0, 127.9, 119.5, 66.5, 52.9, 46.8, 33.8, 22.5, 20.2; IR (Neat Film NaCl) 3063, 2941, 2873, 1735, 1681, 1449, 1276, 1040, 942, 724 cm$^{-1}$; HRMS (MM: ESI-APCI) m/z calc'd for C$_{17}$H$_{20}$NO$_4$ [M+H]$^+$: 302.1387, found 302.1388.

Compound 1a—R is Tosyl

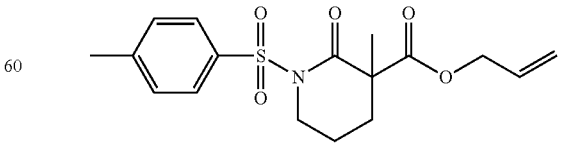

Compound 1a was made by the diallyl malonate method described above, except that the final reaction using lactam SI4 was replaced with the following final reaction scheme.

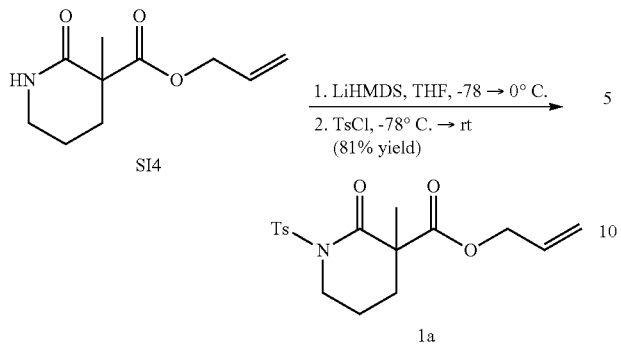

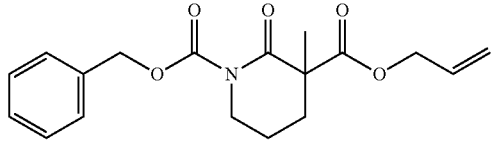

Specifically, to a cooled (−78° C.) solution of LiHMDS (385 mg, 2.30 mmol, 1.15 equiv) in THF (8.0 mL) was added lactam SI4 (394 mg, 2.00 mmol, 1.00 equiv). The reaction mixture warmed to 0° C. and stirred for 30 min, then cooled to −78° C. and treated with TsCl (572 mg, 3.00 mmol, 1.50 equiv). After 5 min, the reaction mixture was allowed to warm to ambient temperature for 30 min and treated with saturated aqueous NH$_4$Cl (10 mL). The phases were separated, and the aqueous phase was extracted with EtOAc (3×20 mL). The combined organic phases were washed with saturated aqueous NaHCO$_3$ (20 mL) and brine (20 mL), dried over Na$_2$SO$_4$, filtered, and concentrated under reduced pressure. The resulting oil was purified by flash chromatography (3×30 cm SiO$_2$, 4:1:1 hexanes-EtOAc-DCM) to afford tosyl lactam 1a as a colorless oil (571 mg, 81% yield). R$_f$=0.58 (33% EtOAc in hexanes); $^1$H NMR (500 MHz, CDCl$_3$) δ 7.93-7.83 (m, 2H), 7.35-7.27 (m, 2H), 5.68 (ddt, J=17.2, 10.5, 5.6 Hz, 1H), 5.17 (dq, J=9.1, 1.4 Hz, 1H), 5.14 (q, J=1.4 Hz, 1H), 4.47 (qdt, J=13.2, 5.6, 1.4 Hz, 2H), 3.98 (ddd, J=12.8, 6.9, 6.1 Hz, 1H), 3.90 (ddt, J=12.4, 6.0, 0.8 Hz, 1H), 2.42 (s, 3H), 2.34-2.26 (m, 1H), 1.95 (tt, J=6.5, 5.5 Hz, 2H), 1.71 (ddd, J=14.2, 8.1, 6.6 Hz, 1H), 1.41 (s, 3H); $^{13}$C NMR (126 MHz, CDCl$_3$) δ 171.8, 169.9, 144.6, 135.7, 131.1, 129.2, 128.6, 118.7, 66.1, 52.8, 46.4, 32.4, 22.3, 21.6, 20.4; IR (Neat Film NaCl) 2942, 1740, 1691, 1353, 1284, 1167, 1090 cm$^{-1}$; HRMS (MM: ESI-APCI) m/z calc'd for C$_{17}$H$_{21}$NO$_5$SNa [M+Na]$^+$: 374.1033, found 374.1042.

Compound 1b—R is BOC (i.e., Tert-Butoxycarbonyl)

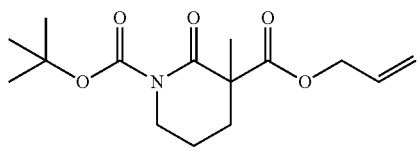 [SMILES: C=CCOC(=O)C1(C)CCCN(C(=O)OC(C)(C)C)C1=O]

Compound 1b was prepared in a manner analogous to the tosyl lactam of Compound 1a, but using lactam SI4 (394 mg, 2.00 mmol, 1.00 equiv) and Boc$_2$O (873 mg, 4.00 mmol, 2.00 equiv). Compound 1b (407 mg, 68% yield) was isolated as an amorphous solid by flash chromatography (SiO$_2$, 9 to 11% Et$_2$O in hexanes). R$_f$=0.54 (25% EtOAc in hexanes); $^1$H NMR (500 MHz, CDCl$_3$) δ 5.95-5.81 (m, 1H), 5.33 (dq, J=17.2, 1.5 Hz, 1H), 5.22 (dq, J=10.5, 1.5 Hz, 1H), 4.64 (m, 2H), 3.80-3.70 (m, 1H), 3.63-3.49 (m, 1H), 2.43-2.33 (m, 1H), 1.98-1.77 (m, 2H), 1.75-1.66 (m, 1H), 1.52 (s, 9H), 1.50 (s, 3H); $^{13}$C NMR (126 MHz, CDCl$_3$) δ 172.5, 170.9, 153.1, 131.5, 118.4, 83.0, 65.9, 53.1, 46.0, 32.6, 28.0, 22.9, 20.1; IR (Neat Film NaCl) 2981, 2939, 1772, 1719, 1457, 1393, 1294, 1282, 1254, 1152, 988, 945, 852 cm$^{-1}$; HRMS (MM: ESI-APCI) m/z calc'd for C$_{15}$H$_{23}$NO$_5$Na [M+Na]$^+$: 320.1468, found 320.1470.

Compound 1c—R is CBZ (i.e., Carboxybenzyl)

Compound 1c was prepared in a manner analogous to the tosyl lactam of Compound 1a, but using lactam SI4 (394 mg, 2.00 mmol, 1.00 equiv) and CbzCl (682 mg, 4.00 mmol, 2.00 equiv). Compound 1c (325 mg, 49% yield) was isolated as a colorless oil by flash chromatography (SiO$_2$, 14 to 17% Et$_2$O in hexanes). R$_f$=0.34 (25% EtOAc in hexanes); $^1$H NMR (500 MHz, CDCl$_3$) δ 7.47-7.40 (m, 2H), 7.39-7.28 (m, 3H), 5.85 (ddt, J=17.1, 10.5, 5.6 Hz, 1H), 5.30 (dq, J=10.5, 1.3 Hz, 1H), 5.29 (s, 2H), 5.19 (dq, J=10.5, 1.3 Hz, 1H), 4.69-4.54 (m, 2H), 3.86-3.79 (m, 1H), 3.71-3.60 (m, 1H), 2.44-2.37 (m, 1H), 1.98-1.78 (m, 2H), 1.73 (ddd, J=14.0, 9.1, 5.1 Hz, 1H), 1.52 (s, 3H); $^{13}$C NMR (126 MHz, CDCl$_3$) δ 172.3, 170.9, 154.4, 135.4, 131.3, 128.5, 128.2, 128.0, 118.7, 68.6, 66.1, 53.3, 46.4, 32.5, 22.8, 20.0; IR (Neat Film NaCl) 2943, 2876, 1776, 1721, 1456, 1378, 1270, 1191, 1167, 1125, 1002, 941, 739, 698 cm$^{-1}$; HRMS (MM: ESI-APCI) m/z calc'd for C$_{18}$H$_{21}$NO$_5$Na [M+Na]$^+$: 354.1312, found 354.1310.

Compound 1d—R is FMOC (i.e., Fluorenyl Methyloxycarbonyl)

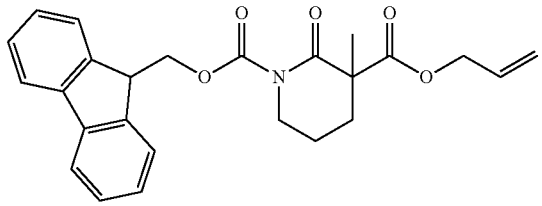 [SMILES: C=CCOC(=O)C1(C)CCCN(C(=O)OCC2c3ccccc3-c3ccccc32)C1=O]

Compound 1d was prepared in a manner analogous to the tosyl lactam of Compound 1a, but using lactam SI4 (394 mg, 2.00 mmol, 1.00 equiv) and FmocCl (621 mg, 2.40 mmol, 1.20 equiv). Compound 1d (352 mg, 42% yield) was isolated as a colorless oil by flash chromatography (SiO$_2$, 2 to 12% Et$_2$O in hexanes). R$_f$=0.28 (25% EtOAc in hexanes); $^1$H NMR (500 MHz, CDCl$_3$) δ 7.77 (dt, J=7.6, 0.9 Hz, 2H), 7.73 (ddd, J=7.5, 5.0, 1.0 Hz, 2H), 7.43-7.38 (m, 2H), 7.32 (tdd, J=7.4, 4.8, 1.2 Hz, 2H), 5.91 (ddt, J=17.2, 10.5, 5.6 Hz, 1H), 5.36 (dq, J=17.2, 1.5 Hz, 1H), 5.25 (dq, J=10.5, 1.3 Hz, 1H), 4.69 (ddt, J=5.6, 2.8, 1.4 Hz, 2H), 4.56-4.43 (m, 2H), 4.33 (t, J=7.5 Hz, 1H), 3.86-3.79 (m, 1H), 3.73-3.61 (m, 1H), 2.44 (dddd, J=13.8, 6.8, 5.0, 0.9 Hz, 1H), 2.00-1.83 (m, 2H), 1.78 (ddd, J=14.0, 9.1, 5.0 Hz, 1H), 1.59 (s, 3H); $^{13}$C NMR (126 MHz, CDCl$_3$) δ 172.3, 170.9, 154.5, 143.6, 141.2, 131.4, 127.8, 127.1, 125.4, 119.9, 118.7, 69.3, 66.1, 53.4, 46.6, 46.4, 32.6, 22.9, 20.0; IR (Neat Film NaCl) 2948, 2892, 1776, 1721, 1451, 1378, 1269, 1191, 997, 759, 742 cm$^{-1}$; HRMS (MM: ESI-APCI) m/z calc'd for C$_{25}$H$_{25}$NO$_5$Na [M+Na]$^+$: 442.1625, found 442.1610.

Compound 1e—R is Acetyl

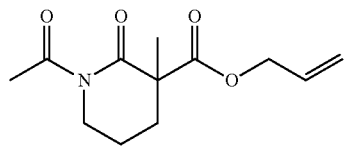 [SMILES: C=CCOC(=O)C1(C)CCCN(C(C)=O)C1=O]

Compound 1e was prepared in a manner analogous to the benzoyl lactam of Compound 1h, but using lactam SI4 (394 mg, 2.00 mmol, 1.00 equiv), acetic anhydride (940 mL, 10.0 mmol, 5.00 equiv), and triethylamine (2.80 mL, 20.0 mmol, 10.0 equiv). Compound 1e (347 mg, 72% yield) was isolated as a colorless oil by flash chromatography (SiO$_2$, 12 to 25% Et$_2$O in hexanes). R$_f$=0.44 (25% EtOAc in hexanes); $^1$H NMR (500 MHz, CDCl$_3$) δ 5.88 (ddt, J=17.1, 10.4, 5.7 Hz, 1H), 5.31 (dq, J=17.2, 1.5 Hz, 1H), 5.25 (dq, J=10.5, 1.2 Hz, 1H), 4.66-4.60 (m, 2H), 3.78 (ddd, J=13.1, 7.6, 5.3 Hz, 1H), 3.71-3.62 (m, 1H), 2.49 (s, 3H), 2.44-2.37 (m, 1H), 1.93-1.77 (m, 2H), 1.78-1.70 (m, 1H), 1.52 (s, 3H); $^{13}$C NMR (126 MHz, CDCl$_3$) δ 174.0, 173.5, 172.4, 131.3, 119.1, 66.2, 53.2, 44.0, 32.9, 27.0, 22.7, 19.9; IR (Neat Film NaCl) 2985, 2942, 1739, 1699, 1457, 1368, 1301, 1261, 1190, 1132, 1048, 990, 959, 936 cm$^{-1}$; HRMS (MM: ESI-APCI) m/z calc'd for C$_{12}$H$_{18}$NO$_4$ [M+H]$^+$: 240.1230, found 240.1237.

Compound 1f—R is 4-OMe-Bz (i.e., 4-Methoxybenzoyl)

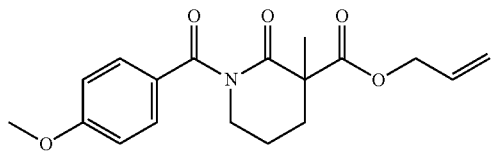 [SMILES: C=CCOC(=O)C1(C)CCCN(C(=O)c2ccc(OC)cc2)C1=O]

Compound 1f was prepared in a manner analogous to the benzoyl lactam of Compound 1h, but using lactam SI4 (394 mg, 2.00 mmol, 1.00 equiv), 4-methoxybenzoyl chloride (682 mg, 4.00 mmol, 2.00 equiv), and triethylamine (840 mL, 6.00 mmol, 3.00 equiv). Compound 1f (425 mg, 64% yield) was isolated as a colorless oil by flash chromatography (SiO$_2$, CHCl$_3$-hexanes-Et$_2$O 6.5:5:1). R$_f$=0.76 (50% EtOAc in hexanes); $^1$H NMR (500 MHz, CDCl$_3$) δ 7.81-7.67 (m, 2H), 6.93-6.79 (m, 2H), 6.05-5.88 (m, 1H), 5.39 (dq, J=17.2, 1.4 Hz, 1H), 5.31 (dq, J=10.4, 1.2 Hz, 1H), 4.71 (dt, J=6.0, 1.3 Hz, 2H), 3.90-3.77 (m, 1H), 3.82 (s, 3H), 3.76-3.63 (m, 1H), 2.48 (ddd, J=13.7, 5.7, 4.3 Hz, 1H), 2.06-1.89 (m, 2H), 1.80 (ddd, J=13.5, 10.0, 5.0 Hz, 1H), 1.49 (s, 3H); $^{13}$C NMR (126 MHz, CDCl$_3$) δ 174.3, 172.6 (2C), 162.7, 131.4, 130.7, 127.7, 119.3, 113.3, 66.3, 55.3, 52.8, 46.9, 33.7, 22.5, 20.2; IR (Neat Film NaCl) 3080, 2941, 1732, 1682, 1604, 1512, 1456, 1390, 1257, 1173, 1139, 1029, 939, 844, 770 cm$^{-1}$; HRMS (MM: ESI-APCI) m/z calc'd for C$_{18}$H$_{22}$NO$_5$ [M+H]$^+$: 332.1492, found 332.1501.

Compound 1g—R is 4-F-Bz (i.e., 4-Fluorobenzoyl)

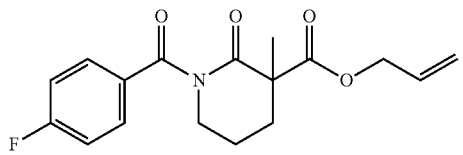

Compound 1g was prepared in a manner analogous to the benzoyl lactam of Compound 1h, but using lactam SI4 (394 mg, 2.00 mmol, 1.00 equiv), 4-fluorobenzoyl chloride (470 mL, 4.00 mmol, 2.00 equiv), and triethylamine (840 mL, 6.00 mmol, 3.00 equiv). Compound 1g (557 mg, 87% yield) was isolated as an amorphous white solid by flash chromatography (SiO$_2$, 15 to 25% Et$_2$O in hexanes). R$_f$=0.37 (25% EtOAc in hexanes); $^1$H NMR (500 MHz, CDCl$_3$) δ 7.84-7.72 (m, 2H), 7.12-6.97 (m, 2H), 5.99 (ddt, J=17.2, 10.4, 5.9 Hz, 1H), 5.41 (dq, J=17.2, 1.4 Hz, 1H), 5.35 (dq, J=10.4, 1.2 Hz, 1H), 4.73 (dt, J=6.0, 1.3 Hz, 2H), 3.89-3.82 (m, 1H), 3.81-3.75 (m, 1H), 2.57-2.42 (m, 1H), 2.09-1.91 (m, 2H), 1.89-1.75 (m, 1H), 1.50 (s, 3H); $^{13}$C NMR (126 MHz, CDCl$_3$) δ 173.8, 172.9, 172.5, 164.8 (d, J$_{C-F}$=252.5 Hz), 131.8 (d, J$_{C-F}$=3.3 Hz), 131.3, 130.7 (d, J$_{C-F}$=9.0 Hz), 119.5, 115.2 (d, J$_{C-F}$=22.0 Hz), 66.5, 52.9, 47.0, 33.8, 22.4, 20.2; IR (Neat Film NaCl) 3079, 2943, 2874, 1734, 1684, 1602, 1508, 1277, 1240, 1193, 1140, 939, 849, 770 cm$^{-1}$; HRMS (MM: ESI-APCI) m/z calc'd for C$_{17}$H$_{19}$NO$_4$F [M+H]$^+$: 320.1293, found 320.1297.

General Procedure for Allylic Alkylation Screening Reactions

The substrates described above (i.e., Compounds 1a through 1h) were then subjected to allylic alkylation reactions using different ligands and solvents and the resulting compounds (i.e., Compounds 2a through 2h) were analyzed for enantiomeric excess. The general procedure for these reactions is described here.

All reagents were dispensed as solutions using a Symyx Core Module within a nitrogen-filled glovebox. Oven-dried half-dram vials were charged with a solution of the palladium source (Pd$_2$dba$_3$ or Pd$_2$pmdba$_3$, 1.68 µmol, 0.05 equiv) in THF (368 µL). The palladium solutions were evaporated to dryness under reduced pressure using a Genevac centrifugal evaporator within the glovebox, and stirbars were added to the vials. The reaction vials were then charged with the desired reaction solvent (500 µL) and a solution of the PHOX ligand (4.20 µmol, 0.125 equiv) in the reaction solvent (250 µL) and stirred at ambient glovebox temperature (~28° C.). After 30 min, solutions of the lactam substrate (33.6 µmol, 1.0 equiv) in the reaction solvent (250 µL) were added. The reaction vials were tightly capped and heated to the desired temperature. When complete consumption of the starting material was observed by colorimetric change (from light green to red-orange) and confirmed by thin layer chromatography on SiO$_2$ (typically less than 72 h), the reaction mixtures were removed from the glovebox, concentrated under reduced pressure, resuspended in an appropriate solvent for analysis (e.g., hexanes), filtered, and analyzed for enantiomeric excess. The methods for determining the enantiomeric excess are reported in Table 4 below.

Results of the Screening of Various Reaction Parameters

The results of the enantiomeric excess analysis (by chiral HPLC (high performance liquid chromatography)) of Compounds 2a through 2h (made from Compounds 1a through 1h) over different N-protecting groups and different solvents are reported in the below Table 2.

TABLE 2

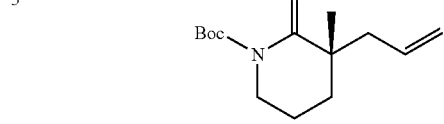

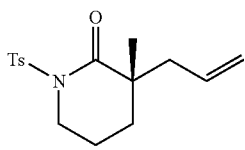

| | THF | MTBE | Toluene | Hex:Tol 2:1 |
|---|---|---|---|---|
| R = Ts[a] | 4.1 | 25.9 | 6.5 | 31.4 |
| | 35.2 | 57.2 | 37.2 | 44.2 |
| R = Boc[a] | 57.3 | 74.5 | 73.6 | 76.7 |
| | 70.3 | 72.1 | 73.0 | 71.0 |
| R = Cbz | 36.3 | 75.2 | 75.1 | 71.5 |
| | 79.9 | 83.5 | 87.3 | 83.2 |
| R = Fmoc | 45.7 | 64.9 | 38.3 | 44.9 |
| | 78.9 | 84.6 | 87.1 | 84.6 |
| R = Ac | 20.0 | 64.1 | 61.6 | 83.2 |
| | 75.1 | 90.6[b] | 90.2[b] | 90.9[b] |
| R = 4-MeO-Bz | 59.5 | 90.7 | 87.4 | 96.8 |
| | 97.1 | 98.3 | 99.0 | 98.5 |
| R = 4-F-Bz | 42.3 | 85.8 | 83.2 | 96.4 |
| | 95.3 | 99.0 | 99.3 | 99.4 |
| R = Bz | 52.2 | 88.3 | 85.8 | 96.4 |
| | 96.2 | 99.2 | 99.0 | 98.8 |

[a]Reactions for these substrates run at 50° C.
[b]Reaction performed at 60° C.

Characterization Data for New Product Compounds 2a through 2h

The new compounds 2a through 2h were formed using the reactions below, and characterized. The results of the characterizations are reported in Table 3 below.

Tosyl Lactam 2a

2a

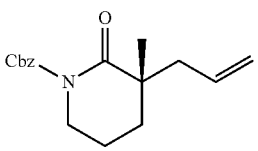

The reaction was performed in MTBE at 40° C. Tosyl lactam 2a was isolated by flash chromatography (SiO$_2$, 3 to 15% Et$_2$O in hexanes) as a light yellow solid. 90.0% yield. R$_f$=0.29 (35% Et$_2$O in hexanes); $^1$H NMR (500 MHz, CDCl$_3$) δ 7.89-7.84 (m, 2H), 7.33-7.27 (m, 2H), 5.41 (dddd, J=16.9, 10.2, 8.1, 6.7 Hz, 1H), 4.99-4.86 (m, 2H), 3.99 (dddd, J=11.9, 5.9, 4.9, 1.3 Hz, 1H), 3.82-3.71 (m, 1H), 2.42 (s, 3H), 2.41-2.34 (m, 1H), 2.07 (ddt, J=13.6, 8.1, 1.0 Hz, 1H), 1.98-1.83 (m, 2H), 1.83-1.75 (m, 1H), 1.55-1.48 (m, 1H), 1.12 (s, 3H); $^{13}$C NMR (126 MHz, CDCl$_3$) δ 175.7, 144.4, 136.2, 132.9, 129.2, 128.5, 118.9, 47.6, 44.2, 44.0, 32.1, 25.5, 21.6, 20.1; IR (Neat Film NaCl) 3074, 2938, 1689, 1597, 1454, 1351, 1283, 1171, 1103, 1089, 1039, 921, 814, 748 cm$^{-1}$; HRMS (MM: ESI-APCI) m/z calc'd for C$_{16}$H$_{21}$NO$_3$SNa [M+Na]$^+$: 330.1134, found 330.1141; [α]$_D^{25}$ –69.2° (c 1.16, CHCl$_3$, 75% ee).

Boc Lactam 2b

2b

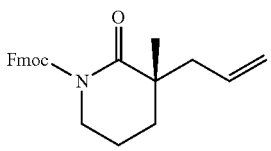

The reaction was performed in toluene at 40° C. Boc lactam 2b was isolated by flash chromatography (SiO$_2$, 8 to 9% Et$_2$O in hexanes) as a colorless oil. 87.1% yield. R$_f$=0.57 (35% Et$_2$O in hexanes); $^1$H NMR (500 MHz, CDCl$_3$) δ 5.74 (dddd, J=17.1, 10.4, 7.8, 7.0 Hz, 1H), 5.14-5.02 (m, 2H), 3.71-3.61 (m, 1H), 3.58-3.48 (m, 1H), 2.48 (dd, J=13.6, 7.0 Hz, 1H), 2.26 (dd, J=13.6, 7.9 Hz, 1H), 1.87-1.76 (m, 3H), 1.61-1.52 (m, 1H), 1.50 (s, 9H), 1.22 (s, 3H); $^{13}$C NMR (126 MHz, CDCl$_3$) δ 177.1, 153.7, 133.7, 118.5, 82.5, 47.4, 44.5, 44.2, 33.0, 28.0, 25.4, 19.7; IR (Neat Film NaCl) 3076, 2978, 2936, 1768, 1715, 1457, 1392, 1368, 1298, 1280, 1252, 1149, 999, 917, 854 cm$^{-1}$; HRMS (MM: ESI-APCI) m/z calc'd for C$_{14}$H$_{23}$NO$_3$Na [M+Na]$^+$: 276.1570, found 276.1574; [α]$_D^{25}$ –73.6° (c 1.025, CHCl$_3$, 81% ee).

Cbz Lactam 2c

2c

The reaction was performed in toluene at 40° C. Cbz lactam 2c was isolated by flash chromatography (SiO$_2$, 8 to 10% Et$_2$O in hexanes) as a colorless oil. 84.6% yield. R$_f$=0.49 (25% EtOAc in hexanes); $^1$H NMR (500 MHz, CDCl$_3$) δ 7.44-7.40 (m, 2H), 7.36 (ddd, J=7.9, 7.0, 1.0 Hz, 2H), 7.33-7.29 (m, 1H), 5.74 (dddd, J=16.6, 10.5, 7.8, 6.9 Hz, 1H), 5.26 (s, 2H), 5.13-5.02 (m, 2H), 3.80-3.72 (m, 1H), 3.67-3.58 (m, 1H), 2.51 (dd, J=13.6, 7.0 Hz, 1H), 2.26 (dd, J=13.6, 7.9 Hz, 1H), 1.90-1.77 (m, 3H), 1.62-1.53 (m, 1H), 1.25 (s, 3H); $^{13}$C NMR (126 MHz, CDCl$_3$) δ 177.0, 154.8, 135.6, 133.4, 128.5, 128.2, 128.0, 118.8, 68.3, 47.8, 44.8, 44.2, 32.8, 25.5, 19.6; IR (Neat Film NaCl) 2940, 1772, 1712, 1456, 1377, 1296, 1270, 1218, 1161, 1001, 918 cm$^{-1}$; HRMS (MM: ESI-APCI) m/z calc'd for C$_{17}$H$_{20}$NO$_3$Na [M+Na]$^+$: 310.1414, found 310.1414; [α]$_D^{25}$ –65.8° (c 1.48, CHCl$_3$, 86% ee).

Fmoc Lactam 2d

2d

The reaction was performed in toluene at 40° C. Fmoc lactam 2d was isolated by flash chromatography (SiO$_2$, 6 to 8% Et$_2$O in hexanes) as a colorless oil. 82.4% yield. R$_f$=0.45 (25% EtOAc in hexanes); $^1$H NMR (500 MHz, CDCl$_3$) δ 7.77 (dt, J=7.6, 1.0 Hz, 2H), 7.71 (ddd, J=7.5, 3.6, 1.0 Hz, 2H), 7.41 (tt, J=7.5, 0.9 Hz, 2H), 7.33 (ddt, J=7.5, 2.0, 1.2 Hz, 2H), 5.80 (dddd, J=17.9, 8.7, 7.9, 6.9 Hz, 1H), 5.18-5.10

(m, 2H), 4.53-4.42 (m, 2H), 4.33 (t, J=7.4 Hz, 1H), 3.80-3.71 (m, 1H), 3.65-3.57 (m, 1H), 2.58 (dd, J=13.6, 7.0 Hz, 1H), 2.32 (ddt, J=13.6, 7.8, 1.1 Hz, 1H), 1.93-1.79 (m, 3H), 1.64-1.57 (m, 1H), 1.31 (s, 3H); $^{13}$C NMR (126 MHz, CDCl$_3$) δ 177.0, 154.9, 143.7, 141.2, 133.5, 127.7, 127.1, 125.4, 119.9, 118.8, 68.9, 47.7, 46.7, 44.8, 44.2, 32.8, 25.5, 19.6; IR (Neat Film NaCl) 3067, 2945, 1770, 1712, 1478, 1451, 1377, 1297, 1269, 1161, 1000, 759, 740 cm$^{-1}$; HRMS (MM: ESI-APCI) m/z calc'd for C$_{24}$H$_{26}$NO$_3$ [M+H]$^+$: 376.1907, found 376.1914; [α]$_D^{25}$ −38.5° (c 2.17, CHCl$_3$, 89% ee).

Acetyl Lactam 2e

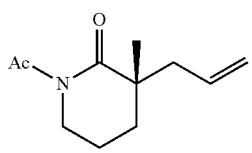

The reaction was performed in toluene at 40° C. Acetyl lactam 2e was isolated by flash chromatography (SiO$_2$, 8 to 10% Et$_2$O in hexanes) as a colorless oil. 47.2% yield. R$_f$=0.38 (25% EtOAc in hexanes); $^1$H NMR (500 MHz, CDCl$_3$) δ 5.73 (dddd, J=16.6, 10.4, 7.8, 7.0 Hz, 1H), 5.14-5.04 (m, 2H), 3.82-3.72 (m, 1H), 3.60-3.49 (m, 1H), 2.50 (ddt, J=13.6, 7.0, 1.2 Hz, 1H), 2.44 (s, 3H), 2.25 (ddt, J=13.6, 7.7, 1.1 Hz, 1H), 1.91-1.71 (m, 3H), 1.64-1.52 (m, 1H), 1.25 (s, 3H); $^{13}$C NMR (126 MHz, CDCl$_3$) δ 179.3, 174.4, 133.3, 118.9, 45.4, 44.8, 44.4, 32.8, 27.2, 25.7, 19.4; IR (Neat Film NaCl) 2941, 1694, 1387, 1367, 1293, 1248, 1177, 1114, 1046, 920 cm$^{-1}$; HRMS (MM: ESI-APCI) m/z calc'd for C$_{11}$H$_{18}$NO$_2$ [M+H]$^+$: 196.1332, found 196.1329; [α]$_D^{25}$ −100.9° (c 0.99, CHCl$_3$, 91% ee).

4-Methoxybenzoyl Lactam 2f

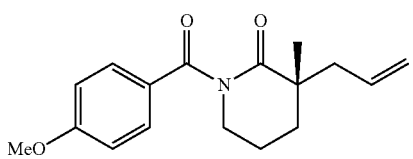

The reaction was performed in toluene at 40° C. 4-Methoxybenzoyl lactam 2f was isolated by flash chromatography (SiO$_2$, 15% EtOAc in hexanes) as a colorless oil. 92.7% yield. R$_f$=0.36 (25% EtOAc in hexanes); $^1$H NMR (500 MHz, CDCl$_3$) δ 7.60-7.48 (m, 2H), 6.92-6.82 (m, 2H), 5.76 (dddd, J=17.2, 10.3, 7.7, 7.0 Hz, 1H), 5.19-5.03 (m, 2H), 3.83 (s, 3H), 3.80 (ddd, J=12.1, 5.3, 1.4 Hz, 1H), 3.73-3.64 (m, 1H), 2.57 (ddt, J=13.6, 7.1, 1.2 Hz, 1H), 2.29 (ddt, J=13.7, 7.6, 1.1 Hz, 1H), 2.05-1.91 (m, 3H), 1.72-1.63 (m, 1H), 1.32 (s, 3H); $^{13}$C NMR (126 MHz, CDCl$_3$) δ 179.0, 174.9, 162.4, 133.4, 130.1, 128.4, 118.9, 113.5, 55.4, 47.3, 43.9, 43.4, 33.3, 25.3, 19.6; IR (Neat Film NaCl) 2937, 1675, 1604, 1511, 1254, 1164, 1029, 922, 840, 770 cm$^{-1}$; HRMS (MM: ESI-APCI) m/z calc'd for C$_{17}$H$_{22}$NO$_3$ [M+H]$^+$: 288.1594, found 288.1595; [α]$_D^{25}$ −94.2° (c 1.00, CHCl$_3$, 99% ee).

4-Fluorobenzoyl Lactam 2g

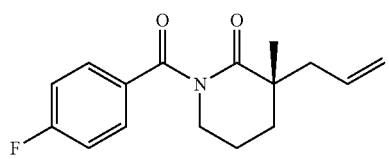

The reaction was performed in toluene at 40° C. 4-Fluorobenzoyl lactam 2g was isolated by flash chromatography (SiO$_2$, 9% Et$_2$O in hexanes) as a colorless oil. 89.4% yield. R$_f$=0.41 (17% EtOAc in hexanes); $^1$H NMR (500 MHz, CDCl$_3$) δ 7.59-7.47 (m, 2H), 7.12-6.99 (m, 2H), 5.74 (ddt, J=17.0, 10.4, 7.3 Hz, 1H), 5.18-5.05 (m, 2H), 3.89-3.77 (m, 1H), 3.77-3.63 (m, 1H), 2.55 (dd, J=13.7, 7.0 Hz, 1H), 2.28 (dd, J=13.7, 7.6 Hz, 1H), 2.07-1.88 (m, 3H), 1.76-1.62 (m, 1H), 1.31 (s, 3H); $^{13}$C NMR (126 MHz, CDCl$_3$) δ 179.1, 174.2, 164.6 (d, J$_{C-F}$=252.4 Hz), 133.2, 132.5 (d, J$_{C-F}$=3.4 Hz), 123.0 (d, J$_{C-F}$=8.9 Hz), 119.1, 115.3 (d, J$_{C-F}$=22.1 Hz), 47.3, 44.0, 43.3, 33.3, 25.2, 19.5; IR (Neat Film NaCl) 3076, 2940, 1679, 1602, 1507, 1384, 1280, 1145, 922, 844, 769 cm$^{-1}$; HRMS (MM: ESI-APCI) m/z calc'd for C$_{16}$H$_{19}$NO$_2$F [M+H]$^+$: 276.1394, found 276.1392; [α]$_D^{25}$ −85.5° (c 1.02, CHCl$_3$, 99% ee).

Benzoyl Lactam 2H

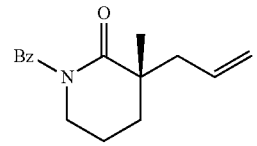

The reaction was performed in toluene at 40° C. Benzoyl lactam 2H was isolated by flash chromatography (SiO$_2$, 5 to 9% Et$_2$O in pentane) as a colorless oil. 84.7% yield. R$_f$=0.55 (25% EtOAc in hexanes); $^1$H NMR (500 MHz, CDCl$_3$) δ 7.54-7.50 (m, 2H), 7.49-7.43 (m, 1H), 7.40-7.35 (m, 2H), 5.75 (dddd, J=17.1, 10.2, 7.7, 7.0 Hz, 1H), 5.19-5.03 (m, 2H), 3.92-3.78 (m, 1H), 3.72 (ddt, J=12.6, 6.4, 6.0, 1.2 Hz, 1H), 2.55 (ddt, J=13.7, 7.0, 1.2 Hz, 1H), 2.29 (ddt, J=13.7, 7.7, 1.1 Hz, 1H), 2.07-1.87 (m, 3H), 1.75-1.60 (m, 1H), 1.31 (s, 3H); $^{13}$C NMR (126 MHz, CDCl$_3$) δ 179.0, 175.3, 136.5, 133.3, 131.3, 128.1, 127.4, 118.9, 47.1, 44.0, 43.3, 33.3, 25.1, 19.5; IR (Neat Film NaCl) 3074, 2939, 2870, 1683, 1478, 1449, 1386, 1282, 1151, 919, 726, 695 cm$^{-1}$; HRMS (MM: ESI-APCI) m/z calc'd for C$_{16}$H$_{20}$NO$_2$ [M+H]$^+$: 258.1489, found 258.1491; [α]$_D^{25}$ −91.2° (c 1.07, CHCl$_3$, 99% ee).

TABLE 3

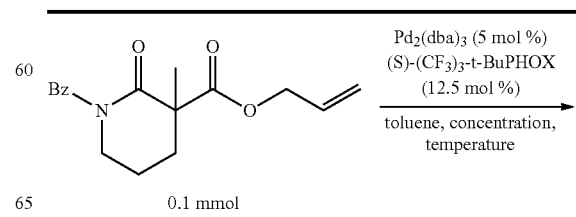

TABLE 3-continued

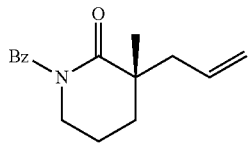

| entry | temperature (° C.) | concentration (M) | time (h) | % ee |
|---|---|---|---|---|
| 1 | 40 | 0.033 | 43 | 99.2 |
| 2 | 45 | 0.033 | 22 | 98.9 |
| 3 | 50 | 0.033 | 12 | 98.7 |
| 4 | 55 | 0.033 | 6 | 98.2 |
| 5 | 40 | 0.10 | 43 | 98.9 |
| 6 | 40 | 0.20 | 43 | 97.4 |

Preparation of Substrates for the Creation of N-acyl Lactam Derivatives

The N-acyl lactam derivatives discussed above and depicted in Table 1, above, were prepared using substrates prepared according to an Acylation and Alkylation Method. A representative reaction scheme for the acylation and alkylation method is depicted in the below Acylation and Alkylation Method Reaction Scheme.

Acylation and Alkylation Method Reaction Scheme

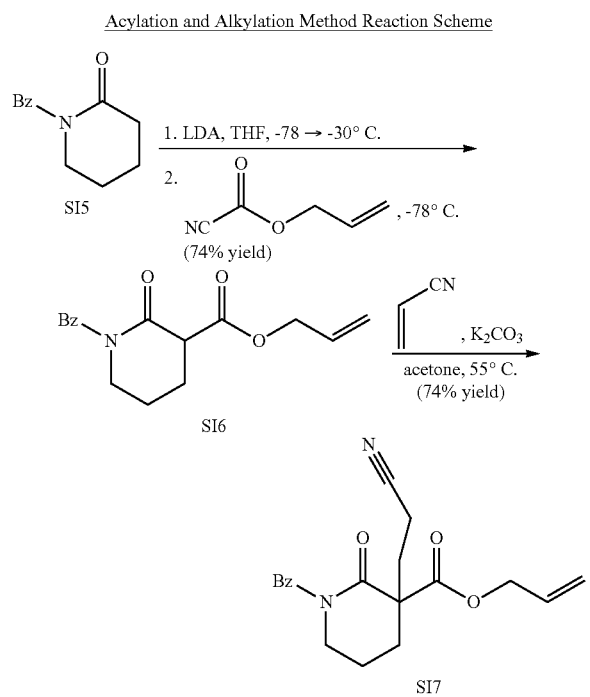

In the above Acylation and Alkylation Method Reaction Scheme, acyl lactam SI6 and benzoyl lactam SI6 were prepared according to the following procedures. Also, although the final reaction depicted in the Acylation and Alkylation Method Reaction Scheme describes the reaction used to form benzoyl lactam SI7, analogous reactions can be used to form substrates for certain of the remaining compounds depicted in Table 1 above. as also described below. Additionally, some of the substrates were formed using the diallyl malonate method described above, as described below.

Acyl Lactam SI6: To a cooled (0° C.) solution of diisopropylamine (3.33 mL, 23.6 mmol, 1.20 equiv) in THF (131 mL) was added a solution of n-BuLi (8.84 mL, 21.7 mmol, 2.45 M in hexanes, 1.10 equiv) dropwise over 10 min. After 30 min at 0° C., the reaction mixture was cooled to −78° C. A solution of benzoyl lactam SI5[7] (4.00 g, 19.7 mmol, 1.00 equiv) in THF (25 mL) was added dropwise over 10 min. After an additional 2 h, the reaction mixture was warmed to −30° C. for 1 h, cooled to −78° C., and treated with allyl cyanoformate (2.41 g, 21.7 mmol, 1.10 equiv). The reaction mixture was maintained at −78° C. for 2 h, allowed to warm to ambient temperature with stirring over 14 h, and diluted with half-saturated brine (100 mL) and EtOAc (100 mL). The phases were separated, and the aqueous phase was extracted with EtOAc (4×100 mL). The combined organic phases were washed with brine (2×100 mL), dried over $Na_2SO_4$, filtered, and concentrated under reduced pressure. The resulting oil was purified by flash chromatography (5×30 cm $SiO_2$, 15 to 30% EtOAc in hexanes) to afford acyl lactam SI6 as a colorless oil (4.18 g, 74% yield). $R_f$=0.43 (35% EtOAc in hexanes); $^1$H NMR (500 MHz, $CDCl_3$) δ 7.75-7.62 (m, 2H), 7.52-7.43 (m, 1H), 7.42-7.33 (m, 2H), 5.95 (ddt, J=17.2, 10.4, 5.9 Hz, 1H), 5.37 (dq, J=17.2, 1.5 Hz, 1H), 5.29 (dq, J=10.4, 1.2 Hz, 1H), 4.75-4.60 (m, 2H), 3.95-3.72 (m, 2H), 3.59 (t, J=6.4 Hz, 1H), 2.42-2.25 (m, 1H), 2.26-2.14 (m, 1H), 2.12-2.03 (m, 1H), 2.01-1.89 (m, 1H); $^{13}$C NMR (126 MHz, $CDCl_3$) δ 174.5, 169.5, 169.2, 135.4, 131.9, 131.4, 128.2, 128.1, 119.3, 66.4, 51.1, 46.3, 25.5, 20.7; IR (Neat Film NaCl) 3063, 2952, 1738, 1682, 1449, 1284, 1152, 730, 700 cm$^{-1}$; HRMS (MM: ESI-APCI) m/z calc'd for $C_{16}H_{18}NO_4$ [M+H]$^+$: 288.1230, found 288.1221.

Benzoyl Lactam SI7: To a mixture of acyl lactam SI6 (750 mg, 2.61 mmol, 1.00 equiv) $K_2CO_3$ (1.80 g, 13.1 mmol, 5.00 equiv) in acetone (10.5 mL) was added acrylonitrile (344 μL, 5.22 mmol, 2.00 equiv). The reaction mixture was heated (55° C.) for 6 h, then cooled to ambient temperature and filtered. The retentate was washed with acetone (2×10 mL). The combined organic phases were concentrated under reduced pressure. The resulting oil was purified by flash chromatography (3×30 cm $SiO_2$, 5 to 30% EtOAc in hexanes) to afford benzoyl lactam SI7 as a colorless oil (654 mg, 74% yield). $R_f$=0.23 (20% EtOAc in hexanes developed twice); $^1$H NMR (500 MHz, $CDCl_3$) δ 7.77-7.66 (m, 2H), 7.56-7.45 (m, 1H), 7.43-7.34 (m, 2H), 6.00 (ddt, J=17.2, 10.3, 6.2 Hz, 1H), 5.44 (dq, J=17.1, 1.3 Hz, 1H), 5.38 (dq, J=10.3, 1.1 Hz, 1H), 4.77 (ddt, J=6.1, 3.1, 1.2 Hz, 2H), 3.85 (ddd, J=13.0, 9.6, 5.4 Hz, 1H), 3.76 (ddt, J=13.0, 4.9, 1.4 Hz, 1H), 2.61 (ddd, J=17.0, 8.4, 6.9 Hz, 1H), 2.53-2.35 (m, 2H), 2.22 (ddd, J=8.8, 6.7, 1.6 Hz, 2H), 2.12-1.95 (m, 2H), 1.89 (ddd, J=13.6, 10.1, 5.3 Hz, 1H); $^{13}$C NMR (126 MHz, $CDCl_3$) δ 174.6, 171.2, 170.6, 135.4, 132.0, 130.8, 128.2, 128.1, 120.5, 119.1, 67.0, 55.4, 46.4, 31.7, 31.5, 20.0, 13.5; IR (Neat Film NaCl) 3067, 2952, 2248, 1733, 1683, 1449, 1271, 1196, 1175, 1152, 943, 725 cm$^{-1}$; HRMS (MM: ESI-APCI) m/z calc'd for $C_{19}H_{21}N_2O_4$ [M+H]$^+$: 341.1496, found 341.1492.

Benzoyl Lactam SI8

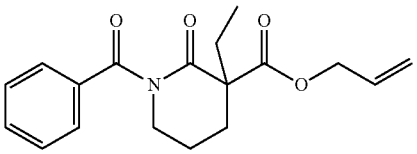 [SMILES: C=CCOC(=O)C1(CC)CCCN(C(=O)c2ccccc2)C1=O]

Benzoyl lactam SI8 was prepared by the diallyl malonate method using diallyl 2-ethylmalonate as a starting material. Benzoyl lactam SI8 was isolated by flash chromatography (SiO$_2$, 15 to 25% Et$_2$O in hexanes) as a colorless oil. R$_f$=0.38 (35% Et$_2$O in hexanes); $^1$H NMR (500 MHz, CDCl$_3$) δ 7.72-7.67 (m, 2H), 7.51-7.43 (m, 1H), 7.37 (dd, J=8.3, 7.1 Hz, 2H), 5.99 (ddt, J=17.3, 10.4, 5.9 Hz, 1H), 5.40 (dq, J=17.2, 1.4 Hz, 1H), 5.33 (dq, J=10.4, 1.2 Hz, 1H), 4.73 (dt, J=6.0, 1.3 Hz, 2H), 3.93-3.63 (m, 2H), 2.43 (ddt, J=13.7, 4.4, 1.4 Hz, 1H), 2.17-1.65 (m, 5H), 0.91 (t, J=7.4 Hz, 3H); $^{13}$C NMR (126 MHz, CDCl$_3$) δ 175.0, 172.0, 171.8, 135.9, 131.6, 131.4, 128.0 (2C), 119.5, 66.4, 56.9, 46.4, 29.8, 28.6, 20.3, 9.0; IR (Neat Film NaCl) 3062, 2943, 2882, 1732, 1678, 1449, 1385, 1268, 1188, 1137, 980, 937, 723, 693, 660 cm$^{-1}$; HRMS (MM: ESI-APCI) m/z calc'd for C$_{18}$H$_{22}$NO$_4$ [M+H]$^+$: 316.1543, found 316.1545.

Benzoyl Lactam SI9

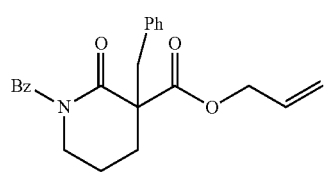

Benzoyl lactam SI9 was prepared by the diallyl malonate method using diallyl 2-benzylmalonate as a starting material. Benzoyl lactam SI9 was isolated by flash chromatography (SiO$_2$, 15 to 35% Et$_2$O in hexanes) as a colorless oil. R$_f$=0.32 (35% Et$_2$O in hexanes); $^1$H NMR (500 MHz, CDCl$_3$) δ 7.72 (dt, J=8.2, 0.9 Hz, 2H), 7.56-7.45 (m, 1H), 7.45-7.35 (m, 2H), 7.30-7.18 (m, 3H), 7.17-7.10 (m, 2H), 6.00 (ddt, J=17.2, 10.4, 6.0 Hz, 1H), 5.43 (dq, J=17.2, 1.4 Hz, 1H), 5.36 (dq, J=10.4, 1.1 Hz, 1H), 4.75 (dq, J=6.1, 1.1 Hz, 2H), 3.70 (dddd, J=12.9, 5.0, 4.3, 1.7 Hz, 1H), 3.59 (ddd, J=12.9, 10.5, 4.6 Hz, 1H), 3.47 (d, J=13.7 Hz, 1H), 3.14 (d, J=13.7 Hz, 1H), 2.36 (ddt, J=13.7, 4.3, 1.7 Hz, 1H), 2.07-1.92 (m, 1H), 1.91-1.75 (m, 2H); $^{13}$C NMR (126 MHz, CDCl$_3$) δ 175.0, 171.5, 171.3, 135.9, 135.7, 131.8, 131.2, 130.9, 128.3, 128.2, 128.0, 127.0, 119.8, 66.7, 57.8, 46.2, 40.6, 29.8, 20.1; IR (Neat Film NaCl) 3062, 3029, 2941, 2890, 1731, 1701, 1682, 1449, 1273, 1190, 1147, 934, 723, 702, 661 cm$^{-1}$; HRMS (MM: ESI-APCI) m/z calc'd for C$_{23}$H$_{24}$NO$_4$ [M+H]$^+$: 378.1700, found 378.1706.

Benzoyl Lactam SI10

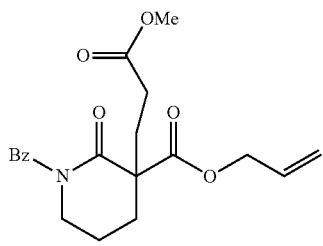

Benzoyl lactam SI10 was prepared by the acylation and alkylation method using methyl acrylate as an alkylating reagent. Benzoyl lactam SI10 was isolated by flash chromatography (SiO$_2$, 40 to 50% Et$_2$O in hexanes) as a colorless oil. R$_f$=0.28 (35% Et$_2$O in hexanes); $^1$H NMR (500 MHz, CDCl$_3$) δ 7.78-7.66 (m, 2H), 7.52-7.42 (m, 1H), 7.38 (t, J=7.7 Hz, 2H), 6.04-5.93 (m, 1H), 5.41 (dq, J=17.1, 1.1 Hz, 1H), 5.35 (dt, J=10.4, 1.0 Hz, 1H), 4.79-4.68 (m, 2H), 3.88-3.79 (m, 1H), 3.79-3.72 (m, 1H), 3.63 (s, 3H), 2.56-2.41 (m, 2H), 2.40-2.28 (m, 1H), 2.27-2.18 (m, 2H), 2.08-1.92 (m, 2H), 1.85 (ddd, J=15.2, 9.8, 5.7 Hz, 1H); $^{13}$C NMR (126 MHz, CDCl$_3$) δ 174.8, 173.1, 171.6, 171.3, 135.7, 131.7, 131.1, 128.0 (2C), 119.9, 66.6, 55.8, 51.7, 46.4, 31.0, 30.5, 29.7, 20.1; IR (Neat Film NaCl) 2952, 1735, 1685, 1449, 1273, 1194, 1174, 726 cm$^{-1}$; HRMS (MM: ESI-APCI) m/z calc'd for C$_{20}$H$_{24}$NO$_6$ [M+H]$^+$: 374.1598, found 374.1592.

Benzoyl Lactam SI11

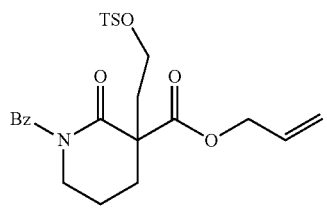

Benzoyl lactam SI11 was prepared the acylation and alkylation method, above, using (2-bromoethoxy)-tert-butyldimethylsilane as an alkylating reagent. Benzoyl lactam SI11 was isolated by flash chromatography (SiO$_2$, 10 to 40% Et$_2$O in hexanes) as a colorless oil. R$_f$=0.18 (10% Et$_2$O in hexanes); $^1$H NMR (500 MHz, CDCl$_3$) δ 7.74-7.62 (m, 2H), 7.52-7.42 (m, 1H), 7.40-7.30 (m, 2H), 5.98 (ddt, J=17.1, 10.4, 6.0 Hz, 1H), 5.40 (dq, J=17.2, 1.4 Hz, 1H), 5.33 (dq, J=10.4, 1.2 Hz, 1H), 4.72 (dt, J=6.0, 1.3 Hz, 2H), 3.80 (ddt, J=6.4, 4.8, 2.4 Hz, 2H), 3.72 (td, J=6.4, 0.8 Hz, 2H), 2.55-2.31 (m, 1H), 2.23 (dt, J=14.1, 6.6 Hz, 1H), 2.16-2.03 (m, 2H), 2.02-1.92 (m, 2H), 0.86 (s, 9H), 0.01 (s, 3H), 0.00 (s, 3H); $^{13}$C NMR (126 MHz, CDCl$_3$) δ 175.0, 171.7 (2C), 136.0, 131.6, 131.4, 128.0 (2C), 119.6, 66.5, 59.5, 55.3, 46.4, 37.8, 30.6, 25.9, 20.3, 18.2, −5.45, −5.47; IR (Neat Film NaCl) 2954, 2929, 2884, 2856, 1735, 1703, 1683, 1276, 1255, 1143, 1092, 836 cm$^{-1}$; HRMS (MM: ESI-APCI) m/z calc'd for C$_{24}$H$_{36}$NO$_5$Si [M+H]$^+$: 446.2357, found 446.2361.

Benzoyl Lactam SI12

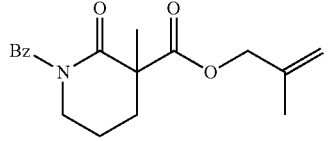

Benzoyl lactam SI12 was prepared by the diallyl malonate using dimethallyl malonate as a starting material. Benzoyl lactam SI12 was isolated by flash chromatography (SiO$_2$, 14 to 20% Et$_2$O in hexanes) as an amorphous white solid. R$_f$=0.47 (25% EtOAc in hexanes); $^1$H NMR δ 7.73-7.68 (m, 2H), 7.49-7.44 (m, 1H), 7.37 (ddd, J=8.1, 6.7, 1.2 Hz, 2H), 5.05 (s, 1H), 5.01 (s, 1H), 4.65 (dd, J=17.5, 10.0 Hz, 2H), 3.87 (ddd, J=12.9, 8.8, 5.6 Hz, 1H), 3.80 (ddt, J=12.9, 5.2, 1.4 Hz, 1H), 2.55-2.46 (m, 1H), 2.08-1.95 (m, 2H), 1.86-1.79 (m, 1H), 1.79 (s, 3H), 1.50 (s, 3H); $^{13}$C NMR (126 MHz, CDCl$_3$) δ 174.9, 172.8, 172.5, 139.3, 135.9, 131.6, 128.0 (2C), 114.2, 69.1, 53.0, 46.8, 33.8, 22.5, 20.3, 19.6; IR (Neat Film NaCl) 2941, 2873, 1735, 1682, 1449, 1276, Benzoyl Lactam SI13

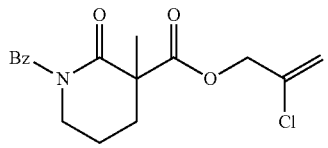

Benzoyl lactam SI13 was prepared by the diallyl malonate method using di-2-chloroallyl malonate as a starting material. Benzoyl lactam SI13 was isolated by flash chromatography (SiO$_2$, 14 to 20% Et$_2$O in hexanes) as a colorless oil. R$_f$=0.47 (25% EtOAc in hexanes); $^1$H NMR (500 MHz, CDCl$_3$) δ 7.76-7.64 (m, 2H), 7.56-7.41 (m, 1H), 7.43-7.31 (m, 2H), 5.54 (dt, J=2.0, 1.1 Hz, 1H), 5.48 (d, J=1.8 Hz, 1H), 4.80 (qd, J=13.4, 1.0 Hz, 2H), 3.89 (ddd, J=12.9, 8.9, 5.1 Hz, 1H), 3.80 (ddt, J=13.0, 5.3, 1.3 Hz, 1H), 2.52 (dddd, J=13.8, 5.6, 4.1, 1.3 Hz, 1H), 2.11-1.94 (m, 2H), 1.85 (ddd, J=13.8, 10.2, 4.5 Hz, 1H), 1.53 (s, 3H); $^{13}$C NMR (126 MHz, CDCl$_3$) δ 174.9, 172.5, 172.1, 135.8, 135.3, 131.7, 128.1, 128.0, 116.4, 67.1, 52.9, 46.7, 33.7, 22.5, 20.1; IR (Neat Film NaCl) 2943, 2873, 1740, 1682, 1449, 1390, 1276, 1192, 1124, 1061, 943, 724, 695 cm$^{-1}$; HRMS (MM: ESI-APCI) m/z calc'd for C$_{17}$H$_{18}$NO$_4$ClNa [M+Na]$^+$: 358.0817 found 358.0819.

Benzoyl Lactam SI14

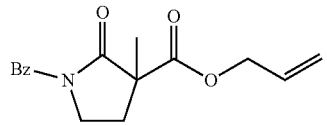

Benzoyl lactam SI14 was prepared by the acylation and alkylation method using N-benzoyl pyrrolidinone as a starting material and methyl iodide as an alkylating reagent. See Amat, et al., "Enantioselective Synthesis of 3,3-Disubstituted Piperidine Derivatives by Enolate Dialkylation of Phenylglycinol-derived Oxazolopiperidone Lactams,"*J. Org. Chem.* 72, 4431-4439 (2007), the entire content of which is incorporated herein by reference. Benzoyl lactam SI14 was isolated by flash chromatography (SiO$_2$, 5 to 20% EtOAc in hexanes) as a colorless oil. R$_f$=0.45 (35% EtOAc in hexanes); $^1$H NMR (500 MHz, CDCl$_3$) δ 7.64-7.55 (m, 2H), 7.56-7.46 (m, 1H), 7.45-7.35 (m, 2H), 5.92 (ddt, J=17.2, 10.5, 5.7 Hz, 1H), 5.34 (dq, J=17.2, 1.5 Hz, 1H), 5.28 (dq, J=10.4, 1.2 Hz, 1H), 4.67 (dt, J=5.7, 1.4 Hz, 2H), 4.02 (ddd, J=11.3, 8.4, 4.6 Hz, 1H), 3.95 (dt, J=11.3, 7.7 Hz, 1H), 2.64 (ddd, J=13.2, 7.7, 4.5 Hz, 1H), 2.06 (ddd, J=13.2, 8.5, 7.6 Hz, 1H), 1.51 (s, 3H); $^{13}$C NMR (126 MHz, CDCl$_3$) δ 173.0, 170.9, 170.5, 133.9, 132.0, 131.2, 128.8, 127.8, 119.0, 66.4, 53.8, 43.3, 30.5, 20.0; IR (Neat Film NaCl) 2985, 2938, 1750, 1738, 1733, 1683, 1449, 1362, 1307, 1247, 1196, 1136, 972, 937, 860, 730, 699, 656 cm$^{-1}$; HRMS (MM: ESI-APCI) m/z calc'd for C$_{16}$H$_{18}$NO$_4$ [M+H]$^+$: 288.1230, found 288.1228.

Benzoyl Lactam SI15

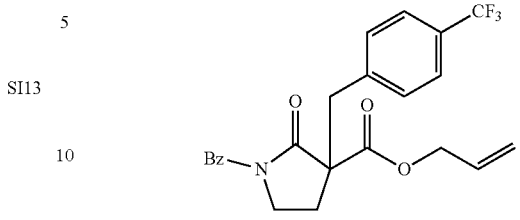

Benzoyl lactam SI15 was prepared by the acylation and alkylation method using N-benzoyl pyrrolidinone as a starting material and 4-(trifluoromethyl)benzyl bromide as an alkylating reagent. See Enders, et al., "Asymmetric Electrophilic Substitutions at the α-Position of γ- and δ-Lactams," *Eur. J. Org. Chem.* 4463-4477 (2011), the entire content of which is incorporated herein by reference. Benzoyl lactam SI15 was isolated by flash chromatography (SiO$_2$, 10 to 20% EtOAc in hexanes) as a colorless oil. R$_f$=0.28 (20% EtOAc in hexanes); $^1$H NMR (500 MHz, CDCl$_3$) δ 7.58 (d, J=7.9 Hz, 2H), 7.56-7.49 (m, 3H), 7.44-7.38 (m, 2H), 7.35 (d, J=7.9 Hz, 2H), 5.92 (ddt, J=17.3, 10.4, 5.8 Hz, 1H), 5.36 (dq, J=17.2, 1.4 Hz, 1H), 5.30 (dq, J=10.5, 1.2 Hz, 1H), 4.70 (dq, J=5.8, 1.2 Hz, 2H), 3.84 (ddd, J=11.2, 8.6, 7.6 Hz, 1H), 3.66 (ddd, J=11.2, 8.8, 3.2 Hz, 1H), 3.39 (d, J=14.0 Hz, 1H), 3.31 (d, J=13.9 Hz, 1H), 2.51 (ddd, J=13.3, 7.6, 3.3 Hz, 1H), 2.15 (dt, J=13.3, 8.7 Hz, 1H); $^{13}$C NMR (126 MHz, CDCl$_3$) δ 171.3, 170.2, 169.8, 139.7 (d, J$_{C-F}$=1.5 Hz), 133.7, 132.3, 131.0, 130.9, 129.8 (q, J$_{C-F}$=32.5 Hz), 128.9, 127.9, 125.5 (q, J$_{C-F}$=3.8 Hz), 124.0 (q, J$_{C-F}$=272.0 Hz), 119.5, 66.8, 59.0, 43.6, 38.4, 26.2; IR (Neat Film NaCl) 3062, 2938, 2913, 1751, 1733, 1683, 1449, 1366, 1326, 1294, 1250, 1193, 1165, 1116, 1068, 861, 728 cm$^{-1}$; HRMS (MM: ESI-APCI) m/z calc'd for C$_{23}$H$_{21}$NO$_4$F$_3$ [M+H]$^+$: 432.1417, found 432.1425.

Benzoyl Lactam SI16

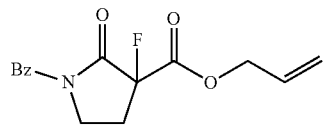

Benzoyl Lactam SI16 was prepared by the acylation and alkylation method using N-benzoyl pyrrolidinone as a starting material and using Selectfluor as a fluorinating agent. See Enders, et al., "Asymmetric Electrophilic Substitutions at the α-Position of γ- and b δ-Lactams," *Eur. J. Org. Chem.* 4463-4477 (2011); Trost, et al., "Asymmetric syntheses of oxindole and indole spirocyclic alkaloid natural products," *Synthesis* 3003-3025 (2009), the entire contents of both which is incorporated herein by reference. Benzoyl lactam SI16 was isolated by flash chromatography (SiO$_2$, 10 to 20% EtOAc in hexanes) as a colorless oil. R$_f$=0.28 (20% EtOAc in hexanes); $^1$H NMR (500 MHz, CDCl$_3$) δ 7.66-7.59 (m, 2H), 7.59-7.50 (m, 1H), 7.46-7.37 (m, 2H), 5.92 (ddt, J=17.2, 10.4, 5.8 Hz, 1H), 5.38 (dq, J=17.2, 1.4 Hz, 1H), 5.32 (dq, J=10.4, 1.1 Hz, 1H), 4.77 (dt, J=5.9, 1.3 Hz, 2H), 4.15 (ddd, J=11.2, 8.8, 4.2 Hz, 1H), 4.01 (dddd, J=11.3, 7.7, 7.0, 2.0 Hz, 1H), 2.80 (dddd, J=14.1, 13.4, 7.8, 4.2 Hz, 1H), 2.53 (dddd, J=23.0, 14.2, 8.8, 7.1 Hz, 1H); $^{13}$C NMR (126 MHz, CDCl$_3$) δ 169.8, 166.0 (d, J=10.2 Hz), 165.8 (d, J=5.5 Hz), 132.9, 132.7, 130.4, 129.0, 128.0, 120.0, 94.4 (d, J=203.6 Hz), 67.2, 42.3 (d, J=2.9 Hz), 29.0 (d, J=21.7 Hz); IR (Neat Film NaCl) 3062, 2987, 2917, 1773, 1690, 1449, 1373, 1290, 1257, 1198, 1161, 1118, 1076, 983, 942, 859, 796, 731 cm$^{-1}$; HRMS (MM: ESI-APCI) m/z calc'd for C$_{16}$H$_{19}$NO$_5$F [M+MeOH+H]$^+$: 324.1242, found 324.1244.

4-Methoxybenzoyl Lactam SI17

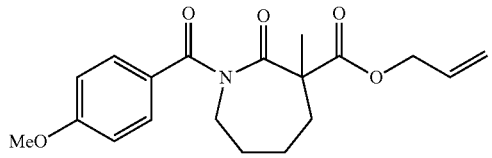

4-Methoxy benzoyl lactam SI17 was prepared by a combination of known methods and the diallyl malonate method. See Badillo, et al., "Enantioselective synthesis of oxindoles and spirooxindoles with applications in drug discovery," Curr. Opin. Drug Disc. Dev. 13, 758-776 (2010), the entire content of which is incorporated herein by reference. Benzoyl lactam SI17 was isolated by flash chromatography (SiO$_2$, 15 to 25% Et$_2$O in hexanes) as a colorless oil. R$_f$=0.38 (35% Et$_2$O in hexanes); $^1$H NMR (500 MHz, CDCl$_3$) δ 7.79-7.68 (m, 2H), 6.94-6.80 (m, 2H), 5.99 (ddt, J=17.1, 10.4, 6.1 Hz, 1H), 5.43 (dq, J=17.2, 1.4 Hz, 1H), 5.34 (dq, J=10.4, 1.1 Hz, 1H), 4.76 (dt, J=6.1, 1.2 Hz, 2H), 4.28-4.16 (m, 1H), 3.84 (s, 3H), 3.15 (ddd, J=15.6, 11.1, 1.2 Hz, 1H), 2.28-2.17 (m, 1H), 2.01-1.87 (m, 2H), 1.87-1.76 (m, 1H), 1.63 (ddd, J=14.8, 11.8, 3.7 Hz, 2H), 1.48 (s, 3H); $^{13}$C NMR (126 MHz, CDCl$_3$) δ 175.1, 174.6, 172.8, 162.6, 131.3, 130.7, 128.2, 119.9, 113.5, 66.2, 55.3, 54.9, 44.6, 34.3, 28.1, 26.9, 24.9; IR (Neat Film NaCl) 2939, 1679, 1604, 1512, 1456, 1281, 1256, 1169, 1139, 1054, 961 cm$^{-1}$; HRMS (MM: ESI-APCI) m/z calc'd for C$_{19}$H$_{24}$NO$_5$ [M+H]$^+$: 346.1649, found 346.1642.

Benzoyl Lactam SI18

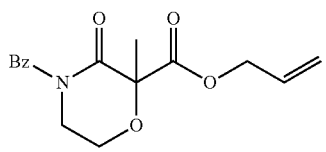

Benzoyl lactam SI8 was prepared by the acylation and alkylation method using 3-morpholinone as a starting material and methyl iodide as an alkylating reagent. See Zhou, et al., "Catalytic asymmetric synthesis of oxindoles bearing a tetrasubstituted stereocenter at the C-3 position," Adv. Synth. Catal. 1381-1407 (2010), the entire content of which is incorporated herein by reference. Benzoyl lactam SI18 was isolated by flash chromatography (SiO$_2$, 5 to 15% EtOAc in hexanes) as a colorless oil. R$_f$=0.40 (20% EtOAc in hexanes); $^1$H NMR (500 MHz, CDCl$_3$) δ 7.70-7.61 (m, 2H), 7.56-7.44 (m, 1H), 7.46-7.33 (m, 2H), 5.98 (ddt, J=17.1, 10.4, 5.9 Hz, 1H), 5.41 (dq, J=17.2, 1.4 Hz, 1H), 5.34 (dq, J=10.4, 1.1 Hz, 1H), 4.76 (dt, J=6.0, 1.3 Hz, 2H), 4.24 (ddd, J=12.4, 10.1, 3.2 Hz, 1H), 4.12 (ddd, J=12.4, 4.1, 3.3 Hz, 1H), 4.02 (ddd, J=13.2, 10.1, 4.1 Hz, 1H), 3.91 (dt, J=13.2, 3.3 Hz, 1H), 1.68 (s, 3H); $^{13}$C NMR (126 MHz, CDCl$_3$) δ 173.0, 169.0 (2C), 134.9, 132.2, 131.0, 128.3, 128.1, 119.8, 81.5, 66.8, 61.6, 45.3, 22.2; IR (Neat Film NaCl) 2943, 2892, 1749, 1689, 1149, 1375, 1311, 1281, 1246, 1124, 1080, 938, 727 cm$^{-1}$; HRMS (MM: ESI-APCI) m/z calc'd for C$_{16}$H$_{18}$NO$_5$ [M+H]$^+$: 304.1179, found 304.1171.

Benzoyl Lactam SI19

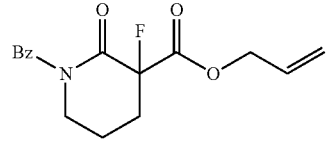

Benzoyl lactam SI19 was prepared by the acylation and alkylation method using Selectfluor as a fluorinating agent. See Amat, et al., "Enantioselective Synthesis of 3,3-Disubstituted Piperidine Derivatives by Enolate Dialkylation of Phenylglycinol-derived Oxazolopiperidone Lactams," J. Org. Chem. 72, 4431-4439 (2007), the entire content of which is incorporated herein by reference. Benzoyl lactam SI19 was isolated by flash chromatography (SiO$_2$, 20 to 35% Et$_2$O in hexanes) as a colorless oil. R$_f$=0.57 (35% Et$_2$O in hexanes developed three times); $^1$H NMR (500 MHz, CDCl$_3$) δ 7.69-7.61 (m, 2H), 7.53-7.45 (m, 1H), 7.42-7.34 (m, 2H), 5.94 (ddt, J=17.2, 10.4, 5.9 Hz, 1H), 5.39 (dq, J=17.2, 1.4 Hz, 1H), 5.31 (dq, J=10.4, 1.1 Hz, 1H), 4.76 (dt, J=6.0, 1.3 Hz, 2H), 3.98 (dddd, J=12.9, 6.0, 4.7, 1.1 Hz, 1H), 3.80 (dddd, J=14.8, 8.8, 4.4, 1.7 Hz, 1H), 2.62-2.45 (m, 1H), 2.45-2.30 (m, 1H), 2.25-2.05 (m, 2H); $^{13}$C NMR (126 MHz, CDCl$_3$) δ 173.8, 166.7 (d, J=26.0 Hz), 166.3 (d, J=23.5 Hz), 134.3, 132.3, 130.6, 128.3, 128.2, 119.9, 92.4 (d, J=194.8 Hz), 67.1, 46.2, 31.9 (d, J=22.4 Hz), 18.6 (d, J=4.0 Hz); IR (Neat Film NaCl) 3064, 2956, 1768, 1711, 1691, 1450, 1396, 1304, 1271, 1190, 1137, 1102, 994, 944, 912, 726, 694, 658 cm$^{-1}$; HRMS (MM: ESI-APCI) m/z calc'd for C$_{16}$H$_{17}$NO$_4$F [M+H]$^+$: 306.1136, found 306.1131.

Benzoyl Glutarimide SI20

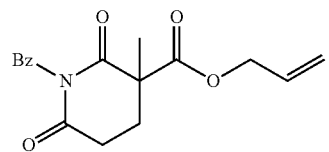

Benzoyl glutarimide SI20 was prepared from glutarimide by a combination of known methods and diallyl malonate method. See Badillo, et al., "Enantioselective synthesis of oxindoles and spirooxindoles with applications in drug discovery," Curr. Opin. Drug Disc. Dev. 13, 758-776 (2010), the entire content of which is incorporated herein by reference. Benzoyl glutarimide SI20 (32 mg, 72% yield) was isolated as a colorless oil by flash chromatography (SiO$_2$, 17 to 25% EtOAc in hexanes). R$_f$=0.18 (25% EtOAc in hexanes); $^1$H NMR (500 MHz, CDCl$_3$) δ 7.99 (d, J=8.22 Hz, 2H), 7.62 (t, J=7.46 Hz, 1H), 7.46 (dd, J=8.22, 7.46 Hz, 2H), 5.93 (ddt, J=17.2, 10.4, 6.0 Hz, 1H), 5.39 (dq, J=17.2, 1.20 Hz, 1H), 5.32 (dq, J=10.4, 1.20 Hz, 1H), 4.75 (ddt, J=12.9, 6.0, 1.20 Hz, 1H), 4.71 (ddt, J=12.9, 6.0, 1.20 Hz, 1H), 2.81-2.70 (m, 2H), 2.40 (ddd, J=14.2, 5.13, 3.56 Hz, 1H), 2.10 (ddd, J=14.2, 11.7, 6.36 Hz, 1H), 1.59 (s, 3H); $^{13}$C NMR (126 MHz, CDCl$_3$) δ 171.1, 170.8, 170.7, 170.4, 134.9, 131.6, 130.8, 130.3, 129.0, 120.0, 66.9, 51.0, 30.0, 29.1, 20.8; IR (Neat Film NaCl) 3070, 2943, 2878, 1755, 1716, 1689, 1450, 1240, 1179, 975, 781 cm$^{-1}$; HRMS (MM: ESI-APCI) m/z calc'd for $C_{17}H_{18}NO_5$ [M+H]$^+$: 316.1179, found 316.1192.

Benzoyl Glutarimide SI21

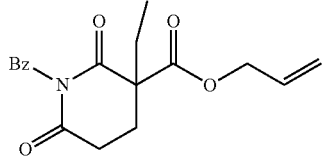

Benzoyl glutarimide SI121 was prepared from glutarimide by a combination of known methods and the diallyl malonate method. See Badillo, et al., "Enantioselective synthesis of oxindoles and spirooxindoles with applications in drug discovery," Curr. Opin. Drug Disc. Dev. 13, 758-776 (2010), the entire content of which is incorporated herein by reference. Benzoyl glutarimide SI21 (67 mg, 85% yield) was isolated as a colorless oil by flash chromatography (SiO$_2$, 17 to 25% EtOAc in hexanes). $R_f$=0.24 (25% EtOAc in hexanes); $^1$H NMR (500 MHz, CDCl$_3$) δ 7.95 (d, J=8.28 Hz, 2H), 7.62 (t, J=7.46 Hz, 1H), 7.46 (dd, J=8.28, 7.46 Hz, 2H), 5.93 (ddt, J=17.0, 10.4, 6.0 Hz, 1H), 5.39 (dq, J=17.0, 1.2 Hz, 1H), 5.32 (dq, J=10.4, 1.2 Hz, 1H), 4.77 (ddt, J=12.9, 6.0, 1.2 Hz, 1H), 4.74 (ddt, J=12.9, 6.0, 1.2 Hz, 1H), 2.84-2.72 (m, 2H), 2.34 (ddd, J=14.1, 5.2, 3.28 Hz, 1H), 2.19 (ddd, J=14.1, 12.2, 5.88 Hz, 1H), 2.15-2.02 (m, 2H), 1.01 (t, J=7.44 Hz, 3H); $^{13}$C NMR (126 MHz, CDCl$_3$) δ 171.1, 170.4, 170.2, 170.1, 134.9, 131.6, 130.8, 130.3, 129.0, 120.0, 66.8, 55.1, 29.9, 27.6, 25.6, 8.9; IR (Neat Film NaCl) 3068, 2975, 2884, 1755, 1716, 1694, 1450, 1270, 1180, 950, 779 cm$^{-1}$; HRMS (MM: ESI-APCI) m/z calc'd for $C_{18}H_{20}NO_5$ [M+H]$^+$: 330.1336, found 330.1334.

Acetyl Lactam SI22

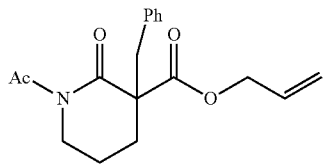

Acetyl lactam SI22 was prepared the diallyl malonate method using diallyl 2-benzylmalonate as a starting material and acetic anhydride as an acetylating reagent. Acetyl lactam SI22 was isolated by flash chromatography (SiO$_2$, 5 to 20% EtOAc in hexanes) as a colorless oil. $R_f$=0.46 (20% EtOAc in hexanes); $^1$H NMR (500 MHz, CDCl$_3$) δ 7.30-7.20 (m, 3H), 7.20-7.14 (m, 2H), 5.88 (ddt, J=17.2, 10.4, 5.8 Hz, 1H), 5.33 (dq, J=17.2, 1.5 Hz, 1H), 5.27 (dq, J=10.4, 1.2 Hz, 1H), 4.65 (dq, J=5.8, 1.4 Hz, 2H), 3.73-3.62 (m, 1H), 3.53 (d, J=13.6 Hz, 1H), 3.35 (ddd, J=13.8, 9.1, 4.8 Hz, 1H), 3.16 (d, J=13.6 Hz, 1H), 2.52 (s, 3H), 2.29-2.19 (m, 1H), 1.89-1.71 (m, 2H), 1.70-1.56 (m, 1H); $^{13}$C NMR (126 MHz, CDCl$_3$) δ 173.9, 172.3, 171.6, 135.8, 131.2, 130.6, 128.3, 127.1, 119.3, 66.4, 58.1, 43.6, 41.2, 29.4, 27.2, 19.8; IR (Neat Film NaCl) 3063, 3029, 2942, 1733, 1699, 1496, 1455, 1368, 1296, 1234, 1177, 1116, 1034, 992, 975, 934, 746, 703 cm$^{-1}$; HRMS (MM: ESI-APCI) m/z calc'd for $C_{18}H_{22}NO_4$ [M+H]$^+$: 316.1543, found 316.1541.

Phenyl Carbamate Lactam SI23

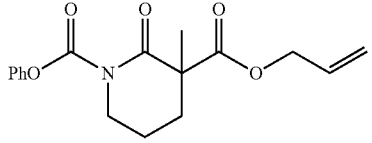

Phenyl carbamate lactam SI23 was prepared in a manner analogous to the tosyl lactam of Compound 1a using lactam SI4 and phenyl chloroformate. Phenyl carbamate lactam SI23 was isolated by flash chromatography (SiO$_2$, 5 to 20% EtOAc in hexanes) as a colorless oil. $R_f$=0.42 (50% EtOAc in hexanes); $^1$H NMR (500 MHz, CDCl$_3$) δ 7.40-7.35 (m, 2H), 7.26-7.21 (m, 1H), 7.20-7.16 (m, 2H), 5.91 (ddt, J=17.2, 10.4, 5.6 Hz, 1H), 5.36 (dq, J=17.2, 1.5 Hz, 1H), 5.26 (dq, J=10.5, 1.3 Hz, 1H), 4.77-4.59 (m, 2H), 3.90 (ddd, J=12.9, 7.6, 5.3 Hz, 1H), 3.85-3.74 (m, 1H), 2.47 (dddd, J=13.8, 6.2, 5.0, 1.0 Hz, 1H), 2.06-1.86 (m, 2H), 1.80 (ddd, J=14.2, 9.3, 5.0 Hz, 1H), 1.56 (s, 3H); $^{13}$C NMR (126 MHz, CDCl$_3$) δ 172.1, 171.2, 153.3, 150.8, 131.3, 129.4, 126.0, 121.4, 118.8, 66.2, 53.4, 46.8, 32.7, 22.7, 20.1; IR (Neat Film NaCl) 2943, 1786, 1732, 1494, 1457, 1297, 1267, 1204, 1161, 1134, 982, 943, 752, 689, 665 cm$^{-1}$; HRMS (MM: ESI-APCI) m/z calc'd for $C_{17}H_{20}NO_5$ [M+H]$^+$: 318.1336, found 318.1332.

Benzyl Carbamate Lactam SI24

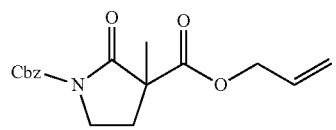

Benzyl carbamate lactam SI24 was prepared by the acylation and alkylation method using N-benzyloxycarbonylpyrrolidin-2-one as a starting material and methyl iodide as an alkylating reagent. See Ohmatsu, et al., "Chiral 1,2,3-triazoliums as New Cationic Organic Catalysts with Anion-Recognition Ability: Application to Asymmetric Alkylation of Oxindoles," J. Am. Chem. Soc. 133, 1307-1309 (2011), the entire content of which is incorporated herein by reference. Cbz lactam SI24 was isolated by flash chromatography (SiO$_2$, 5 to 15% EtOAc in hexanes) as a colorless oil. $R_f$=0.40 (20% EtOAc in hexanes); $^1$H NMR (500 MHz, CDCl$_3$) δ 7.46-7.40 (m, 2H), 7.40-7.28 (m, 3H), 5.87 (ddt, J=17.1, 10.4, 5.6 Hz, 1H), 5.30 (dq, J=17.2, 1.5 Hz, 1H) 5.30 (s, 2H), 5.23 (dq, J=10.5, 1.2 Hz, 1H), 4.69-4.55 (m, 2H), 3.82 (ddq, J=10.7, 8.4, 5.8 Hz, 2H), 2.54 (ddd, J=13.1, 7.4, 4.2 Hz, 1H), 1.93 (dt, J=13.2, 8.3 Hz, 1H), 1.50 (s, 3H); $^{13}$C NMR (126 MHz, CDCl$_3$) δ 171.9, 170.7, 151.4, 135.1, 131.3, 128.6, 128.4, 128.1, 118.8, 68.3, 66.3, 53.3, 43.7, 30.5, 20.2; IR (Neat Film NaCl) 2984, 2939, 1793, 1758, 1725, 1456, 1383, 1300, 1202, 1138, 1009, 983, 774, 739, 698 cm$^{-1}$; HRMS (MM: ESI-APCI) m/z calc'd for $C_{17}H_{20}NO_5$ [M+H]$^+$: 318.1336, found 318.1136.

4-Phenylbenzoyl Lactam SI25

2-Naphthoyl Lactam SI27

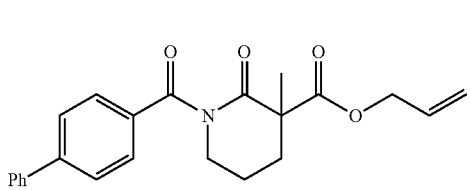

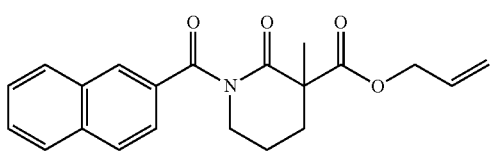

4-phenylbenzoyl lactam SI25 was prepared the diallyl malonate method using lactam SI4 and 4-phenylbenzoyl chloride. 4-Phenylbenzoyl lactam SI25 was isolated by flash chromatography (SiO$_2$, 5 to 15% EtOAc in hexanes) as an off-white solid. R$_f$=0.27 (20% EtOAc in hexanes); $^1$H NMR (500 MHz, CDCl$_3$) δ 7.84-7.77 (m, 2H), 7.65-7.54 (m, 4H), 7.49-7.40 (m, 2H), 7.40-7.34 (m, 1H), 6.00 (ddt, J=17.2, 10.4, 5.9 Hz, 1H), 5.41 (dq, J=17.2, 1.5 Hz, 1H), 5.34 (dq, J=10.4, 1.2 Hz, 1H), 4.75 (dt, J=5.9, 1.3 Hz, 2H), 3.95-3.84 (m, 1H), 3.81 (ddt, J=12.9, 5.1, 1.4 Hz, 1H), 2.52 (dddd, J=13.8, 5.7, 4.3, 1.4 Hz, 1H), 2.10-1.94 (m, 2H), 1.90-1.76 (m, 1H), 1.52 (s, 3H); $^{13}$C NMR (126 MHz, CDCl$_3$) δ 174.7, 172.9, 172.5, 144.5, 140.3, 134.5, 131.4, 128.8, 128.7, 127.8, 127.3, 126.8, 119.5, 66.5, 52.9, 46.89, 33.8, 22.5, 20.3; IR (Neat Film NaCl) 3030, 2942, 2874, 1733, 1679, 1607, 1486, 1449, 1389, 1278, 1191, 1139, 939, 749, 698 cm$^{-1}$; HRMS (MM: ESI-APCI) m/z calc'd for C$_{23}$H$_{24}$NO$_4$ [M+H]$^+$: 378.1700, found 378.1708.

1-Naphthoyl Lactam SI26

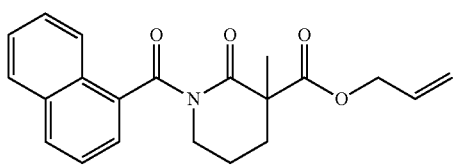

1-naphthoyl lactam SI26 was prepared by the diallyl malonate method using lactam SI4 and 1-naphthoyl chloride. 1-Naphthoyl lactam SI26 was isolated by flash chromatography (SiO$_2$, 10 to 20% EtOAc in hexanes) as a colorless oil. R$_f$=0.50 (35% EtOAc in hexanes); $^1$H NMR (500 MHz, CDCl$_3$) δ 8.07-8.01 (m, 1H), 7.90 (dd, J=8.2, 1.4 Hz, 1H), 7.88-7.83 (m, 1H), 7.57-7.47 (m, 3H), 7.42 (td, J=7.6, 7.0, 1.2 Hz, 1H), 5.99-5.86 (m, 1H), 5.35 (dq, J=17.3, 1.3 Hz, 1H), 5.30 (dq, J=10.6, 1.0 Hz, 1H), 4.66 (ddt, J=5.4, 4.2, 1.3 Hz, 2H), 4.13-3.91 (m, 2H), 2.49 (ddd, J=13.6, 6.1, 4.5 Hz, 1H), 2.14-1.97 (m, 2H), 1.83 (ddd, J=14.3, 9.9, 4.6 Hz, 1H), 1.42 (s, 3H); $^{13}$C NMR (126 MHz, CDCl$_3$) δ 173.8, 172.4, 172.1, 134.9, 133.6, 131.3, 130.3, 129.8, 128.4, 127.0, 126.1, 124.9, 124.4, 123.9, 119.3, 66.3, 52.9, 45.7, 33.4, 22.4, 20.1; IR (Neat Film NaCl) 3050, 2984, 2942, 1737, 1704, 1682, 1509, 1456, 1387, 1290, 1254, 1194, 1144, 1130, 935, 806, 783 cm$^{-1}$; HRMS (MM: ESI-APCI) m/z calc'd for C$_{21}$H$_{22}$NO$_4$ [M+H]$^+$: 352.1543, found 352.1542.

2-naphthoyl lactam SI27 was prepared by the diallyl malonate method using lactam SI4 and 2-naphthoyl chloride. 2-Naphthoyl lactam SI27 was isolated by flash chromatography (SiO$_2$, 20 to 33% Et$_2$O in hexanes) as a colorless oil. R$_f$=0.25 (35% Et$_2$O in hexanes); $^1$H NMR (500 MHz, CDCl$_3$) δ 8.30 (t, J=1.2 Hz, 1H), 7.90 (dd, J=8.1, 1.4 Hz, 1H), 7.85-7.79 (m, 2H), 7.76 (dd, J=8.6, 1.7 Hz, 1H), 7.54 (ddd, J=8.1, 6.8, 1.4 Hz, 1H), 7.50 (ddd, J=8.1, 6.9, 1.4 Hz, 1H), 6.01 (ddt, J=17.2, 10.4, 5.8 Hz, 1H), 5.42 (dq, J=17.2, 1.4 Hz, 1H), 5.34 (dq, J=10.4, 1.1 Hz, 1H), 4.77 (dt, J=5.9, 1.3 Hz, 2H), 3.93 (ddd, J=12.8, 8.9, 5.3 Hz, 1H), 3.85 (ddt, J=12.9, 5.1, 1.3 Hz, 1H), 2.52 (dddd, J=13.8, 5.6, 4.2, 1.3 Hz, 1H), 2.12-1.93 (m, 2H), 1.84 (ddd, J=13.7, 10.2, 4.7 Hz, 1H), 1.51 (s, 3H); $^{13}$C NMR (126 MHz, CDCl$_3$) δ 174.9, 172.8, 172.5, 134.8, 133.2, 132.5, 131.4, 129.2, 129.0, 127.7 (2C), 127.6, 126.3, 124.4, 119.4, 66.4, 52.9, 46.8, 33.7, 22.4, 20.2; IR (Neat Film NaCl) 3059, 2941, 2873, 1730, 1680, 1456, 1385, 1285, 1234, 1186, 1131, 936, 778, 762 cm$^{-1}$; HRMS (MM: ESI-APCI) m/z calc'd for C$_{21}$H$_{22}$NO$_4$ [M+H]$^+$: 352.1543, found 352.1530.

General Procedure for Preparative Allylic Alkylation Reactions to Form N-acyl Lactam Derivatives The N-acyl lactam substrates described above were subjected to allylic alkylation reactions to form N-acyl lactam derivative building block compounds. The general procedure for these reactions is described here.

In a nitrogen-filled glovebox, an oven-dried 20 mL vial was charged with Pd$_2$pmdba$_3$ (27.4 mg, 0.025 mmol, 0.05 equiv) or Pd$_2$dba$_3$ (22.9 mg, 0.025 mmol, 0.05 equiv), (S)—(CF$_3$)$_3$-t-BuPHOX (37.0 mg, 0.0625 mmol, 0.125 equiv), toluene (15 mL or 13 mL if the substrate is an oil), and a magnetic stir bar. See Franckevicius, et al., "Asymmetric Decarboxylative Alkylation of Oxindoles," Org. Lett. 13, 4264-4267 (2011), the entire content of which is incorporated herein by reference. The vial was stirred at ambient glovebox temperature (~28° C.) for 30 min and the substrate (0.50 mmol, 1.00 equiv) was added either as a solid or as a solution of an oil dissolved in toluene (2 mL). The vial was sealed and heated to 40° C. When complete consumption of the starting material was observed by colorimetric change (from light green to red-orange) and confirmed by thin layer chromatography on SiO$_2$, the reaction mixtures were removed from the glovebox, concentrated under reduced pressure, and purified by flash chromatography to afford the desired alkylated product.

Characterization Data for the N-acyl Lactam Derivative Building Blocks

The N-acyl lactam Derivatives were isolated as described below and characterized. The characterization data is reported below.

Benzoyl Lactam 3

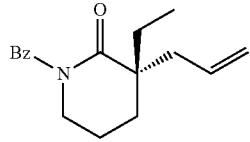

See Jakubec, et al., "Cyclic Imine Nitro-Mannich/Lactamization Cascades: A Direct Stereoselective Synthesis of Multicyclic Piperidinone Derivatives," Org. Lett. 10, 4267-4270 (2008), the entire content of which is incorporated by reference. Benzoyl lactam 3 was isolated by flash chromatography (SiO$_2$, 15 to 20% Et$_2$O in hexanes) as a colorless oil. 97.2% yield. R$_f$=0.39 (20% Et$_2$O in hexanes); $^1$H NMR (500 MHz, CDCl$_3$) δ 7.53-7.49 (m, 2H), 7.48-7.43 (m, 1H), 7.41-7.34 (m, 2H), 5.74 (dddd, J=16.7, 10.4, 7.6, 7.0 Hz, 1H), 5.19-5.02 (m, 2H), 3.84-3.70 (m, 2H), 2.51 (ddt, J=13.8, 7.0, 1.3 Hz, 1H), 2.28 (ddt, J=13.8, 7.6, 1.2 Hz, 1H), 2.06-1.91 (m, 2H), 1.91-1.74 (m, 3H), 1.74-1.63 (m, 1H), 0.91 (t, J=7.4 Hz, 3H); $^{13}$C NMR (126 MHz, CDCl$_3$) δ 178.0, 175.6, 136.7, 133.6, 131.2, 128.1, 127.4, 118.6, 47.4, 46.9, 41.3, 30.3 (2C), 19.6, 8.3; IR (Neat Film NaCl) 3072, 2970, 2941, 2880, 1678, 1448, 1384, 1283, 1147, 916, 725, 694 cm$^{-1}$; HRMS (MM: ESI-APCI) m/z calc'd for C$_{17}$H$_{22}$NO$_2$ [M+H]$^+$: 272.1645, found 272.1649; [α]$_D^{25}$ −28.6° (c 1.15, CHCl$_3$, 99% ee).

Benzoyl Lactam 4

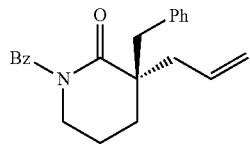

See Jakubec, et al., "Cyclic Imine Nitro-Mannich/Lactamization Cascades: A Direct Stereoselective Synthesis of Multicyclic Piperidinone Derivatives," Org. Lett. 10, 4267-4270 (2008), the entire content of which is incorporated by reference. Benzoyl lactam 4 was isolated by flash chromatography (SiO$_2$, 10% Et$_2$O in hexanes) as a white solid. 84.8% yield. R$_f$=0.48 (35% Et$_2$O in hexanes); $^1$H NMR (500 MHz, CDCl$_3$) δ 7.54 (dd, J=8.1, 1.4 Hz, 2H), 7.52-7.46 (m, 1H), 7.43-7.37 (m, 2H), 7.32-7.22 (m, 3H), 7.18-7.11 (m, 2H), 5.80 (dddd, J=16.8, 10.1, 7.6, 6.8 Hz, 1H), 5.21-5.06 (m, 2H), 3.70 (ddd, J=12.2, 7.0, 4.8 Hz, 1H), 3.63 (ddd, J=12.5, 7.7, 4.4 Hz, 1H), 3.34 (d, J=13.4 Hz, 1H), 2.73-2.64 (m, 1H), 2.68 (d, J=13.3 Hz, 1H), 2.25 (ddt, J=13.8, 7.7, 1.1 Hz, 1H), 2.03-1.91 (m, 1H), 1.91-1.83 (m, 1H), 1.81 (dd, J=6.7, 5.3 Hz, 2H); $^{13}$C NMR (126 MHz, CDCl$_3$) δ 177.4, 175.5, 136.9, 136.6, 133.2, 131.4, 130.8, 128.2, 128.1, 127.6, 126.7, 119.3, 48.8, 46.8, 43.0, 42.9, 28.9, 19.6; IR (Neat Film NaCl) 3061, 3028, 2942, 1679, 1449, 1286, 1149, 919, 724, 704, 695 cm$^{-1}$; HRMS (MM: ESI-APCI) m/z calc'd for C$_{22}$H$_{24}$NO$_2$ [M+H]$^+$: 334.1802, found 334.1800; [α]$_D^{25}$ +48.1° (c 0.825, CHCl$_3$, 99% ee).

Benzoyl Lactam 5

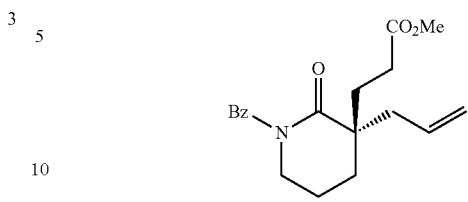

Benzoyl lactam 5 was isolated by flash chromatography (SiO$_2$, 25% Et$_2$O in hexanes) as a light yellow oil. 91.8% yield. R$_f$=0.39 (35% Et$_2$O in hexanes); $^1$H NMR (500 MHz, CDCl$_3$) δ 7.53-7.49 (m, 2H), 7.49-7.44 (m, 1H), 7.41-7.31 (m, 2H), 5.72 (ddt, J=17.4, 10.3, 7.3 Hz, 1H), 5.23-5.05 (m, 2H), 3.78 (t, J=6.0 Hz, 2H), 3.67 (s, 3H), 2.58-2.47 (m, 1H), 2.42-2.24 (m, 3H), 2.08-1.97 (m, 4H), 1.93 (ddd, J=14.0, 7.8, 4.6 Hz, 1H), 1.78 (ddd, J=13.9, 7.1, 4.9 Hz, 1H); $^{13}$C NMR (126 MHz, CDCl$_3$) δ 177.4, 175.5, 173.7, 136.5, 132.6, 131.4, 128.2, 127.4, 119.4, 51.7, 47.0, 46.6, 41.2, 32.2, 31.2, 29.0, 19.4; IR (Neat Film NaCl) 3073, 2950, 2874, 1736, 1679, 1448, 1281, 1150, 920, 727, 696, 665 cm$^{-1}$; HRMS (MM: ESI-APCI) m/z calc'd for C$_{19}$H$_{24}$NO$_4$ [M+H]$^+$: 330.1700, found 330.1704; [α]$_D^{25}$ +14.0° (c 0.72, CHCl$_3$, 99% ee).

Benzoyl Lactam 6

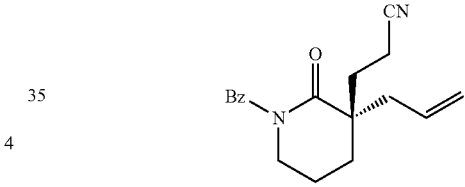

Benzoyl lactam 6 was isolated by flash chromatography (SiO$_2$, 15 to 25% EtOAc in hexanes) as a colorless oil. 88.2% yield. R$_f$=0.43 (35% EtOAc in hexanes); $^1$H NMR (500 MHz, CDCl$_3$) δ 7.52-7.47 (m, 3H), 7.41 (ddt, J=8.7, 6.6, 1.0 Hz, 2H), 5.71 (ddt, J=17.4, 10.1, 7.3 Hz, 1H), 5.28-5.15 (m, 2H), 3.88-3.79 (m, 1H), 3.76 (ddd, J=12.9, 8.7, 4.2 Hz, 1H), 2.57 (ddt, J=14.1, 7.3, 1.2 Hz, 1H), 2.44-2.29 (m, 3H), 2.13-2.04 (m, 2H), 2.03-1.89 (m, 3H), 1.87-1.78 (m, 1H); $^{13}$C NMR (126 MHz, CDCl$_3$) δ 176.8, 175.2, 136.2, 131.7, 131.5, 128.3, 127.3, 120.3, 119.5, 47.0, 46.5, 41.1, 32.7, 30.8, 19.2, 12.5; IR (Neat Film NaCl) 3074, 2945, 2876, 1678, 1448, 1389, 1282, 1151, 922, 727, 696 cm$^{-1}$; HRMS (MM: ESI-APCI) m/z calc'd for C$_{18}$H$_{21}$N$_2$O$_2$ [M+H]$^+$: 297.1598, found 297.1603; [α]$_D^{25}$ +46.9° (c 0.83, CHCl$_3$, 99% ee).

Benzoyl Lactam 7

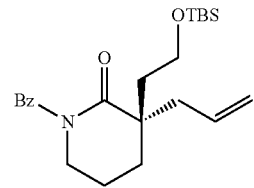

Benzoyl lactam 7 was isolated by flash chromatography (SiO$_2$, 5 to 15% Et$_2$O in hexanes) as a colorless oil. 85.4% yield. R$_f$=0.32 (10% Et$_2$O in hexanes); $^1$H NMR (500 MHz, CDCl$_3$) δ 7.54-7.48 (m, 2H), 7.48-7.42 (m, 1H), 7.41-7.33 (m, 2H), 5.76 (ddt, J=17.3, 10.2, 7.3 Hz, 1H), 5.18-5.06 (m, 2H), 3.81-3.75 (m, 2H), 3.75-3.64 (m, 2H), 2.55 (ddt, J=13.8, 7.1, 1.2 Hz, 1H), 2.33 (ddt, J=13.8, 7.5, 1.1 Hz, 1H), 2.10-1.94 (m, 4H), 1.94-1.85 (m, 1H), 1.81 (ddd, J=13.9, 7.3, 5.6 Hz, 1H), 0.88 (s, 9H), 0.04 (s, 6H); $^{13}$C NMR (126 MHz, CDCl$_3$) δ 177.6, 175.5, 136.8, 133.4, 131.2, 128.1, 127.4, 118.9, 59.2, 46.9, 46.3, 42.2, 39.7, 30.8, 25.9, 19.6, 18.2, −5.4; IR (Neat Film NaCl) 2953, 2928, 2884, 2856, 1681, 1280, 1257, 1151, 1093, 836, 776, 725, 694 cm$^{-1}$; HRMS (MM: ESI-APCI) m/z calc'd for C$_{23}$H$_{36}$NO$_3$Si [M+H]$^+$: 402.2459, found 402.2467; [α]$_D^{25}$ −3.71° (c 1.40, CHCl$_3$, 96% ee).

Benzoyl Lactam 8

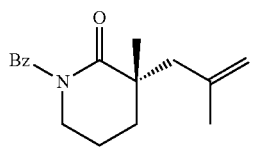

Benzoyl lactam 8 was isolated by flash chromatography (SiO$_2$, 5 to 9% EtOAc in hexanes) as a colorless oil. 78.0% yield. R$_f$=0.54 (25% EtOAc in hexanes); $^1$H NMR (500 MHz, CDCl$_3$) δ 7.54-7.50 (m, 2H), 7.48-7.43 (m, 1H), 7.41-7.35 (m, 2H), 4.89 (t, J=1.8 Hz, 1H), 4.70 (dt, J=2.1, 1.0 Hz, 1H), 3.94-3.84 (m, 1H), 3.74-3.63 (m, 1H), 2.75 (dd, J=13.8, 1.3 Hz, 1H), 2.13 (dd, J=13.8, 0.8 Hz, 1H), 2.08-1.94 (m, 3H), 1.69 (s, 3H), 1.68-1.61 (m, 1H), 1.37 (s, 3H); $^{13}$C NMR (126 MHz, CDCl$_3$) δ 178.8, 175.5, 141.9, 136.5, 131.3, 128.1, 127.4, 115.5, 47.2, 46.2, 44.0, 32.9, 26.9, 24.7, 19.8; IR (Neat Film NaCl) 3070, 2940, 1678, 1448, 1274, 1144, 726 cm$^{-1}$; HRMS (MM: ESI-APCI) m/z calc'd for C$_{17}$H$_{22}$NO$_2$ [M+H]$^+$: 272.1645, found 272.1655; [α]$_D^{25}$ −105.6° (c 0.99, CHCl$_3$, 97% ee).

Benzoyl Lactam 9

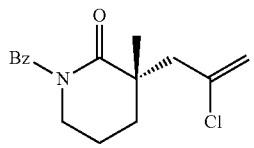

Benzoyl lactam 9 was isolated by flash chromatography (SiO$_2$, 8 to 10% Et$_2$O in hexanes) as a colorless oil. 60.3% yield. R$_f$=0.39 (25% EtOAc in hexanes); $^1$H NMR (500 MHz, CDCl$_3$) δ 7.55-7.49 (m, 2H), 7.49-7.43 (m, 1H), 7.42-7.34 (m, 2H), 5.32 (d, J=1.7 Hz, 1H), 5.18 (s, 1H), 3.92 (ddt, J=12.7, 4.8, 1.7 Hz, 1H), 3.75-3.66 (m, 1H), 3.04 (dd, J=14.5, 1.0 Hz, 1H), 2.50 (d, J=14.5 Hz, 1H), 2.16 (ddd, J=13.4, 10.2, 4.4 Hz, 1H), 2.12-1.98 (m, 2H), 1.86-1.77 (m, 1H), 1.43 (s, 3H); $^{13}$C NMR (126 MHz, CDCl$_3$) δ 177.9, 175.3, 138.3, 136.4, 131.4, 128.1, 127.4, 117.1, 47.0 (2C), 44.2, 32.8, 26.3, 19.7; IR (Neat Film NaCl) 2944, 2872, 1679, 1628, 1448, 1386, 1277, 1151, 894, 726 cm$^{-1}$; HRMS (MM: ESI-APCI) m/z calc'd for C$_{16}$H$_{19}$NO$_2$Cl [M+H]$^+$: 292.1099, found 292.1102; [α]$_D^{25}$ −91.4° (c 0.94, CHCl$_3$, 95% ee).

Benzoyl Lactam 10

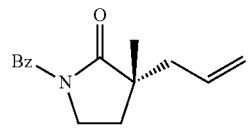

Benzoyl lactam 10 was isolated by flash chromatography (SiO$_2$, 5 to 10% Et$_2$O in hexanes) as a colorless oil. 90.3% yield. R$_f$=0.35 (35% Et$_2$O in hexanes); $^1$H NMR (500 MHz, CDCl$_3$) δ 7.58-7.54 (m, 2H), 7.53-7.48 (m, 1H), 7.43-7.38 (m, 2H), 5.78 (dddd, J=17.1, 10.2, 7.8, 7.0 Hz, 1H), 5.22-5.09 (m, 2H), 3.87 (dd, J=7.7, 6.7 Hz, 2H), 2.36 (dd, J=13.8, 7.0 Hz, 1H), 2.24 (dd, J=13.7, 7.8 Hz, 1H), 2.15 (dt, J=12.9, 7.6 Hz, 1H), 1.85 (dt, J=13.1, 6.7 Hz, 1H), 1.22 (s, 3H); $^{13}$C NMR (126 MHz, CDCl$_3$) δ 178.6, 170.8, 134.4, 133.0, 131.8, 128.8, 127.7, 119.3, 46.2, 42.8, 41.8, 29.3, 22.8; IR (Neat Film NaCl) 3075, 2974, 2902, 1742, 1674, 1448, 1377, 1357, 1306, 1243, 1156, 921, 860, 731, 694, 656 cm$^{-1}$; HRMS ESI-APCI m/z calc'd for C$_{14}$H$_{18}$NO$_2$ [M+H]$^+$: 244.1332, found 244.1336; [α]$_D^{25}$ −31.6° (c 1.04, CHCl$_3$, 98% ee).

Benzoyl Lactam 11

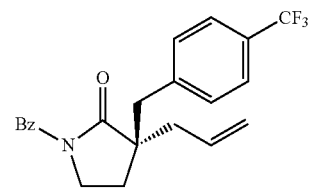

Benzoyl lactam 11 was isolated by flash chromatography (SiO$_2$, 10 to 20% Et$_2$O in hexanes) as a colorless oil. 89.3% yield. R$_f$=0.24 (20% Et$_2$O in hexanes); $^1$H NMR (500 MHz, CDCl$_3$) δ 7.60-7.56 (m, 2H), 7.56-7.51 (m, 1H), 7.49-7.45 (m, 2H), 7.42 (ddt, J=7.8, 6.7, 1.0 Hz, 2H), 7.31 (d, J=7.7 Hz, 2H), 5.83 (dddd, J=17.1, 10.1, 7.8, 6.9 Hz, 1H), 5.28-5.10 (m, 2H), 3.70 (dt, J=11.4, 7.5 Hz, 1H), 3.39 (dt, J=11.4, 6.9 Hz, 1H), 3.10 (d, J=13.4 Hz, 1H), 2.76 (d, J=13.5 Hz, 1H), 2.48 (dd, J=13.8, 7.0 Hz, 1H), 2.32 (dd, J=13.8, 7.8 Hz, 1H), 2.05 (t, J=7.3 Hz, 2H); $^{13}$C NMR (126 MHz, CDCl$_3$) δ 177.1, 170.5, 140.9, 134.2, 132.3, 131.9, 130.7, 129.4 (q, J$_{C-F}$=32.5 Hz), 128.7, 127.7, 125.3 (q, J$_{C-F}$=3.7 Hz), 124.1 (q, J$_{C-F}$=272.2 Hz), 120.1, 51.3, 43.0, 41.9 (2C), 25.2; IR (Neat Film NaCl) 3080, 2977, 2913, 1738, 1677, 1325, 1294, 1244, 1164, 1121, 1067, 859, 728, 701, 665 cm$^{-1}$; HRMS (FAB) m/z calc'd for C$_{22}$H$_{21}$NO$_2$F$_3$ [M+H]$^+$: 388.1524, found 388.1525; [α]$_D^{25}$ +78.3° (c 1.90, CHCl$_3$, 93% ee).

Benzoyl Lactam 12

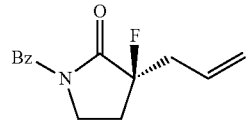

Benzoyl lactam 12 was isolated by flash chromatography (SiO$_2$, 10 to 20% Et$_2$O in hexanes) as a white solid. 85.7% yield. $R_f$=0.35 (35% Et$_2$O in hexanes); $^1$H NMR (500 MHz, CDCl$_3$) δ 7.63-7.58 (m, 2H), 7.58-7.52 (m, 1H), 7.49-7.40 (m, 2H), 5.87-5.73 (m, 1H), 5.32-5.20 (m, 2H), 4.00 (ddd, J=11.5, 7.7, 6.5 Hz, 1H), 3.90-3.80 (m, 1H), 2.81-2.70 (m, 1H), 2.62-2.48 (m, 1H), 2.46-2.27 (m, 2H); $^{13}$C NMR (126 MHz, CDCl$_3$) δ 170.3, 169.7 (d, $J_{C-F}$=23.1 Hz), 133.4, 132.4, 129.7 (d, $J_{C-F}$=7.1 Hz), 129.0, 127.9, 121.0, 97.0 (d, $J_{C-F}$=185.4 Hz), 42.0 (d, $J_{C-F}$=2.3 Hz), 38.4 (d, $J_{C-F}$=25.2 Hz), 28.5 (d, $J_{C-F}$=22.6 Hz); IR (Neat Film NaCl) 3076, 1760, 1676, 1365, 1314, 1253, 1132, 1058, 1008, 980, 920, 863, 791, 729 cm$^{-1}$; HRMS (MM: ESI-APCI) m/z calc'd for C$_{14}$H$_{15}$NO$_2$F [M+H]$^+$: 248.1081, found 248.1092; $[α]_D^{25}$ −120.5° (c 1.11, CHCl$_3$, 98% ee).

4-Methoxybenzoyl Lactam 13:

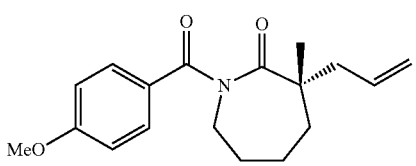

The reaction was performed in MTBE at 40° C. 4-Methoxybenzoyl lactam 13 was isolated by flash chromatography (SiO$_2$, 8% Et$_2$O in hexanes) as a colorless oil. 83.2% yield. $R_f$=0.48 (25% EtOAc in hexanes); $^1$H NMR (500 MHz, CDCl$_3$) δ 7.56-7.48 (m, 2H), 6.91-6.82 (m, 2H), 5.86-5.66 (m, 1H), 5.18-5.02 (m, 2H), 4.03 (ddd, J=15.0, 8.0, 2.4 Hz, 1H), 3.88 (ddd, J=15.1, 8.5, 2.1 Hz, 1H), 3.83 (s, 3H), 2.50 (ddt, J=13.6, 7.0, 1.2 Hz, 1H), 2.35 (ddt, J=13.7, 7.6, 1.1 Hz, 1H), 1.92-1.77 (m, 4H), 1.77-1.62 (m, 2H), 1.31 (s, 3H); $^{13}$C NMR (126 MHz, CDCl$_3$) δ 182.3, 174.7, 162.2, 133.9, 130.0, 128.9, 118.6, 113.5, 55.4, 47.7, 44.7, 43.0, 35.1, 28.2, 25.0, 23.4; IR (Neat Film NaCl) 3074, 2932, 1673, 1605, 1511, 1279, 1255, 1168, 1112, 1025, 837 cm$^{-1}$; HRMS (MM: ESI-APCI) m/z calc'd for C$_{18}$H$_{24}$NO$_3$ [M+H]$^+$: 302.1751, found 302.1744; $[α]_D^{25}$ −34.7° (c 0.75, CHCl$_3$, 93% ee).

Benzoyl Lactam 14

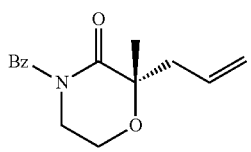

Benzoyl lactam 14 was isolated by flash chromatography (SiO$_2$, 10 to 20% Et$_2$O in hexanes) as a colorless oil. 91.4% yield. $R_f$=0.36 (35% Et$_2$O in hexanes); $^1$H NMR (500 MHz, CDCl$_3$) δ 7.55-7.52 (m, 2H), 7.52-7.47 (m, 1H), 7.42-7.37 (m, 2H), 5.90 (ddt, J=17.3, 10.3, 7.2 Hz, 1H), 5.26-5.10 (m, 2H), 4.12-3.95 (m, 3H), 3.94-3.81 (m, 1H), 2.71 (ddt, J=14.1, 7.3, 1.2 Hz, 1H), 2.47 (ddt, J=14.1, 7.0, 1.3 Hz, 1H), 1.48 (s, 3H); $^{13}$C NMR (126 MHz, CDCl$_3$) δ 174.3, 173.1, 135.7, 132.1, 131.7, 128.1, 127.7, 119.3, 80.3, 59.4, 45.7, 43.1, 23.3; IR (Neat Film NaCl) 3075, 2978, 2894, 1685, 1448, 1373, 1283, 1227, 1111, 1092, 921, 726, 694 cm$^{-1}$; HRMS (FAB) m/z calc'd for C$_{15}$H$_{18}$NO$_3$ [M+H]$^+$: 260.1287, found 260.1277; $[α]_D^{25}$ −72.1° (c 0.97, CHCl$_3$, 99% ee).

Benzoyl Lactam 15

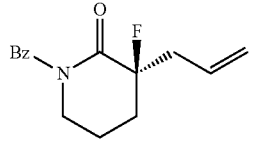

Benzoyl lactam 15 was isolated by flash chromatography (SiO$_2$, 5 to 10% EtOAc in hexanes) as a colorless oil. 88.8% yield. $R_f$=0.35 (35% Et$_2$O in hexanes); $^1$H NMR (500 MHz, CDCl$_3$) δ 7.62-7.57 (m, 2H), 7.53-7.47 (m, 1H), 7.44-7.37 (m, 2H), 5.87-5.70 (m, 1H), 5.28-5.15 (m, 2H), 3.91 (dddd, J=12.8, 6.0, 4.7, 1.4 Hz, 1H), 3.74 (dddd, J=13.6, 9.2, 4.5, 2.4 Hz, 1H), 2.86-2.60 (m, 2H), 2.33-2.14 (m, 2H), 2.13-1.89 (m, 2H); $^{13}$C NMR (126 MHz, CDCl$_3$) δ 174.5, 170.8 (d, $J_{C-F}$=23.5 Hz), 135.0, 132.0, 130.6 (d, $J_{C-F}$=6.5 Hz), 128.3, 128.0, 120.4, 93.9 (d, $J_{C-F}$=179.3 Hz), 46.4, 40.0 (d, $J_{C-F}$=23.6 Hz), 32.1 (d, $J_{C-F}$=22.5 Hz), 19.1 (d, $J_{C-F}$=4.6 Hz); IR (Neat Film NaCl) 3078, 2956, 1715, 1687, 1478, 1449, 1435, 1390, 1288, 1273, 1175, 1152, 1000, 930, 725, 694, 662 cm$^{-1}$; HRMS (MM: ESI-APCI) m/z calc'd for C$_{15}$H$_{16}$NO$_2$F [M+H]$^+$: 262.1238, found 262.1244; $[α]_D^{25}$ −120.6° (c 1.09, CHCl$_3$, 99% ee).

Benzoyl Glutarimide 16

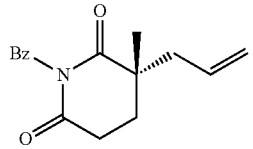

Benzoyl glutarimide 16 was isolated by flash chromatography (SiO$_2$, 17 to 25% EtOAc in hexanes) as a colorless oil. 81% yield. $R_f$=0.21 (25% EtOAc in hexanes); $^1$H NMR (500 MHz, CDCl$_3$) δ 7.83 (d, J=8.29 Hz, 2H), 7.63 (t, J=7.45 Hz, 1H), 7.48 (dd, J=8.29, 7.45 Hz, 2H), 5.77 (dddd, J=17.4, 10.2, 7.4, 7.0 Hz, 1H), 5.22-5.16 (m, 2H), 2.87-2.77 (m, 2H), 2.59 (ddt, J=13.8, 7.0, 1.0 Hz, 1H), 2.40 (ddt, J=13.8, 7.4, 1.0 Hz, 1H), 2.12 (ddd, J=14.2, 7.73, 6.81 Hz, 1H), 1.85 (ddd, J=14.2, 6.5, 6.1 Hz, 1H), 1.37 (s, 3H); $^{13}$C NMR (126 MHz, CDCl$_3$) δ 176.6, 171.6, 170.9, 134.8, 132.0, 131.9, 130.0, 129.1, 120.0, 41.9, 41.7, 29.2, 28.2, 22.8; IR (Neat Film NaCl) 3077, 2975, 2935, 1750, 1713, 1683, 1450, 1340, 1239, 1198, 981, 776 cm$^{-1}$; HRMS (MM: ESI-APCI) m/z calc'd for C$_{16}$H$_{18}$NO$_3$ [M+H]$^+$: 272.1281, found 272.1281; $[α]_D^{25}$ −31.3° (c 1.00, CHCl$_3$, 94% ee).

Benzoyl Glutarimide 17

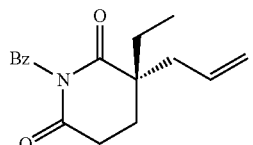

Benzoyl glutarimide 17 was isolated by flash chromatography (SiO$_2$, 17 to 25% EtOAc in hexanes) as a colorless oil. 86% yield. $R_f$=0.24 (25% EtOAc in hexanes); $^1$H NMR (500 MHz, CDCl$_3$) δ 7.83 (d, J=8.38 Hz, 2H), 7.64 (t, J=7.46 Hz, 1H), 7.48 (dd, J=8.38, 7.46 Hz, 2H), 5.75 (dddd, J=17.2, 10.2, 7.7, 7.0 Hz, 1H), 5.20-5.15 (m, 2H), 2.86-2.76 (m, 2H), 2.60 (ddt, J=14.0, 7.0, 1.1 Hz, 1H), 2.37 (ddt, J=14.0, 7.7, 1.1 Hz, 1H), 2.05 (ddd, J=14.3, 7.85, 6.81 Hz, 1H), 1.97 (ddd, J=14.3, 6.56, 6.24 Hz, 1H), 1.87-1.75 (m, 2H), 0.97 (t, J=7.46, 3H); $^{13}$C NMR (126 MHz, CDCl$_3$) δ 175.9, 171.6, 171.0, 134.8, 132.4, 131.9, 130.0, 129.0, 119.8, 45.4, 39.3, 29.0, 28.1, 25.4, 8.1; IR (Neat Film NaCl) 3076, 2974, 2940, 2882, 1750, 1713, 1683, 1450, 1340, 1239, 1195, 1001, 923, 778 cm$^{-1}$; HRMS (MM: ESI-APCI) m/z calc'd for C$_{17}$H$_{20}$NO$_3$ [M+H]$^+$: 286.1438, found 286.1432; $[α]_D^{25}$ −16.2° (c 1.00, CHCl$_3$, 96% ee).

Acyl Lactam 18

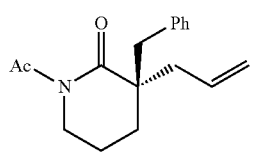

Acyl lactam 18 was isolated by flash chromatography (SiO$_2$, 10 to 20% Et$_2$O in hexanes) as a colorless oil. 88.4% yield. R$_f$=0.40 (35% Et$_2$O in hexanes); $^1$H NMR (500 MHz, CDCl$_3$) δ 7.32-7.17 (m, 3H), 7.17-7.09 (m, 2H), 5.77 (dddd, J=17.0, 10.3, 7.9, 6.8 Hz, 1H), 5.19-5.05 (m, 2H), 3.60-3.48 (m, 1H), 3.44 (dddd, J=13.0, 7.0, 4.6, 1.0 Hz, 1H), 3.27 (d, J=13.3 Hz, 1H), 2.68 (d, J=13.2 Hz, 1H), 2.66-2.62 (m, 1H), 2.51 (s, 3H), 2.23 (ddt, J=13.5, 7.9, 1.1 Hz, 1H), 1.90-1.61 (m, 3H), 1.57-1.38 (m, 1H); $^{13}$C NMR (126 MHz, CDCl$_3$) δ 178.0, 174.2, 137.1, 133.2, 130.4, 128.3, 126.8, 119.2, 49.7, 45.1, 44.8, 44.5, 29.0, 27.6, 19.6; IR (Neat Film NaCl) 3028, 2941, 1691, 1367, 1291, 1247, 111178, 1131, 1031, 923 cm$^{-1}$; HRMS (MM: ESI-APCI) m/z calc'd for C$_{17}$H$_{22}$NO$_2$ [M+H]$^+$: 272.1645, found 272.1646; $[α]_D^{25}$ +11.4° (c 1.03, CHCl$_3$, 88% ee).

Phenyl Carbamate Lactam 19

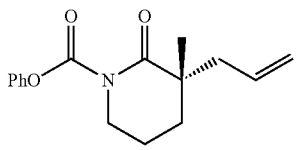

Phenyl Carbamate lactam 19 was isolated by flash chromatography (SiO$_2$, 10 to 20% Et$_2$O in hexanes) as a colorless oil. 82.2% yield. R$_f$=0.39 (35% Et$_2$O in hexanes); $^1$H NMR (500 MHz, CDCl$_3$) δ 7.40-7.35 (m, 2H), 7.25-7.21 (m, 1H), 7.20-7.15 (m, 2H), 5.79 (dddd, J=16.7, 10.4, 7.8, 7.0 Hz, 1H), 5.18-5.08 (m, 2H), 3.89-3.82 (m, 1H), 3.78-3.70 (m, 1H), 2.55 (ddt, J=13.6, 7.0, 1.2 Hz, 1H), 2.33 (ddt, J=13.6, 7.8, 1.1 Hz, 1H), 2.00-1.85 (m, 3H), 1.70-1.59 (m, 1H), 1.30 (s, 3H); $^{13}$C NMR (126 MHz, CDCl$_3$) δ 177.3, 153.8, 150.8, 133.3, 129.3, 125.9, 121.5, 118.9, 48.2, 45.0, 44.1, 33.0, 25.3, 19.6; IR (Neat Film NaCl) 3074, 2939, 2870, 1783, 1733, 1718, 1494, 1299, 1265, 1203, 1153, 991, 920 cm$^{-1}$; HRMS (MM: ESI-APCI) m/z calc'd for C$_{16}$H$_{20}$NO$_3$ [M+H]$^+$: 274.1438, found 274.1444; $[α]_D^{25}$ −81.6° (c 1.11, CHCl$_3$, 94% ee).

Benzyl Carbamate Lactam 20

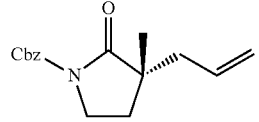

Benzyl carbamate lactam 20 was isolated by flash chromatography (SiO$_2$, 10 to 30% Et$_2$O in hexanes) as a colorless oil. 85.9% yield. R$_f$=0.41 (35% Et$_2$O in hexanes); $^1$H NMR (500 MHz, CDCl$_3$) δ 7.46-7.42 (m, 2H), 7.37 (ddd, J=7.4, 6.3, 1.5 Hz, 2H), 7.35-7.30 (m, 1H), 5.74 (dddd, J=15.9, 11.0, 7.9, 6.9 Hz, 1H), 5.28 (s, 2H), 5.18-5.06 (m, 2H), 3.77-3.63 (m, 2H), 2.33 (ddt, J=13.8, 6.9, 1.2 Hz, 1H), 2.24 (ddt, J=13.8, 7.9, 1.0 Hz, 1H), 2.03 (ddd, J=12.9, 8.1, 6.9 Hz, 1H), 1.74 (ddd, J=13.2, 7.7, 5.9 Hz, 1H), 1.19 (s, 3H); $^{13}$C NMR (126 MHz, CDCl$_3$) δ 178.0, 151.7, 135.3, 133.0, 128.6, 128.3, 128.1, 119.1, 68.0, 45.5, 42.9, 41.7, 29.5, 22.6; IR (Neat Film NaCl) 3066, 2973, 2930, 2903, 1789, 1750, 1719, 1456, 1380, 1363, 1301, 1217, 1001, 919, 776, 736 cm$^{-1}$; HRMS (MM: ESI-APCI) m/z calc'd for C$_{16}$H$_{20}$NO$_3$[M+H]$^+$: 274.1438, found 274.1438; $[α]_D^{25}$ −41.4° (c 1.02, CHCl$_3$, 91% ee).

4-Phenylbenzoyl Lactam 21

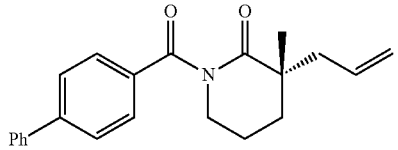

4-Phenylbenzoyl lactam 21 was isolated by flash chromatography (SiO$_2$, 10 to 15% Et$_2$O in pentane) as a colorless oil. 84.6% yield. R$_f$=0.43 (35% Et$_2$O in hexanes); $^1$H NMR (500 MHz, CDCl$_3$) δ 7.64-7.57 (m, 6H), 7.45 (ddd, J=7.8, 6.7, 1.1 Hz, 2H), 7.40-7.34 (m, 1H), 5.84-5.70 (m, 1H), 5.20-5.09 (m, 2H), 3.91-3.82 (m, 1H), 3.74 (ddd, J=12.1, 7.4, 5.7 Hz, 1H), 2.59 (ddd, J=13.7, 7.0, 1.3 Hz, 1H), 2.32 (ddt, J=13.7, 7.7, 1.2 Hz, 1H), 2.10-1.91 (m, 3H), 1.77-1.64 (m, 1H), 1.34 (s, 3H); $^{13}$C NMR (126 MHz, CDCl$_3$) δ 179.1, 175.1, 144.2, 140.2, 135.1, 133.3, 128.8, 128.1, 127.8, 127.2, 126.9, 119.0, 47.2, 44.0, 43.3, 33.3, 25.2, 19.5; IR (Neat Film NaCl) 3073, 2938, 2869, 1677, 1607, 1478, 1383, 1295, 1279, 1145, 922, 849, 743, 698 cm$^{-1}$; HRMS (MM: ESI-APCI) m/z calc'd for C$_{22}$H$_{24}$NO$_2$ [M+H]$^+$: 334.1802, found 334.1812; $[α]_D^{25}$ −82.6° (c 0.75, CHCl$_3$, 99% ee).

1-Naphthoyl Lactam 22

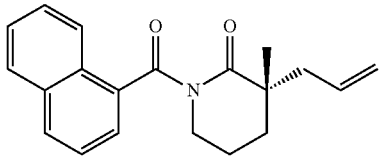

1-Naphthoyl lactam 22 was isolated by flash chromatography (SiO$_2$, 10 to 20% Et$_2$O in hexanes) as a white solid. 86.3% yield. R$_f$=0.42 (35% Et$_2$O in hexanes); $^1$H NMR (500 MHz, CDCl$_3$) δ 8.03-7.97 (m, 1H), 7.90-7.83 (m, 2H), 7.55-7.46 (m, 2H), 7.42 (dd, J=8.1, 7.1 Hz, 1H), 7.37 (dd, J=7.1, 1.3 Hz, 1H), 5.64 (dddd, J=17.2, 10.2, 7.6, 7.1 Hz, 1H), 5.16-4.97 (m, 2H), 4.05 (dddd, J=12.8, 6.3, 5.2, 1.3 Hz, 1H), 3.95-3.82 (m, 1H), 2.43 (ddt, J=13.7, 7.1, 1.2 Hz, 1H), 2.19 (ddt, J=13.7, 7.6, 1.1 Hz, 1H), 2.11-1.99 (m, 2H), 1.99-1.91 (m, 1H), 1.73-1.64 (m, 1H), 1.18 (s, 3H); $^{13}$C NMR (126 MHz, CDCl$_3$) δ 178.5, 174.3, 135.8, 133.6, 133.1, 130.0, 129.8, 128.4, 126.9, 126.2, 124.9, 124.5, 123.3, 118.9, 46.4, 44.1, 43.3, 33.2, 24.8, 19.5; IR (Neat Film NaCl) 3062, 2937, 2869, 1702, 1677, 1381, 1295, 1251, 1147, 923, 781 cm$^{-1}$; HRMS (MM: ESI-APCI) m/z calc'd for C$_{20}$H$_{22}$NO$_2$ [M+H]$^+$: 308.1645, found 308.1648; $[\alpha]_D^{25}$ −102.3° (c 1.12, CHCl$_3$, 99% ee).

2-Naphthoyl Lactam 23

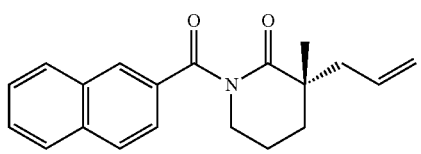

2-Naphthoyl lactam 23 was isolated by flash chromatography (SiO$_2$, 10 to 20% Et$_2$O in hexanes) as a colorless oil. 82.1% yield. R$_f$=0.42 (35% Et$_2$O in hexanes); $^1$H NMR (500 MHz, CDCl$_3$) δ 8.10 (dd, J=1.8, 0.8 Hz, 1H), 7.93-7.76 (m, 3H), 7.63-7.43 (m, 3H), 5.87-5.67 (m, 1H), 5.21-5.06 (m, 2H), 3.95-3.84 (m, 1H), 3.84-3.72 (m, 1H), 2.58 (ddt, J=13.8, 7.1, 1.2 Hz, 1H), 2.33 (ddt, J=13.7, 7.6, 1.1 Hz, 1H), 2.12-1.89 (m, 3H), 1.71 (ddt, J=10.9, 4.9, 4.3, 2.4 Hz, 1H), 1.34 (s, 3H); $^{13}$C NMR (126 MHz, CDCl$_3$) δ 179.0, 175.3, 134.6, 133.7, 133.3, 132.5, 128.9, 128.1, 127.7 (2C), 127.5, 126.4, 124.1, 118.9, 47.2, 44.0, 43.3, 33.3, 25.1, 19.5; IR (Neat Film NaCl) 3059, 2938, 2869, 1677, 1467, 1383, 1293, 1234, 1165, 1139, 923, 862, 822, 780, 762 cm$^{-1}$; HRMS (FAB) m/z calc'd for C$_{20}$H$_{22}$NO$_2$ [M+H]$^+$: 308.1650, found 308.1638; $[\alpha]_D^{25}$ −257.4° (c 0.92, CHCl$_3$, 97% ee).

Procedures for the Conversion of Benzoyl Lactam 3 to Various Derivatives

The benzoyl lactam 3 compound was converted to various derivatives via the reactions described below (and depicted in Benzoyl Lactam 3 Reaction Schemes 1 and 2).

and diluted with saturated aqueous NaHCO$_3$ (100 mL) and EtOAc (75 mL). The phases were separated, and the aqueous phase was extracted with EtOAc (4×75 mL). The combined organic phases were washed with brine (2×30 mL), dried (Na$_2$SO$_4$), filtered, and concentrated under reduced pressure. The resulting oil was purified by flash chromatography (3×25 cm SiO$_2$, 40 to 60% EtOAc in hexanes) to afford known lactam 24 as a colorless oil (1.18 g, 96% yield). See Jakubec, et al., "Cyclic Imine Nitro-Mannich/Lactamization Cascades: A Direct Stereoselective Synthesis of Multicyclic Piperidinone Derivatives," Org. Lett. 10, 4267-4270 (2008), the entire content of which is incorporated by reference. R$_f$=0.21 (50% EtOAc in hexanes); $^1$H NMR (500 MHz, CDCl$_3$) δ 6.05 (br s, 1H), 5.88-5.66 (m, 1H), 5.12-4.95 (m, 2H), 3.25 (td, J=5.8, 1.9 Hz, 2H), 2.48 (ddt, J=13.6, 6.7, 1.3 Hz, 1H), 2.18 (ddt, J=13.6, 8.1, 1.0 Hz, 1H), 1.87-1.62 (m, 5H), 1.49 (dq, J=13.5, 7.4 Hz, 1H), 0.89 (t, J=7.5 Hz, 3H); $[\alpha]_D^{25}$ −13.7° (c 0.57, CHCl$_3$, 99% ee).

Piperidine 25

To a solution of piperidin-2-one 24 (250 mg, 1.49 mmol, 1.00 equiv) in ether (14.9 mL) was added lithium aluminum hydride (170 mg, 4.48 mmol, 3.0 equiv) (Caution: Gas evolution and exotherm). After stirring at ambient temperature for 5 min, the reaction mixture was heated to reflux for 36 h, cooled (0° C.), and quenched with saturated aqueous K$_2$CO$_3$ (20 mL, Caution: Gas evolution and exotherm). The phases were separated, and the aqueous phase was extracted with Et$_2$O (4×75 mL). The combined organic phases were washed with brine (2×30 mL), dried (Na$_2$SO$_4$), filtered, and concentrated under reduced pressure to provide piperidine 23 (206 mg, 90% yield) as a colorless oil. R$_f$=0.29 (20% MeOH in DCM); $^1$H NMR (500 MHz, CDCl$_3$) δ 5.76 (ddt, J=16.4, 10.6, 7.5 Hz, 1H), 5.10-4.96 (m, 2H), 2.81-2.68 (m, 2H), 2.53 (dd, J=13.0, 20.0 Hz, 2H), 2.06 (d, J=7.5 Hz, 2H), 2.02 (br s, 1H), 1.55-1.42 (m, 2H), 1.40-1.30 (m, 2H), 1.32 (q, J=7.5 Hz, 2H), 0.80 (t, J=7.6 Hz, 3H); $^{13}$C NMR (126 MHz, CDCl$_3$) δ 134.6, 116.9, 55.1, 47.0, 39.2, 34.9, 33.6, 27.7, 22.4, 7.1; IR (Neat Film NaCl) 3298, 3073, 2963, 2931, 2853, 2799, 1638, 1462, 1125, 996, 911 cm$^{-1}$; HRMS (MM: ESI-APCI) m/z calc'd for C$_{10}$H$_{20}$N [M+H]$^+$: 154.1590, found 154.1590; $[\alpha]_D^{25}$ −7.5° (c 0.80, MeOH, 96% ee).

Benzoyl Lactam 3 Reaction Scheme 1

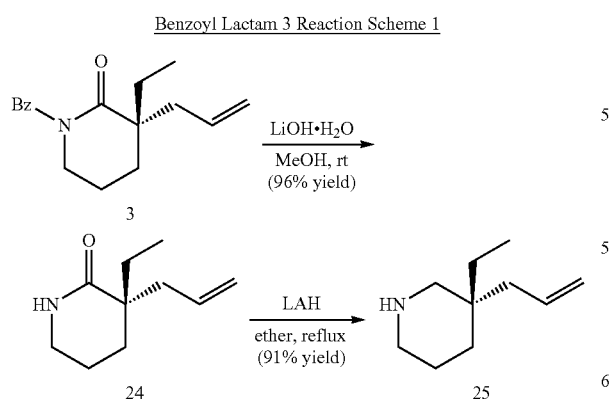

Benzoyl Lactam 3 Reaction Scheme 2

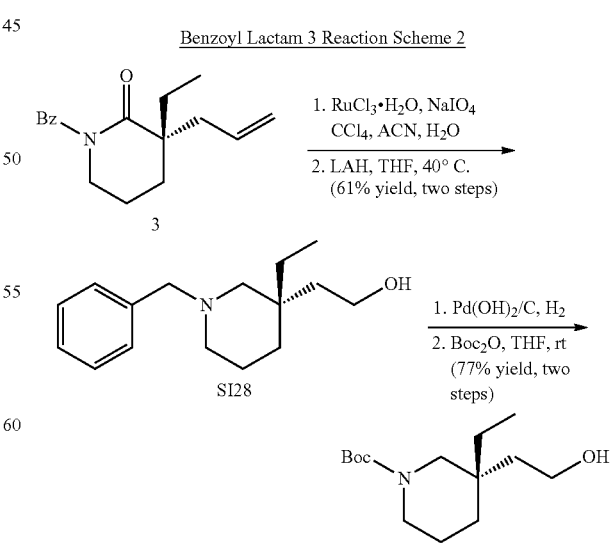

Piperidin-2-one 24

To a solution of lactam 3 (2.00 g, 7.37 mmol, 1.00 equiv) in MeOH (188 mL) was added a solution of LiOH.H$_2$O (464 mg, 11.1 mmol, 1.50 equiv) in H$_2$O (75 mL). After 20 h, the reaction mixture was concentrated under reduced pressure Alcohol SI28

See Moss, et al., "Catalytic enantio- and diastereoselective alkylations with cyclic sulfamidates," *Angew. Chem. Int. Ed.* 49, 568-571 (2010), the entire content of which is incorporated by reference. To a vigorously stirred mixture of benzoyl lactam 3 (291 mg, 1.07 mmol, 1.00 equiv) and NaIO$_4$ (915 mg, 4.28 mmol, 4.00 equiv) in CCl$_4$ (4.3 mL), MeCN (4.3 mL), and H$_2$O (6.5 mL) was added RuCl$_3$·H$_2$O (11.0 mg, 0.053 mmol, 0.05 equiv). After 28 h, the reaction mixture was diluted with half-saturated brine (30 mL) and extracted with DCM (5×25 mL). The combined organics were washed with half-saturated brine, dried (Na$_2$SO$_4$), and concentrated under reduced pressure. The resulting residue was suspended in Et$_2$O (30 mL) and filtered through a pad of celite. The celite pad was washed with Et$_2$O (2×15 mL), and the combined filtrate was concentrated under reduced pressure. This crude residue was used in the next step without further purification.

With cooling from a room temperature bath, the above residue was dissolved in THF (19 mL) and then treated with lithium aluminum hydride (487 mg, 12.9 mmol, 12.0 equiv) (Caution: Gas evolution and exotherm). The reaction mixture was stirred at ambient temperature for 12 h and then warmed to 40° C. for an addition 12 h. The reaction mixture was then cooled (0° C.) and dropwise treated with brine (20 mL, Caution: Gas evolution and exotherm). Once gas evolution had ceased the reaction mixture was diluted with half-saturated brine (20 mL) and EtOAc (20 mL). The phases were separated and the aqueous phase was extracted with EtOAc (5×50 mL). The combined organic phases were dried (Na$_2$SO$_4$), filtered, and concentrated under reduced pressure. The resulting oil was purified by flash chromatography (3×12 cm SiO$_2$, 35 to 70% EtOAc in hexanes) to afford alcohol SI28 as a colorless oil (162 mg, 61% yield for two steps). R$_f$=0.36 (75% EtOAc in hexanes); $^1$H NMR (500 MHz, CDCl$_3$) δ 7.35-7.24 (m, 5H), 3.80-3.72 (m, 1H), 3.71-3.60 (m, 2H), 3.31 (br s, 1H), 2.85-2.70 (br s, 2H), 2.00-1.70 (br s, 4H), 1.66-1.45 (m, 3H), 1.35-1.10 (m, 3H), 0.81 (t, J=7.5 Hz, 3H); $^{13}$C NMR (126 MHz, CDCl$_3$) δ 129.5, 128.4, 127.4, 63.9, 63.4, 59.4, 52.9, 39.9, 35.9, 35.1, 33.4, 22.4, 7.5; IR (Neat Film NaCl) 3345 (br), 2933, 2793, 1453, 1350, 1115, 1040, 1028, 739 cm$^{-1}$; HRMS (MM: ESI-APCI) m/z calc'd for C$_{16}$H$_{26}$NO [M+H]$^+$: 248.2009, found 248.2016.

Alcohol SI29

A mixture of alcohol SI28 (162.3 mg, 0.656 mmol, 1.00 equiv) and 20% Pd(OH)$_2$/C (50 mg) in MeOH (15 mL) was stirred under an H2 atmosphere for 3.5 h. The reaction mixture was filtered through a pad of celite. The celite pad was washed with MeOH (2×15 mL), and the combined filtrate was concentrated under reduced pressure. This crude residue was used in the next step without further purification.

To a solution of the above residue in THF (10 mL) was added Boc$_2$O (150 mg, 0.689 mmol, 1.05 equiv). After stirring for 24 h, the reaction mixture was concentrated under reduced pressure and partitioned between DCM (20 mL) and saturated aqueous NaHCO$_3$ (20 mL). The organic layer was dried (Na$_2$SO$_4$), filtered, and concentrated under reduced pressure. The resulting oil was purified by flash chromatography (2×20 cm SiO$_2$, 15 to 35% EtOAc in hexanes) to afford alcohol SI29 as a colorless oil (130 mg, 77% yield for two steps). R$_f$=0.34 (35% EtOAc in hexanes); $^1$H NMR (500 MHz, CDCl$_3$) δ 3.74-3.60 (m, 2H), 3.48 (br s, 1H), 3.31 (br s, 1H), 3.20 (br s, 1H), 2.96 (br s, 1H), 2.16 (br s, 1H), 1.66-1.55 (m, 1H), 1.55-1.42 (m, 3H), 1.44 (s, 9H), 1.40-1.27 (m, 2H), 1.25-1.15 (m, 1H), 0.83 (t, J=7.5 Hz, 3H); $^{13}$C NMR (126 MHz, CDCl$_3$) δ 155.2, 79.4, 58.7, 52.5, 44.5, 36.1, 35.3, 34.6, 28.4, 27.6, 21.2, 7.4; IR (Neat Film NaCl) 3439 (br), 2967, 2934, 2861, 1693, 1670, 1429, 1365, 1275, 1248, 1162, 1045, 865, 767 cm$^{-1}$; HRMS (MM: ESI-APCI) m/z calc'd for C$_{14}$H$_{28}$NO$_3$[M+H]$^+$: 258.2064, found 258.2069; [α]$_D^{25}$ −7.0° (c 1.13, CHCl$_3$, 96% ee).

TABLE 4

Methods for the Determination of Enantiomeric Excess for the above Examples
In the below Table, HPLC refers to high performance liquid chromatography and SFC refers supercritical fluid chromatography. Also, ChiralPak and Chiralcel refer to the companies from which the column resin (i.e., stationary phase) was obtained, and the lettering appearing after the company name refers to the specific material used.

| entry | product | assay conditions | retention time of major isomer (min) | retention time of minor isomer (min) | % ee |
|---|---|---|---|---|---|
| 1 | 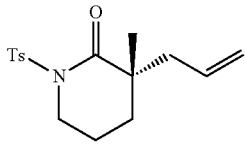<br>2a | HPLC<br>Chiralpak AD-H<br>5% EtOH in hexanes<br>isocratic, 1.0 mL/min<br>254 nm | 19.10 | 15.77 | 75 |
| 2 | 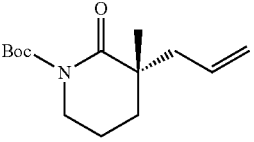<br>2b | HPLC<br>Chiralcel OJ-H<br>0.1% IPA in hexanes<br>isocratic, 1.0 mL/min<br>220 nm | 15.22 | 18.10 | 81 |

TABLE 4-continued

Methods for the Determination of Enantiomeric Excess for the above Examples
In the below Table, HPLC refers to high performance liquid chromatography and SFC refers supercritical fluid chromatography. Also, ChiralPak and Chiralcel refer to the companies from which the column resin (i.e., stationary phase) was obtained, and the lettering appearing after the company name refers to the specific material used.

| entry | product | assay conditions | retention time of major isomer (min) | retention time of minor isomer (min) | % ee |
|---|---|---|---|---|---|
| 3 | 2c | HPLC Chiralcel OJ-H 3% EtOH in hexanes isocratic, 1.0 mL/min 220 nm | 18.68 | 17.60 | 86 |
| 4 | 2d | HPLC Chiralcel OD 3% EtOH in hexanes isocratic, 1.0 mL/min 254 nm | 28.89 | 21.47 | 89 |
| 5 | 2e | HPLC Chiralcel OJ 1% IPA in hexanes isocratic, 1.0 mL/min 254 nm | 10.15 | 9.71 | 91 |
| 6 | 2f | HPLC Chiralcel OD-H 3% IPA in hexanes isocratic, 1.0 mL/min 254 nm | 15.73 | 18.12 | 99 |
| 7 | 2g | HPLC Chiralcel OJ-H 2% IPA in hexanes isocratic, 1.0 mL/min 254 nm | 29.12 | 19.74 | 99 |
| 8 | 2h | HPLC Chiralcel OJ-H 5% IPA in hexanes isocratic, 1.0 mL/min 254 nm | 32.97 | 31.16 | 99 |
| 9 | 3 | SFC Chiralcel OJ-H 3% MeOH in $CO_2$ isocratic, 5.0 mL/min 254 nm | 3.85 | 2.49 | 99 |

TABLE 4-continued

Methods for the Determination of Enantiomeric Excess for the above Examples
In the below Table, HPLC refers to high performance liquid chromatography and SFC refers supercritical fluid chromatography. Also, ChiralPak and Chiralcel refer to the companies from which the column resin (i.e., stationary phase) was obtained, and the lettering appearing after the company name refers to the specific material used.

| entry | product | assay conditions | retention time of major isomer (min) | retention time of minor isomer (min) | % ee |
|---|---|---|---|---|---|
| 10 | 4 | SFC Chiralcel OD-H 10% MeOH in $CO_2$ isocratic, 5.0 mL/min 254 nm | 3.84 | 3.20 | 99 |
| 11 | 5 | HPLC Chiralpak AD-H 3% EtOH in hexane isocratic, 1.0 mL/min 254 nm | 32.69 | 27.83 | 99 |
| 12 | 6 | SFC Chiralpak IC 10% MeOH in $CO_2$ isocratic, 5.0 mL/min 254 nm | 2.67 | 3.84 | 99 |
| 13 | 7 | HPLC Chiralcel OJ-H 3% IPA in hexane isocratic, 1.0 mL/min 254 nm | 7.75 | 5.95 | 96 |
| 14 | 8 | HPLC Chiralcel OJ-H 8% IPA in hexane isocratic, 1.0 mL/min 254 nm | 25.94 | 19.12 | 97 |
| 15 | 9 | HPLC Chiralpak AD 2% IPA in hexane isocratic, 1.0 mL/min 254 nm | 18.72 | 27.05 | 95 |

TABLE 4-continued

Methods for the Determination of Enantiomeric Excess for the above Examples
In the below Table, HPLC refers to high performance liquid chromatography and SFC refers supercritical fluid chromatography. Also, ChiralPak and Chiralcel refer to the companies from which the column resin (i.e., stationary phase) was obtained, and the lettering appearing after the company name refers to the specific material used.

| entry | product | assay conditions | retention time of major isomer (min) | retention time of minor isomer (min) | % ee |
|---|---|---|---|---|---|
| 16 | 10 | SFC Chiralcel OJ-H 10% MeOH in $CO_2$ isocratic, 5.0 mL/min 254 nm | 2.93 | 1.84 | 98 |
| 17 | 11 | SFC Chiralcel OJ-H 5% MeOH in $CO_2$ isocratic, 5.0 mL/min 254 nm | 2.31 | 3.73 | 93 |
| 18 | 12 | SFC Chiralpak AD-H 15% MeOH in $CO_2$ isocratic, 5.0 mL/min 254 nm | 4.16 | 5.05 | 99 |
| 19 | 13 | HPLC Chiralcel OJ-H 5% IPA in hexane isocratic, 1.0 mL/min 254 nm | 29.16 | 24.82 | 93 |
| 20 | 14 | SFC Chiralpak AD-H 10% MeOH in $CO_2$ isocratic, 5.0 mL/min 254 nm | 1.96 | 1.41 | 99 |
| 21 | 15 | SFC Chiralcel OJ-H 5% MeOH in $CO_2$ isocratic, 5.0 mL/min 254 nm | 2.55 | 2.25 | 99 |
| 22 | 16 | SFC Chiralcel OJ-H 3% MeOH in $CO_2$ isocratic, 5.0 mL/min 254 nm | 3.05 | 2.72 | 94 |

TABLE 4-continued

Methods for the Determination of Enantiomeric Excess for the above Examples
In the below Table, HPLC refers to high performance liquid chromatography and SFC refers supercritical fluid chromatography. Also, ChiralPak and Chiralcel refer to the companies from which the column resin (i.e., stationary phase) was obtained, and the lettering appearing after the company name refers to the specific material used.

| entry | product | assay conditions | retention time of major isomer (min) | retention time of minor isomer (min) | % ee |
|---|---|---|---|---|---|
| 23 | 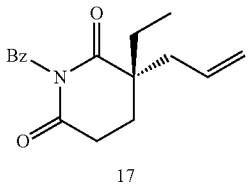 17 | SFC Chiralpak OJ-H 3% MeOH in $CO_2$ isocratic, 5.0 mL/min 254 nm | 3.28 | 2.87 | 96 |
| 24 | 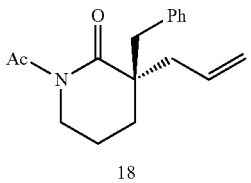 [SMILES: C=CC[C@]1(Cc2ccccc2)CCCN(C(C)=O)C1=O] 18 | SFC Chiralpak AD-H 3% MeOH in $CO_2$ isocratic, 3.0 mL/min 235 nm | 4.03 | 4.69 | 88 |
| 25 | 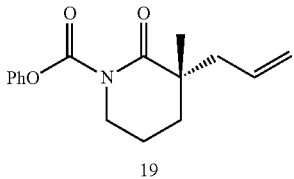 [SMILES: C=CC[C@]1(C)CCCN(C(=O)Oc2ccccc2)C1=O] 19 | SFC Chiralcel OB-H 10% MeOH in $CO_2$ isocratic, 5.0 mL/min 210 nm | 2.65 | 2.39 | 94 |
| 26 | 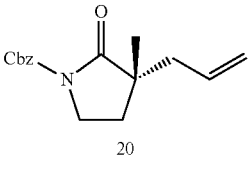 [SMILES: C=CC[C@]1(C)CCN(C(=O)OCc2ccccc2)C1=O] 20 | SFC Chiralpak AD-H 15% MeOH in $CO_2$ isocratic, 5.0 mL/min 210 nm | 4.23 | 2.51 | 91 |
| 27 | 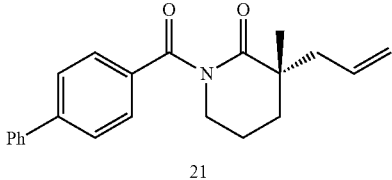 [SMILES: C=CC[C@]1(C)CCCN(C(=O)c2ccc(-c3ccccc3)cc2)C1=O] 21 | SFC Chiralcel OJ-H 10% MeOH in $CO_2$ isocratic, 5.0 mL/min 254 nm | 4.53 | 3.80 | 99 |
| 28 | 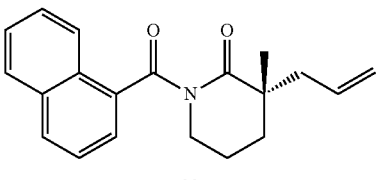 22 | SFC Chiralcel OB-H 10% MeOH in $CO_2$ isocratic, 5.0 mL/min 210 nm | 4.05 | 4.60 | 99 |
| 29 | 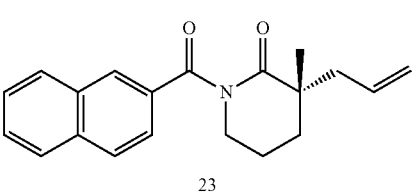 [SMILES: C=CC[C@]1(C)CCCN(C(=O)c2ccc3ccccc3c2)C1=O] 23 | SFC Chiralpak AD-H 20% MeOH in $CO_2$ isocratic, 5.0 mL/min 254 nm | 3.73 | 2.93 | 97 |

Piperazinone Examples

Some exemplary piperazinone building blocks were prepared according to the below reaction schemes.

Preparation of Piperazinone Building Block Compound 2

Piperazinone building block compound 2 was prepared according the following Piperazinone Reaction Scheme 1 according to the following reaction particulars.

Piperazinone Reaction Scheme 1

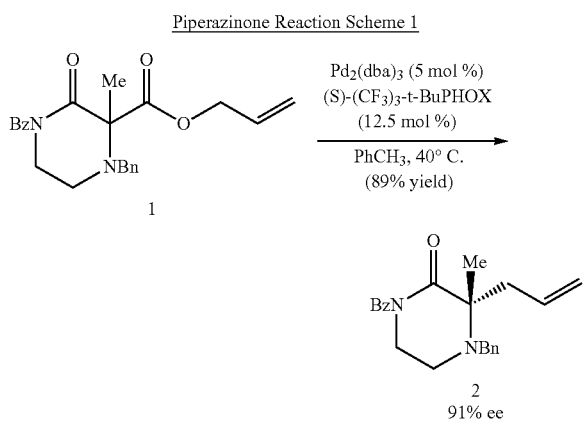

According to the above Piperazinone Reaction Scheme 1, in a nitrogen-filled glovebox, an oven-dried 2 dram vial was charged with $Pd_2dba_3$ (21.3 mg, 0.023 mmol, 0.05 equiv), (S)—$(CF_3)_3$-t-Bu-PHOX (34.3 mg, 0.058 mmol, 0.125 equiv), toluene (10 mL), and a magnetic stir bar. The vial was stirred at ambient glovebox temperature (~28° C.) for 30 min and 1 (182 mg, 0.464 mmol, 1.00 equiv) was added as a solution in toluene (5 mL). The vial was sealed and heated to 40° C. After 17 hours, complete consumption of the starting material was observed by colorimetric change (from light green to red-orange) and confirmed by thin layer chromatography on $SiO_2$. The reaction mixture was removed from the glovebox, concentrated under reduced pressure, and purified by flash chromatography ($SiO_2$, 4:1 hexane:ethyl acetate) to afford piperazinone 2 (145 mg, 0.413 mmol, 89% yield) as a pale yellow oil; $^1$H NMR (500 MHz, $CDCl_3$) δ 7.57-7.55 (m, 2H), 7.50-7.47 (m, 1H), 7.42-7.26 (m, 7H), 6.10-6.02 (m, 1H), 5.19-5.13 (m, 2H), 4.02 (d, J=13.5 Hz, 1H), 3.89-3.86 (m, 1H), 3.62-3.57 (m, 1H), 3.42 (d, J=13.5 Hz, 1H), 2.91-2.79 (m, 3H), 2.66-2.62 (m, 1H), 1.41 (s, 3H).

Preparation of Piperazinone Building Block Compound 4

Piperazinone building block compound 4 was prepared according the following Piperazinone Reaction Scheme 2 according to the following reaction particulars.

Piperazinone Reaction Scheme 2

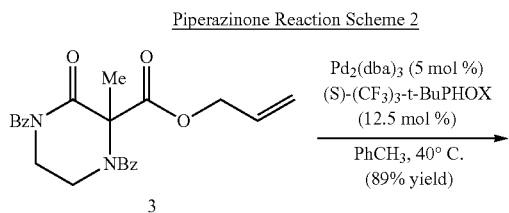

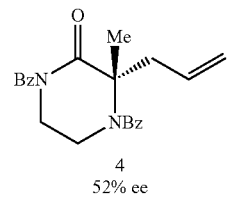

According to Piperazinone Reaction Scheme 2, in a nitrogen-filled glovebox, an oven-dried 2 dram vial was charged with $Pd_2dba_3$ (22.9 mg, 0.025 mmol, 0.05 equiv), (S)—$(CF_3)3$-t-Bu-PHOX (37.0 mg, 0.063 mmol, 0.125 equiv), toluene (10 mL), and a magnetic stir bar. The vial was stirred at ambient glovebox temperature (~28° C.) for 30 min and 3 (203 mg, 0.50 mmol, 1.00 equiv) was added as a solution in toluene (5 mL). The vial was sealed and heated to 40° C. After 7 hours, complete consumption of the starting material was observed by colorimetric change (from light green to red-orange) and confirmed by thin layer chromatography on $SiO_2$. The reaction mixture was removed from the glovebox, concentrated under reduced pressure, and purified by flash chromatography ($SiO_2$, 4:1 hexane:ethyl acetate) to afford piperazinone 4 (161 mg, 0.445 mmol, 89% yield) as a pale yellow oil; $^1$H NMR (500 MHz, $CDCl_3$) δ 7.57-7.51 (m, 3H), 7.46-7.40 (m, 7H), 5.89-5.81 (m, 1H), 5.26-5.18 (m, 2H), 4.16-4.12 (m, 1H), 3.82-3.69 (m, 2H), 3.63-3.50 (m, 2H), 2.90-2.85 (m, 1H), 1.99 (s, 3H).

Preparation of Piperazinone Building Block Compound 6

Piperazinone building block compound 6 was prepared according the following Piperazinone Reaction Scheme 3 according to the following reaction particulars.

Piperazinone Reaction Scheme 3

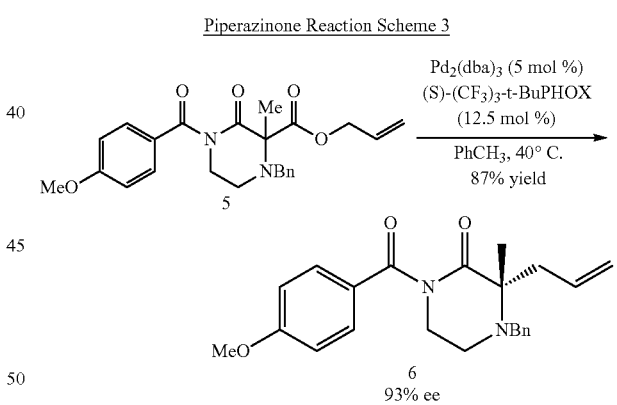

According to Piperazinone Reaction Scheme 3, in a nitrogen-filled glovebox, an oven-dried 2 dram vial was charged with $Pd_2dba_3$ (1.7 mg, 0.002 mmol, 0.05 equiv), (S)—$(CF_3)_3$-t-Bu-PHOX (2.5 mg, 0.0047 mmol, 0.125 equiv), toluene (0.5 mL), and a magnetic stir bar. The vial was stirred at ambient glovebox temperature (~28° C.) for 30 min and 5 (15.5 mg, 0.038 mmol, 1.00 equiv) was added as a solution in toluene (0.5 mL). The vial was sealed and heated to 40° C. After 18 hours, complete consumption of the starting material was observed by colorimetric change (from light green to red-orange) and confirmed by thin layer chromatography on $SiO_2$. The reaction mixture was removed from the glovebox, concentrated under reduced pressure, and purified by flash chromatography ($SiO_2$, 4:1 hexane:ethyl acetate) to afford piperazinone 6 (12.5 mg, 0.033 mmol, 87% yield) as a pale yellow oil; $^1$H NMR (500 MHz, CDCl$_3$) δ 7.66-7.58 (m, 2H), 7.42-7.26 (m, 5H), 6.90-6.86 (m, 2H), 5.63 (ddt, J=17.0, 10.3, 7.0 Hz, 1H), 5.19-5.12 (m, 2H), 4.02 (d, J=13.7 Hz, 2H), 3.85 (s, 3H), 3.83-3.77 (m, 1H), 3.62-3.53 (m, 1H), 3.41 (d, J=13.7 Hz, 2H), 2.91-2.79 (m, 3H), 2.66-2.59 (m 1H), 1.45 (s, 3H).

Additional Examples

Some additional building block compounds were prepared according to the below reaction schemes.

Preparation of Acyclic Building Block Compound 2

Acyclic building block compound 2 was prepared from acyclic substrate compound 1 according to the following Acyclic Reaction Scheme.

Acyclic Reaction Scheme

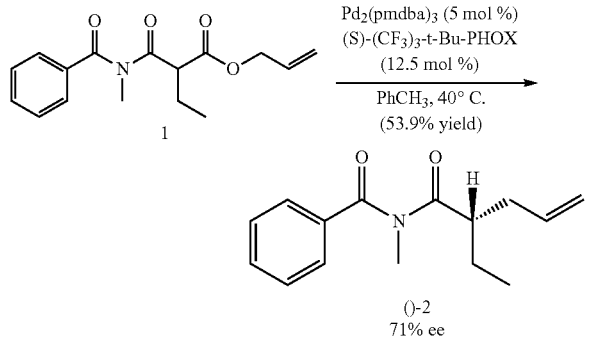

According to the Acyclic Reaction Scheme above, in a nitrogen-filled glovebox, an oven-dried 20 mL vial was charged with Pd$_2$pmdba$_3$ (27.4 mg, 0.025 mmol, 0.05 equiv), (S)—(CF3)3-t-Bu-PHOX (37.0 mg, 0.0625 mmol, 0.125 equiv), toluene (13 mL), and a magnetic stir bar. The vial was stirred at ambient glovebox temperature (~28° C.) for 30 min and 1 (144.6 mg, 0.50 mmol, 1.00 equiv) was added as a solution in toluene (2 mL). The vial was sealed and heated to 40° C. After 37 hours, complete consumption of the starting material was observed by colorimetric change (from light green to red-orange) and confirmed by thin layer chromatography on SiO$_2$. The reaction mixture was removed from the glovebox, concentrated under reduced pressure, and purified by flash chromatography (SiO$_2$, 3×25 cm, 19:1→14:1→9:1 hexane:diethyl ether) to afford imide 2 (66.2 mg, 0.013 mmol, 53.9% yield) as a pale yellow oil; $^1$H NMR (500 MHz, CDCl$_3$) δ 7.68-7.52 (m, 3H), 7.52-7.43 (m, 2H), 5.70 (ddt, J=17.2, 10.2 Hz, 1H), 2.28-2.18 (m, 1, 7.1 Hz, 1H), 5.09-4.97 (m, 2H), 3.19 (s, 3H), 2.99 (tt, J=7.6, 6.0 Hz, 1H), 2.40 (dtt, J=13.9, 7.5, 11H), 1.72 (dp, J=13.4, 7.5 Hz, 1H), 1.60-1.47 (m, 1H), 0.88 (t, J=7.4 Hz, 3H).

Preparation of Lactone Building Block Compound 4

Lactone building block compound 4 was prepared from lactone substrate compound 3 according to the following Lactone Reaction Scheme.

Lactone Reaction Scheme

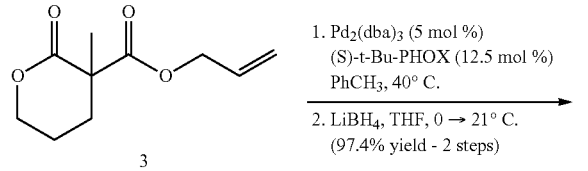

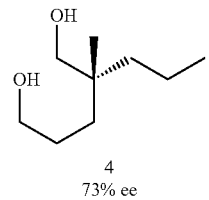

According to the Lactone Reaction Scheme, above, in a nitrogen-filled glovebox, an oven-dried 20 mL vial was charged with Pd$_2$dba$_3$ (27.4 mg, 0.025 mmol, 0.05 equiv), (S)-t-Bu-PHOX (24.2 mg, 0.0625 mmol, 0.125 equiv), toluene (13 mL), and a magnetic stir bar. The vial was stirred at ambient glovebox temperature (~28° C.) for 30 min and 3 (99.0 mg, 0.50 mmol, 1.00 equiv) was added as a solution in toluene (2 mL). The vial was sealed and heated to 40° C. After 30 hours, complete consumption of the starting material was observed by colorimetric change (from light green to red-orange) and confirmed by thin layer chromatography on SiO$_2$. The reaction mixture was removed from the glovebox, concentrated under reduced pressure, and taken up in 10 mL THF. The solution was cooled to 0° C. with an ice-water bath and LiBH$_4$ (1.0 mL 2.0 M solution in THF, 2.0 mmol, 4 equiv) was added. After 30 minutes stirring, an additional charge of LiBH4 1.0 mL 2.0 M solution in THF, 2.0 mmol, 4 equiv) was added. After 40 additional minutes of stirring, the ice-water bath was removed to allow the reaction to warm to room temperature (~21° C.). After more hours stirring at room temperature, the reaction was complete as observed by thin layer chromatography on SiO$_2$. The reaction mixture was poured into a mixture of water and ethyl acetate. A 1.0 M solution of HCl in water was added slowly. The aqueous phase was extracted five times with ethyl acetate. The combined organic layers were washed with brine and concentrated under reduced pressure. The resulting crude product was purified by flash chromatography (SiO$_2$, 1.5×20 cm, 19:1→7:3→1:1→7:3 hexane:diethyl ether) to afford diol 4 (77.1 mg, 0.049 mmol, 97.4% yield) as a pale yellow oil; $^1$H NMR (500 MHz, CDCl$_3$) δ 5.84 (ddt, J=16.4, 10.5, 7.5 Hz, 1H), 5.11-5.02 (m, 2H), 4.12 (q, J=7.1 Hz, 1H), 3.69-3.51 (m, 2H), 3.37 (d, J=0.8 Hz, 2H), 2.08-1.92 (m, 3H), 1.62-1.42 (m, 2H), 1.42-1.18 (m, 2H), 0.86 (s, 3H).

Preparation of Imide Building Block Compound 6

Imide building block compound 6 was prepared from imide substrate compound 6 according to the following Imide Reaction Scheme.

Imide Reaction Scheme

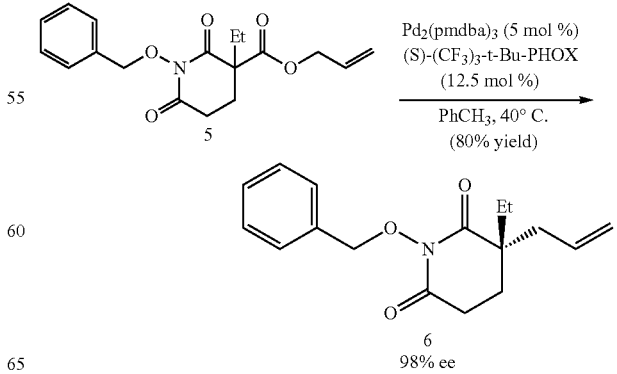

According to the Imide Reaction Scheme, above, in a nitrogen-filled glovebox, an oven-dried 2 dram vial was charged with Pd$_2$pmdba$_3$ (5.0 mg, 0.005 mmol, 0.05 equiv), (S)—(CF3)3-t-Bu-PHOX (7.7 mg, 0.013 mmol, 0.125 equiv), toluene (3 mL), and a magnetic stir bar. The vial was stirred at ambient glovebox temperature (~28° C.) for 30 min and 5 (33 mg, 0.10 mmol, 1.00 equiv) was added as a solution in toluene (0.3 mL). The vial was sealed and heated to 40° C. After 5 days, complete consumption of the starting material was observed by colorimetric change (from light green to red-orange) and confirmed by thin layer chromatography on SiO$_2$. The reaction mixture was removed from the glovebox, concentrated under reduced pressure, and purified by flash chromatography (SiO$_2$, 4:1 hexane:ethyl acetate) to afford imide 6 (23 mg, 0.08 mmol, 80% yield) as a pale yellow oil; $^1$H NMR (500 MHz, CDCl$_3$) δ 7.55-7.47 (m, 2H), 7.36 (dd, J=5.0, 2.0 Hz, 3H), 5.63 (ddt, J=17.3, 10.3, 7.4 Hz, 1H), 5.15-5.06 (m, 2H), 4.99 (s, 2H), 2.80-2.65 (m, 2H), 2.45 (ddt, J=14.2, 7.0, 1.3 Hz, 1H), 2.26 (ddt, J=14.0, 8.0, 1.1 Hz, 1H), 1.84-1.63 (m, 3H), 0.86 (t, J=7.5 Hz, 3H).

While certain exemplary embodiments of the present invention have been illustrated and described, those of ordinary skill in the art will understand that various modifications and changes can be made to the described embodiments without departing from the spirit and scope of the present invention, as defined by the following claims.

What is claimed is:

1. A method comprising
treating a compound of Formula (III):

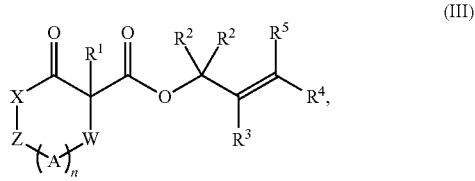
(III)

with a transition metal catalyst under alkylation conditions, thereby preparing a compound of Formula (IV):

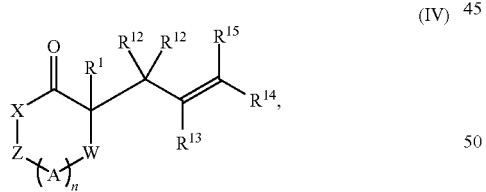
(IV)

wherein the compound of Formula (IV) comprises one of a (+) enantiomer or a (−) enantiomer in an enantiomeric excess of greater than 50%,
wherein the transition metal catalyst is selected from Mo(CO)$_6$, Mo(MeCN)$_3$(CO)$_3$, W(CO)$_6$, W(MeCN)$_3$(CO)$_3$, [Ir-(1,5-cyclooctadiene)Cl]$_2$, [Ir(1,5-cyclooctadiene)Cl]$_2$, [Ir(1,5-cyclooctadiene)Cl]$_2$, Rh(PPh$_3$)$_3$Cl, [Rh(1,5-cyclooctadiene)Cl]$_2$, Ru(pentamethylcyclopentadienyl)(MeCN)$_3$PF$_6$, Ni(1,5-cyclooctadiene)2, Ni[P(OEt)$_3$]$_4$, tris(dibenzylideneacetone)dipalladium(0), tris(dibenzylideneacetone)dipalladium(0)-chloroform adduct, bis(4-methoxybenzylidene)acetone)dipalladium(0), Pd(OC(=O)CH$_3$)$_2$, Pd(3,5-dimethyoxy-dibenzylideneacetone)$_2$, PdCl$_2$(R$^{23}$CN)$_2$; PdCl$_2$(PR$^{24}$R$^{25}$R$^{26}$)$_2$; [Pd(η$^3$-allyl)Cl]$_2$; and Pd(PR$^{24}$R$^{25}$R$^{26}$)$_4$, whrein R$^{23}$, R$^{24}$, R$^{25}$, and R$^{26}$ are independently selected from H, alkyl, alkenyl, alkynyl, carbocycle, substituted hydrocarbyl, heteroatom-containing hydrocarbyl, and substituted heteroatom-containing hydrocarbyl, allylchloro[1,3-bis(2,6-di-i-propylphenyl)imidazol-2-ylidene]palladium(II-), ([2S, 3S]-bis[diphenylphosphino]butane)(η$^3$-allyl)palladium(II) perchlorate, [S]-4-tert-butyl-2-(2-diphenylphosphanyl-phenyl)-4,5-dihydro-oxazole(η-$^3$-allyl)palladium(II) hexafluorophosphate, [Pd(S-tBu-PHOX)(allyl)]PF$_6$, and cyclopentadienyl(η$^3$-allyl) palladium(II);

wherein, as valence and stability permit,

X is selected from NR$^6$— and —O—;
Z is selected from —C(O)— and CR$^7$R$^7$—;
A is independently selected at each occurrence from —CR$^8$R$^8$— and —NR$^9$—;
W is absent or selected from —O—, —NR$^{10}$—, and —CR$^{11}$R$^{11}$—;
R$^1$ is selected from optionally substituted alkyl, alkenyl, alkynyl, carbocyclyl, heterocycle, aryl, heteroaryl, and halogen;
R$^2$, R$^3$, R$^4$, R$^5$, R$^{12}$, R$^{13}$, R$^{14}$, and R$^{15}$ are independently selected at each occurrence from hydrogen, hydroxyl, halogen, nitro, alkyl, alkenyl, alkynyl, cyano, carboxyl, sulfate, amino, alkoxy, alkylamino, alkylthio, hydroxyalkyl, alkoxyalkyl, aminoalkyl, thioalkyl, ether, thioether, ester, amide, thioester, carbonate, carbamate, urea, sulfonate, sulfone, sulfoxide, sulfonamide, acyl, acyloxy, acylamino, aryl, heteroaryl, carbocyclyl, heterocyclyl, aralkyl, aralkyloxy, hetaralkyl, carbocyclylalkyl, and heterocyclylalkyl;
R$^7$, R$^8$, and R$^{11}$ are independently selected at each occurrence from hydrogen, halogen, nitro, alkyl, alkenyl, alkynyl, cyano, hydroxyl, thiol, carboxyl, sulfate, amino, alkoxy, alkylamino, alkylthio, hydroxyalkyl, alkoxyalkyl, aminoalkyl, thioalkyl, ether, thioether, ester, amide, thioester, carbonate, carbamate, urea, sulfonate, sulfone, sulfoxide, sulfonamide, acyl, acyloxy, acylamino, aryl, heteroaryl, carbocyclyl, heterocyclyl, aralkyl, aralkyloxy, hetaralkyl, carbocyclylalkyl, and heterocyclylalkyl;
wherein R$^7$ and R$^8$ may combine with the carbons to which they are bound to form an optionally substituted 3-8-membered ring, R$^8$ and R$^{11}$ may combine with the carbons to which they are bound to form an optionally substituted 3-8-membered ring, and when n is 2 or 3, R$^8$ attached to one carbon may combine with R$^8$ attached to another carbon to combine with the carbons to which they are bound to form a 3-8-membered ring;
R$^6$, R$^9$ and R$^{10}$ are independently selected at each occurrence from hydrogen, hydroxyl and optionally substituted alkyl, alkoxy, alkylthio, aryloxy, carbocyclyl, aryl, heteroaryl, aralkyl, heteroaralkyl, aralkyloxy, heteroaryloxy, acyl, arylcarbonyl, aralkylcarbonyl, acyloxy, sulfone, alkoxycarbonyl, aryloxycarbonyl, aralkoxycarbonyl, and amide; and
n is 0-3.

2. The method of claim 1, wherein:
X is —NR$^6$—;
A at each occurrence is —CR$^8$R$^8$—;
W is selected from —NR$^{10}$— and —CR$^{11}$R$^{11}$—; and
n is 0-2.

3. The method of claim 1, wherein:
X is —O—;
A at each occurrence is —CR$^8$R$^8$—;

W is selected from —NR¹⁰—, and —CR¹¹R¹¹—; and
n is 0-2.

4. The method of claim 1, wherein the method further comprises a chiral ligand.

5. The method of claim 1, wherein a pharmaceutical product or a natural product is prepared.

6. The method of claim 5, wherein the pharmaceutical product is a 3,3-disubstituted pyrrolidinone, a 3,3-disubstituted piperidinone, or a 3,3-disubstituted caprolactam.

7. The method of claim 5, wherein the natural product is (+)-quebrachamine.

8. The method of claim 7, wherein the compound of Formula (IV) is

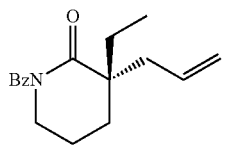

3

9. The method of claim 5, wherein the natural product is (+)-rhazinilam.

10. The method of claim 9, wherein the compound of Formula (IV) is

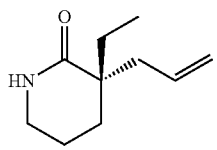

24

11. The method of claim 1, wherein the compound of Formula (IV) is

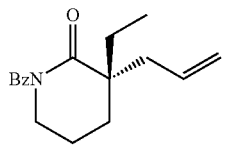

3 further comprising treating the compound of Formula (IV) with lithium hydroxide in the presence of a solvent, thereby preparing the compound

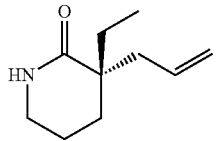

24

12. The method of claim 1, wherein the compound of Formula (IV) is

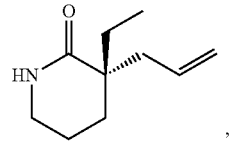

24 further comprising treating the compound of Formula (IV) with lithium aluminum hydride, in the presence of a solvent, thereby preparing the compound

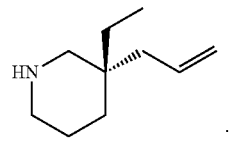

25

13. The method of claim 1, wherein the compound of Formula (IV) is

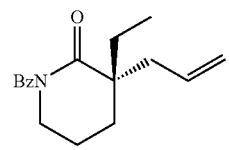

3 further comprising treating the compound of Formula (IV) with, successively,
a) sodium periodate, carbon tetrachloride, acetonitrile, water, and ruthenium(III) chloride; and
b) lithium aluminum hydride in the presence of a solvent;
thereby preparing the compound

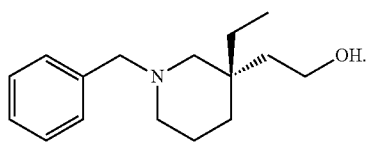

S128

14. The method of claim 13, further comprising treating the compound

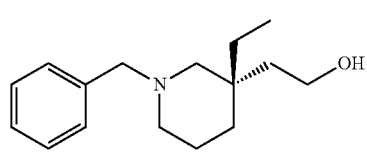

S128 with, successively,
a) Pd(OH)₂/C in the presence of hydrogen and a first solvent; and
b) Boc₂O in the presence of a second solvent;

thereby preparing the compound
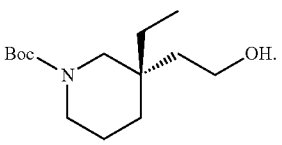
* * * * *